US011019411B2

(12) United States Patent
Mandapaka et al.

(10) Patent No.: US 11,019,411 B2
(45) Date of Patent: *May 25, 2021

(54) SYSTEM AND METHOD FOR COMMUNICATION OF ANALYTE DATA

(71) Applicant: DexCom, Inc., San Diego, CA (US)

(72) Inventors: Aditya Mandapaka, San Diego, CA (US); Douglas William Burnette, San Diego, CA (US); Hari Hampapuram, Portland, OR (US); Francis William Pascual, Valley Center, CA (US); James Stephen Amidei, Escondido, CA (US); Darin Edward Chum Dew, San Diego, CA (US); Apurv Ullas Kamath, San Diego, CA (US); Nathanael Paul, Knoxville, TN (US); William A. Pender, Hollywood, FL (US); Michael A. Ploof, Del Mar, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/782,782

(22) Filed: Oct. 12, 2017

(65) Prior Publication Data

US 2018/0110077 A1 Apr. 19, 2018

Related U.S. Application Data

(63) Continuation of application No. 15/782,702, filed on Oct. 12, 2017.
(Continued)

(51) Int. Cl.
*H04B 7/00* (2006.01)
*H04Q 9/00* (2006.01)
(Continued)

(52) U.S. Cl.
CPC ............ *H04Q 9/00* (2013.01); *A61B 5/0004* (2013.01); *A61B 5/0031* (2013.01);
(Continued)

(58) Field of Classification Search
CPC ... A61B 5/14532; A61B 5/742; A61B 5/0031; A61B 5/14503; A61B 5/14546;
(Continued)

(56) References Cited

U.S. PATENT DOCUMENTS 4,076,385 A 2/1978 Kondo
6,001,067 A 12/1999 Shults et al.
(Continued)

FOREIGN PATENT DOCUMENTS

WO WO-2008138006 A2 11/2008
WO WO-2013096789 A1 6/2013

OTHER PUBLICATIONS

Examination Report No. 1 for Australian Application No. 2020201726 dated Aug. 6, 2020, 5 pages.
(Continued)

*Primary Examiner* — Mahendra R Patel
(74) *Attorney, Agent, or Firm* — Knobbe Martens Olson & Bear LLP

(57) ABSTRACT

Systems, devices, and methods are disclosed for wireless communication of analyte data. In this regard, in embodiments, a mobile includes a transceiver configured to transmit and receive wireless signals. The mobile device includes circuitry operatively coupled to the transceiver. The mobile device also includes a non-transitory computer-readable medium operatively coupled to the circuitry and storing instructions that, when executed, cause the mobile device to perform a number of operations. One such operation is to obtain a derivative of a first signal received via a first link. Another such operation is to obtain a derivative of a second
(Continued)

signal received via a second link; and. Yet another such operation is to generate a selection for connection to an analyte sensor system, based on a comparison of the derivative of the first signal and the derivative of the second signal.

7 Claims, 41 Drawing Sheets

Related U.S. Application Data

(60) Provisional application No. 62/409,677, filed on Oct. 18, 2016.

(51) Int. Cl.

| | | |
|---|---|---|
| *H04W 4/38* | (2018.01) | |
| *H04W 12/02* | (2009.01) | |
| *H04L 29/06* | (2006.01) | |
| *H04W 12/033* | (2021.01) | |
| *H04W 12/037* | (2021.01) | |
| *H04W 12/065* | (2021.01) | |
| *H04W 12/06* | (2021.01) | |
| *H04W 12/069* | (2021.01) | |
| *H04W 12/084* | (2021.01) | |
| *H04W 4/70* | (2018.01) | |
| *H04W 76/23* | (2018.01) | |
| *H04W 76/14* | (2018.01) | |
| *A61B 5/00* | (2006.01) | |
| *A61B 5/145* | (2006.01) | |
| *H04W 76/10* | (2018.01) | |
| *H04W 76/25* | (2018.01) | |
| *H04W 76/30* | (2018.01) | |

(52) U.S. Cl.
CPC ...... *A61B 5/14503* (2013.01); *A61B 5/14532* (2013.01); *H04L 63/08* (2013.01); *H04L 63/0869* (2013.01); *H04W 4/38* (2018.02); *H04W 4/70* (2018.02); *H04W 12/02* (2013.01); *H04W 12/033* (2021.01); *H04W 12/037* (2021.01); *H04W 12/065* (2021.01); *H04W 12/068* (2021.01); *H04W 12/069* (2021.01); *H04W 12/084* (2021.01); *H04W 76/10* (2018.02); *H04W 76/14* (2018.02); *H04W 76/23* (2018.02); *A61B 5/14546* (2013.01); *H04Q 2209/40* (2013.01); *H04Q 2209/43* (2013.01); *H04Q 2209/826* (2013.01); *H04Q 2209/86* (2013.01); *H04Q 2209/88* (2013.01); *H04W 76/25* (2018.02); *H04W 76/30* (2018.02)

(58) Field of Classification Search
CPC . A61B 5/0004; G04F 19/00; G06F 196/3418; G16H 40/63; H04Q 9/00; H04Q 2209/86; H04Q 2209/43; H04Q 2209/826; H04Q 2209/88; H04Q 2209/40; H04W 12/033; H04W 12/037; H04W 12/065; H04W 12/068; H04W 12/069; H04W 12/084; H04W 4/38; H04W 12/02; H04W 76/10; H04W 76/25; H04W 76/30; H04W 4/70; H04W 76/23; H04W 76/14; H04L 63/08; H04L 63/0869; Y02A 90/10
USPC .................................................. 455/41.2
See application file for complete search history.

(56) References Cited

U.S. PATENT DOCUMENTS

| | | |
|---|---|---|
| 6,424,847 B1 | 7/2002 | Mastrototaro et al. |
| 6,477,395 B2 | 11/2002 | Schulman et al. |
| 6,484,046 B1 | 11/2002 | Say et al. |
| 6,512,939 B1 | 1/2003 | Colvin et al. |
| 6,565,509 B1 | 5/2003 | Say et al. |
| 6,579,690 B1 | 6/2003 | Bonnecaze et al. |
| 6,718,179 B1* | 4/2004 | Forssell ............... H04W 76/25 455/509 |
| 6,931,327 B2 | 8/2005 | Goode et al. |
| 7,310,544 B2 | 12/2007 | Brister et al. |
| 8,372,351 B2 | 2/2013 | Ow-Wing |
| 9,317,656 B2 | 4/2016 | Hayter et al. |
| 9,463,325 B1* | 10/2016 | Young ............... A61N 1/37217 |
| 9,526,420 B2* | 12/2016 | Fish ................... G08C 17/02 |
| 9,814,389 B2* | 11/2017 | DeHennis ............ G16H 40/63 |
| 2003/0208133 A1* | 11/2003 | Mault ................... A61B 5/097 600/532 |
| 2005/0027463 A1 | 2/2005 | Goode et al. |
| 2005/0043598 A1 | 2/2005 | Goode et al. |
| 2005/0154271 A1 | 7/2005 | Rasdal et al. |
| 2005/0192557 A1 | 9/2005 | Brauker et al. |
| 2005/0203360 A1 | 9/2005 | Brauker et al. |
| 2006/0020187 A1 | 1/2006 | Brister et al. |
| 2006/0222566 A1 | 10/2006 | Brauker et al. |
| 2007/0016381 A1 | 1/2007 | Kamath et al. |
| 2007/0027385 A1 | 2/2007 | Brister et al. |
| 2007/0032706 A1 | 2/2007 | Kamath et al. |
| 2007/0043290 A1 | 2/2007 | Goepp et al. |
| 2007/0197890 A1 | 8/2007 | Boock et al. |
| 2007/0203966 A1 | 8/2007 | Brauker et al. |
| 2007/0208245 A1 | 9/2007 | Brauker et al. |
| 2007/0208246 A1 | 9/2007 | Brauker et al. |
| 2007/0217556 A1 | 9/2007 | Pietraski |
| 2008/0033254 A1 | 2/2008 | Kamath et al. |
| 2008/0108942 A1 | 5/2008 | Brister et al. |
| 2008/0119703 A1 | 5/2008 | Brister et al. |
| 2008/0177570 A1 | 7/2008 | Craine |
| 2009/0036747 A1* | 2/2009 | Hayter ................. A61B 5/01 600/300 |
| 2009/0054754 A1* | 2/2009 | McMahon ............ G16H 20/17 600/365 |
| 2009/0092060 A1* | 4/2009 | Goto .................. H04L 63/0428 370/254 |
| 2009/0240120 A1 | 9/2009 | Mensinger et al. |
| 2009/0240193 A1 | 9/2009 | Mensinger et al. |
| 2009/0307517 A1* | 12/2009 | Fehr .................... H04B 1/7156 713/500 |
| 2010/0000862 A1* | 1/2010 | Rao .................... G01N 27/3273 204/403.02 |
| 2010/0094111 A1* | 4/2010 | Heller ................. G01N 27/3274 600/345 |
| 2010/0133099 A1* | 6/2010 | Norgaard ............ A61B 5/14532 204/403.01 |
| 2010/0138197 A1* | 6/2010 | Sher .................... G16H 50/50 703/2 |
| 2010/0265073 A1* | 10/2010 | Harper .................. H04W 4/80 340/573.1 |
| 2011/0053121 A1 | 3/2011 | Heaton |
| 2011/0184265 A1* | 7/2011 | Hayter ................. A61B 5/01 600/347 |
| 2012/0116196 A1* | 5/2012 | Tubb .................. A61B 5/14532 600/365 |
| 2012/0120886 A1* | 5/2012 | He ...................... H04W 52/262 370/329 |
| 2012/0271557 A1* | 10/2012 | Sekimoto ............. A61B 5/743 702/19 |
| 2013/0044028 A1* | 2/2013 | Lea .................... H01Q 21/24 342/359 |
| 2013/0059541 A1 | 3/2013 | Sloan et al. |
| 2013/0069865 A1 | 3/2013 | Hart et al. |
| 2013/0076531 A1* | 3/2013 | San Vicente ......... A61B 5/0015 340/870.02 |

(56) References Cited

U.S. PATENT DOCUMENTS

| | | | |
|---|---|---|---|
| 2013/0078912 A1* | 3/2013 | San Vicente | A61B 5/0004 455/39 |
| 2013/0132416 A1 | 5/2013 | Hayter et al. | |
| 2013/0197445 A1* | 8/2013 | Schabbach | A61M 5/31 604/189 |
| 2013/0328572 A1 | 12/2013 | Wang et al. | |
| 2013/0331036 A1 | 12/2013 | Baker et al. | |
| 2014/0012117 A1* | 1/2014 | Mensinger | A61B 5/6898 600/365 |
| 2014/0039383 A1* | 2/2014 | Dobbies | A61B 5/14532 604/66 |
| 2014/0066735 A1* | 3/2014 | Engelhardt | A61B 5/7221 600/365 |
| 2014/0094743 A1* | 4/2014 | Bengtsson | G16H 40/63 604/66 |
| 2014/0095081 A1* | 4/2014 | Doniger | G16H 40/63 702/19 |
| 2014/0107449 A1* | 4/2014 | Ecoff | A61B 5/0015 600/365 |
| 2014/0118159 A1 | 5/2014 | Fish et al. | |
| 2014/0197946 A1 | 7/2014 | Park et al. | |
| 2014/0266776 A1* | 9/2014 | Miller | A61B 5/0002 340/870.01 |
| 2014/0275876 A1 | 9/2014 | Hansen et al. | |
| 2014/0322815 A1 | 10/2014 | Carlsgaard et al. | |
| 2014/0324020 A1* | 10/2014 | Stefansen | A61M 5/31535 604/506 |
| 2015/0112264 A1 | 4/2015 | Kamen et al. | |
| 2015/0123810 A1* | 5/2015 | Hernandez-Rosas | H04W 4/70 340/870.02 |
| 2015/0149689 A1* | 5/2015 | Hua | G06F 12/0215 711/102 |
| 2015/0182115 A1 | 7/2015 | DeHennis | |
| 2015/0199165 A1 | 7/2015 | Chopde et al. | |
| 2015/0205930 A1 | 7/2015 | Shaanan et al. | |
| 2015/0205947 A1* | 7/2015 | Berman | A61B 5/14532 726/16 |
| 2015/0207796 A1* | 7/2015 | Love | H04L 63/10 600/345 |
| 2015/0241407 A1* | 8/2015 | Ou | A61B 5/14532 702/19 |
| 2015/0356263 A1* | 12/2015 | Chatterjee | G16H 40/67 705/3 |
| 2016/0058341 A1 | 3/2016 | Heller et al. | |
| 2016/0089066 A1 | 3/2016 | Hernandez-Rosas et al. | |
| 2016/0094648 A1 | 3/2016 | Han et al. | |
| 2016/0117532 A1* | 4/2016 | Lin | G06K 19/0717 340/10.51 |
| 2016/0174272 A1* | 6/2016 | Rabii | H04W 8/005 455/422.1 |
| 2016/0210099 A1* | 7/2016 | Hampapuram | G06F 3/1423 |
| 2016/0331310 A1* | 11/2016 | Kovatchev | A61B 5/7275 |
| 2016/0345874 A1* | 12/2016 | Raisoni | A61B 5/002 |
| 2017/0000426 A1 | 1/2017 | Harper et al. | |
| 2017/0048722 A1* | 2/2017 | Van Phan | H04W 16/16 |
| 2017/0181671 A1 | 6/2017 | Varsaysky et al. | |
| 2017/0201931 A1* | 7/2017 | Swanzey | H04W 76/10 |
| 2017/0367104 A1* | 12/2017 | Raisoni | H04W 72/12 |
| 2018/0109852 A1 | 4/2018 | Mandapaka et al. | |
| 2018/0110078 A1 | 4/2018 | Mandapaka et al. | |
| 2018/0256208 A1* | 9/2018 | Altschul | A61B 17/34 |
| 2018/0325434 A1* | 11/2018 | Bernstein | G16H 50/20 |
| 2018/0359689 A1* | 12/2018 | Lee | H04W 48/18 |

OTHER PUBLICATIONS

Extended European Search Report for Application No. 17862878 dated Mar. 30, 2020, 7 pages.
International Preliminary Report on Patentability for Application No. PCT/US2017/056389 dated May 9, 2019, 9 pages.
International Search Report and Written opinion for Application No. PCT/US2017/056389 dated Feb. 2, 2018, 11 pages.

* cited by examiner

|  | Address 805 | Description 810 | Value 815 |
|---|---|---|---|
| 800a | Range 805a | Preamble 810a | Bytes 815a |
| 800b | Range 805b | Access Address 810b | Bytes 815b |
| 800c | Range 805c | Header 810c | Bytes 815c |
| 800d | Range 805d | MAC Address 810d | Bytes 815d |
| 800e | Range 805e | Device Name 810e | Bytes 815e |
| 800f | Range 805f | Flags 810f | Bytes 815f |
| 800g | Range 805g | Identifier 810g | Bytes 815g |
| 800h | Range 805h | Manufacturing Data 810h | Bytes 815h |
| 800i | Range 805i | Error Checking 810i | Bytes 815i |

SYSTEM AND METHOD FOR COMMUNICATION OF ANALYTE DATA

INCORPORATION BY REFERENCE TO RELATED APPLICATION

Any and all priority claims identified in the Application Data Sheet, or any correction thereto, are hereby incorporated by reference under 37 CFR 1.57. This application is a continuation of U.S. application Ser. No. 15/782,702, filed Oct. 12, 2017, which claims the benefit of U.S. Provisional Appl. No. 62/409,677, filed on Oct. 18, 2016. The aforementioned application is incorporated by reference herein in its entirety, and is hereby expressly made a part of this specification.

TECHNICAL FIELD

The present disclosure relates generally to the monitoring of analyte values received from a sensor. More particularly, the present disclosure is directed to systems, methods, apparatuses, and devices, for the communication of analyte (e.g., glucose) data.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which may require uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is not only unlikely that a diabetic will take a timely SMBG value, but will not know if his blood glucose value is going up (higher) or down (lower), due to limitations of conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display. The transmission to wireless display devices can be wireless.

With respect to the wireless transmission of glucose and other analyte data gathered using an implanted sensor, battery life of the transmitter acting in conjunction with the sensor is typically a concern. In order to conserve battery life or to increase the efficiency associated with the transmission of glucose and other analyte data, transmissions may, for example, need to be intermittent. The intermittent transmission of monitored data can introduce reliability issues, however. In some cases, reliability is thus sacrificed for battery life in conventional sensor systems.

SUMMARY

In a first aspect, a method for identifying a device for connection includes a display device receiving input that identifies an analyte sensor system from among a set of analyte sensor systems. The method further includes the display device selecting the analyte sensor system for connection, based on the input.

In certain implementations of the first aspect, which may be generally applicable but are also particularly applicable in connection with any other implementation of the first aspect, the input is identification information associated with the analyte sensor system. The identification information may include a number string associated with the analyte sensor system. In embodiments the input uniquely identifies the analyte sensor system. In embodiments, the input is received from a user via a GUI of the display device.

In certain implementations of the first aspect, which may be generally applicable but are also particularly applicable in connection with any other implementation of the first aspect, the method further includes presenting, via the GUI, a list of one or more discoverable analyte sensor systems from among the set of analyte sensor systems. In embodiments, the display device selecting the analyte sensor system for connection is done responsive to the user manually selecting the analyte sensor system from the list using the GUI and a touch screen interface of the display device. In embodiments, the list includes respective identification information for one or more of the discoverable analyte sensor systems. In embodiments, the identification information includes at least one of a graphic, a symbol, a code, and a character string.

In certain implementations of the first aspect, which may be generally applicable but are also particularly applicable in connection with any other implementation of the first aspect, the input is based on one of an encoded element and an image. The encoded element may include one of capacitive ink, a bar code, a QR code, and a sticker. In embodiments, the display device receiving the input includes scanning the encoded element from the analyte sensor system or product packaging of the analyte sensor system.

In a second aspect, a mobile device is configured for wireless communication of analyte data. The mobile device includes a touch screen, a camera, a transceiver configured to transmit and receive wireless signals, and a processor operatively coupled to the touch screen, the camera, and the transceiver. The processor is configured to cause the display device to perform a number of operations. One such operation is to receive, via one or more of the touch screen and the camera, input that identifies an analyte sensor system from among a set of analyte sensory systems. Another such operation is to select the analyte sensor system for connection, based on the input.

In certain implementations of the second aspect, which may be generally applicable but are also particularly applicable in connection with any other implementation of the second aspect, the processor is further configured to cause a GUI of the display device to present a list of one or more discoverable analyte sensor systems from among the set of analyte sensor systems. In embodiments, the processor is further configured to cause the touch screen to receive the input manually from the user based on the list presented via the GUI of the display device.

In certain implementations of the second aspect, which may be generally applicable but are also particularly applicable in connection with any other implementation of the second aspect, the processor is further configured to cause the touch screen or the camera of the display device to obtain the input from one or more of an encoded element and an image.

In a third aspect, a method for identifying a device for connection includes a display device receiving a first signal from an analyte sensor system of a set of analyte sensor systems. The first signal is received via a first link. The method further includes the display device determining a derivative of the first signal. Additionally, the method includes the display device identifying the analyte sensor system for selection, based on the derivative of the first signal In certain implementations of the third aspect, which may be generally applicable but are also particularly applicable in connection with any other implementation of the third aspect, identifying the analyte sensor system for selection includes comparing the derivative of the first signal to a first threshold. In embodiments, identifying the analyte sensor system for selection further includes determining whether the derivative of the first signal at least meets the first threshold. In embodiments, the method further includes selecting the analyte sensor system for connection, based on determining that the derivative of the first signal at least meets the first threshold.

In certain implementations of the third aspect, which may be generally applicable but are also particularly applicable in connection with any other implementation of the third aspect, the method further includes the display device receiving a second signal from the analyte sensor system. The signal may be received via a second link. In embodiments, the method further includes the display device determining a derivative of the second signal. Additionally, the method may include selecting the analyte sensor system for connection, based on the derivative of the second signal. In some cases, selecting the analyte sensor system for connection includes comparing the derivative of the second signal to a second threshold. Selecting the analyte sensor system for connection may further include determining whether the derivative of the second signal at least meets the second threshold. In embodiments, selecting the analyte sensor system for connection is done responsive to determining that the derivative of the second signal at least meets the second threshold.

In certain implementations of the third aspect, which may be generally applicable but are also particularly applicable in connection with any other implementation of the third aspect, selecting the analyte sensor system for connection further includes comparing the derivative of the first signal to the second threshold; determining whether the derivative of the first signal does not at least meet the second threshold. In embodiments, selecting the analyte sensor system for connection is done responsive to determining that the derivative of the second signal at least meets the second threshold and that the derivative of the first signal does not at least meet the second threshold.

In certain implementations of the third aspect, which may be generally applicable but are also particularly applicable in connection with any other implementation of the third aspect, selecting the analyte sensor system for connection includes comparing the derivative of the second signal to the first threshold. In embodiments, selecting the analyte sensor system for connection further includes determining whether the derivative of the second signal does not at least meet the first threshold. In embodiments, selecting the analyte sensor system for connection is done responsive to determining that the derivative of the second signal does not at least meet the first threshold.

In certain implementations of the third aspect, which may be generally applicable but are also particularly applicable in connection with any other implementation of the third aspect, the derivative of the first signal is based on a signal strength of the first signal. In some cases, the derivative of the first signal is a received signal strength indication ("RSSI") associated with the first signal. In some cases, the derivative of the second signal is based on a signal strength of the second signal. The derivative of the second signal may include an RSSI associated with the second signal.

In certain implementations of the third aspect, which may be generally applicable but are also particularly applicable in connection with any other implementation of the third aspect, the derivative of the first signal is based on a bit error rate ("BER") associated with the first signal. In some cases, the derivative of the second signal is based on a BER associated with the second signal. The derivative of the second signal may include a BER associated with the second signal.

In a fourth aspect, a mobile device is configured for wireless communication of analyte data. The mobile device includes a transceiver configured to transmit and receive wireless signals. The mobile device includes circuitry operatively coupled to the transceiver. Further, the mobile device includes a non-transitory computer-readable medium operatively coupled to the circuitry and storing instructions that, when executed, cause the display device to perform a number of operations. One such operation is to receive, via a first link, a first signal from an analyte sensor system of a set of analyte sensor systems. Another such operation is to determine a derivative of the first signal. Another such operation is to identify the analyte sensor system for selection, based on the derivative of the first signal.

In certain implementations of the fourth aspect, which may be generally applicable but are also particularly applicable in connection with any other implementation of the fourth aspect, the non-transitory computer-readable medium further stores instructions that, when executed, cause the display device to perform additional operations. One such operation is to compare the derivative of the first signal to a first threshold. Another such operation is to determine whether the derivative of the first signal at least meets the first threshold. Yet another such operation is to select the analyte sensor system for connection, based on a determination that the derivative of the first signal at least meets the first threshold.

In certain implementations of the fourth aspect, which may be generally applicable but are also particularly applicable in connection with any other implementation of the fourth aspect, the non-transitory computer-readable medium further stores instructions that, when executed, cause the display device to perform additional operations. One such operation is to receive a second signal from the analyte sensor system. Another such operation is to determine a derivative of the second signal. Yet another such operation is to select the analyte sensor system for connection, based on the derivative of the second signal. In embodiments, another such operation is to compare the derivative of the second signal to a second threshold. In embodiments, another such operation is to determine whether the derivative of the second signal at least meets the second threshold. The display device may select the analyte sensor system for connection further based on a determination that the derivative of the second signal at least meets the second threshold.

In certain implementations of the fourth aspect, which may be generally applicable but are also particularly applicable in connection with any other implementation of the fourth aspect, the non-transitory computer-readable medium further stores instructions that, when executed, cause the display device to perform additional operations. One such operation is to compare the derivative of the first signal to a second threshold. Another such operation is to determine whether the derivative of the first signal does not at least meet the second threshold. In embodiments, another such operation is to select the analyte sensor system for connection further based on a determination that the derivative of the first signal does not at least meet the second threshold.

In certain implementations of the fourth aspect, which may be generally applicable but are also particularly applicable in connection with any other implementation of the fourth aspect, the non-transitory computer-readable medium further stores instructions that, when executed, cause the display device to perform additional operations. One such operation is to compare the derivative of the second signal to the first threshold. Another such operation is to determine whether the derivative of the second signal does not at least meet the first threshold. Yet another such operation is to select the analyte sensor system for connection further based on a determination that the derivative of the second signal does at least meet the first threshold.

In a fifth aspect, a method for identifying a device for connection includes a display device receiving a first signal from an analyte sensor system of a set of analyte sensor systems. The first signal is received via a first link. The method also includes the display device obtaining a derivative of the first signal. Further, the method includes the display device identifying the analyte sensor system for selection, based on the derivative of the first signal meeting or being above a lower threshold.

In certain implementations of the fifth aspect, which may be generally applicable but are also particularly applicable in connection with any other implementation of the fifth aspect, the method additionally includes selecting the analyte sensor system for connection based on the derivative of the first signal meeting or being above an upper threshold. In embodiments, the method further includes the display device receiving a second signal from the analyte sensor system. The second signal may be received via a second link. In embodiments, the method also includes the display device obtaining a derivative of the second signal. Selecting the analyte sensor system for connection may be further based on the derivative of the second signal being below the lower threshold.

In certain implementations of the fifth aspect, which may be generally applicable but are also particularly applicable in connection with any other implementation of the fifth aspect, the method further includes the display device receiving a second signal from the analyte sensor system. In embodiments, the second signal is received via a second link. In embodiments, the second signal is received via the first link. In embodiments, the method also includes the display device obtaining a derivative of the second signal. The method may also include the display device selecting the analyte sensor system for connection, based on the derivative of the second signal meeting or being above an upper threshold. In some cases, selecting the analyte sensor system for connection is further based on the derivative of the first signal not meeting or being above the upper threshold.

In certain implementations of the fifth aspect, which may be generally applicable but are also particularly applicable in connection with any other implementation of the fifth aspect, the method also includes generating an indication to configure the display device according to a second link, based on the derivative of the first signal being below the upper threshold. In embodiments, the indication includes a communication representing an instruction for the display device to be moved closer to the analyte sensor system. The method may also include the displace device providing the indication to a user of the display device. The indication comprises one or more of an audible communication, a visual communication, and a tactile communication.

In certain implementations of the fifth aspect, which may be generally applicable but are also particularly applicable in connection with any other implementation of the fifth aspect, the method also includes generating an indication to configure the display device according to the second link, based on the derivative of the first signal meeting or being above the upper threshold.

In certain implementations of the fifth aspect, which may be generally applicable but are also particularly applicable in connection with any other implementation of the fifth aspect, the method includes the display device receiving a third signal from the analyte sensor system, wherein the third signal is received via a third link. In embodiments, the method also includes the display device obtaining a derivative of the third signal. Further, the method may include the display device selecting the analyte sensor system for connection is further based on the derivative of the third signal being below the lower threshold.

In certain implementations of the fifth aspect, which may be generally applicable but are also particularly applicable in connection with any other implementation of the fifth aspect, the method includes the display device receiving a third signal from the analyte sensor system, wherein the third signal is received via a third link. In embodiments, the method also includes the display device obtaining a derivative of the third signal. The display device selecting the analyte sensor system for connection may further be based on the derivative of the third signal being below the lower threshold.

In certain implementations of the fifth aspect, which may be generally applicable but are also particularly applicable in connection with any other implementation of the fifth aspect, the method also includes the display device receiving a second signal from the analyte sensor system, wherein the second signal is received via a second link. In embodiments, the method further includes the display device obtaining a derivative of the second signal. Additionally, the method may include the display device selecting the analyte sensor system for connection, based on a comparison of the derivative of the second signal and the derivative of the first signal. In embodiments, selecting the analyte sensor system for connection is further based on the derivative of the first signal meeting or exceeding the upper threshold, where the derivative of the second signal is less than the derivative of the first signal. In embodiments, selecting the analyte sensor system for connection is further based on the derivative of the second signal meeting or exceeding the upper threshold, where the derivative of the first signal is less than the derivative of the second signal.

In certain implementations of the fifth aspect, which may be generally applicable but are also particularly applicable in connection with any other implementation of the fifth aspect, the method also includes the display device receiving a third signal from the analyte sensor system, wherein the third signal is received via a third link. In embodiments, the method further includes the display device obtaining a derivative of the third signal. Additionally, the display device selecting the analyte sensor system for connection may further be based on a comparison of the derivative of the third signal and the derivative of the second signal. In embodiments of the method, the derivative of the second signal exceeds the upper threshold, and the derivative of the third signal is less than the derivative of the second signal. In embodiments of the method, the derivative of the second signal falls below the upper threshold, and the derivative of the third signal is greater than the derivative of the second signal.

In certain implementations of the fifth aspect, which may be generally applicable but are also particularly applicable in connection with any other implementation of the fifth aspect, the method also includes the display device sending a first response signal to the analyte sensor system via the first link. In embodiments, the method also includes the display device obtaining a derivative of the first response signal. Also, the display device identifying the analyte sensor system for selection may further be based on a comparison of the derivative of the first signal and the derivative of the first response signal. In embodiments, the method also includes the display device receiving the derivative of the first response signal from the analyte sensor system, where the derivative of the first response signal is generated by the analyte sensor system.

In certain implementations of the fifth aspect, which may be generally applicable but are also particularly applicable in connection with any other implementation of the fifth aspect, each of the analyte sensor systems includes a wakeup circuit that initiates transmission of advertisement signals after a predetermined amount of time from when a sensor is connected to a sensor electronics module of the analyte system. In embodiments, the predetermined amount of time is common to the analyte sensor systems.

In a sixth aspect, a mobile device is configured for wireless communication of analyte data. The mobile device includes a transceiver configured to transmit and receive wireless signals. The mobile device also includes circuitry operatively coupled to the transceiver. Additionally, the mobile device includes a non-transitory computer-readable medium operatively coupled to the circuitry and storing instructions that, when executed, cause the display device to perform a number of operations. One such operation is to receive, via a first link, a first signal from an analyte sensor system of a set of analyte sensor systems. Another such operation is to obtain a derivative of the first signal. Yet another such operation is to identify the analyte sensor system for selection, based on the derivative of the first signal meeting or being above a lower threshold.

In certain implementations of the sixth aspect, which may be generally applicable but are also particularly applicable in connection with any other implementation of the sixth aspect, the non-transitory computer-readable medium further stores instructions that, when executed, cause the display device to additional operations. One such operation is to select the analyte sensor system for connection based on the derivative of the first signal meeting or being above an upper threshold. One such operation is to receive, via a second link, a second signal from the analyte sensor system. Another such operation is to obtain a derivative of the second signal. Yet another such operation is to select the analyte sensor system for connection further based on the derivative of the second signal being below the lower threshold or meeting or being above the upper threshold. Another such operation is to generate an indication to configure the display device according to the second link, based on a determination that the derivative of the first signal is below the upper threshold. Yet another such operation is to generate an indication to configure the display device according to the second link, based on a determination that the derivative of the first signal meets or is above the upper threshold.

In a seventh aspect, a method for identifying a device for connection includes an analyte sensor system receiving a first signal from a display device of a set of display devices, wherein the first signal is received via a first link. The method also includes the analyte sensor system identifying the display device for selection, based on a derivative of the first signal meeting or being above a lower threshold.

In certain implementations of the seventh aspect, which may be generally applicable but are also particularly applicable in connection with any other implementation of the seventh aspect, the method also includes selecting the display device for connection based on the derivative of the first signal meeting or being above an upper threshold. In embodiments, the method also includes the analyte sensor system receiving a second signal from the display device. The second signal may be received via a second link. Selecting the display device for connection may further based on the derivative of the second signal being below the lower threshold.

In certain implementations of the seventh aspect, which may be generally applicable but are also particularly applicable in connection with any other implementation of the seventh aspect, the method also includes the analyte sensor system receiving a second signal from the display device. The second signal may be received via a second link. The second signal may be received via the first link. In embodiments, the method also includes the analyte sensor system obtaining a derivative of the second signal. In embodiments, the method further includes the analyte sensor system selecting the display device for connection, based on the derivative of the second signal meeting or being above an upper threshold. Selecting the display device for connection may further be based on the derivative of the first signal not meeting or being above the upper threshold.

In certain implementations of the seventh aspect, which may be generally applicable but are also particularly applicable in connection with any other implementation of the seventh aspect, the method also includes generating an indication to configure the display device according to a second link, based on the derivative of the first signal being below the upper threshold. The indication may include a communication representing an instruction for the display device to be moved closer to the analyte sensor system. In embodiments, the method also includes sending the indication to the displace device for the indication to be provided to a user of the display device. The indication may include one or more of an audible communication, a visual communication, and a tactile communication. In embodiments, the method also includes generating an indication to configure the display device according to the second link, based on the derivative of the first signal meeting or being above the upper threshold.

In certain implementations of the seventh aspect, which may be generally applicable but are also particularly applicable in connection with any other implementation of the seventh aspect, the method also includes the analyte sensor system receiving a third signal from the display device, wherein the third signal is received via a third link. The method may also include the analyte sensor system obtaining a derivative of the third signal. The analyte sensor system selecting the display device for connection may further be based on the derivative of the third signal being below the lower threshold.

In certain implementations of the seventh aspect, which may be generally applicable but are also particularly applicable in connection with any other implementation of the seventh aspect, the method also includes the analyte sensor system receiving a third signal from the display device, wherein the third signal is received via a third link. In embodiments, the method further includes the analyte sensor system determining a derivative of the third signal. The analyte sensor system selecting the display device for connection may further be based on the derivative of the third signal being below the lower threshold.

In certain implementations of the seventh aspect, which may be generally applicable but are also particularly applicable in connection with any other implementation of the seventh aspect, the method also includes the analyte sensor system receiving a second signal from the display device. The second signal may be received via a second link. In embodiments, the method also includes the analyte sensor system obtaining a derivative of the second signal.

In embodiments, the method also includes the analyte sensor system selecting the display device for connection, based on a comparison of the derivative of the second signal and the derivative of the first signal. Selecting the display device for connection may further be based on the derivative of the first signal meeting or exceeding the upper threshold, where the derivative of the second signal is less than the derivative of the first signal. Selecting the display device for connection may further be based on the derivative of the second signal meeting or exceeding the upper threshold, where the derivative of the first signal is less than the derivative of the second signal.

In certain implementations of the seventh aspect, which may be generally applicable but are also particularly applicable in connection with any other implementation of the seventh aspect, the method also includes the analyte sensor system receiving a third signal from the display device. The third signal may be received via a third link. In embodiments, the method also includes the analyte sensor system obtaining a derivative of the third signal. The analyte sensor system selecting the display device for connection may further be based on a comparison of the derivative of the third signal and the derivative of the second signal. In embodiments, the derivative of the second signal meets or exceeds the upper threshold, and the derivative of the third signal is less than the derivative of the second signal. In embodiments, the derivative of the second signal falls below the upper threshold, and the derivative of the third signal is greater than the derivative of the second signal.

In certain implementations of the seventh aspect, which may be generally applicable but are also particularly applicable in connection with any other implementation of the seventh aspect, the method also includes generating a representation of user input from an accelerometer. In embodiments, selecting the display device for connection is further based on the representation of the user input from the accelerometer. In embodiments, the method also includes initiating a prompt for the user to provide the user input. The user input may be based on the user physically contacting the analyte sensor system.

In an eighth aspect, an analyte sensor system is configured for wireless communication of analyte data. The analyte sensor system includes an analyte sensor. The analyte sensor system includes a transceiver configured to transmit and receive wireless signals. The analyte sensor system also a processor operatively coupled to the analyte sensor and the transceiver and configured to cause the analyte sensor system to perform a number of operations. One such operation is to receive, via a first link, a first signal from a display device of a set of display devices. Another such operation is to obtain a derivative of the first signal. Another such operation is to identify the display device for selection, based on the derivative of the first signal meeting or being above a lower threshold.

In certain implementations of the eighth aspect, which may be generally applicable but are also particularly applicable in connection with any other implementation of the eighth aspect, the processor is further configured to cause the analyte sensor system to perform a number of additional operations. One such operation is to select the display device for connection based on the derivative of the first signal meeting or being above an upper threshold. Another such operation is to receive, via a second link, a second signal from the display device. Yet another such operation is to obtain a derivative of the second signal. Another such operation is to select the display device for connection further based on the derivative of the second signal being below the lower threshold or meeting or being above the upper threshold. Another such operation is to generate an indication to configure the display device according to the second link, based on a determination that the derivative of the first signal is below the upper threshold. Another such operation is to generate an indication to configure the display device according to the second link, based on a determination that the derivative of the first signal meets or is above the upper threshold.

In a ninth aspect, a method for identifying a device for connection includes a display device obtaining a derivative of a first signal received via a first link. The method also includes the display device generating an identification for selection, based on the derivative of the first signal meeting or being above a lower threshold.

In certain implementations of the ninth aspect, which may be generally applicable but are also particularly applicable in connection with any other implementation of the ninth aspect, the method also includes generating a selection for connection, based on the derivative of the first signal meeting or being above an upper threshold. In embodiments, the method further includes the display device obtaining a derivative of a second signal received via a second link. Generating the selection for connection may further be based on the derivative of the second signal being below the lower threshold.

In certain implementations of the ninth aspect, which may be generally applicable but are also particularly applicable in connection with any other implementation of the ninth aspect, the method also includes the display device obtaining a derivative of a second signal. The second signal may be received via a second link. The second signal may be received via the first link. In embodiments, the method also includes the display device generating a selection for connection, based on the derivative of the second signal meeting or being above an upper threshold. Generating the selection for connection may further be based on the derivative of the first signal not meeting or being above the upper threshold.

In certain implementations of the ninth aspect, which may be generally applicable but are also particularly applicable in connection with any other implementation of the ninth aspect, the method also includes generating an indication to configure the display device according to a second link, based on the derivative of the first signal being below the upper threshold. The indication may include a communication representing an instruction for the display device to be moved closer to the analyte sensor system. In embodiments, the method further includes sending the indication to the displace device for the indication to be provided to a user of the display device. The indication may include one or more of an audible communication, a visual communication, and a tactile communication. In embodiments, the method also includes generating an indication to configure the display device according to a second link, based on the derivative of the first signal meeting or being above the upper threshold.

In certain implementations of the ninth aspect, which may be generally applicable but are also particularly applicable in connection with any other implementation of the ninth aspect, the method also includes the display device obtaining a derivative of a third signal received via a third link. The display device generating the selection for connection may further be based on the derivative of the third signal being below the lower threshold.

In certain implementations of the ninth aspect, which may be generally applicable but are also particularly applicable in connection with any other implementation of the ninth aspect, the method also includes the display device obtaining a derivative of a third signal received via a third link. The display device generating the selection connection is further based on the derivative of the third signal meeting or being above the upper threshold.

In certain implementations of the ninth aspect, which may be generally applicable but are also particularly applicable in connection with any other implementation of the ninth aspect, the method also includes the display device obtaining a derivative of a second signal received via a second link. In embodiments, the method also includes the display device generating a selection for connection, based on a comparison of the derivative of the second signal and the derivative of the first signal. In embodiments, the display device generating the selection for connection is further based on the derivative of the first signal meeting or exceeding the upper threshold, where the derivative of the second signal is less than the derivative of the first signal. In embodiments, the display device generating the selection for connection is further based on the derivative of the second signal meeting or exceeding the upper threshold, where the derivative of the first signal is less than the derivative of the second signal.

In certain implementations of the ninth aspect, which may be generally applicable but are also particularly applicable in connection with any other implementation of the ninth aspect, the method also includes the display device obtaining a derivative of the third signal received via a third link. Generating the selection for connection may further be based on a comparison of the derivative of the third signal and the derivative of the second signal. In embodiments of the method, the derivative of the second signal meets or exceeds the upper threshold; and the derivative of the third signal is less than the derivative of the second signal. In embodiments of the method, the derivative of the second signal is below the upper threshold, and the derivative of the third signal is greater than the derivative of the second signal.

In certain implementations of the ninth aspect, which may be generally applicable but are also particularly applicable in connection with any other implementation of the ninth aspect, the method also includes receiving a representation of user input to an accelerometer. In embodiments, generating the selection for connection is further based on the representation of the user input. In embodiments, the method also includes presenting a prompt for the user to provide the user input to the analyte sensor system. The user input may be based on the user tapping the analyte sensor system.

In certain implementations of the ninth aspect, which may be generally applicable but are also particularly applicable in connection with any other implementation of the ninth aspect, the method also includes the display device prompting the user to physically contact an analyte sensor system in order to trigger the analyte sensor system to send the first signal to the display device.

In a tenth aspect, a mobile device is configured for wireless communication of analyte data. The mobile device includes a transceiver configured to transmit and receive wireless signals. The mobile device also includes circuitry operatively coupled to the transceiver. Further, the mobile device includes a non-transitory computer-readable medium operatively coupled to the circuitry and storing instructions that, when executed, cause the display device to perform a number of operations. One such operation is to obtain a derivative of a first signal received via a first link. Another such operation is to generate an identification for selection, based on a derivative of the first signal meeting or being above a lower threshold.

In certain implementations of the tenth aspect, which may be generally applicable but are also particularly applicable in connection with any other implementation of the tenth aspect, the non-transitory computer-readable medium further stores instructions that, when executed, cause the mobile device to perform a number of additional operations. One such operation is to generate a selection for connection, based on the derivative of the first signal meeting or being above an upper threshold. Another such operation is to obtain a derivative of a second signal received via a second link. Yet another such operation is to generate the selection for connection further based on the derivative of the second signal being below the lower threshold or meeting or being above the upper threshold. Another such operation is to generate the selection for connection further based on the derivative of the first signal not meeting or being above the upper threshold. Another such operation is to obtain a derivative of a third signal received via a third link. Yet another such operation is to generate the selection for connection further based on the derivative of the third signal meeting or being above the upper threshold or being below the lower threshold.

In certain implementations of the tenth aspect, which may be generally applicable but are also particularly applicable in connection with any other implementation of the tenth aspect, the non-transitory computer-readable medium further stores instructions that, when executed, cause the mobile device to perform a number of additional operations. One such operation is to obtain a derivative of a second signal received via a second link. Another such operation is to generate the selection for connection based on a comparison of the derivative of the second signal to the derivative of the first signal. Another such operation is to obtain a derivative of a third signal received via a third link. Yet another such operation is to generate the selection for connection further based on a comparison of the derivative of the third signal to the derivative of the second signal.

In certain implementations of the tenth aspect, which may be generally applicable but are also particularly applicable in connection with any other implementation of the tenth aspect, the non-transitory computer-readable medium further stores instructions that, when executed, cause the mobile device to perform a number of additional operations. One such operation is to receive a representation of user input to the accelerometer. Another such operation is to generate the selection for connection further based on a comparison of the representation of the user input.

In an eleventh aspect, a method for identifying a device for connection includes a display device obtaining a derivative of a first signal received via a first link. The method also includes the display device obtaining a derivative of a second signal received via a second link. Additionally, the method includes the display device generating a selection for connection, based on a comparison of the derivative of the first signal to the derivative of the second signal.

In certain implementations of the eleventh aspect, which may be generally applicable but are also particularly applicable in connection with any other implementation of the eleventh aspect, the method also includes calculating a difference between the derivative of the first signal and the derivative of the second signal. In embodiments, the method also includes generating the comparison by comparing the difference to a predetermined value.

In certain implementations of the eleventh aspect, which may be generally applicable but are also particularly applicable in connection with any other implementation of the eleventh aspect, the method also includes calculating a difference between the derivative of the first signal and the derivative of the second signal. In embodiments, the method also includes generating the comparison by comparing an absolute value of the difference to a predetermined value.

In certain implementations of the eleventh aspect, which may be generally applicable but are also particularly applicable in connection with any other implementation of the eleventh aspect, the method also includes the display device obtaining a derivative of a third signal received via a third link. In embodiments, the display device generating the selection for connection is further based on a comparison of the second derivative to the third derivative.

In certain implementations of the eleventh aspect, which may be generally applicable but are also particularly applicable in connection with any other implementation of the eleventh aspect, the method also includes calculating a first difference between the derivative of the first signal and the derivative of the second signal. In embodiments, the method further includes the display device obtaining a derivative of a third signal received via a third link. In embodiments, the method includes calculating a second difference between the derivative of the third signal and the derivative of the second signal. In embodiments, the display device generating the selection for connection is further based on a comparison of the first difference to the second difference.

In a twelfth aspect, a mobile device is configured for wireless communication of analyte data. The mobile device includes a transceiver configured to transmit and receive wireless signals. The mobile device also includes circuitry operatively coupled to the transceiver. Further, the mobile device includes a non-transitory computer-readable medium operatively coupled to the circuitry and storing instructions that, when executed, cause the mobile device to perform a number of operations. One such operation is to obtain a derivative of a first signal received via a first link. Another such operation is to obtain a derivative of a second signal received via a second link. Yet another such operation is to generate a selection for connection, based on a comparison of the derivative of the first signal and the derivative of the second signal.

In certain implementations of the twelfth aspect, which may be generally applicable but are also particularly applicable in connection with any other implementation of the twelfth aspect, the non-transitory computer-readable medium further stores instructions that, when executed, cause the mobile device to perform a number of additional operations. One such operation is to calculate a difference between the derivative of the first signal and the derivative of the second signal. Another such operation is to generate the comparison by comparing the difference to a predetermined value.

In a twelfth aspect, a method for identifying a device for connection includes a display device of a set of display devices establishing a connection with an analyte sensor system of a set of analyte sensor systems. The method further includes the display device generating a confirmation for connection to the analyte sensor system based on a duration of the connection exceeding a pre-determined amount of time.

In a thirteenth aspect, a mobile device of a set of mobile devices is configured for wireless communication of analyte data. The mobile device includes a transceiver configured to transmit and receive wireless signals. The mobile device also includes circuitry operatively coupled to the transceiver. Additionally, the mobile device includes a non-transitory computer-readable medium operatively coupled to the circuitry and storing instructions that, when executed, cause the mobile device to perform a number of operations. One such operation is to establish connection with an analyte sensor system of a set of analyte sensor systems. Another such operation is to generate a confirmation for connection to the analyte sensor system based on a duration of the connection exceeding a pre-determined about of time.

In a fourteenth aspect, a method for identifying a device for connection includes operating in one of a plurality of modes for generating a selection for connection between a display device and an analyte sensor system. Operating in a first mode of the plurality of modes includes receiving input regarding the analyte sensor system that identifies the analyte sensor system from among a set of analyte sensor systems. Operating in the first mode also includes generating the selection for connection with the analyte sensor system based on the input. Operating in a second mode of the plurality of modes includes obtaining a derivative of a first signal received via a first link. Operating in the second mode also includes generating an identification for selection based on the derivative of the first signal. Operating in the second mode also includes generating a selection for connection based on the identification for selection and one or more of a derivative of a second signal and user input. Operating in a third mode of the plurality of modes includes forming a connecting between the display device and the analyte sensor system. Operating in the third mode also includes generating a confirmation for connection based on maintaining the connection for at least a pre-determined amount of time.

In certain implementations of the fourteenth aspect, which may be generally applicable but are also particularly applicable in connection with any other implementation of the fourteenth aspect, the input regarding the analyte sensor system that identifies the analyte sensor system includes one of: an identification number for the analyte sensor system; a character identifier for the analyte sensor system; a captured encoded element; a captured image; and input selecting the analyte sensor system from a list.

In certain implementations of the fourteenth aspect, which may be generally applicable but are also particularly applicable in connection with any other implementation of the fourteenth aspect, the derivative of the first signal is based on an RSSI of the first signal, and the derivative of the second signal is based on an RSSI of the second signal. In embodiments, the method also includes calculating a difference the derivative of the first signal and the derivative of the second signal. Further, the method includes comparing the difference to a threshold. The method may also include, if the difference exceeds the threshold, confirming the selection for connection.

In certain implementations of the fourteenth aspect, which may be generally applicable but are also particularly applicable in connection with any other implementation of the fourteenth aspect, the method also includes presenting an instruction to the user to provide input to an accelerometer of the analyte sensor system for the analyte sensor system to initiate transmission of the first signal.

In a fifteenth aspect, a system for identifying a device for connection includes an analyte sensor system. The system also includes a mobile device. The analyte sensor system and the mobile device are configured to operate in one of a plurality of modes for generating a selection for connection between the mobile device and the analyte sensor system. For operation in a first mode of the plurality of modes, the mobile device is configured to perform a number of operations. One such operation is to receive input regarding the analyte sensor system that identifies the analyte sensor system from among a set of analyte sensor systems. Another such operation is to generate the selection for connection with the analyte sensor system based on the input. For operation in a second mode of the plurality of modes, the mobile device is configured to perform a number of operations. One such operation is to obtain a derivative of a first signal received via a first link. Another such operation is to generate an identification for selection based on the derivative of the first signal. Yet another such operation is to generate a selection for connection based on the identification for selection and one or more of a derivative of a second signal and user input. For operation in a third mode of the plurality of modes, the mobile device is configured to perform a number of operations. One such operation is to form a connecting between the display device and the analyte sensor system. Another such operation is to generate a confirmation for connection based on maintaining the connection for at least a pre-determined amount of time.

In a sixteenth aspect, a method for wireless communication of analyte data includes establishing a first connection between an analyte sensor system and a display device. The method also includes during the first connection, exchanging information related to authentication between the analyte sensor system and the display device. The information related to authentication includes an application key. The method further includes the analyte sensor system transmitting an encrypted analyte value to the display device. The encrypted analyte value has been generated based on the application key.

In certain implementations of the sixteenth aspect, which may be generally applicable but are also particularly applicable in connection with any other implementation of the sixteenth aspect, the method also includes modifying the application key responsive to one or more of: the passage of a predetermined amount of time; the analyte sensor system or the display device being restarted; a trigger related to another device attempting to connect to the analyte sensor system; and user input.

In certain implementations of the sixteenth aspect, which may be generally applicable but are also particularly applicable in connection with any other implementation of the sixteenth aspect, the application key was received by the display device from a server. In embodiments, for each analyte sensor system, the server associates the application key with identification information for the analyte sensor system. In embodiments, the application key was received by the display device from the server responsive to the display device providing the server with the identification information for the analyte sensor system.

In a seventeenth aspect, an analyte sensor system is configured for wireless communication of analyte data. The analyte sensor system includes an analyte sensor. The analyte sensor system includes a transceiver configured to transmit and receive wireless signals. The analyte sensor system also includes a processor operatively coupled to the analyte sensor and the transceiver and configured to cause the analyte sensor system to perform a number of operations. One such operation is to establish a first connection between the analyte sensor system and a display device. Another such operation is to, during the first connection, exchange information related to authentication between the analyte sensor system and the display device, where the information related to authentication includes an application key. Another such operation is to make a determination regarding whether authentication was performed during the first interval. Yet another such operation is to transmit an encrypted analyte value to the display device, where the encrypted analyte value was generated based on the application key. In embodiments, the application key was received from a server responsive to the server being provided with the identification information for the analyte sensor system.

In an eighteenth aspect, a method for wireless communication of analyte data includes receiving a proposal for a connection parameter. The proposal includes one or more proposed values for the connection parameter. The method also includes determining whether the proposal is acceptable. The method includes generating a response to the proposal, based on determining whether the proposal is acceptable.

In certain implementations of the eighteenth aspect, which may be generally applicable but are also particularly applicable in connection with any other implementation of the eighteenth aspect, the method also includes modifying a connection between a display device and an analyte sensor system based on an acceptable proposed value of the one or more proposed values, if the response indicates an acceptance of the acceptable proposed value.

In certain implementations of the eighteenth aspect, which may be generally applicable but are also particularly applicable in connection with any other implementation of the eighteenth aspect, the method also includes establishing a connection between a display device and the analyte sensor system based on an acceptable proposed value of the one or more proposed values, if the response indicates an acceptance of the acceptable proposed value.

In certain implementations of the eighteenth aspect, which may be generally applicable but are also particularly applicable in connection with any other implementation of the eighteenth aspect, the method also includes sending a counter-proposal, if the response indicates a preference of a value for the connection parameter other than the proposed values for the connection parameter. The counter-proposal comprises one or more counter-proposal values for the connection parameter.

In certain implementations of the eighteenth aspect, which may be generally applicable but are also particularly applicable in connection with any other implementation of the eighteenth aspect, the method also includes receiving a response to the counter-proposal. In embodiments, the method further includes modifying a connection between a display device and an analyte sensor system based on at least one of the counter-proposal values, if the response to the counter-proposal indicates an acceptance of one or more of the counter-proposal values.

In certain implementations of the eighteenth aspect, which may be generally applicable but are also particularly applicable in connection with any other implementation of the eighteenth aspect, the method also includes receiving a response to the counter-proposal. In embodiments, the method further includes terminating a connection between a display device and an analyte sensor system, if the response to the counter-proposal indicates a denial of the counter-proposal values.

In certain implementations of the eighteenth aspect, which may be generally applicable but are also particularly applicable in connection with any other implementation of the eighteenth aspect, the method also includes receiving a response to the counter-proposal. In embodiments, the method further includes establishing a connection between a display device and an analyte sensor system based on at least one of the counter-proposal values, if the response to the counter-proposal indicates an acceptance of one or more of the counter-proposal values.

In certain implementations of the eighteenth aspect, which may be generally applicable but are also particularly applicable in connection with any other implementation of the eighteenth aspect, the method also includes receiving a response to the counter-proposal. In embodiments, the method further includes generating a negative connection decision, if the response to the counter-proposal indicates a denial of the counter-proposal values.

In certain implementations of the eighteenth aspect, which may be generally applicable but are also particularly applicable in connection with any other implementation of the eighteenth aspect, the connection parameter is one of a connection interval, a slave latency, and a supervision timeout.

In certain implementations of the eighteenth aspect, which may be generally applicable but are also particularly applicable in connection with any other implementation of the eighteenth aspect, the proposal is based on an expected operating time of the analyte sensor system.

In certain implementations of the eighteenth aspect, which may be generally applicable but are also particularly applicable in connection with any other implementation of the eighteenth aspect, the proposal is based on a glucose level of a user.

In certain implementations of the eighteenth aspect, which may be generally applicable but are also particularly applicable in connection with any other implementation of the eighteenth aspect, the proposal is based on one or more of a quality of service, a time of day, a location, or battery conditions.

In certain implementations of the eighteenth aspect, which may be generally applicable but are also particularly applicable in connection with any other implementation of the eighteenth aspect, the method also includes requesting a connection according to a first connection model. In embodiments, the method further includes requesting a connection according to a second connection model, responsive to determining that the proposal is not acceptable.

In certain implementations of the eighteenth aspect, which may be generally applicable but are also particularly applicable in connection with any other implementation of the eighteenth aspect, the method also includes terminating a connecting between a display device and an analyte sensor system, responsive to determining that the proposal is not acceptable. In embodiments, the method also includes providing a notification related to terminating the connection.

In a nineteenth aspect, an analyte sensor system is configured for wireless communication of analyte data. The analyte sensor system includes an analyte sensor. The analyte sensor system includes a transceiver configured to transmit and receive wireless signals. The analyte sensor system includes a processor operatively coupled to the analyte sensor and the transceiver and configured to cause the analyte sensor system to perform a number of operations. One such operation is to receive a proposal for a connection parameter, wherein the proposal comprises one or more proposed values for the connection parameter. Another such operation is to determine whether the proposal is acceptable. Yet another such operation is to generate a response to the proposal, based on a determination that the proposal is acceptable.

In certain implementations of the nineteenth aspect, which may be generally applicable but are also particularly applicable in connection with any other implementation of the nineteenth aspect, the processor is further configured to perform a number of additional operations. One such operation is to modify a connection between a display device and the analyte sensor system based on an acceptable proposed value of the one or more proposed values, if the response indicates an acceptable of the acceptable proposed value. Another such operation is to establish a connection between a display device and the analyte sensor system based on an acceptable proposed value of the one or more proposed values, if the response indicates an acceptable of the acceptable proposed value. Another such operation is to send a counter-proposal, if the response indicates a preference of a value for the connection parameter other than the proposed values for the connection parameter. The counter-proposal may include one or more counter-proposal values for the connection parameter. Another such operation is to receive a response to the counter-proposal. Another such operation is to modify a connection between a display device and the analyte sensor system based on at least one of the counter-proposal values, if the response to the counter-proposal indicates an acceptance of one or more of the counter-proposed values. Another such operation is to terminate a connection between a display device and the analyte sensor system, if the response to the counter-proposal indicates a denial of the counter-proposed values. Another such operation is to establish a connection between a display device and the analyte sensor system based on at least one of the counter-proposal values, if the response to the counter-proposal indicates an acceptance of one or more of the counter-proposed values. Another such operation is to request a connection according to a first connection model. Another such operation is to request a connection according to a second connection model, responsive to a determination that the proposal is not acceptable.

In a twentieth aspect, a method for wireless communication of analyte data includes responsive to input from an application running on a display device, the display device sending to an analyte sensor system a message comprising a value for a connection parameter. The method also includes the display device receiving from the analyte sensor system the value for the connection parameter. Additionally, the method includes an operating system of the display device applying the value for the connection parameter, based on a determination that the value is acceptable.

In certain implementations of the twentieth aspect, which may be generally applicable but are also particularly applicable in connection with any other implementation of the twentieth aspect, the determination that the value is acceptable is received by the display device from the analyte sensor system.

In a twenty-first aspect, a method for wireless communication of analyte data includes operating in a first mode. Operating in the first mode includes an analyte sensor system periodically exchanging messages with a display device such that the analyte sensor system and the display device remain connected. Operating in the first mode includes, while the analyte sensor system and the display device remain connected, the analyte sensor system transmitting the analyte data to the display device. The method also includes operating in a second mode. Operating in the second mode includes periodically establishing a connection between the analyte sensor system and the display device. Operating in the second mode includes, while the connection is established, transmitting the analyte data to the display device.

In certain implementations of the twenty-first aspect, which may be generally applicable but are also particularly applicable in connection with any other implementation of the twenty-first aspect, the method includes switching from operating in the first mode to operating in the second mode or switching from operating in the second mode to operating in the first mode. In embodiments, the switching is based on user input. In embodiments, the switching is based on one or more switching criteria. In embodiments, the switching criteria include a type of display device; user information; the availability of display devices for connection; a priority scheme regarding display devices; quality of service; battery life; time of day; and a location.

In certain implementations of the twenty-first aspect, which may be generally applicable but are also particularly applicable in connection with any other implementation of the twenty-first aspect, the method further includes receiving an indication related to battery management; wherein the switching is done based on the indication.

In certain implementations of the twenty-first aspect, which may be generally applicable but are also particularly applicable in connection with any other implementation of the twenty-first aspect, the method also includes presenting a notification to the user related to the switching.

In certain implementations of the twenty-first aspect, which may be generally applicable but are also particularly applicable in connection with any other implementation of the twenty-first aspect, while the analyte sensor system and the display device remain connected, the analyte sensor system transmitting the analyte data to the display device is done upon the analyte data becoming available for transmission.

In a twenty-second aspect, an analyte sensor system is configured for wireless communication of analyte data. The analyte sensor system includes an analyte sensor. The analyte sensor system includes a transceiver configured to transmit and receive wireless signals. The analyte sensor system includes a processor operatively coupled to the analyte sensor and the transceiver and configured to cause the analyte sensor system to perform a number of operations. One such operation is to operate in a first mode. For operation in the first mode, the analyte sensor system is configured to perform a number of operations. One such operation for the first mode is periodically exchange messages with a display device such that the analyte sensor system and the display device remain connected. Another such operation for the first mode is to, while the analyte sensor system and the display device remain connected, transmit the analyte data to the display device. Another such operation is to operate in a second mode. For operation in the second mode, the analyte sensor system is configured to perform a number of operations. One such operation for the second mode is to periodically establish a connection with a display device. Another such operation for the second mode is to, while the connection is established, transmit the analyte data to the display device. Another such operation is to switch between operation in the first mode and operation in the second mode.

In a twenty-third aspect, a method for wireless communication of analyte data includes an analyte sensor system periodically exchanging messaging with a display device such that the analyte sensor system and the display device maintain a connection. The method also includes the analyte sensor system transmitting the analyte data to the display device while the analyte sensor system and the display device maintain the connection.

In certain implementations of the twenty-third aspect, which may be generally applicable but are also particularly applicable in connection with any other implementation of the twenty-third aspect, the method also includes the analyte sensor system sending a proposal for a set of connection parameters to the display device, responsive to receiving a connection request from the display device. The set of connection parameters may include a connection interval, slave latency, and supervision timeout. In embodiments, the method also includes receiving a connection decision from the display device; wherein the connection decision is based on the proposal. In embodiments, periodically exchanging messaging is done based on the set of connection parameters, responsive the connection decision comprising an acceptance of the proposal.

In certain implementations of the twenty-third aspect, which may be generally applicable but are also particularly applicable in connection with any other implementation of the twenty-third aspect, the method also includes terminating the connection, based on a violation of one or more of the connection parameters. In embodiments, the method also includes the analyte sensor system transmitting advertisement messages, responsive terminating the connection.

In certain implementations of the twenty-third aspect, which may be generally applicable but are also particularly applicable in connection with any other implementation of the twenty-third aspect, the method also includes requesting to modify one or more of the connection parameters, responsive to a violation of one or more of the connection parameters.

In a twenty-fourth aspect, an analyte sensor system is configured for wireless communication of analyte data. The analyte sensor system includes an analyte sensor. The analyte sensor system includes a transceiver configured to transmit and receive wireless signals. The analyte sensor system also includes a processor operatively coupled to the analyte sensor and the transceiver and configured to cause the analyte sensor system to perform a number of operations. One such operation is to periodically exchange messaging with a display device such that the analyte sensor system and the display device maintain a connection. One such operation is to transmit the analyte data to the display device while the analyte sensor system and the display device remain connected.

In a twenty-fifth aspect, a method for wireless communication of analyte data includes establishing a connection between an analyte sensor system and a display device. The method also includes receiving a set of characteristics associated with the analyte sensor system. The characteristics are arranged in a sequence. The method also includes sending to the analyte sensor system a request to read one or more of the characteristics in an order different from the sequence.

In certain implementations of the twenty-fifth aspect, which may be generally applicable but are also particularly applicable in connection with any other implementation of the twenty-fifth aspect, the request to read one or more of the characteristics includes a request to read an estimated glucose value.

In certain implementations of the twenty-fifth aspect, which may be generally applicable but are also particularly applicable in connection with any other implementation of the twenty-fifth aspect, the method also includes performing a characteristic of the set of characteristics. In embodiments, the characteristic is associated with reading the estimated glucose value. In embodiments, the characteristic is performed without having performed one or more other characteristics preceding the characteristic in the sequence.

In a twenty-sixth aspect, a mobile device is configured for wireless communication of analyte data. The mobile device includes a transceiver configured to transmit and receive wireless signals. The mobile device includes circuitry operatively coupled to the transceiver. And the mobile device includes a non-transitory computer-readable medium operatively coupled to the circuitry and storing instructions that, when executed, cause the mobile device to perform a number of operations. One such operation is to establish a connection with an analyte sensor system. Another such operation is to receive a set of characteristics associated with the analyte sensor system. The characteristics may be arranged in a sequence. Another such operation is to send to the analyte sensor system a request to read one or more of the characteristics in an order different from the sequence.

In a twenty-seventh aspect, a method for wireless communication of analyte data includes obtaining a derivative of a first signal received via a first link. The method also includes generating an identification for selection, based on the derivative of the first signal. The method also includes obtaining a derivative of a second signal received via a second link. Further, the method includes generating a selection for connection, based on the derivative of the second signal. The method includes establishing a connection between a display device and an analyte sensor system, based on the selection for connection. And the method includes periodically exchanging messaging to maintain the connection.

In certain implementations of the twenty-seventh aspect, which may be generally applicable but are also particularly applicable in connection with any other implementation of the twenty-seventh aspect, the method also includes the analyte sensor system transmitting the analyte data to the display device while the analyte sensor system and the display device maintain the connection. In embodiments, the method also includes receiving a connection decision from the display device, where the connection decision is based on the proposal.

In certain implementations of the twenty-seventh aspect, which may be generally applicable but are also particularly applicable in connection with any other implementation of the twenty-seventh aspect, the method also includes the analyte sensor system sending a proposal for a set of connection parameters to the display device, responsive to receiving a connection request from the display device.

In certain implementations of the twenty-seventh aspect, which may be generally applicable but are also particularly applicable in connection with any other implementation of the twenty-seventh aspect, periodically exchanging messaging is done based on the set of connection parameters, responsive the connection decision comprising an acceptance of the proposal.

In a twenty-eighth aspect, a method for wireless communication of analyte data includes authenticating a display device for a first connection by exchanging information related to authentication between an analyte sensor system and the display device. The method also includes, based on authenticating the display device, the analyte sensor system periodically exchanging messaging with the display device to maintain the first connection. Further, the method includes the analyte sensor system transmitting encrypted analyte data to the display device during the time the first connection is maintained.

In certain implementations of the twenty-eighth aspect, which may be generally applicable but are also particularly applicable in connection with any other implementation of the twenty-eighth aspect, the method also includes terminating the first connection. In embodiments, the method also includes establishing a second connection between analyte sensor system and the display device. In embodiments, the method also includes the analyte sensor system periodically exchanging messaging with the display device to maintain the second connection. In embodiments, the method also includes the analyte sensor system transmitting encrypted analyte data to the display device during the time the second connection is maintained. For the second connection, in some cases, the periodically exchanging the messaging and the transmitting encrypted analyte data are based on authenticating the display device for the first connection.

In a twenty-ninth aspect, a method for wireless communication of analyte data between a display device and one or more analyte sensor systems includes the display device obtaining a derivative of a first signal received from a first analyte sensor system of the one or more analyte sensor systems or from one or more of the analyte sensor systems other than the first analyte sensor system. The method additionally includes the display device generating a selection for connection with the first analyte sensor system using the derivative of the first signal and a condition. Further, the method includes establishing a first connection between the display device and the first analyte sensor system using the selection for connection. The first connection is established if, during an amount of time, the display device does not receive an advertisement message from the one or more analyte sensor systems other than the first analyte sensor system, or the display device does not obtain a derivative of a second signal that satisfies the condition. The second signal is received from the one or more analyte sensor systems other than the first analyte sensor system.

In certain implementations of the twenty-ninth aspect, which may be generally applicable but are also particularly applicable in connection with any other implementation of the twenty-ninth aspect, the method also includes obtaining a derivative of a signal received from a second analyte sensor system among the one or more analyte sensor systems other than the first analyte sensor system. In embodiments, the method also includes establishing a second connection between the display device and the second analyte sensor system using at least the derivate of the signal received from the second analyte sensor system.

In a thirtieth aspect, a method for wireless communication of analyte data includes a display device receiving advertisement messages from a number of analyte sensor systems. The number is two or more. If the number does not exceed a threshold, the method includes further operations, as follows. The method may further include the display device obtaining respective derivatives of signals received from the number of analyte sensor systems. The method may also include the display device determining whether any of the derivatives satisfies a condition for an amount of time. Additionally, the method may include, responsive to the display device determining that a first derivative of the derivatives satisfies the condition for the amount of time, the display device generating a selection for connection with a first analyte sensor system of the number of analyte sensor systems. The first analyte sensor system sent the signal used to obtain the first derivative. Further, the method may include establishing a first connection between the display device and the first analyte sensor system using the selection for connection.

In certain implementations of the thirtieth aspect, which may be generally applicable but are also particularly applicable in connection with any other implementation of the thirtieth aspect, if the number exceeds the threshold, the method includes further operations, as follows. The method may include the display device providing a prompt to a user of the display device, wherein the prompt relates to connection establishment. The method may further include establishing a second connection between the display device and one of the analyte sensor systems selected for connection using input received by the display device in response to the prompt.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

FIG. 8 illustrates an example structure for an advertisement message in accordance with embodiments of the present disclosure.

Figure 1A:
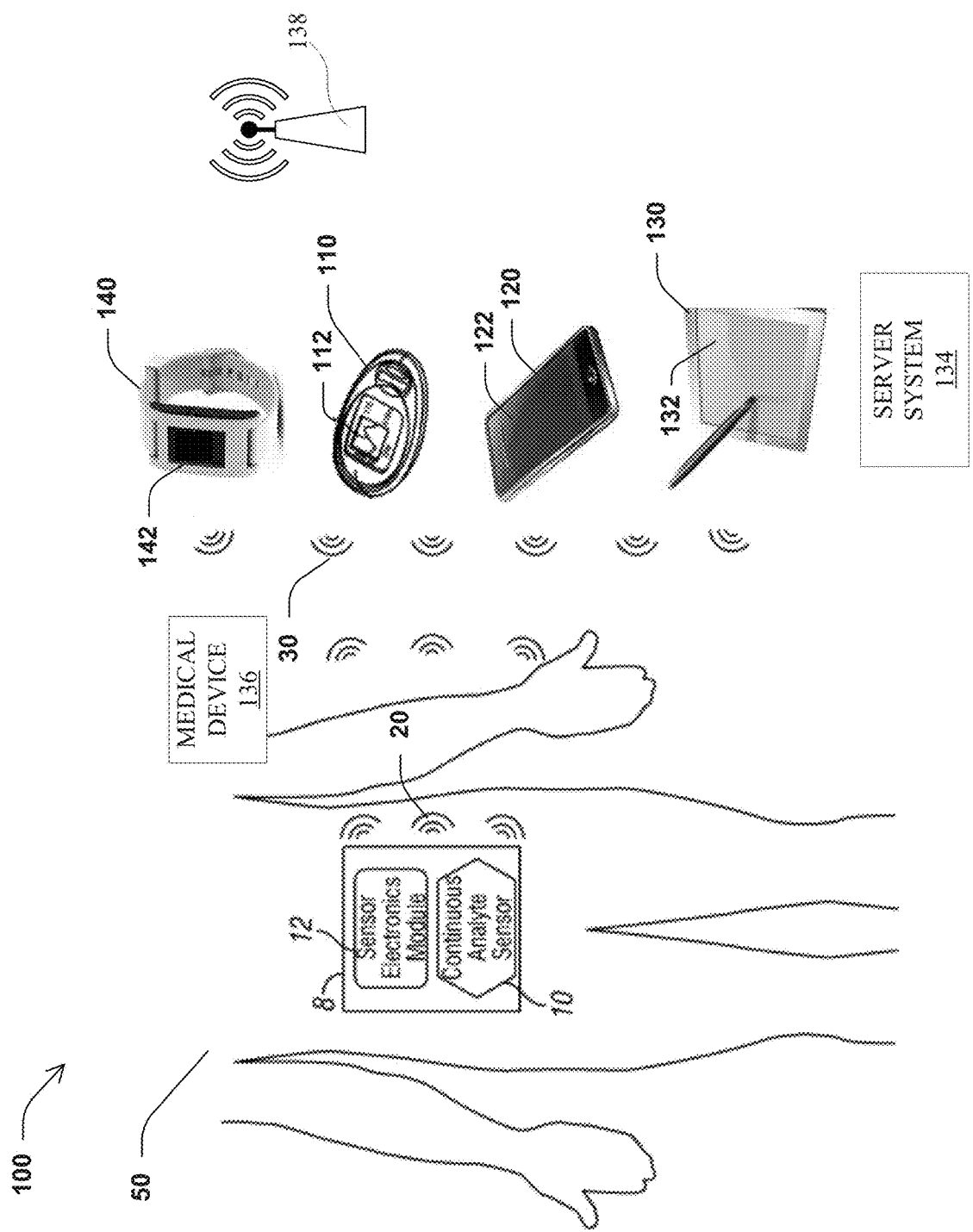
FIG. 1A illustrates aspects of an example system that may be used in connection with implementing embodiments of the disclosure.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure may be practiced with modification or alteration, and that the disclosure may be limited only by the claims and the equivalents thereof.

DETAILED DESCRIPTION

Embodiments of the present disclosure are directed to systems, methods, and devices for wireless communication of analyte data. In various deployments described herein, the analyte data is glucose data generated by an analyte sensor system configured to connect to display devices and the like. Implementing aspects of the present disclosure, as described in detail herein, may reduce the power consumption of the analyte sensor system by increasing the efficiency thereof with respect to wireless communications the analyte sensor system and other devices. Moreover, implementing aspects of the present disclosure may also allow for reduced power consumption while maintaining and/or improving performance with respect to the reliability, speed, and accuracy of wireless communications, as well as the connection protocols associated therewith. Additionally, in some cases, power consumption may be less critical than other aspects of performance (e.g., reliability and/or latency), and in such cases, different modes of connection may be employed to increase performance. In particular, some aspects of the disclosure relate to, for example, authentication and encryption, connection protocols and timing for devices, advertisement message structure and content, and device pairing.

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

A. Overview

In some embodiments, a system is provided for continuous measurement of an analyte in a host. The system may include: a continuous analyte sensor configured to continuously measure a concentration of the analyte in the host, and a sensor electronics module physically connected to the continuous analyte sensor during sensor use. In certain embodiments, the sensor electronics module includes electronics configured to process a data stream associated with an analyte concentration measured by the continuous analyte sensor, in order to generate sensor information that includes raw sensor data, transformed sensor data, and/or any other sensor data, for example. The sensor electronics module may further be configured to generate sensor information that is customized for respective display devices, such that different display devices may receive different sensor information.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, rickettsia (scrub typhus), *Schistosoma mansoni, Toxoplasma gondii, Trepenoma pallidium, Trypanosoma cruzi/rangeli,* vesicular stomatis virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

B. Alerts

In certain embodiments, one or more alerts are associated with a sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In certain embodiments, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In certain embodiments, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data package indicating an alarm should be initiated by one or a plurality of display devices (e.g., sequentially and/or simultaneously). In certain embodiments, the sensor electronics module merely provides a data field indicating that an alarm conditions exists and the display device, upon reading the data field indicating the existence of the alarm condition, may decide to trigger an alarm. In some embodiments, the sensor electronics module determines which of the one or more alarms to trigger based on one or more alerts that are triggered. For example, when an alert trigger indicates severe hypoglycemia, the sensor electronics module can perform multiple actions, such as activating an alarm on the sensor electronics module, transmitting a data package to a monitoring device indicating activation of an alarm on the display, and transmitting a data package as a text message to a care provider. As an example, a text message can appear on a custom monitoring device, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

C. Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one example embodiment, the sensor electronics module is configured to search for and attempt to alarm a host or care provider sequentially using a list of display devices, such as: (1) a default display device or a custom analyte monitoring device; (2) a mobile phone via auditory and/or visual methods, such as, text message to the host and/or care provider, voice message to the host and/or care provider, and/or 911); (3) a tablet; (4) a smart watch.

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may include software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, tablets, PDAs, PCs and the like).

In some embodiments, certain display devices may be in direct wireless communication with the sensor electronics module, but intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In certain embodiments, the sensor electronics module directly wirelessly transmits displayable sensor information to one or a plurality of display devices, such that the displayable sensor information transmitted from the sensor electronics module is received by the display device without intermediate processing of the displayable sensor information.

In certain embodiments, one or more display devices include built-in authentication mechanisms, wherein authentication is required for communication between the sensor electronics module and the display device. In some embodiments, to authenticate the data communication between the sensor electronics module and display devices, a challenge-response protocol, such as key authentication is provided, where the challenge is a request for the key or a hash or other value based on or derived from the key, and the valid response is the correct key or a hash or other value based on or derived from the key, such that pairing of the sensor electronics module with the display devices can be accomplished by the user and/or manufacturer via the key. This may be referred to in some cases as two-way authentication. The key may be a software or hardware level key. Additionally, the key may be a password (e.g., randomly generated or set by a user or other entity), and/or may be derived from uniquely identifying features (e.g., finger print or retinal information) or information, etc.

In some embodiments, one or more display devices are configured to query the sensor electronics module for displayable sensor information, wherein the display device acts as a master device requesting sensor information from the sensor electronics module (e.g., a slave device) on-demand, for example, in response to a query. Although in some cases the display device acts as a master and the sensor electronics module acts as a slave, in other cases, these roles may be reversed. For example, the roles can reverse depending on the nature of the communication and so on. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how sensor information is obtained.

In some embodiments, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with embodiments disclosed herein.

In general, a plurality of display devices (e.g., a custom analyte monitoring device (which may also be referred to as an analyte display device), a mobile phone, a tablet, a smart watch, a reference analyte monitor, a drug delivery device, a medical device and a personal computer) may be configured to wirelessly communicate with the sensor electronics module. The plurality of display devices may be configured to display at least some of the displayable sensor information wirelessly communicated from the sensor electronics module. The displayable sensor information may include sensor data, such as raw data and/or transformed sensor data, such as analyte concentration values, rate of change information, trend information, alert information, sensor diagnostic information and/or calibration information, for example.

D. Continuous Sensor

With reference to FIG. 1A, in some embodiments, analyte sensor 10 includes a continuous glucose sensor, for example, a subcutaneous, transdermal (e.g., transcutaneous), or intravascular device. In some embodiments, such a sensor or device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. According to one example embodiment described below, an implantable glucose sensor may be used. However, it should be understood that the devices and methods described herein can be applied to any device capable of detecting a concentration of glucose and providing an output signal that represents the concentration of glucose (e.g., as a form of analyte data).

In certain embodiments, analyte sensor 10 is an implantable glucose sensor, such as described with reference to U.S. Pat. No. 6,001,067 and U.S. Patent Publication No. US-2005-0027463-A1. In embodiments, analyte sensor 10 is a transcutaneous glucose sensor, such as described with reference to U.S. Patent Publication No. US-2006-0020187-A1. In embodiments, analyte sensor 10 is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In embodiments, the continuous glucose sensor includes a transcutaneous sensor such as described in U.S. Pat. No. 6,565,509 to Say et al., for example. In embodiments, analyte sensor 10 is a continuous glucose sensor that includes a subcutaneous sensor such as described with reference to U.S. Pat. No. 6,579,690 to Bonnecaze et al. or U.S. Pat. No. 6,484,046 to Say et al., for example. In embodiments, the continuous glucose sensor includes a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

Figure 2A:
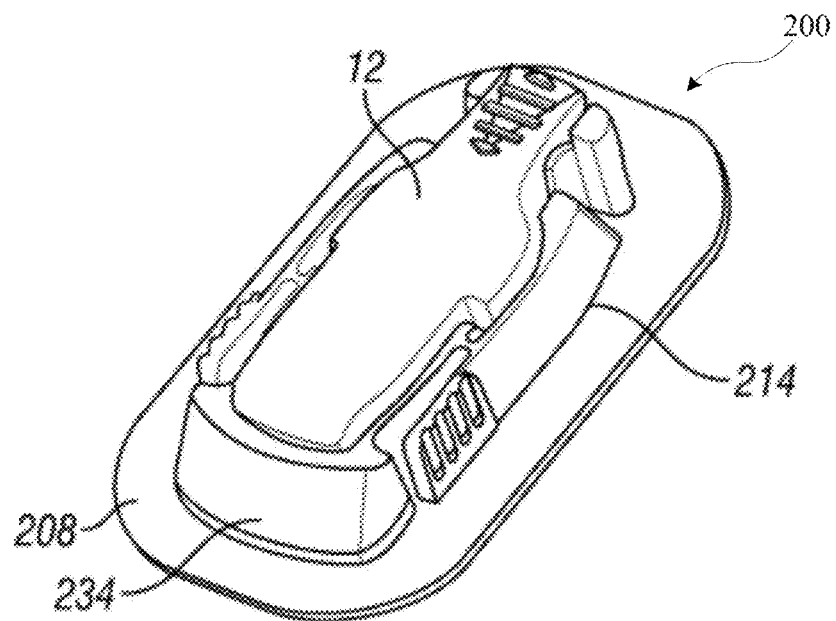
FIG. 2A is a perspective view of an example enclosure that may be used in connection with implementing embodiments of an analyte sensor system.
Figure 2B:
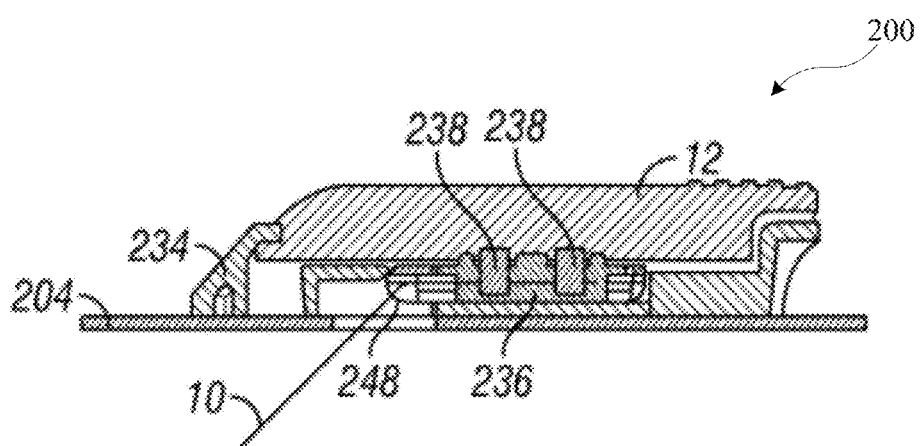
FIG. 2B is a side view of an example enclosure that may be used in connection with implementing embodiments of an analyte sensor system.

FIGS. 2A and 2B are perspective and side views of enclosure 200 that may be used in connection with implementing embodiments of analyte sensor system 8, according to certain aspects of the present disclosure. Enclosure 200 includes mounting unit 214 and sensor electronics module 12 attached thereto in certain embodiments. Enclosure 200 is shown in a functional position, including mounting unit 214 and sensor electronics module 12 matingly engaged therein. In some embodiments, mounting unit 214, also referred to as a housing or sensor pod, includes base 234 adapted for fastening to a host's or user's skin. Base 234 can be formed from a variety of hard or soft materials, and can include a low profile for minimizing protrusion of the device from the host during use. In some embodiments, base 234 is formed at least partially from a flexible material, which may provide numerous advantages over other transcutaneous sensors, which, unfortunately, can suffer from motion-related artifacts associated with the host's movement when the host is using the device. Mounting unit 214 and/or sensor electronics module 12 can be located over the sensor insertion site to protect the site and/or provide a minimal footprint (utilization of surface area of the host's skin).

In some embodiments, a detachable connection between mounting unit 214 and sensor electronics module 12 is provided, which enables improved manufacturability, namely, the potentially relatively inexpensive mounting unit 214 can be disposed of when refurbishing or maintaining analyte sensor system 8, while the relatively more expensive sensor electronics module 12 can be reusable with multiple sensor systems. In some embodiments, sensor electronics module 12 is configured with signal processing (programming), for example, configured to filter, calibrate, and/or execute other algorithms useful for calibration and/or display of sensor information. However, an integral (non-detachable) sensor electronics module can be configured.

In some embodiments, contacts 238 are mounted on or in a subassembly hereinafter referred to as contact subassembly 236 configured to fit within base 234 of mounting unit 214 and hinge 248 that allows contact subassembly 236 to pivot between a first position (for insertion) and a second position (for use) relative to mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, contacts 238 are formed from a conductive elastomeric material, such as a carbon black elastomer, through which sensor 10 extends.

With further reference to FIGS. 2A and 2B, in certain embodiments, mounting unit 214 is provided with adhesive pad 208, disposed on the mounting unit's back surface and includes a releasable backing layer. Thus, removing the backing layer and pressing at last a portion of base 234 of mounting unit 214 onto the host's skin adheres mounting unit 214 to the host's skin. Additionally or alternatively, an adhesive pad can be placed over some or all of analyte sensor system 8 and/or sensor 10 after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. US-2009-0240120-A1, which is incorporated herein by reference in its entirety for all purposes.

E. Example Configurations

Referring again to FIG. 1A, system 100 that may be used in connection with implementing aspects of an analyte sensor system is depicted. In some cases, system 100 may be used to implement various systems described herein. System 100 in embodiments includes analyte sensor system 8 and display devices 110, 120, 130, and 140, according to certain aspects of the present disclosure. Analyte sensor system 8 in the illustrated embodiment includes sensor electronics module 12 and continuous analyte sensor 10 associated with the sensor electronics module 12. Sensor electronics module 12 may be in wireless communication (e.g., directly or indirectly) with one or more of display devices 110, 120, 130, and 140. In embodiments, system 100 also includes medical device 136 and server system 134. Sensor electronics module 12 may also be in wireless communication (e.g., directly or indirectly) with medical device 136 and/or server system 134. Likewise, in some examples, display devices 110-140 may also be in wireless communication (e.g., directly or indirectly) with medical devices 136 and/or server system 134. Various couplings shown in FIG. 1A can be facilitated with wireless access point 138, as also mentioned below.

In certain embodiments, sensor electronics module 12 includes electronic circuitry associated with measuring and processing the continuous analyte sensor data, including prospective algorithms associated with processing and calibration of the sensor data. Sensor electronics module 12 can be physically connected to continuous analyte sensor 10 and can be integral with (non-releasably attached to) or releasably attachable to continuous analyte sensor 10. Sensor electronics module 12 may include hardware, firmware, and/or software that enables measurement of levels of the analyte via a glucose sensor. For example, sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor.

Sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Referring again to FIG. 1A, display devices 110, 120, 130, and/or 140 are configured for displaying (and/or alarming) the displayable sensor information that may be transmitted by sensor electronics module 12 (e.g., in a customized data package that is transmitted to the display devices based on their respective preferences). Each of display devices 110, 120, 130, or 140 can include a display such as a touchscreen display 112, 122, 132,/or 142 for displaying sensor information and/or analyte data to a user and/or receiving inputs from the user. For example, a graphical user interface may be presented to the user for such purposes. In some embodiments, the display devices may include other types of user interfaces such as voice user interface instead of or in addition to a touchscreen display for communicating sensor information to the user of the display device and/or receiving user inputs. In some embodiments, one, some, or all of the display devices is configured to display or otherwise communicate the sensor information as it is communicated from the sensor electronics module (e.g., in a data package that is transmitted to respective display devices), without any additional prospective processing required for calibration and real-time display of the sensor data.

Figure 1B:
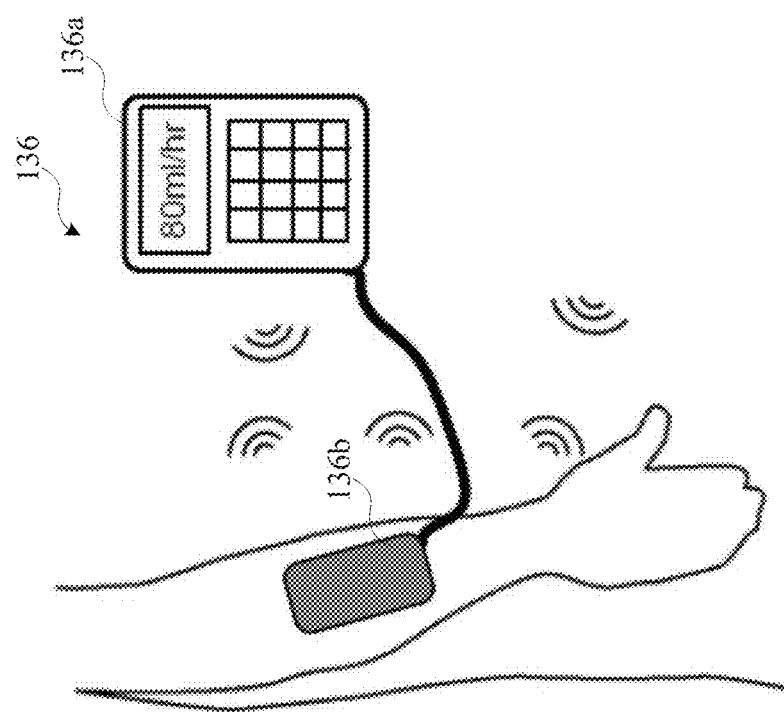
FIG. 1B illustrates aspects of an example system that may be used in connection with implementing embodiments of the disclosure.

Medical device 136 may be a passive device in example embodiments of the disclosure. For example medical device 136 may be an insulin pump for administering insulin to a user, as shown in FIG. 1B. For a variety of reasons, it may be desirable for such an insulin pump to receive and track glucose values transmitted from analyte sensor system 8. One reason is to provide the insulin pump a capability to suspend/activate insulin administration based on a glucose value being below/above a threshold value. One solution that allows a passive device (e.g., medical device 136) to receive analyte data (e.g., glucose values) without being bonded to analyte sensor system 8 is to include the analyte data in the advertisement messages transmitted from analyte sensor system 8. The data included in the advertisement messages can be encoded so that only a device that has the identification information associated with analyte sensor system 8 can decode the analyte data. Medical device 136 may include input/output portion 136a, in which, for example, glucose and other values may be displayed and input may be received via buttons, wireless connection, or other mechanisms. Medical device 136 may also include attachment portion 136b that interfaces with the user to, for example, administrate insulin responsive to the input received at input/output portion 136a. In some cases, attachment portion 136b may provide sensory alerts or other notifications to the user based on, for example, the input received and/or values calculated at input/output portion 136a.

With further reference to FIG. 1A, the plurality of display devices may include a custom display device specially designed for displaying certain types of displayable sensor information associated with analyte data received from sensor electronics module 12 (e.g., a numerical value and an arrow, in some embodiments). Analyte display device 110 is an example of such a custom device. In some embodiments, one of the plurality of display devices is smartphone, such as mobile phone 120 based on an Android, iOS or other operating system, and configured to display a graphical representation of the continuous sensor data (e.g., including current and historic data). Other display devices can include other hand-held devices, such as tablet 130, smart watch 140, medical device 136 (e.g., an insulin delivery device or a blood glucose meter), and/or a desktop or laptop computer.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1A, a plurality of different display devices can be in direct wireless communication with a sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

As further illustrated in FIG. 1A, system 100 may also include wireless access point (WAP) 138 that may be used to couple one or more of analyte sensor system 8, the plurality display devices, server system 134, and medical device 136 to one another. For example, WAP 138 may provide WiFi and/or cellular connectivity within system 100. Near Field Communication (NFC) may also be used among devices of system 100. Server system 134 may be used to collect analyte data from analyte sensor system 8 and/or the plurality of display devices, for example, to perform analytics thereon, generate universal or individualized models for glucose levels and profiles, and so on.

Figure 3A:
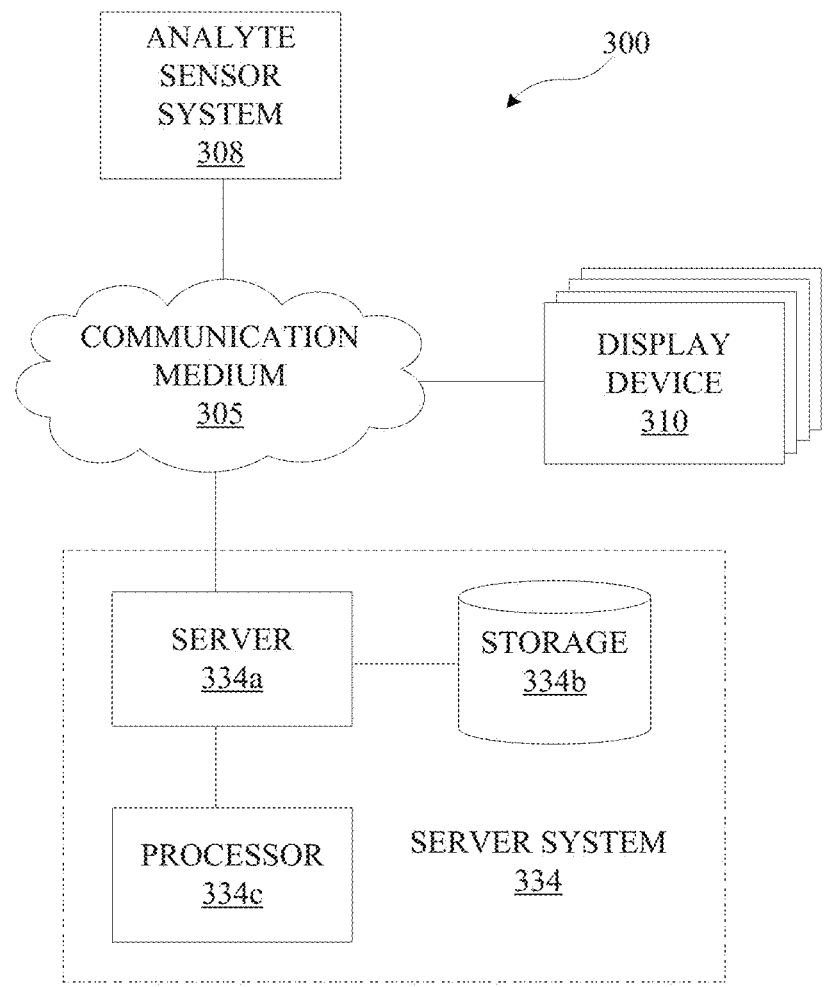
FIG. 3A illustrates aspects of an example system that may be used in connection with implementing embodiments of the disclosure.

Referring now to FIG. 3A, system 300 is depicted. System 300 may be used in connection with implementing embodiments of the disclosed systems, methods, and devices. By way of example, the various below-described components of FIG. 3A may be used to provide wireless communication of glucose data, for example between an analyte sensor system and a plurality of display devices, medical devices, servers and so on.

As shown in FIG. 3A, system 100 may include analyte sensor system 308 and one or more display devices 310. Additionally, in the illustrated embodiment, system 300 includes server system 334, which in turn includes server 334a coupled to processor 334c and storage 334b. Analyte sensor system 308 may be coupled to display devices 310 and/or server system 334 via communication medium 305. Many details of the processing, gathering, and exchanging data by analyte sensor system 308 and/or display device 310 etc. are provided, for example, with reference to FIG. 6, below.

As will be described in detail herein, analyte sensor system 308 and display devices 310 may exchange messaging via communication medium 305, and communication medium 305 may also be used to deliver analyte data to display devices 310 and/or server system 334. As alluded to above, display devices 310 may include a variety of electronic computing devices, such as, for example, a smartphone, tablet, laptop, wearable device, etc. Display devices 310 may also include analyte display device 110 and medical device 136. Here, it will be noted that a GUI of display device 310 may perform such functions as accepting user input and displaying menus as well as information derived from analyte data. The GUI may be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. In various embodiments, communication medium 305 may be based on one or more wireless communication protocols such as Bluetooth, Bluetooth Low Energy (BLE), ZigBee, WiFi, 802.11 protocols, Infrared (IR), Radio Frequency (RF), 2G, 3G, 4G, etc., and/or wired protocols and media.

In various embodiments, the elements of system 300 may be used to perform various processes described herein and/or may be used to execute various operations described herein with regard to one or more disclosed systems and methods. Upon studying the present disclosure, one of skill in the art will appreciate that system 300 may include multiple analyte sensor systems, communication media 305, and/or server systems 334.

As mentioned, communication medium 305 may be used to connect or communicatively couple analyte sensor system 308, display devices 310, and/or server system 334 to one another or to a network, and communication medium 305 may be implemented in a variety of forms. For example, communication medium 305 may include an Internet connection, such as a local area network (LAN), a wide area network (WAN), a fiber optic network, internet over power lines, a hard-wired connection (e.g., a bus), and the like, or any other kind of network connection. Communication medium 305 may be implemented using any combination of routers, cables, modems, switches, fiber optics, wires, radio (e.g., microwave/RF links), and the like. Further, communication medium 305 may be implemented using various wireless standards, such as Bluetooth®, BLE, Wi-Fi, 3GPP standards (e.g., 2G GSM/GPRS/EDGE, 3G UMTS/CDMA2000, or 4G LTE/LTE-U), etc. Upon reading the present disclosure, one of skill in the art will recognize other ways to implement communication medium 305 for communications purposes.

Server 334a may receive, collect, or monitor information, including analyte data and related information, from analyte sensor system 308 and/or display device 310, such as input responsive to the analyte data or input received in connection with an analyte monitoring application running on analyte sensor system or display device 310. In such cases, server 334a may be configured to receive such information via communication medium 305. This information may be stored in storage 334b and may be processed by processor 334c. For example, processor 334c may include an analytics engine capable of performing analytics on information that server 334a has collected, received, etc. via communication medium 305. In embodiments, server 334a, storage 334b, and/or processor 334c may be implemented as a distributed computing network, such as a Hadoop® network, or as a relational database or the like.

Server 334a may include, for example, an Internet server, a router, a desktop or laptop computer, a smartphone, a tablet, a processor, a module, or the like, and may be implemented in various forms, including, for example, an integrated circuit or collection thereof, a printed circuit board or collection thereof, or in a discrete housing/package/rack or multiple of the same. In embodiments, server 334a at least partially directs communications made over communication medium 305. Such communications include the delivery and/or messaging (e.g., advertisement, command, or other messaging) and analyte data. For example, server 334a may process and exchange messages between analyte sensor system 308 and display devices 310 related to frequency bands, timing of transmissions, security, alarms, and so on. Server 334a may update information stored on analyte sensor system 308 and/or display devices 310, for example, by delivering applications thereto. Server 334*a* may send/receive information to/from analyte sensor system 308 and/or display devices 310 in real time or sporadically. Further, server 334*a* may implement cloud computing capabilities for analyte sensor system 308 and/or display devices 310.

Figure 3B:
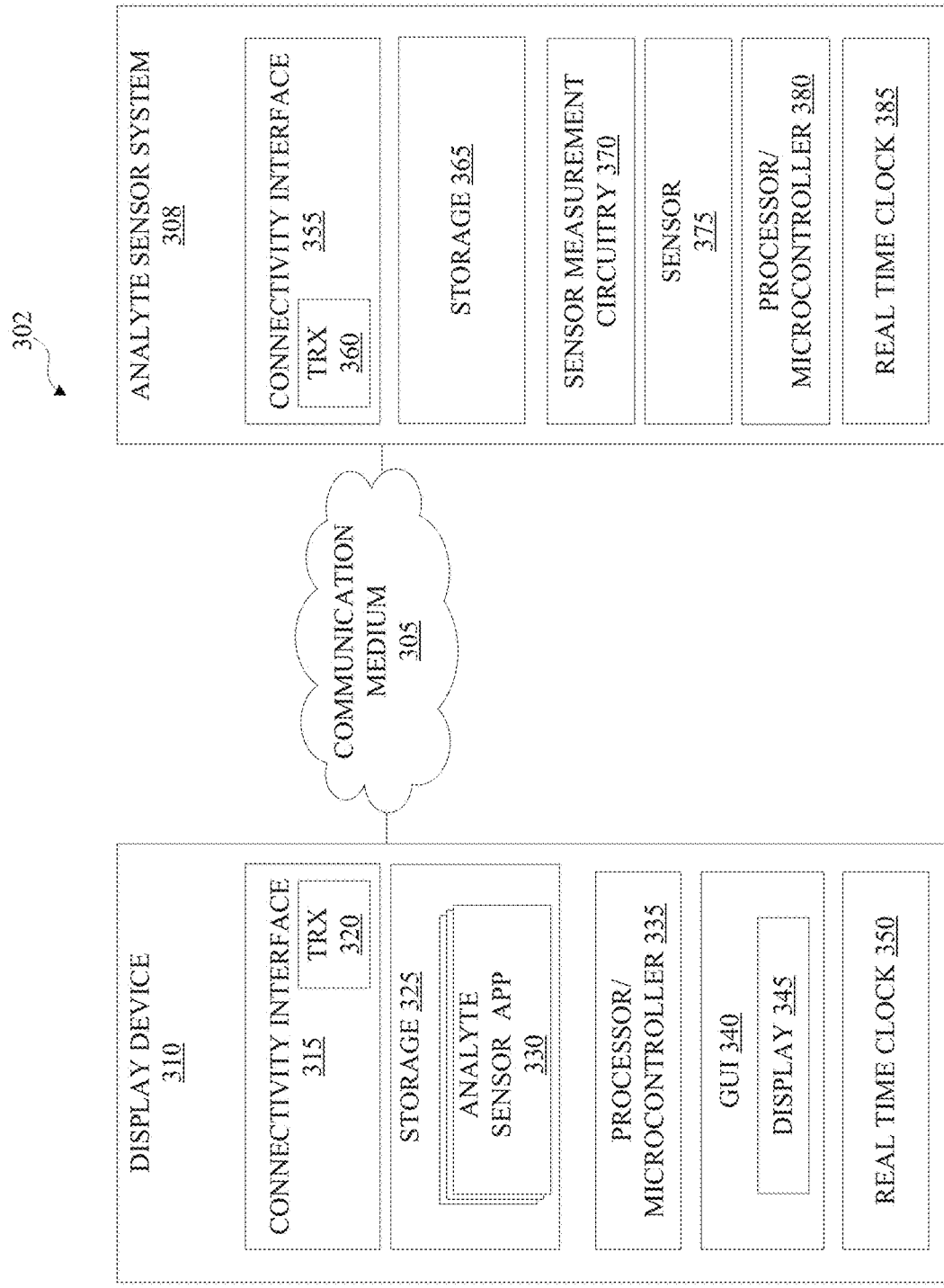
FIG. 3B illustrates aspects of an example system that may be used in connection with implementing embodiments of the disclosure.

FIG. 3B depicts system 302, which includes examples of additional aspects of the present disclosure that may be used in connection implementing an analyte sensor system. Many details of the processing, gathering, and exchanging data by analyte sensor system 308 and/or display device 310 etc. are provided, for example, with reference to FIG. 6, below. As illustrated in FIG. 3B, system 302 may include analyte sensor system 308. As shown, analyte sensor system 308 may include analyte sensor 375 (e.g., which may also be designated with the numeral 10 in FIG. 1A) coupled to sensor measurement circuitry 370 for processing and managing sensor data. Sensor measurement circuitry 370 may be coupled to processor/microprocessor 380 (e.g., which may be part of item 12 in FIG. 1A). In some embodiments, processor 380 may perform part or all of the functions of the sensor measurement circuitry 370 for obtaining and processing sensor measurement values from sensor 375. Processor 380 may be further coupled to a radio unit or transceiver 320 (e.g., which may be part of item 12 in FIG. 1A) for sending sensor data and receiving requests and commands from an external device, such as display device 310, which may be used to display or otherwise provide the sensor data (or analyte data) to a user. As used herein, the terms "radio unit" and "transceiver" are used interchangeably and generally refer to a device that can wirelessly transmit and receive data. Analyte sensor system 308 may further include storage 365 (e.g., which may be part of item 12 in FIG. 1A) and real time clock (RTC) 380 (e.g., which may be part of item 12 in FIG. 1A) for storing and tracking sensor data.

As alluded to above, wireless communication protocols may be used to transmit and receive data between analyte sensor system 308 and the display device 310 via communication medium 305. Such wireless protocols may be designed for use in a wireless network that is optimized for periodic and small data transmissions (that may be transmitted at low rates if necessary) to and from multiple devices in a close range (e.g., a personal area network (PAN)). For example, one such protocol may be optimized for periodic data transfers where transceivers may be configured to transmit data for short intervals and then enter low power modes for long intervals. The protocol may have low overhead requirements both for normal data transmissions and for initially setting up communication channels (e.g., by reducing overhead) to reduce power consumption. In some embodiments, burst broadcasting schemes (e.g., one way communication) may be used. This may eliminate overhead required for acknowledgement signals and allow for periodic transmissions that consume little power. In other embodiments, passive or active proximity-based protocols may be employed to reduce overhead (e.g., overhead associated with typical pairing operations) and/or increase security, with NFC being one specific example.

The protocols may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as WiFi, Bluetooth and Bluetooth Low Energy (BLE). The wireless protocol may operate in various frequency bands such as an open ISM band such as 2.4 GHz. Furthermore, to reduce power usage, the wireless protocol may adaptively configure data rates according to power consumption.

With further reference to FIG. 3B, system 302 may include display device 310 communicatively coupled to analyte sensor system 308 via communication medium 305. In the illustrated embodiment, display device 310 includes connectivity interface 315 (which in turn includes transceiver 320), storage 325 (which in turn stores analyte sensor application 330 and/or additional applications), processor/microprocessor 335, graphical user interface (GUI) 340 that may be presented using display 345 of display device 310, and real time clock (RTC) 350. A bus (not shown here) may be used to interconnect the various elements of display device 310 and transfer data between these elements.

Display device 310 may be used for alerting and providing sensor information or analyte data to a user, and may include a processor/microprocessor 335 for processing and managing sensor data. Display device 310 may include display 345, storage 325, analyte sensor application 330, and real time clock 350 for displaying, storing, and tracking sensor data. Display device 310 may further include a radio unit or transceiver 320 coupled to other elements of display device 310 via connectivity interface 315 and/or a bus. Transceiver 320 may be used for receiving sensor data and for sending requests, instructions, and/or data to analyte sensor system 308. Transceiver 320 may further employ a communication protocol. Storage 325 may also be used for storing an operating system for display device 310 and/or a custom (e.g., proprietary) application designed for wireless data communication between a transceiver and display device 310. Storage 325 may be a single memory device or multiple memory devices and may be a volatile or non-volatile memory for storing data and/or instructions for software programs and applications. The instructions may be executed by processor 335 to control and manage transceiver 320.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, processor 335, 380 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver 320, 360.

Components of analyte sensor system 308 may require replacement periodically. For example, analyte sensor system 308 may include an implantable sensor 375 that may be attached to a sensor electronics module that includes sensor measurement circuitry 370, processor 380, storage 365, and transceiver 360, and a battery (not shown). Sensor 375 may require periodic replacement (e.g., every 7 to 30 days). The sensor electronics module may be configured to be powered and active for much longer than sensor 375 (e.g., for three to six months or more) until the battery needs replacement. Replacing these components may be difficult and require the assistance of trained personnel. Reducing the need to replace such components, particularly the battery, significantly improves the convenience and cost of using analyte sensor system 308, including to the user. In some embodiments, when a sensor electronic module is used for the first time (or reactivated once a battery has been replaced in some cases), it may be connected to sensor 375 and a sensor session may be established. As will be further described below, there may be a process for initially establishing communication between display device 310 and the sensor electronics module when the module is first used or re-activated (e.g., the battery is replaced). Once display device 310 and sensor electronics module have established communication, display device 310 and the sensor electronics module may periodically and/or continuously be in communication over the life of several sensors 375 until, for example, the battery needs to be replaced. Each time sensor 375 is replaced, a new sensor session may be established. The new sensor session may be initiated through a process completed using display device 310 and the process may be triggered by notifications of a new sensor via the communication between the sensor electronics module and display device 310 that may be persistent across sensor sessions.

Analyte sensor system 308 in example implementations gathers analyte data from sensor 375 and transmits the same to display device 310. Data points regarding analyte values may be gathered and transmitted over the life of sensor 375 (e.g., in the range of 1 to 30 days or more). New measurements may be transmitted often enough to adequately monitor glucose levels. Rather than having the transmission and receiving circuitry of each of analyte sensor system 308 and display device 310 continuously communicating, analyte sensor system 308 and display device 310 may regularly and/or periodically establish a communication channel between them. Thus, analyte sensor system 308 can in some cases communicate via wireless transmission with display device 310 (e.g., a hand-held computing device, medical device, or proprietary device) at predetermined time intervals. The duration of the predetermined time interval can be selected to be long enough so that analyte sensor system 308 does not consume too much power by transmitting data more frequently than needed, yet frequent enough to provide substantially real-time sensor information (e.g., measured glucose values or analyte data) to display device 310 for output (e.g., via display 345) to a user. While the predetermined time interval is every five minutes in some embodiments, it is appreciated that this time interval can be varied to be any desired length of time.

With continued reference to FIG. 3B, as shown, connectivity interface 315 interfaces display device 310 to communication medium 305, such that display device 310 may be communicatively coupled to analyte sensor system 308 via communication medium 305. Transceiver 320 of connectivity interface 315 may include multiple transceiver modules operable on different wireless standards. Transceiver 320 may be used to receive analyte data and associated commands and messages from analyte sensor system 308. Additionally, connectivity interface 315 may in some cases include additional components for controlling radio and/or wired connections, such as baseband and/or Ethernet modems, audio/video codecs, and so on.

Storage 325 may include volatile memory (e.g. RAM) and/or non-volatile memory (e.g. flash storage), may include any of EPROM, EEPROM, cache, or may include some combination/variation thereof. In various embodiments, storage 325 may store user input data and/or other data collected by display device 310 (e.g., input from other users gathered via analyte sensor application 330). Storage 325 may also be used to store volumes of analyte data received from analyte sensor system 308 for later retrieval and use, e.g., for determining trends and triggering alerts. Additionally, storage 325 may store analyte sensor application 330 that, when executed using processor 335, for example, receives input (e.g., by a conventional hard/soft key or a touch screen, voice detection, or other input mechanism), and allows a user to interact with the analyte data and related content via GUI 340, as will be described in further detail herein.

In various embodiments, a user may interact with analyte sensor application 330 via GUI 340, which may be provided by display 345 of display device 310. By way of example, display 345 may be a touchscreen display that accepts various hand gestures as inputs. Application 330 may process and/or present analyte-related data received by display device 310, according to various operations described herein, and present such data via display 345. Additionally, application 330 may be used to obtain, access, display, control, and/or interface with analyte data and related messaging and processes associated with analyte sensor system 308, as is described in further detail herein.

Application 330 may be downloaded, installed, and initially configured/setup on display device 310. For example, display device 310 may obtain application 330 from server system 334, or from another source accessed via a communication medium (e.g., communication medium 305), such as an application store or the like. Following installation and setup, application 330 may be used to access and/or interface with analyte data (e.g., whether stored on server system 334, locally from storage 325, or from analyte sensor system 308). By way of illustration, application 330 may present a menu that includes various controls or commands that may be executed in connection with the operating of analyte sensor system 308 and one or more display devices 310. Application 330 may also be used to interface with or control other display devices 310, for example, to deliver or make available thereto analyte data, including for example by receiving/sending analyte data directly to the other display device 310 and/or by sending an instruction for analyte sensor system 308 and the other display device 310 to be connected, etc., as will be described herein. Additionally, application 330 in some implementations may interact with one or more additional applications supported by display device 310, for example to retrieve or supply relevant data. Such applications may include, by way of example, fitness/lifestyle monitoring applications, social media applications, and so on.

Analyte sensor application 330 may include various code/functional modules, such as, for example, a display module, a menu module, a list module, and so on as will become clear in light of the description of various functionalities herein (e.g., in connection with disclosed methods). These modules may be implemented separately or in combination. Each module may include computer-readable media and have computer-executable code stored thereon, such that the code may be operatively coupled to and/or executed by processor 335 (which, e.g., may include a circuitry for such execution) to perform specific functions (e.g., as described herein with regard to various operations and flow charts etc.) with respect to interfacing with analyte data and performing tasks related thereto. As will be further described below, a display module may present (e.g., via display 345) various screens to a user, with the screens containing graphical representations of information provided by application 330. In further embodiments, application 330 may be used to display to the user an environment for viewing and interacting with various display devices that may be connectable to analyte sensor system 308, as well as with analyte sensor system 308 itself. Sensor application 330 may include a native application modified with a software design kit (e.g., depending on the operating system) in order to carry out the functionalities/features described herein.

Referring again to FIG. 3B, display device 310 also includes processor/microcontroller 335. Processor 335 may include processor sub-modules, including, by way of example, an applications processor that interfaces with and/or controls other elements of display device 310 (e.g., connectivity interface 315, application 330, GUI 340, display 345, RTC 350, etc.). Processor 335 may include a controller and/or microcontroller that provides various controls (e.g., interfaces with buttons and switches) related to device management, such as, for example, lists of available or previously paired devices, information related to measurement values, information related to network conditions (e.g., link quality and the like), information related to the timing, type, and/or structure of messaging exchanged between analyte sensor system 308 and display device 310, and so on. Additionally, the controller may include various controls related to the gathering of user input, such as, for example, a user's finger print (e.g., to authorize the user's access to data or to be used for authorization/encryption of data, including analyte data), as well as analyte data.

Processor 335 may include circuitry such as logic circuits, memory, a battery and power circuitry, and other circuitry drivers for periphery components and audio components. Processor 335 and any sub-processors thereof may include logic circuits for receiving, processing, and/or storing data received and/or input to display device 310, and data to be transmitted or delivered by display device 310. Processor 335 may be coupled by a bus to display 345 as well as connectivity interface 315 and storage 325 (including application 330). Hence, processor 335 may receive and process electrical signals generated by these respective elements and thus perform various functions. By way of example, processor 335 may access stored content from storage 325 at the direction of application 330, and process the stored content for display and/or output by display 345. Additionally, processor 335 may process the stored content for transmission via connectivity interface 315 and communication medium 305 to other display devices 310, analyte sensor system 308, or server system 334. Display device 310 may include other peripheral components not shown in detail in FIG. 3B.

In further embodiments, processor 335 may further obtain, detect, calculate, and/or store data input by a user via display 345 or GUI 340, or data received from analyte sensor system 308 (e.g., analyte sensor data or related messaging), over a period of time. Processor 335 may use this input to gauge the user's physical and/or mental response to the data and/or other factors (e.g., time of day, location, etc.). In various embodiments, the user's response or other factors may indicate preferences with respect to the use of certain display devices 310 under certain conditions, and/or the use of certain connection/transmission schemes under various conditions, as will be described in further detail herein.

It should be noted at this juncture that like-named elements as between display device 310 and analyte sensor system 308 may include similar features, structures, and/or capabilities. Therefore, with respect to such elements, the description of display device 310 above may in some cases be applied to analyte sensor system 308.

Figure 3C:
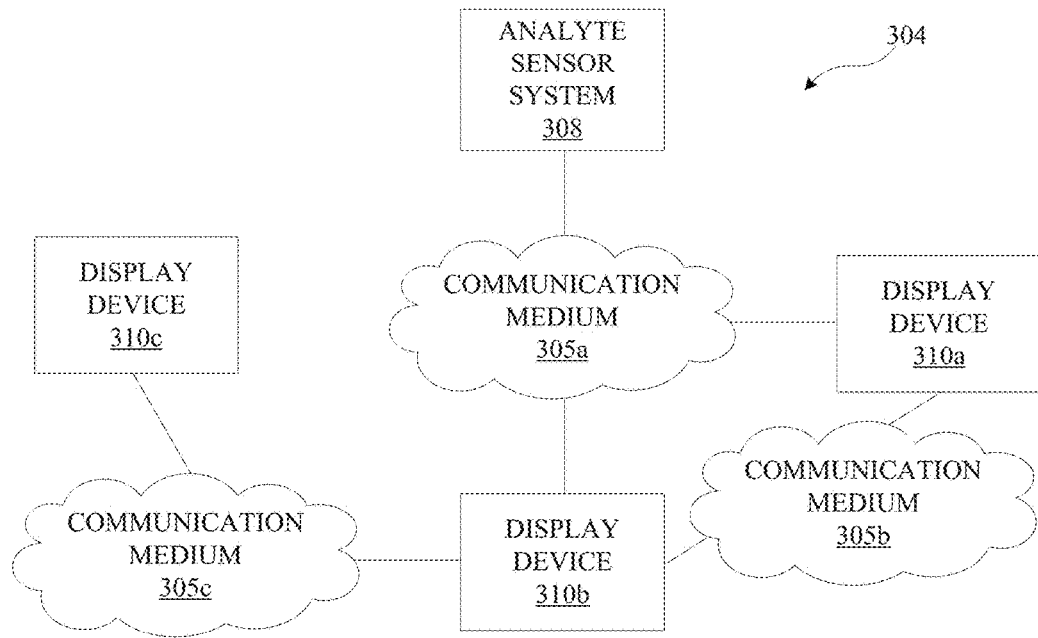
FIG. 3C illustrates aspects of an example system that may be used in connection with implementing embodiments of the disclosure.

Turning now to FIG. 3C, system 304 is depicted in accordance with embodiments of the present disclosure. As shown, system 304 includes analyte sensor system 308 communicatively coupled display devices 310a, 310b via communication medium 305a. Display device 310a is also communicatively coupled to display device 310b via communication medium 305b. By way of example, FIG. 3C illustrates that in example implementations of the disclosure, display device 310a may connect to analyte sensor system 308 using a first connection scheme and a first wireless protocol (e.g., BLE). In turn, display device 310a may also connect to display device 310b using a second connection scheme and a second wireless protocol (e.g., Wi-Fi, NFC, etc.). In embodiments, the connection between display device 310a and analyte sensor system 308 may subsequently be closed, and display device 310b may establish a connection with analyte sensor system 308 while maintaining the connection with display device 310a. Further, for example, display devices 310a and 310b may exchange analyte data with one another via communication medium 305b, where each display device 310a, 310b received the analyte data via communication medium 305a, that is, from analyte sensor system 308. Display device 310c may also connect to display device 310b via communication medium 305c. Additional aspects and features represented by FIG. 3C will become apparent upon studying the entirety of the present disclosure, including, by way of example, FIGS. 3D and 3E.

Figure 3D:
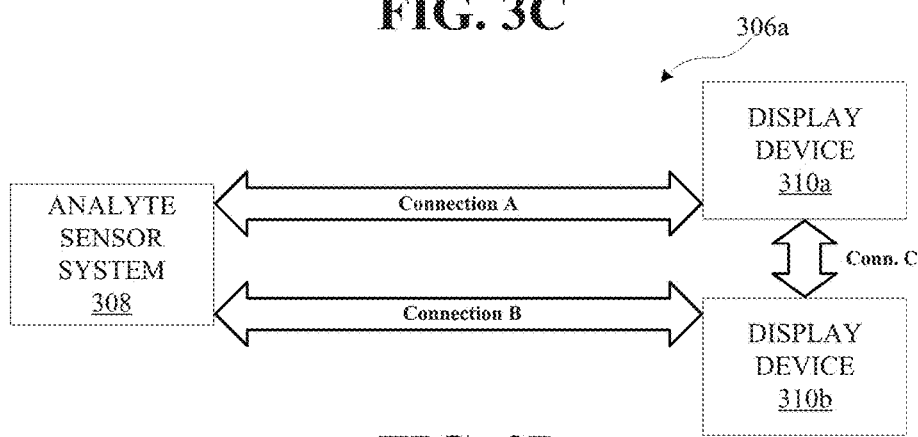
FIG. 3D illustrates aspects of an example system that may be used in connection with implementing embodiments of the disclosure.
Figure 3E:
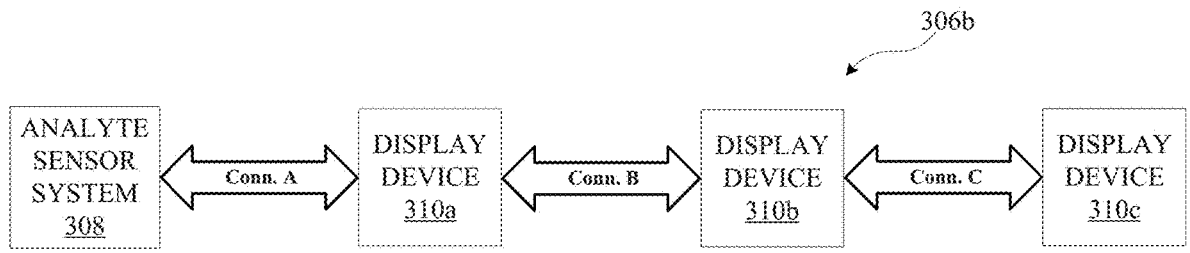
FIG. 3E illustrates aspects of an example system that may be used in connection with implementing embodiments of the disclosure.
Figure 3F:
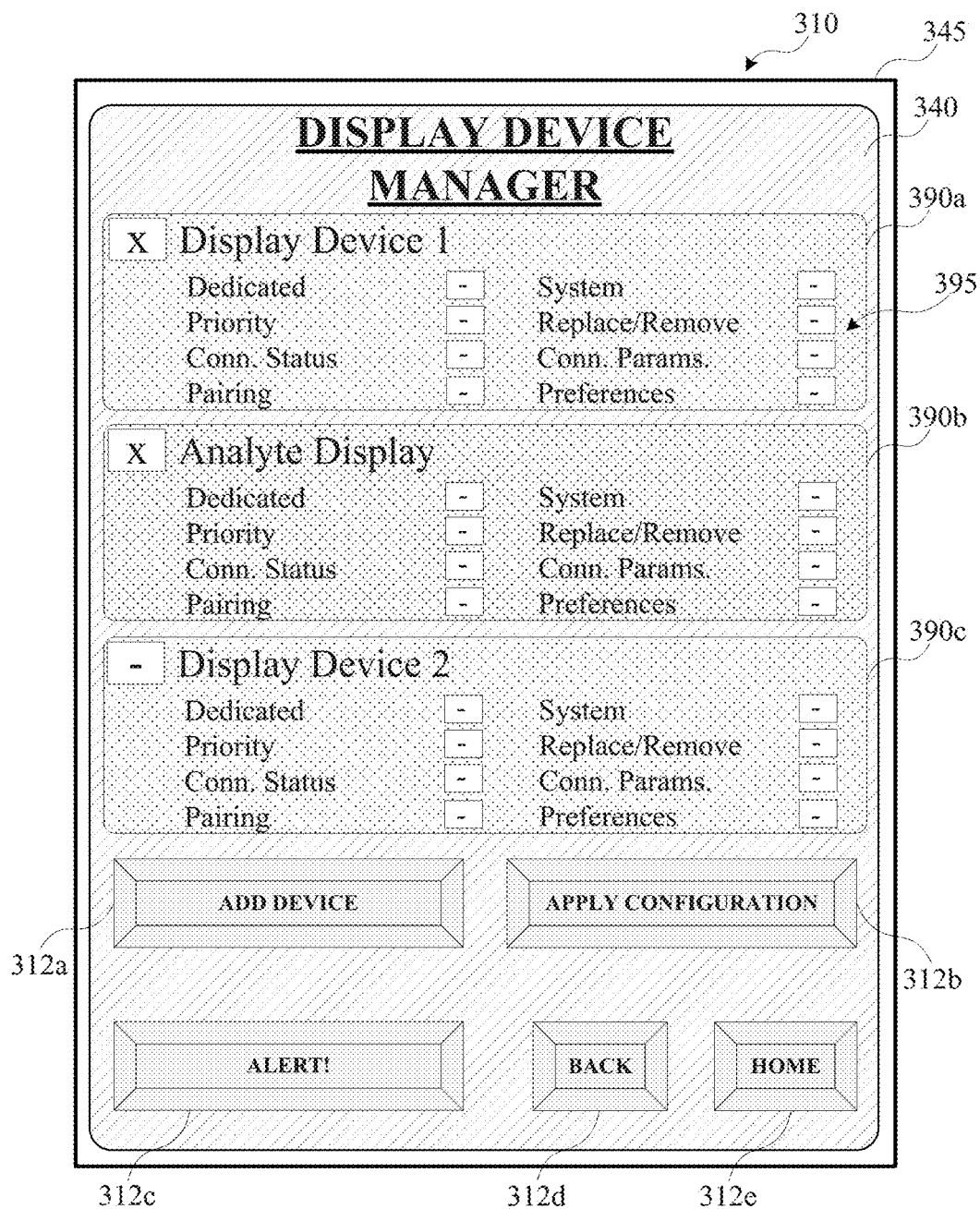
FIG. 3F illustrates aspects of an example user interface according to embodiments of the disclosure.

FIG. 3F illustrates an example implementation of GUI 340 that may be employed in accordance with embodiments of the present disclosure. As shown in FIG. 3F, GUI 340 may be presented via display 345 of display device 310, for example in connection with sensor application 330. Generally speaking, the functionality and features of GUI 340 will be described in further detail with reference to systems and methods described herein. By way of illustration, GUI 340 may present interfaces associated with application 330, including, for example, a display device manager. Such a display device manager may be used for configuring aspects of systems involving analyte monitoring, such as systems 300, 302, 304, 306a, and 306b (referencing by way of example FIGS. 3A-3E). For example, the display device manages (and in some cases more generally, interfaces associated with application 330) may be used to set up connection parameters for a connection established (or to be established) between analyte 308 and display device 310, may be used to select a dedicated display device 310, may be used to tether one display device 310a to another display device 310b, and so on (referencing by way of example FIGS. 3A-3E).

As shown in FIG. 3F, the display device manager may include an interface module for each of one or more display devices 310 that may be coupled to analyte sensor system 308 (see, e.g., FIGS. 3A and 3B). Interface module 390a may be used to interface with a first display device of display devices 310 ("Display Device 1" or "DD1"); interface module 390b may be used to interface with an analyte display device of display devices 310 ("Analyte Display"); and interface module 390c may be used to interface with a second display device of display devices 310 ("Display Device 2" or "DD2"). Each interface module 390a, 390b, 390c may in turn include configuration menu 395, which may include a number of buttons (e.g., touch-sensitive soft keys) to configure various settings for the device being managed. The available buttons of configuration menu 395 and their functionality can be modified, for example, based on characteristics of the display device being managed as well as other parameters.

As will be described in connection with FIG. 3G, configuration menus 395 may be used to access sub-menus that may be used to select specific management options for the display device of interest. Additional buttons that can be included in GUI 340 are buttons 312a-e. For example, button 312a may be used to add a device to the device manager; button 312b may be used to apply a pre-set configuration to the device manager; button 312c may be used to notify the user of an alert or to manage alert settings; button 312d may be used to navigate back to a previous screen shown in GUI 340 (e.g., in connection with application 330); and button 312e may be used as a soft key to return to the home screen of display device 310.

Figure 3G:
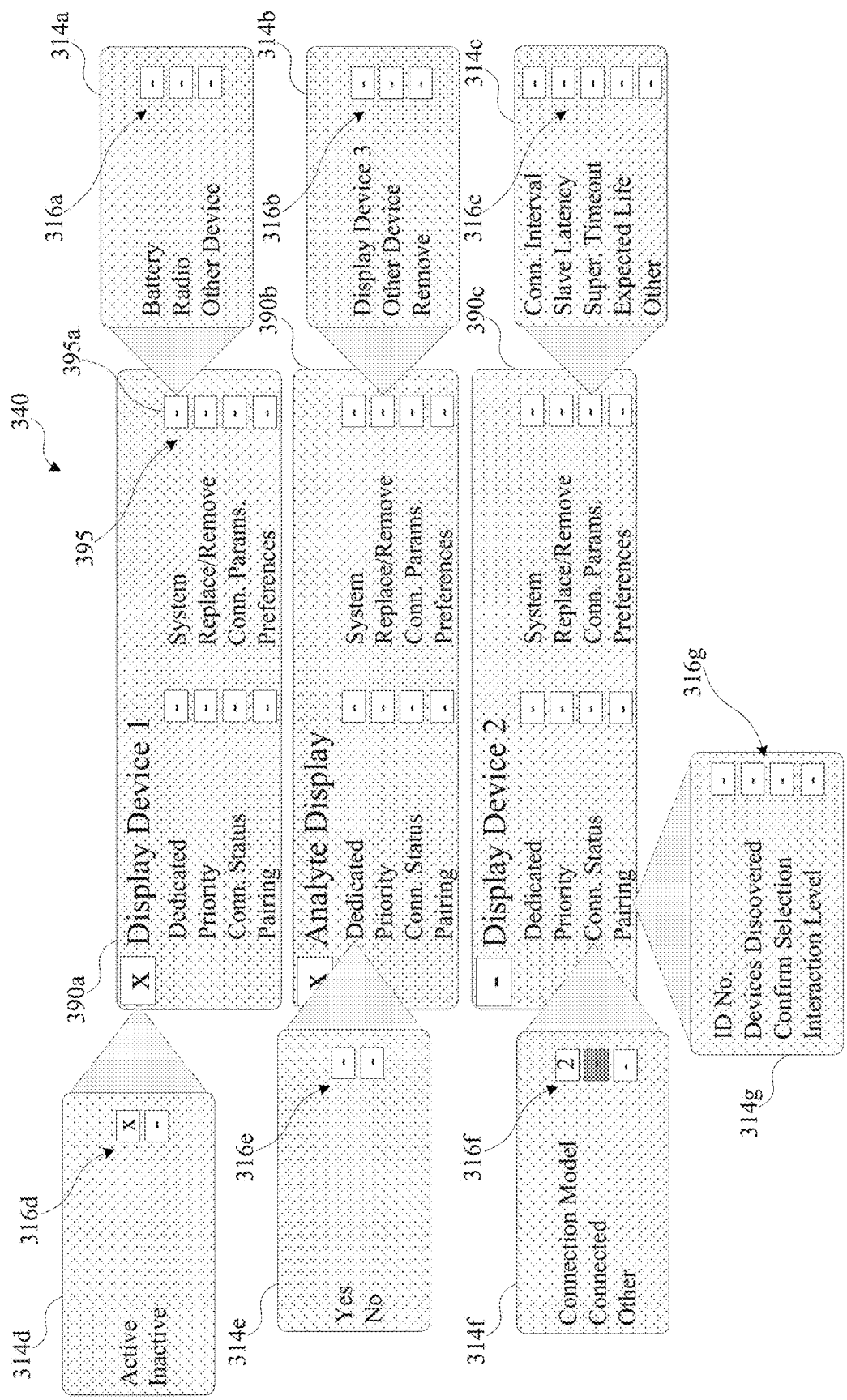
FIG. 3G illustrates aspects of an example user interface according to embodiments of the disclosure.

Turning now to FIG. 3G, additional aspects that may be implemented in connection with GUI 340 are provided. As shown in FIG. 3G, embodiments of GUI 340 involve sub-menus 314a-g of interface modules 390a, 390b, and 390c. Sub-menu 314a may be accessed via configuration menu 395 of interface module 390a. In this instance, sub-menu 314a corresponds to a "System" option. In this regard, when selected (e.g., via touch gesture on display 345) sub-menu 314a presents options 316a for management and viewing of Battery characteristics of Display Device 1, Radio configuration and measurements of Display Device 1, and aspects of Other Devices. Options 316a may be used to select a device to tether to (e.g., through the Other Devices option 316a. With reference to FIG. 3C by way of specific example, tethering in this case may involve, for example, two display devices 310a and 310b connecting via communication medium 305b. In some cases, Analyte Display and Display Device 2 may correspond to known devices, whereas selecting the Other Device option may initiate a scan for other display devices 310 available for connection. In other examples, the Other Device option can be used to tether to a known device. It will be appreciated that sub-menu 314a may be implemented in connection with any other interface module (e.g., 390b etc.)

Sub-menu 314b corresponds to a "Replace/Remove" option. In this regard, when selected (e.g., via touch gesture on display 345) sub-menu 314b presents options 316b, which include options for replacing Analyte Display with another display device 310, namely Display Device 3 ("DD3") or Other Device. Within options 316b, sub-menu 314b also presents an options for to Remove Analyte Display from a list of devices (e.g., a whitelist), as will be further described herein (see, e.g., FIG. 10B). Here again, in some cases Display Device 3 may correspond to a known device, whereas selecting the Other Device option may initiate a scan for other display devices 310 available for connection to Analyte Display. It will be appreciated that sub-menu 314b may be implemented in connection with any other interface module (e.g., 390a etc.). For example, sub-menu may be used to replace a user's old smartphone with the user's new smartphone in terms of use with analyte sensor system 308.

Sub-menu 314c corresponds to a "Config. Params." or Configuration Parameters option. In this regard, when selected (e.g., via touch gesture on display 345) sub-menu 314c presents options 316c, which include options for modifying or setting various configuration parameters regarding connection with analyte sensor system 8 and the transmission of data from the same. Within options 316c, sub-menu 314c presents options concerning whether specific Configuration Parameters are Enabled and then lists additional options related to Configuration Parameters that may be specifically controlled by the user. In some examples, these connection parameters may additionally or alternatively be monitored and adjusted without user intervention (e.g., by display device 310 and/or analyte sensor system 308), for example by comparing monitored parameter values to predetermined and/or configurable/adaptable thresholds. In this regard, the user may be able to select which parameters should be monitored/adjusted by display device 310. In other cases, the selection can be made on the fly based on monitored parameter values and/or other inputs. Thus, it will be appreciated that in some cases, the user may not have access to or permission with respect to the connection parameters.

Accordingly, notwithstanding the above, it will be appreciated that in embodiments of GUI 340, various combinations and implementations of configuration 395 (395a, etc.), sub-menus 314a-g, and options 316a-g, are contemplated in connection with the present disclosure. By way of example, sub-menu 314c corresponding to "Config. Params." may be omitted such that the connection parameters may not by default be visible to the user and/or are accessible to or changeable by the user. In such examples, the connection parameters may be stored in storage 325 of display device 310 and may be in conjunction with establishing and/or maintaining a connection between display device 310 and analyte sensor system 308 (and/or in some cases another display device 310).

In embodiments, a Quality option (not shown) may be adjusted by the user to control or interface with Configuration Parameters related to quality of service (QoS), as will be described further herein. Further, as mentioned elsewhere herein in further detail, QoS-related parameters may also be monitored/adjusted by analyte sensor system 308 and/or display device 310, for example based thresholds related to link quality and so on. The Quality Option may be accessed through the Preferences configuration 395. The Location option may be adjusted by the user to control or interface with Configuration Parameters related to location, as will be described further herein. The Time option may be adjusted by the user to control or interface with Configuration Parameters related to time of day, as will be described further herein. The Power option may be adjusted by the user to at least indirectly control and/or interface with Configuration Parameters related to battery power, as will be described further herein. These Options may be accessed through the Preferences configuration 395, for example.

Sub-menu 314d corresponds to a pop-up window option related to the device to which interface module 390a pertains (i.e., in this example, Display Device 1 (DD1)). More specifically, sub-menu 314d indicates via greyed out options 316d whether the device of interest is on the whitelist, as will be described further herein. Options 316d in this example are greyed out to indicate that they are in some cases not selectable but rather are used to present information regarding whitelist status. A different sub-menu ("Whitelist/Blacklist"), not described specifically with reference to FIG. 3G, may be used to add/remove specific devices from the whitelist (or to/from a blacklist). It will be appreciated that sub-menu 314d may be implemented in connection with any other interface module (e.g., 390a etc.).

Sub-menu 314e corresponds to a "Dedicated" option. In this regard, when selected (e.g., via touch gesture on display 345), sub-menu 314e presents options 316e, which include options for making a display device of interest (here, Analyte Display) a dedicated display device with respect to connecting to analyte sensor system 308 and receiving data from and/or exchanging control signaling with the same. Options 316e of sub-menu 314e present options for indicating Yes or No regarding whether Analyte Display is a dedicated display device, as will be described further herein. It will be appreciated that sub-menu 314e may be implemented in connection with any other interface module (e.g., 390a etc.).

Sub-menu 314f corresponds to a "Connection Status" option. In this regard, when selected (e.g., via touch gesture on display 345) sub-menu 314f presents options 316f, which include options for setting or configuring a connection mode as between the display device of interest (here, Display Device 2) and analyte sensor system 308, for example. Within options 316f, sub-menu 314f presents options for Connection Model, Connected, and Other, regarding a connection, as will be described further herein. By way of example, sub-menu 314f may provide a user with information regarding the connection model employed without allowing the user modify the connection model or select a connection model from among a set of options. In other cases, however, the user may be able to manually choose a connection model to be employed using this option. Additionally, the Connected option 316f may indicate to the user whether Display Device 2 is presently connected to analyte sensor system 308. It will be appreciated that sub-menu 314f may be implemented in connection with any other interface module (e.g., 390a etc.).

Sub-menu 314g corresponds to a "Pairing" option. In this regard, when selected (e.g., via touch gesture on display 345) sub-menu 314g presents options 316g, which include options relating to identification of, selection of, and or pairing with analyte sensor system 308 and/or display devices 310a, 310b, etc. Within options 316g, sub-menu 314g presents an ID No. option, which is related to identification-related information (e.g., with respect to analyte sensor system 308); Devices Discovered, which is related to a set of identified display devices 310a, 310b, etc.; Confirm Selection, which may be used by a user to manually confirm a selection for connection between analyte sensor system 308 and display device 310; and Interaction Level, which can be used to set and/or modify the amount of user interaction to be employed with respect to the identification and/or selection of devices in connection with the pairing process. It will be appreciated that sub-menu 314f may be implemented in connection with any other interface module (e.g., 390a etc.).

Certain sub-menus and/or options etc. disclosed in connection with FIG. 3G and the present disclosure have not been described in detail here with reference to FIG. 3G, but aspects of embodiments shown in FIG. 3G are further described hereinbelow. Additionally, one of ordinary skill in the art will appreciate upon studying the present disclosure that GUI 340 may present various addition sub-menus and/or options, and will also appreciate that additional sub-menus and options are within the scope and spirit of the present disclosure.

Figure 4:
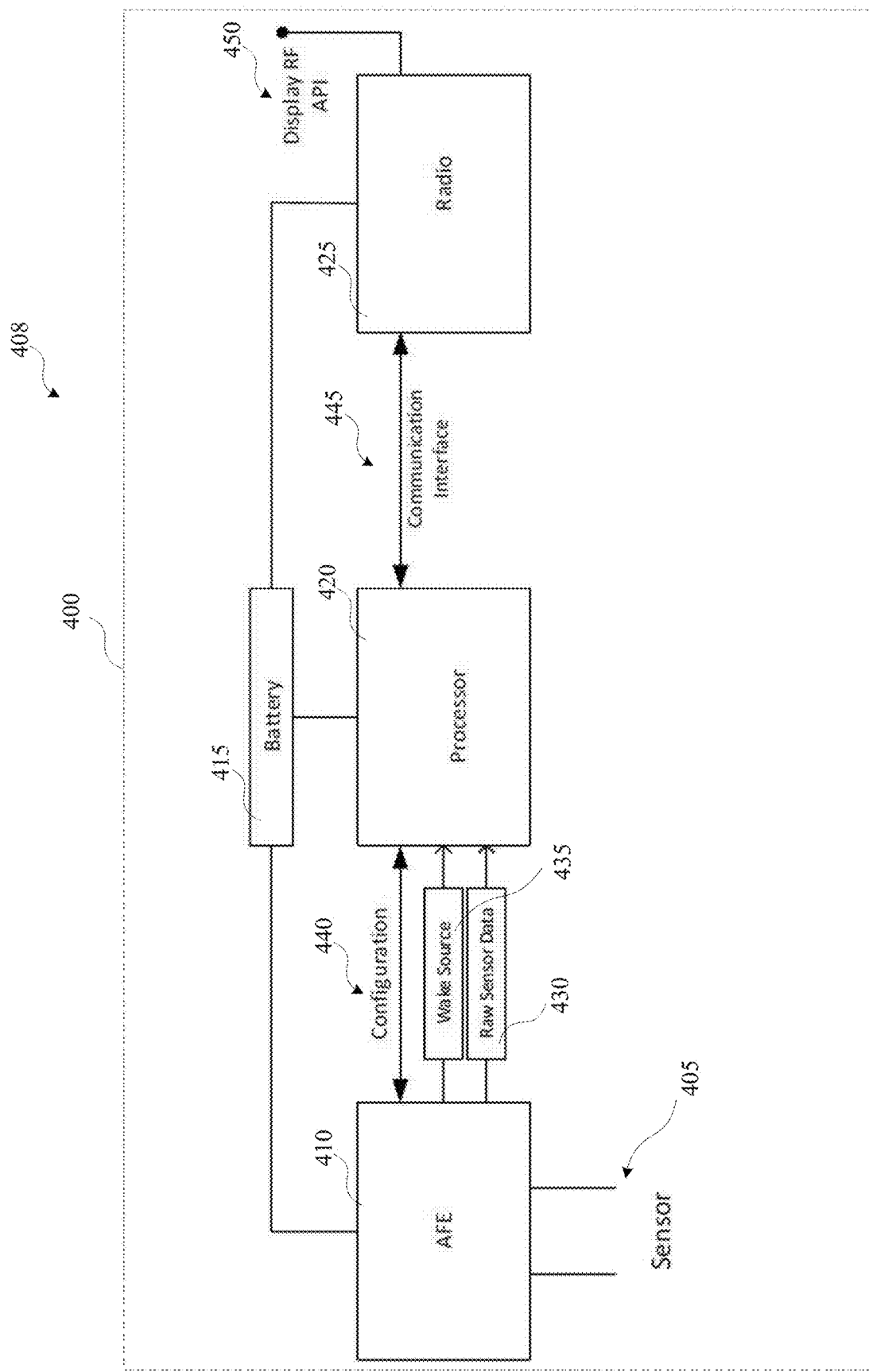
FIG. 4 is a block diagram illustrating aspects of an example analyte sensor system according to embodiments of the disclosure.

FIG. 4 is a block diagram illustrating potential aspects of analyte sensor system 408 according to embodiments of the present disclosure that are in example implementations associated with operation according to the intermittent connection model. The aspects of analyte sensor system 408 shown in FIG. 4 may be implemented within subsystem 400 of analyte sensor system 408 and may in general be used to manage a radio interface between analyte sensor system 408 and any display devices communicatively coupled thereto via a wireless protocol, such as BLE. For example, application programming interface (API) 450 may be provided for display devices to communicate with processor 420 (e.g., processor 380) via radio 425, which may include a BLE or other RF or microwave transceiver (e.g., transceiver 360). Processor 420 may be used to process analyte data gathered by sensor 405 (e.g., sensor 375).

As shown, within analyte sensor system 408, subsystem 400 may include sensor 405 (e.g., sensor 10), analog front end (AFE) 410 (e.g., sensor electronics module 12), battery 415, processor 420, and radio 425. The design of analyte sensor system 408, including with respect to subsystem 400 as well as related software, enables multi-chip operation and management, and particularly where such operation and/or management is carried out in accordance with power savings principles described herein and may involve implementing system configurations that support/maximize power savings. For example, the design enables system startup, inter-chip communication, application task scheduling, maximization of battery life in storage as well as active modes, and utilization of control points and indications by API 450 associated with radio 425.

A storage mode may be used for the operation of analyte sensor system 408 before analyte sensor system 408 has been inserted into a host. For example, upon detecting that sensor 405 has been inserted into the host, analyte sensor system 408 can automatically exit storage mode and enter an active mode. In storage mode, radio 425 can be at least partially disabled in order to save power. Likewise, processor 420 can be at least partially disabled, for example by disabling a clock used by processor 420 (e.g., RTC 350). Furthermore, it is contemplated that, in the storage mode, radio 425 may be configured to be in a deep sleep mode. This may advantageously extend/maximize the battery life of analyte sensor system 408. It is further contemplated that in implementations, upon interacting with display device 310, for example via NFC, analyte sensor system 408 may exit the storage mode.

In active mode, a low power mode (LPM) may still be used (e.g., to extend/maximize battery life), but RTC 350 may be activated/enabled. This may allow processor 420 to track time accurately and perform other clock-based functions while still allowing for power savings. For example, RTC 350 may be used to perform error recovery using time-based counters and interrupts. The following error recovery scenarios are provided by way of illustration. In one example, if no response messages are received from radio 425 for a given amount of time, processor 420 may reset radio 425. In another example, a periodic interrupt may be used where if logic of RTC 350 fails, analyte sensor system 408 can be reset by hardware logic. In additional implementations, if message or signal associated with wake source 435 (or AFE 410) is not received or fails, an interrupt (e.g., RTC interrupt) can be used to bring processor 420 out of LPM and perform communication functions.

Processor 420 may act as a system controller for subsystem 400 within analyte sensor system 408. For example, after initializing, radio 425 may enter a sleep state and wait for instruction from processor 420. AFE 410 may initialize to a default state and likewise wait for configuration instructions/commands from processor 420. Processor 420 may control resetting AFE 410 and/or radio 425 in case errors are detected. Processor 420 may also self-reset if internal error conditions are detected (e.g., using a hardware watchdog).

Subsystem 400 of analyte sensor system 8 may utilize a multi-chip (or multi-module) design, in which case a hardware communication bus may be used for the exchange of data among the various chips (or modules). Examples of viable options for the hardware communication bus include Inter-Integrated Circuit (I2C or I2C) and Serial Peripheral Interface (SPI). SPI may be used to achieve a reduction in powers as well as an increase in speed relative to I2C.

Wake source 435 and raw sensor data 430 may be used to maximize the battery life of analyte sensor system 408. AFE 410 may in examples be used as a wake source for components of subsystem 400. Nevertheless, other wake sources may be utilized. During normal operation, AFE 410 may allow processor 420 to enter an energy efficient lower power mode (LPM). Wake source 435 can be used to signal processor 420 to exit LPM such that, e.g., processor 420 can execute operations that in examples may not be available during LPM. Wake source 435 may signal processor 420 in this manner periodically and trigger processor 420 to start processing or executing operations. Analyte sensor system 408 may include multiple processors, and as mentioned below with reference to FIG. 5, staged task processing may be implemented, in some cases in connection with wake source 435, such that not all processors are active simultaneously. This technique may reduce power consumption and hence extend battery life. By way of example, wake source 435 may first signal processor 420 to exit LPM and begin configuring the pertinent hardware and software of analyte sensor system 408 to initiate the transfer of raw sensor (analyte) data from AFE 410.

Raw sensor data 430 may include hardware that transfers sensor data gathered by sensor 405 from AFE 410 to processor 420. Such data may be referred to herein as raw sensor data or raw analyte data. Configuration 440 may be a two-way interface between processor 420 and AFE 410. In some cases, configuration 440 may be implemented using I2C, but SPI or another interface configuration may also be used. Processor 420 and radio 425 may likewise use a SPI and/or I2C bus for communication and data transfer. In some cases, additional hardware and software may be used to create an asynchronous interface between processor 420 and radio 425 when using synchronous protocols (e.g., SPI and the like).

Figure 5:
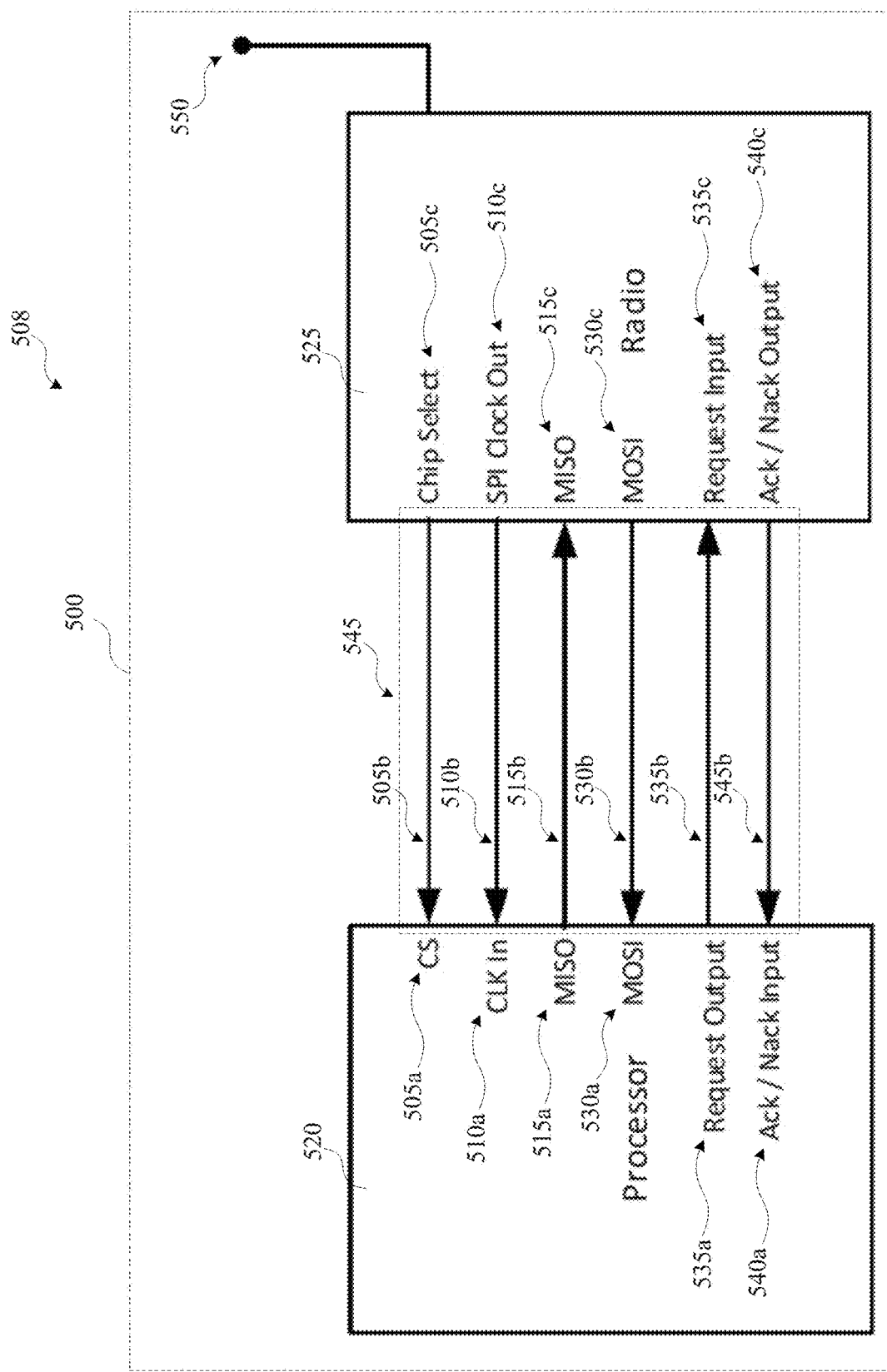
FIG. 5 is a block diagram illustrating aspects of an example analyte sensor system according to embodiments of the disclosure.

Turning now to FIG. 5, a block diagram illustrating potential aspects of analyte sensor system 508 is provided in accordance with embodiments of the present disclosure that are in some cases associated with operation according to the intermittent connection model. The aspects of analyte sensor system 508 shown in FIG. 5 may be implemented within subsystem 500 of analyte sensor system 508. In particular, subsystem 500 includes processor 520 and radio 525 that may be modified to include a SPI bus and additional general purpose input/out (GPIO) relative to communication interface 445 and thus create asynchronous interface 545 that couples processor 520 to radio 525. Asynchronous interface 545 may in some cases be referred to as a message transport layer.

As shown in the example of FIG. 5, asynchronous interface 545 includes connection 505*b* that provides chip select (CS) output 505*c* of radio 525 to CS input 505*a* of processor 520. Further, asynchronous interface 545 includes connection 510*b* that provides SPI clock out 515*c* of radio 525 to CLK in 510*a* of processor 520. Asynchronous interface 545 includes connection 515*b* that provides MISO (multiple input single output) 530*a* of processor 520 to MISO input 530*c* of radio 525. Asynchronous interface 545 further includes connection 530*b* that provides MOSI (multiple output single input) output 530*c* of radio 525 to MOSI input 530*a* of processor 520. In addition, asynchronous interface 545 includes connection 535*b* that provides request output 535*a* of processor 520 to request input 535*c* of radio 525.

Asynchronous interface 545 also includes connection 545*b* that provides ACK/NACK (acknowledgement/negative-acknowledgement) output 540*c* of radio 525 to ACK/NACK input 540*a* of processor 520.

Asynchronous interface 545 may provide an asynchronous communication link between processor 520 (which may be used to process analyte data) and a radio processor within radio 525 (e.g., a baseband processor). Further, asynchronous interface 545 may allow for the removal of a master/slave topology from the application layer logic. Asynchronous interface 545 may also allow for messages to be sent/received in an interrupt context, such that processor 520 and/or the radio processor remain in a low power mode until a complete message is ready to be communicated over the interface. In example implementations, messages sent by processor 520 use an ACK/NACK as well as a response packet to confirm/deny receipt of the message. With respect to subsystem 500, staged task processing may also be employed to limit the run-time of each of processor 520 and a processor within radio 525, so that there is as little run-time overlap as possible. This may reduce stress on battery 415 and minimize asynchronous messaging issues.

Returning again to FIG. 4, AFE 410 may sample raw analyte data from sensor 405 for a period of time (e.g., 5 minutes). During the sampling, processor 420 and a processor (e.g., baseband processor) within radio 425 may be held in low power mode (LPM). Once AFE 410 completes the sample, AFE 410 may send a signal to processor 420 indicating that processor 420 should exit LPM (i.e., should wake up). AFE 410 may then transfer the raw analyte data to processor 420 via configuration 440. AFE 410 may then re-enter LPM. Processor 420 may then process the raw analyte data (e.g., to generate an estimated glucose value) and store the processed analyte data. Processor 420 may then signal the processor of radio 425 via communication interface 445 to communicate the processed analyte data to radio 425. Processor 420 may subsequently enter LPM while waiting for radio 425 to connect to a display device (e.g., display device 310). Once such a connection is made, processor 420 may exit LPM, and the display device and processor 420 may exchange data, commands, and/or messaging via radio 425.

API 450 may be used to interface with devices remote from analyte sensor system 408 over various wireless protocols. One example of such a protocol is BLE. In this regard, API 450 may allow analyte sensor system 408 to be configured by a user of a display device (e.g., display device 310) running an application such as, for example, analyte sensor application 330. Analyte sensor application 330 may have been developed by the manufacturer of analyte sensor system 408 and/or display device 310, or may be developed by any individual or entity. In the case that the BLE standard is used to couple a display device to analyte sensor system 408, BLE Characteristics can be configurable according to system design parameters.

Figure 6:
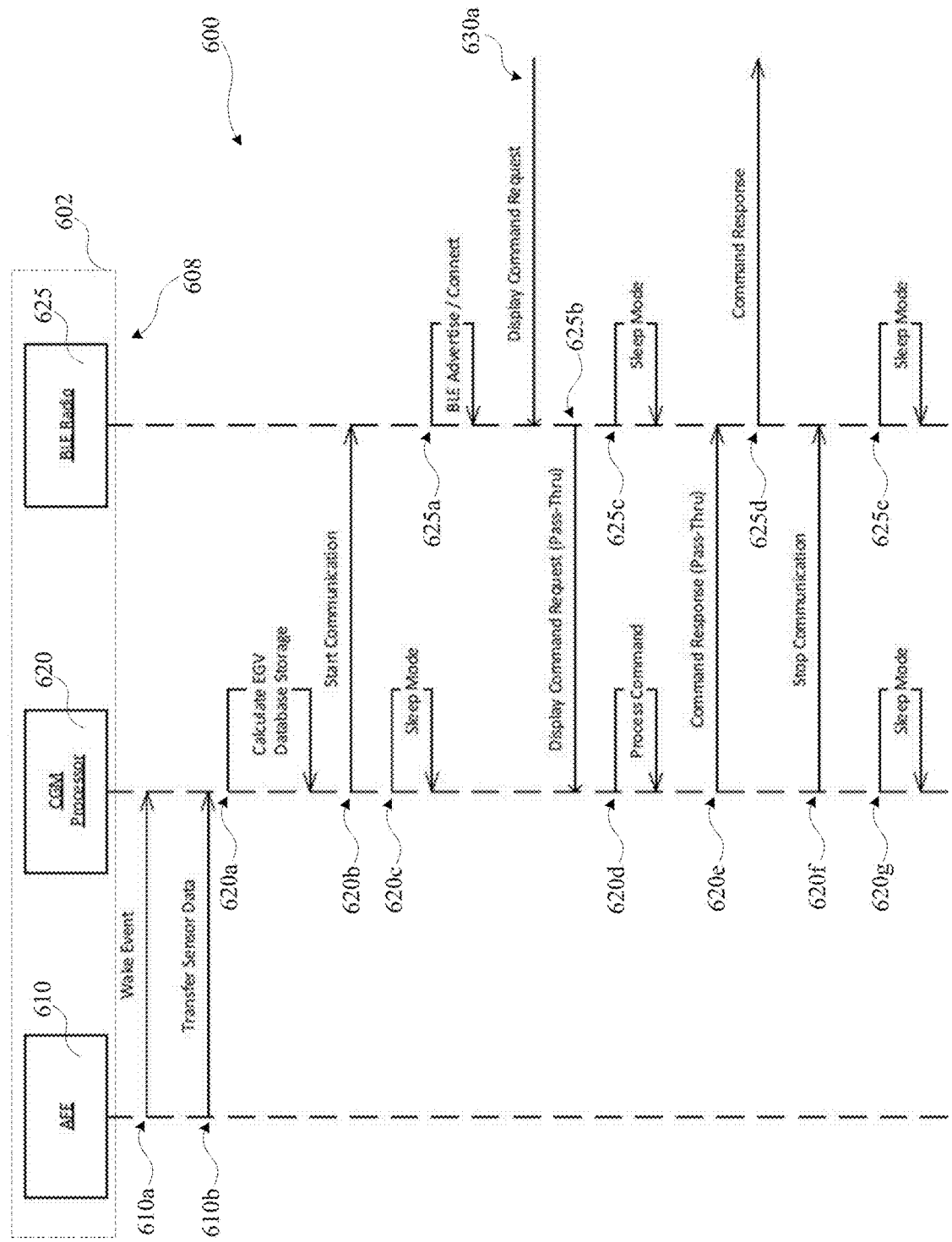
FIG. 6 is an operational flow diagram illustrating various operations that may be performed in accordance with embodiments of the disclosure.

FIG. 6 is an operational flow diagram illustrating various operations that may be implemented by, for example, analyte sensor system 408, in connection with embodiments of method 600 according to the present disclosure, wherein such embodiments are in examples associated with operation according to the intermittent connection model. It will be appreciated up studying the present disclosure, however, that FIG. 6 may be modified for operation according to the continuous connection model. For context purposes, FIG. 6 includes analyte sensor system 608 and subsystem 602. As shown, within subsystem 602, analyte sensor system 608 may include AFE 610, processor 620 (which may be used to process CGM data), and radio 625. Analyte sensor system 608 may be used to execute various operations shown in FIG. 6 in order to connect (e.g., wirelessly) to a remote device such as a display device (e.g., display device 310 or medical device 136). In this manner, analyte data may be transmitted to and processed by the display device. Further, analyte sensor system 608 and the display device may exchange messaging related to configuring the communication protocol used for connection between analyte sensor system and the display device. The operations shown in FIG. 6 may in some instances herein be described with reference to the BLE protocol, but it will in any case be appreciated by one of skill in the art upon studying the present disclosure that aspects shown in and described with reference to FIG. 6 can be applied to other communications protocols.

Before operation 610a, analyte sensor system 608 may be in LPM or a related mode in which power consumption is reduced, e.g., a "sleep mode". At operation 610a, AFE 610 signals processor 620 to initiate processing. For example, AFE 610 can signal processor 620 with a wake event that instructs processor 620 to exit a low power mode. As alluded to above, AFE 610 may act as a wake source, and operation 610a may correspond to wake source 435 referenced in FIG. 4. At operation 610b, AFE 610 passes sensor data (e.g., raw analyte or sensor data) to processor 620. In example implementations in which the analyte data relates to glucose data, processor 620 may be referred to as a continuous glucose monitor (CGM) processor.

Having been signaled to initiate processing (e.g., at operation 610a), processor 620 may, at operation 620a, processor the sensor data passed thereto at operation 610b. For example, as referenced in FIG. 6, processor 620 can calculate an estimated glucose value (EGV) from the sensor data. Processor 620 can also store the sensor data and/or another value derived therefrom (e.g., EGV) in storage and/or a database (e.g., storage 365 shown in FIG. 3B, which in some cases is flash memory). At operation 620b, processor 620 may signal radio 625 (which may in some cases be a BLE radio) to start communication. At operation 620c, processor 620 may then enter LPM or a related mode in which power consumption is reduced, e.g., a "sleep mode". In embodiments, operation 620c may be omitted such that the processor does not necessarily enter the LPM mode etc. In response to the signal to start communication send at operation 620b, radio 625 may at operation 625a advertise and/or connect to a display device. Examples of advertisement messaging and associated connect/disconnect protocols will be described in further detail herein.

After advertisement/connection per operation 625a, radio 625 may at operation 630a receive request signaling (e.g., a command request). The request signaling may be received from a display device and may be a request for the transmission of analyte data, and/or may relate to various configuration parameters of analyte sensor system 608 associated with advertisement and/or data transmission. In response to receiving the signaling, at operation 625b radio 625 may pass the signaling to processor 620. This may be done using interface 445 or 545 (e.g., a message transport layer). In other words, radio 625 may be configured to pass such signaling through to processor 620 using a message transport layer such that, for example, analyte sensor system 608 does not appear to be a multi-chip system to a display device sending the signaling. After passing (at operation 625b) the signaling to processor 620, at operation 625c radio 625 may enter LPM or a related mode in which power consumption is reduced, e.g., a "sleep mode". For the continuous connection model, operation 625c may be omitted, such that sleep mode is not entered but instead the connection is maintained as described herein with reference to FIG. 7J, for example.

At operation 625d, after receiving the request signaling from radio 625 (operation 625b), processor 620 may process the signaling to generate response signaling (e.g., a command response). The response signaling may be passed to radio 625 at operation 620e. This may be done using interface 445 or 545 (e.g., a message transport layer). In other words, processor 620 may be configured to pass such signaling through to radio 625 using a message transport layer. Upon receiving the response signaling (sent at operation 620e), radio 625 may exit LPM or the related mode (entered at operation 625c) and send the response signaling to the display device. In short, by way of example, after receiving (at operation 630a) a request from a display device for analyte data, analyte sensor system 608 can transmit response signaling (at operation 625d).

At operation 620f, processor 620 signals radio 625 to stop communication. In this manner, after sending the response signaling (at operation 625d), radio 625 may close the connection with the display device and, at operation 625e, enter LPM or the like. Likewise, processor 620 may, at operation 620g, enter LPM or the like after signaling radio 625 to stop communication. In embodiments, operation 620g may be omitted such that the processor does not necessarily enter the LPM mode etc. Analyte sensor system 608 may remain in LPM or the like until AFE 610 subsequently signals processor 620 to re-imitation the implementation of various of the above-described operations. For the continuous connection model, operation 625e may be omitted, such that sleep mode is not entered and/or the connection is not closed, but instead the connection is maintained as described herein with reference to FIG. 7J, for example.

With the above description of aspects of the presently disclosed systems and methods for wireless communication of analyte data, a number of specific improvements will now be provided. It will be appreciated by one of skill in the art upon studying the present disclosure that these improvements may be implemented using features and combinations of features of the example configurations described above, whether or not explicit reference is made to the same. Moreover, with respect to FIGS. 4, 5, and 6, though embodiments related thereto are in some cases associated with operation according to the intermittent connection model, it will be appreciated by one of ordinary skill in the art upon studying the present disclosure that such embodiments may be modified for operation according to the continuous connection model described herein.

F. Advertisement Timing and Structure

An additional aspect involves the order and manner in which various devices (e.g., display devices 710) connect to the analyte sensor system (e.g., analyte sensor system 708), which can depend upon the order, timing, structure, and manner of advertisement messages transmitted to such display devices 710 devices. Here it will be noted that the numerals 708 and 710 are referred to, but the description can apply to any of the analyte sensor systems and/or display devices described herein, as will be appreciated by one of ordinary skill in the art upon studying the present disclosure. One potential scheme for the ordering of connection for various devices may be described as follows.

Analyte sensor system 708 advertises and connects to display devices 710 that are available for connection, that is, to in-range display devices 710. This may be done, for example, by transmitting advertisement messages. By way of example, reference is made to operation 705a shown in FIG. 7A. On the display device side, display devices 710 seeking to connect to analyte sensor system 708 may in example embodiments scan for analyte sensor system 708 or another like sensor system to connect to. This generally entails receiving and processing advertisement messages that are being broadcast by analyte sensor system 708 etc., in order to determine whether any such messages are being transmitted by a compatible/desirable analyte sensor system 708.

Display device 710 may then respond to the advertisement message by sending a connection request back to analyte sensor system 708. By way of example, reference is made to operation 705b shown in FIG. 7A. Upon receiving the connection request, analyte sensor system 708 may accept, deny, or simply ignore the request. In example implementations, analyte sensor system 708 serves only one display device 710 connection at a time. Therefore, one ground for denying or ignoring a connection request is that analyte sensor system 708 is already connected to a display device 710. If there are no grounds for denying or ignoring a connection request, analyte sensor system 708 may accept the request and connect to the display device 710 that sent the request. For example, operation 705b shows analyte sensor system 708 accepting the request by sending signaling to display device 710 to indicate that the connection is granted. Aspects of advertisement and related contexts are also illustrated by way of example with reference to FIGS. 7B-7K. See, e.g., operations 735a, 765a, 795a. Detailed discussions of these FIGS. are included further below.

Referring back to FIG. 7A, once display device 710 and analyte sensor system 708 are connected may exchange messaging, including analyte sensor system 708 transmitting analyte data to display device 710. By way of example, reference is made to operation 705d shown in FIG. 7A. In embodiments, in order to prevent display device 710 from staying connected to analyte sensor system 708 longer than is expected or desired, analyte sensor system 708 may enforce timeouts, and/or may cause timeouts to be enforced. That is, for example, there may be a predetermined limit set with respect to the duration of the connection, and upon the expiry of the same, the connection to analyte sensor system 708 may be terminated. By way of example, reference is made to operation 715 shown in FIG. 7A. This may allow for other display devices 710 to connect or attempt to connect to analyte sensor system 708. Analyte sensor system 708 may maintain a list of display devices 710 that have recently connected to analyte sensor system 708. In some cases, this may be known as a whitelist. Analyte sensor system 708 may use this list to permit only listed display devices (i.e., that have recently connected) to connect to analyte sensor system 708.

Figure 9:
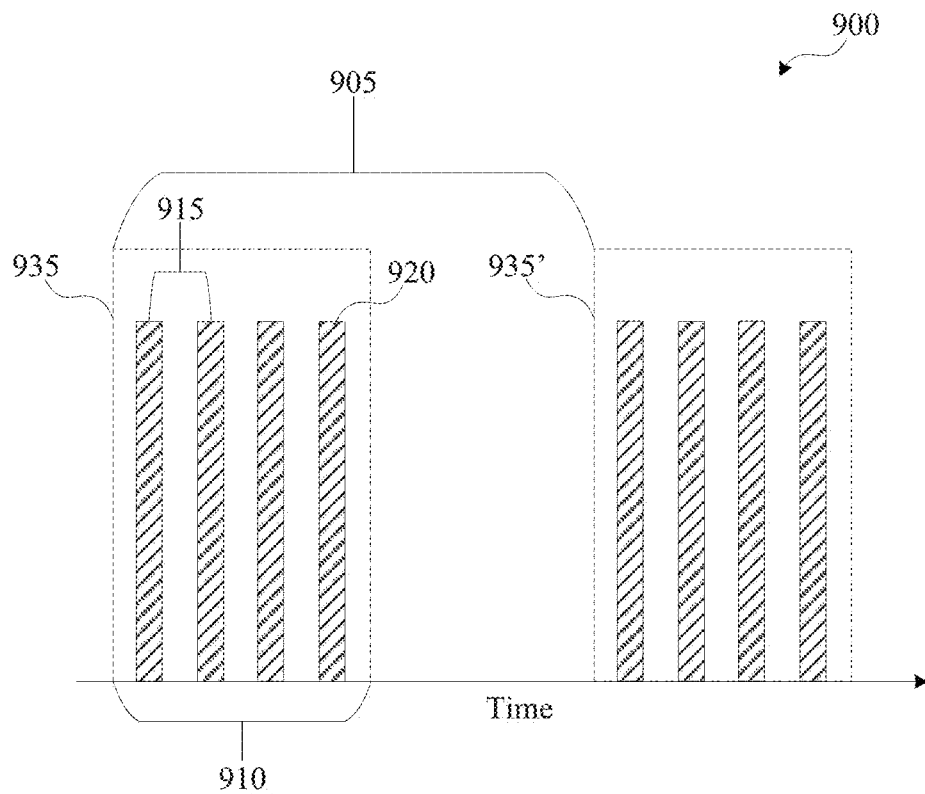
FIG. 9 is a timing diagram illustrating the transmission of advertisement messages in accordance with embodiments of the present disclosure.

FIG. 9 is a timing diagram illustrating an example of the transmission of advertisement messages in accordance with the present disclosure. More specifically, FIG. 9 provides an example embodiment of advertisement duration structure 935 that may be used in connection with pairing or connecting analyte sensor system 708 to display device 710 and/or analyte display device 110. In connection with the above and in accordance with embodiments of advertisement duration structure 935, advertisement messages 920 may be sent according to a time interval that occurs periodically based on a schedule. This may be known in some cases as an advertisement window interval 905. This period of repetition of the occurrence of this interval may be any length of time, but in one specific example is 5 minutes. Nevertheless advertisement window interval may be configured or set to vary depending upon the nature of the operation of analyte sensor system 708 with respect to gathering and processing analyte data. Thus, every 5 minutes (in this example), there will be a time window for advertisement messages to be transmitted. The time window for advertisement messages may be considered a duration of time during which advertisement messages may actually be transmitted. This may also be referred to in some cases as advertisement duration 910. By way of example, this window may range from 7 to 22 seconds. It will be appreciated by one of ordinary skill in the art upon studying the present disclosure, however, that the window for the advertisement duration may range from 0 to any reasonable amount of time. In some cases, the duration of the window is shorter than advertisement window interval 905.

During advertisement duration window 910, advertisement messages 920 may be transmitted, in some cases periodically, though not necessarily so, according to advertisement message interval 915. Advertisement message interval 915 may be thought of as a time interval between sequential or successive advertisement messages 920. One specific example range for the advertisement interval 915 is between 20 and 90 msec, though it will be appreciated upon studying the present disclosure that the advertisement message interval 915 may be shorter or longer, and/or may be adaptively variable or configurable in length, depending on the relevant circumstances, including adapting or reconfiguring message interval 915 during advertisement duration window 910. After advertisement window interval has elapsed, advertisement messages 920 may resume transmission, and advertisement duration structure 935 may be repeated (e.g., as 935'). It should also be noted that one or more of the advertisement message interval, advertisement duration length, and advertisement window interval can be reconfigured as between advertisement duration structures 935 and 935' and/or within the respective advertisement duration 935, 935', etc.

For convenience for the purposes of the following discussion, display devices will be referred to as display devices 710, whereas analyte display devices will be referred to as analyte display device 110. It will be appreciated, however, that in other places herein, the term display devices 710 is broad enough to cover any display device or collection of display devices, including analyte display device 110 and medical devices 136.

The above-mentioned advertisement window interval 905, advertisement duration 910, and advertisement message interval 915 can each vary based on a variety of factors. For example, the values of these parameters may vary based on the type and/or number of display devices 710 present, and/or on how recently such display devices 710 have connected to analyte sensor system 708. These values of these parameters can also vary in order to optimize battery life, to speed up connection time, etc. Any one of a decreased advertisement window interval 905, an increased advertisement duration 910, and a decreased advertisement message interval 915 may increase the likelihood that a particular display device 710 successfully connects to the targeted analyte sensor system 708. In examples, however, there may be a concomitant increase in power consumption.

In terms of connecting to display devices 710 in a particular order, during a time window corresponding to advertisement duration 910, analyte sensor system 708 may in some cases first attempt to connect with display device 710 (e.g., a smartphone) and then with analyte display device 110 (e.g., a proprietary device, which can be a device be designed for the purpose of receiving and present analyte data). One potential issue with this connection protocol, in terms of the order used, is that more time of advertisement duration 910 may need to be dedicated for the connection with display device 710 as compared to the connection with analyte display device 110, for example since being a proprietary display device, analyte display device 110 may be optimized for use with analyte sensor system 708.

Furthermore, there may occasionally be difficulties connecting with display device 710. If display device 710 is unable to connect during a time segment (not shown FIG. 9) of advertisement duration 910 specifically allocated to display device 710, analyte display device 110 may still be able to connect subsequently by sending advertisement messages 920 during other portions or time segments within advertisement duration 910. But in some cases, the time segment allocated to display device 710 within advertisement duration 910 is bounded by another time segment dedicated to the analyte display device 110, such that it may not be feasible to allocate display device 710 additional time segments in which to connect. Alternatively, if additional time from advertisement duration 910 is allocated to display device 710, the analyte display device 110 may not be left with sufficient time available to make a connection.

Accordingly, aspects of the present disclosure also include configuring the ordering of connection for various display devices 710, including with respect to analyte display device 110, as well as configuring advertisement window interval 905, advertisement duration 910, and advertisement message interval 915, and other features associated with advertisement messaging and/or related thereto. Configuring the ordering of connection for various display devices 710 and analyte display device 110 according to the present disclosure may increase the likelihood of establishing a connection between such display devices, including display devices 710 and analyte display device 110, on the one hand, and analyte sensor system 708 on the other hand, while also reducing power consumption due to increased efficiency of the connection protocol. In this manner, the overall reliability of communications related to analyte data is increased, while the power consumption is decreased. In this connection, methods for connecting analyte sensor system 708 to analyte display device 110 and display device 710 are provided.

G. Advertisement Messages

Figure 7A:
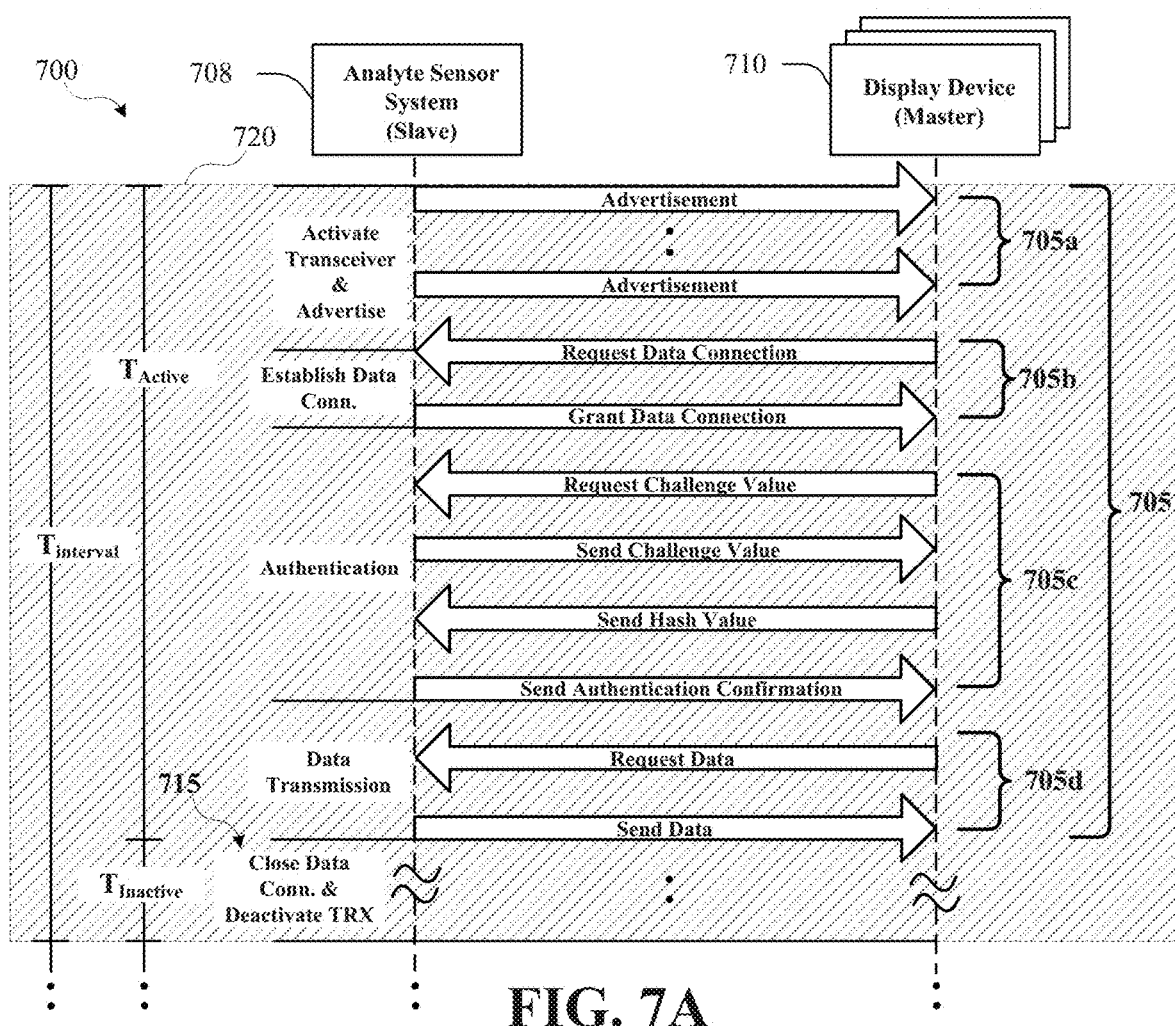
FIG. 7A is an operational flow diagram illustrating various operations that may be performed in accordance with embodiments of the disclosure.

FIG. 8 illustrates an example structure for advertisement message 800 that in some cases may be transmitted for purposes of establishing a connection between two devices, according to various aspects of the present disclosure (e.g., with reference to FIG. 7A, at operation 705, and the like). In some cases, advertisement message 800 may be considered to be a packet or an advertisement packet. In the illustrated example, advertisement message 800 includes rows (fields) 800a-800i and columns 805', 810', and 815'. Though advertisement message 800 is represented in matrix form for visual/organization convenience, one of skill in the art will appreciate upon studying the present disclosure that in terms of a digital signal, advertisement message 800 may be represented by a one-dimensional array of bits or bytes that may be arranged in a pre-determined fashion, for example, according to fields and sub-fields. In other words, if rows 800a-i of the matrix format of advertisement message 800 were to be unstacked and concatenated end to end, message 800 would appear as a one-dimensional array. Each field 800a, 800b, . . . 800i may be considered to correspond to a row of advertisement message 800, while a sub-field may be considered to correspond to a cell of a particular column within a particular row. Accordingly, in example implementations, within field 800a, range 805a is a sub-field or cell corresponding to column 805'.

Column 805' in example embodiments corresponds to address 805. Address 805 includes ranges 805a-i, where each range 805a-i may represent a range of bytes reserved for the corresponding field. Within each field 800a-i, a number of bytes may be reserved for each cell. That is, by way of illustration, one byte (address 805a may refer to byte zero "0" as the address of field 800a within message 800) may be used for preamble 810a. The number of bytes need not but in some cases may be the same for each cell of a column across various fields 800a-i. That is, by way of illustration, two bytes may be used for each cell 805a-i of address 805 and two bytes may be used for each cell 810a-i of description 810. Moreover, a variable number of bytes may be used in cells 815a-i of value 815. In other examples, different numbers of bytes may be used and numerous variations are contemplated within the scope and spirit of the present disclosure. It will also be appreciated that any number of rows and columns may be used, subject of course to the laws of physics and in some cases standardized communication protocols.

With further reference to FIG. 8, Column 805' in this example corresponds to address 805. Cells 805a-i may each contain a value (e.g., binary or hexadecimal or the like) that represents the length of the corresponding field 800a-i. Each length may in some cases be represented by a starting and ending position for the respective field. Column 810' in this example corresponds to description 810. Cells 810a-i may each contain a value that represents a description of the corresponding field 800a-i. For example, field 800a in this example is described by the value in cell 810a as a preamble for advertisement message 800. Column 815' in the illustrated example corresponds to value 815. Cells 815a-i may each contain a value that represents the value (e.g., as opposed to address or description) of the corresponding field 800a-i. By way of example, cell 815e may contain bytes amounting to a value that represents the devices name (e.g., for analyte sensor system 708). MAC address 810d may include an address for analyte sensor system 708.

Embodiments of the present disclosure may involve exploiting aspects of message 800 to improve the reliability, speed, and/or efficiencies of aspects related to the wireless communication of analyte data. In some cases, the value 815d of the MAC address field 810d may be dynamically configurable to be made specific to a particular display device 710 or set of display devices 710, or other remote devices connectable to and being targeted by analyte sensor system 708. In some cases, analyte data and/or related control signaling and the like, or portions thereof, may be included in reserved slots within advertisement packets (e.g., operation 765a with reference to FIG. 7E). For example, analyte data and such can be included in manufacturing data field 800h. Other slots may be used for similar purposes in accordance with various implementations. Other such embodiments utilizing aspects of advertisement message 800 advantageously will become apparent upon studying the present disclosure.

H. Identification, Selection, and Pairing

In example implementations, before analyte sensory system 308 is connected to a device such as display device 310 (with reference to FIG. 3A), the appropriate analyte sensor system 308 and/or display device 310 may need to be identified and/or selected. In some example use cases, display device 310 may be presented with more than one analyte sensor system 308 available for connection. One such use case may occur in a hospital room, for example, where multiple analyte sensor systems 308 are activated for patients. In such a case, for each patient's respective display device 310 to connect to that patient's analyte sensor system 308, techniques for identifying the appropriate analyte sensor system 308 are discussed herein.

In some example use cases, a single analyte sensor system 308 may at times be provided with opportunities to connect to more than one display device 310. One such use case may occur, for example, in a user's home where the user may be in proximity to multiple display devices 310 such as a an analyte display device, a smartphone, a tablet, a watch, and a television, among other devices. In such a case, techniques for identifying one or more of display devices 310 for connection, as well as for determining aspects of the connection that are suitable, are discussed herein.

Once the appropriate system/device is identified and selected, display device 310 and analyte sensor system 308 may be paired and/or bonded. Further, in some cases, authentication procedures may be implemented, for example for data security/privacy purposes. Ultimately, data such as analyte data and control signaling can then be exchanged between analyte sensor system 308 and display device 310 pursuant to an established connection (whether using a continuous connection model or an intermittent connection model, as discussed hereinbelow).

In connection with embodiments of the present disclosure, device/system selection may refer to the choosing of a device to connect to, pairing may refer to exchanging information to make/establish a connection, and bonding may refer to storing pairing information from previous exchanges such that the stored information can be used in establishing subsequent connections. Furthermore, the term pairing as used herein may in some cases additionally include identification, selection and/or bonding, and may in some cases be used to refer to one or more of identification, selection, pairing, and bonding, as will be apparent to a person of ordinary skill in the art upon studying the present disclosure.

It will be appreciated that the pairing of analyte sensor system 308 and display device 310 in some cases involves user interaction. For example, a user may provide information, such as information related to an analyte sensor system 308 to be selected. Such information may be provided manually into display device 310 (e.g., via GUI 340) in order to initiate and perform aspects of the identification, selection, pairing, and authentication process discussed above. While this manual process has benefits, some a more automated selection/identification/pairing process that involves less user interaction may in some cases be preferable. Accordingly, embodiments of the present disclosure involve adjusting the amount of user interaction involved in the selection/identification/pairing process. For example, the amount of user interaction involved may be adjusted according to tiers, or levels of user interaction involved in identifying and/or selecting (or pairing with) a display device 310 and/or analyte sensor system 308 for connection.

By way of example, the amount of user interaction involved may be adjusted according to the tiers based on user input directly or indirectly relating to modifying the amount of user interaction involved, and/or in the absence of user input. In embodiments, the amount of user interaction may be adjusted automatically (including, e.g., on the fly).

The automatic adjustment may be based on information gathering in an archive related to previous attempts (successful or not) is identify and select analyte sensor system 308 and/or 310 according to the tiers described below. In some cases, one or more of the approaches described in the tiers below may be preferable based on criteria such as the time of day, battery life of a device, quality of service, radio environment, location and/or the like. The suitability of one or more of the tiers may be determined and implemented based on these criteria and/or other criteria.

A first tier or level of user interaction involved in the selection/identification process may be associated with a higher level of user interaction. For example, the user according to the first tier may provide information manually in order to facilitate the selection and/or identification of (or pairing with) analyte sensor system 308. This may be done by the user manually inputting, for example, an identification number and/or other identifying information associated with analyte sensor system 308. For example, with reference to FIG. 3G, GUI 340 of display device 310 may provide an entry for the identification information associated with analyte sensor system 308 using option 314*g*. Display device 310 can then identify the corresponding analyte sensor system 308, by way of example based on information received from advertisement messages sent by analyte sensor system 308. Such advertisement messages may include the identification information (e.g., identification number, manufacture information, etc.).

In example implementations, the amount of user interaction may be reduced or altered by display device 310 receiving identification information related to analyte sensor system 308 (including, e.g., an identification number associated with analyte sensor system 308 and/or with a manufacturer thereof) from a remote source, such as, for example, server system 334 (with reference, e.g., to FIG. 3A). That is, instead of or in addition to the user entering identification information manually into display device 310, display device 310 may receive this information from server system 334 or another remote source.

One way this may be done is that a manufacturer, retailer, etc. of analyte sensor system 308 may upload or otherwise provide identification information to server system 334, where the information may be received via server 334*a*, processed by processor 334*c*, and/or stored in storage 334*b*. A user or individual etc. may then purchase or obtain analyte sensor system 308. For example, the purchase may be made in a brick-and-mortar-type store, from an online marketplace, or from a proprietary web-market offered by the manufacturer of analyte sensor system 308. In some cases, at the time of purchase, the user may provide user information associated with the user (e.g., one or more of a login, password, email address, phone number, etc.), for example to the seller or to the manufacturer directly or indirectly. This information can then be provided to server system 334 and associated (e.g., in a database or cluster residing within server system 334) with the identification information of analyte sensor system 308 purchased by the user.

After obtaining analyte sensor system 308, the user may, for example, obtain and/or launch application 330 on the user's display device 310. The user may login to application 330, whereupon display device 310 may communicate with server system 334. The user may also provide application 330 with additional information associated with the user. Application 330 may then interface with server system 334 to provide server system 334 with at least some of the user information provided to application 330 by the user. Server system 334 may then use at least some of the received user information to identify the identification information for analyte sensor system 308 purchased by the user. The relevant identification information can then be provided to display device 310. In some cases, this information may be transmitted to display device 310 and conveyed to application 330 via an application program interface. In some cases, the information may be provided to the user via email or other message. Display device 310 may use this identification information to pair with analyte sensor system 308 and/or confirm/validate an identified/selection analyte sensor system 308.

Alternatively or additionally, the user may scan a code or image using display device 310. This may provide a check for verifying the manually input the identification number. Or, for example, this may allow for at least partial automation of inputting the transmitter identification number. That is, the user need not manually enter the identification number, but rather need only scan the encoded identification number. The identification number in example implementations may be included in one or more of capacitive ink, thermochromatic ink, fluorescent ink, a bar or QR code employing that may in some cases employ such inks, and a removable sticker. Each of these may be included on the packaging of analyte sensor system 308, or may in some cases be provided in another manner (e.g., via email, text message, tangibly, etc.). In embodiments, image recognition/matching may facilitate or be used for inputting of the identification number.

In embodiments, a list of available analyte sensor systems 308 may be provided via GUI 340 of display device 310. The list may include analyte sensor systems 308 discoverable to display device 310, and may include codes, icons, or other identifying information with respect to display devices 310. Corresponding codes, icons, etc. may be printed on analyte sensor systems 308, printed on a piece of paper or the like, or may be provided electronically (e.g., via email, etc.). The user may then match the code/icon/etc. from the desired analyte sensor system 308 with the corresponding element shown on display device 310 and select the element desired. In some cases, the code/icon/etc. may be formed from applying a hash function to identification information associated with analyte sensor system 308.

Alternatively or additionally, the provided list may include display devices 310 discoverable to analyte sensor system 308. These lists may be sorted/filtered according to various factors (e.g., RSSI, BER, type of device, devices recently connect to or otherwise known, other identifying information, etc.). The user may then select an analyte sensor system 308 and/or a display device 310 for connection. With reference to FIG. 3G, for example, option 314g may be used to select display device 310 from a list and/or to confirm the selection of a display devices 310. In some cases, once a device's identification information is scanned (e.g., using received advertisement messages or otherwise), the user may be prompted to confirm the selection of the device. The display device 310 used to make the selection, including where the selection is facilitated by manually inputting information and/or by scanning information, may not be the device ultimately connected to analyte sensor system 308. Rather, in some cases, a first display device 310 may be used to facilitate connection of analyte sensor system 308 to a second display device 310.

Figure 13A:
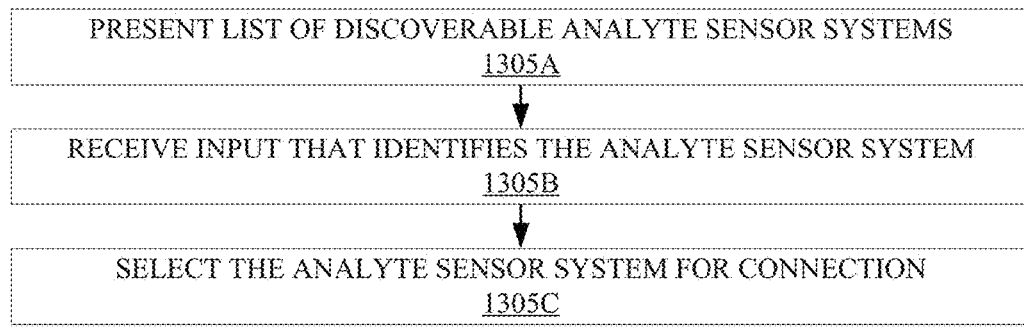
FIG. 13A is an operational flow diagram illustrating various operations that may be performed in accordance with embodiments of the disclosure.

FIG. 13A is an operational flow diagram illustrating various operations that may be performed in accordance with embodiments of the present disclosure, for example in connection with the first tier or level of user interaction. For illustration purposes, reference is made here to FIGS. 10D and 10E and numerals of components shown therein. Nevertheless, one of ordinary skill in the art will appreciate upon studying the present disclosure that like components from other FIGS. of the present disclosure may be included in the scope of the present description of FIG. 13A.

Embodiments shown in FIG. 13A involve aspects of method 1300 for identifying a device for connection. Method 1300 optionally includes, at operation 1305A, presenting (e.g., via GUI 340) a list of one or more analyte sensor systems 308a, 308b (e.g., with reference to FIGS. 10D and 10E) from among a set of analyte sensor systems 308. At operation 1305B, method 1300 involves display device 310 receiving input (e.g., via GUI 340 and/or via connectivity interface 315 or a subsystem thereof) that identifies an analyte sensor system 308a from among the set of analyte sensor systems 308. At operation 1305C, method 1300 involves display device 310 selecting analyte sensor system 308a of connection based on the received input.

Figure 13B:
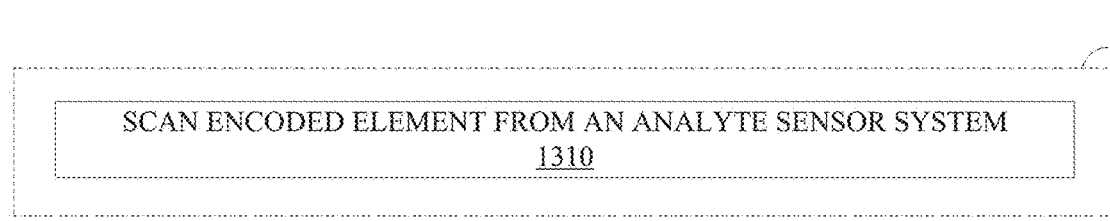
FIG. 13B is an operational flow diagram illustrating various operations that may be performed in accordance with embodiments of the disclosure.

FIG. 13B illustrated method 1302, which includes further details regarding operation 1305B, mentioned above with reference to FIG. 13A. As shown in FIG. 13B, operation 1305B includes at operation 1310, scanning an encoded element from analyte sensor system 308a or product packaging of analyte sensor system 308b. Operation 1310 may thus provide an example deployment with respect to receiving input that identifies analyte sensor system 308a from among a set of analyte sensor system 308, for example, as the analyte sensor system appropriate for connection to display device 310.

While the first tier or level of user interaction is suitable for many cases, in some users or use cases less user interaction may be preferable. Accordingly, a second tier or level of user interaction involved in the selection/identification/pairing process may be associated with a moderate amount of user interaction. For example, the selection/identification/pairing and connection process according to the second tier may be semi-automated, and in some cases the user may manually perform a relatively simple and/or quick task in order to facilitate the selection and/or identification of a particular analyte sensor system 308 and/or display device 310.

In example embodiments, in connection with a more automated portion of the selection/identification/pairing process related to the second tier, display device 310 may be configured to detect the presence of one or more signals from one or more analyte sensor systems 308, and may be further configured to monitor such signals to determine whether any of the signals meet a set of selection criteria, for example based on a derivative of the signal or the like. If a signal or a derivative thereof meets one or more selection criteria, the particular analyte sensor system 308 sending the signal, for example, may be initially selected for connection with display device 310.

For some detected signals monitored in conjunction with embodiments of this selection process, measurements and/or characterizations may be employed to derive or otherwise generate statistical measures and/or other derivatives related to the detected signals. By way of example, such derivatives may include or be related to the strength or quality of a detected signal as determined over a measuring period. For example, the signal strength or quality may be gleaned from bit error rate (BER) or received signal strength indication (RSSI), taken over measuring period (predetermined or adjustable/adaptable). One or more such measures or information derived based on a detected signal may be compared to threshold such that decisions may be based on the comparison. For example, the pair of a display device 310 and an analyte sensor system 310 with the least amount of distance therebetween would in some cases be associated with the largest RSSI measurements, and could thus be selected for pairing and/or connection based on a comparison of the RSSI or the like to a threshold value. Likewise, a field of discoverable display devices 310 and/or analyte sensor systems 308 could be narrowed by filtering out those devices whose RSSI does not surpass a threshold. In another example, the pair of a display device 310 and analyte sensor system 308 having the lowest BER could be selected for pairing.

Either analyte sensor system 308 or display device 310 or both can monitor signals, generate derivatives therefrom, and determine whether the signals meet a set of selection criteria being employed. In some cases, different selection criteria may be used depending on the device monitoring the signal and/or depending on the device sending the signal. With respect to RSSI, both analyte sensor system 308 and display device 310 may be used to determine the RSSI or a like derivative of signals received. One or more of the respective RSSI values can then be shared as between analyte sensor system 308 and display device 310 and compared. If in agreement or within a predetermined range of one another, RSSI pairing can be confirmed. The determination of whether the RSSI values are in agreement can be performed at the analyte sensor system 308, display device 310, or both. By way of illustration, a first RSSI value may be calculated at display device 310 based on a signal received from analyte sensor system 308. A second RSSI value may be calculated at analyte sensor system 308 based on an at least similar signal received from display device 310. The first RSSI value may then be sent to analyte sensor system 308 for comparison to the second RSSI value, and/or the second RSSI value may then be sent to display device 310 for comparison to the first RSSI signal. Agreement between the first/second RSSI values can then be used to confirm pairing.

Figure 10A:
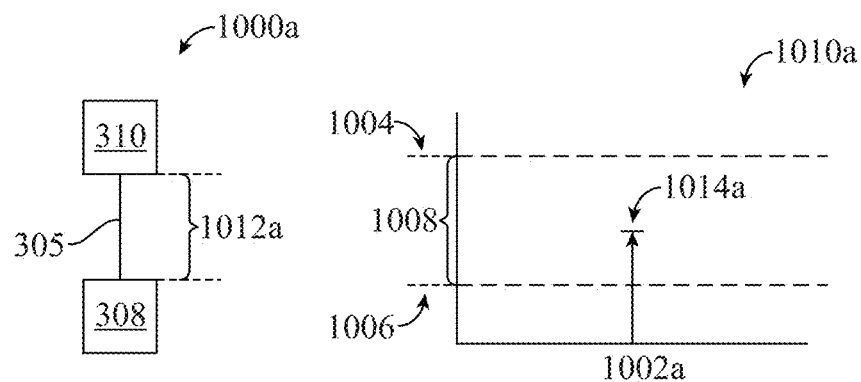
FIG. 10A illustrates aspects of an example system that may be used in connection with implementing embodiments of the disclosure.
Figure 10B:
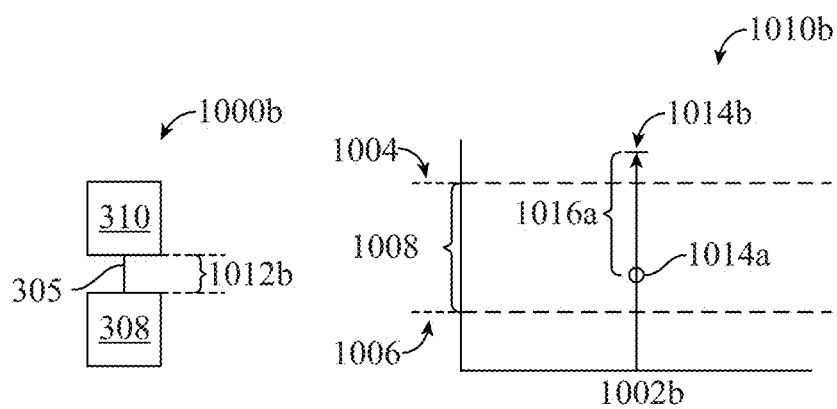
FIG. 10B illustrates aspects of an example system that may be used in connection with implementing embodiments of the disclosure.
Figure 10C:
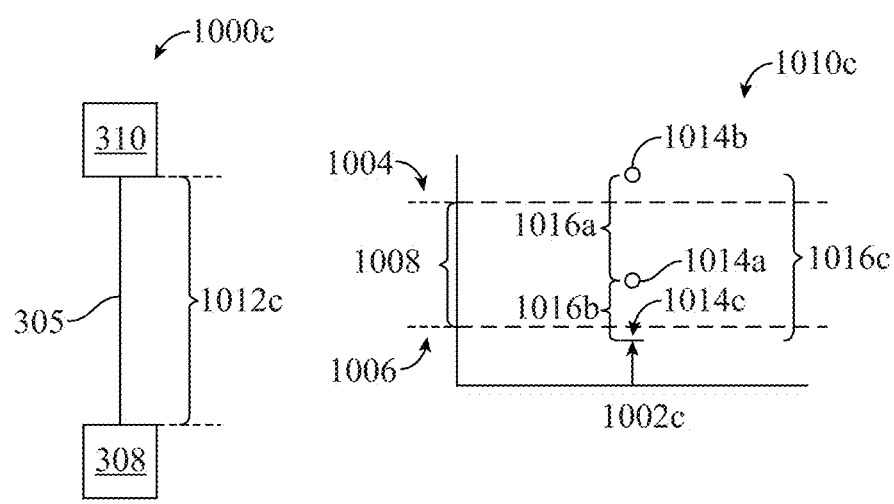
FIG. 10C illustrates aspects of an example system that may be used in connection with implementing embodiments of the disclosure.
Figure 10D:
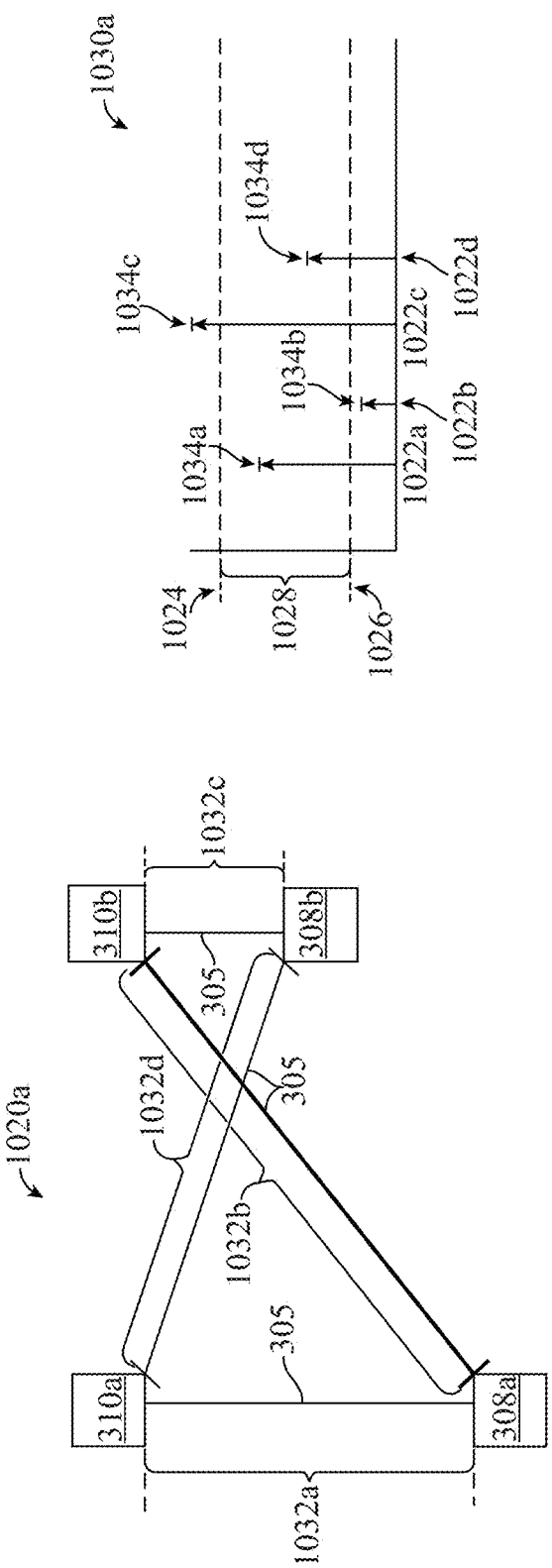
FIG. 10D illustrates aspects of an example system that may be used in connection with implementing embodiments of the disclosure.

FIG. 10D illustrates an example of how characteristics of a received or detected signal may be used for functionality related to device identification, selection, and/or pairing. Namely, FIG. 10D shows arrangement 1020a that includes analyte sensor systems 308a and 308b and display devices 310a. Analyte sensor systems 308a, 308b are connectable to display devices 310a, 310b via communication medium 305, including by employing various connection models discussed herein.

Display device 310a is connectable to analyte sensor system 308a by link 1032a (e.g., signals may be passed between analyte sensor system 308a and display device 310 via link 1032a). Link 1032a may represent various arrangements and/or configurations described herein. For example, link 1032a may be associated with a distance between analyte sensor system 308a and display device 310a. In some cases, link 1032a may be associated with signal or path conditions (e.g., signal strength, fading, etc.) as between display device 310a and analyte sensor system 308a. Display device 310a is connectable to analyte sensor system 308b by link 1032d (e.g., via communication medium 305). Here again, link 1032d may be associated with a distance and/or with signal or path conditions. Display device 310b is connectable to analyte sensor system 308a by link 1032b and to analyte sensor system 308b by link 1032c.

As further illustrated in FIG. 10D, arrangement 1020a in this example may result in measurement profile 1030a. Namely, with respect to measurement profile 1030a, FIG. 10D shows upper and lower thresholds 1024 and 1026, as well as threshold delta 1028 that, in this example, represents a difference between upper and lower thresholds 1024 and 1026. Such a difference may be determined by comparing two signals or derivatives of the signals to one another. Furthermore, measurement values are shown that correspond to each of links 1032a through 1032d. More specifically, measurement values 1034a through 1034d are shown respectively for measurements 1022a through 1022d, where measurements 1022a through 1022d correspond respectively to links 1032a through 1032d. That is, for example, measurement value 1034a for measurement 1022a corresponds to link 1032a, and so on. As shown in this particular example illustration, measurement values 1034a and 1034d are within upper and lower thresholds 1024 and 1026 (e.g., measurement value 1034a meets or is above first threshold 1026 but is below second threshold 1024), whereas measurement value 1034b is below lower threshold 1026 and measurement value 1034c is above both upper and lower thresholds 1024 and 1026.

Upper and lower thresholds 1024 and 1026 may be employed in various ways in accordance with embodiments of the present disclosure. For example, referring to both the first and second tiers or levels of user interaction, either or both of upper and/or lower thresholds 1024 and 1026 may be used in connection with a manual or semi-automatic identification, selection, pairing, and/or connection processes. With respect to the more manual process discussed above, for example, upper and/or lower thresholds 1024, 1026 may be employed to filter out analyte sensor systems 308 and/or display devices 310 from appearing on a user-presentable list of devices available for connection (e.g., discoverable devices). In this regard, for example with respect to analyte sensor system 308a, display device 310b could be filtered out since measurement value 1034b falls below lower threshold 1026. Alternatively or in addition, upper and/or lower thresholds 1024, 1026 may be employed to automatically select a particular analyte sensor system 308 and/or display device 310 where information about the selected devices can then be presented to the user for manual verification (e.g., via GUI 340). With respect to display device 310b, for example, analyte sensor system 308b may be selected since measurement value 1034c is above upper threshold 1024.

In embodiments, once a particular analyte sensor system 308 and/or display device 310 is initially selected, then a relatively simple and/or quick input, task, action, and/or event may be provided, performed, and/or take place to confirm/validate that the selection is appropriate/desirable. For example, following an initial selection, the user may be prompted (e.g., via GUI 340 and/or other means, such as audio and/or haptic feedback) to perform such tasks and/or provide such inputs or the like. In example implementations involving derivatives of signals where the derivatives are based on RSSI measurements, once display device 310 and analyte sensor system 308 are initially selected for pairing/connection, the user may be prompted to move display device 310 closer to or further from analyte sensor system 308. Examples of how these features may be used in connection device selection/pairing/etc. will now be provided with reference to FIGS. 10A-10E.

FIG. 10A illustrates arrangement 1000a of analyte sensor system 308 and display device 310. As shown, analyte sensor system 308 is connectable to display device 310 via communication medium 305 and is connectable to display device 310 by link 1012a. FIG. 10A also illustrates measurement profile 1010a that may result from environment 1000a. In particular, with respect to measurement profile

1010*a*, FIG. 10A includes upper and lower thresholds 1004 and 1006, as well as threshold delta 1008 that, in this example represents a difference between upper threshold 1004 and lower threshold 1006. Moreover, in measurement profile 1010*a*, measurement value 1014*a* for measurement 1002*a* corresponds to link 1012*a* between display device 310 and analyte sensor system 308 (e.g., where measurement value 1014*a* may be a derivative related to RSSI as between analyte sensor system 308 and display device 310). It should be appreciated that the measurement values herein may be or represent, or may be used to generate, derivatives of a signal received via a link (e.g., link 1012*a*, etc.).

In measurement profile 1010*a*, measurement value 1014*a* is within upper and lower thresholds 1004 and 1006. That is, in this example, measurement value 1014*a* meets or exceeds (or is above) lower threshold 1006 but falls below (or is below) upper threshold 1004. In example implementations, because measurement value 1014*a* meets or is above lower threshold 1006, display device 310 and/or analyte sensor system 308 may be initially identified/selected. In embodiments, at this point, the user can be prompted (e.g., graphically, audibly, haptically, or one or more of these in combination) to bring display device 310 closer to analyte sensor 308 to confirm/verify the initial selection. Alternatively, the user can be prompted to move display device 310 farther away from analyte sensor 308 to confirm/verify the initial selection. These two scenarios will be further described in connection with FIGS. 10B and 10C.

FIG. 10B illustrates arrangement 1000*b* of analyte sensor system 308 and display device 310. As shown, analyte sensor system 308 is connectable to display device 310 via communication medium 305 and by link 1012*b*. In example implementations, arrangement 1000*b* can result from the user being prompted to move display device 310 closer to analyte sensor 308 relative to arrangement 1000*a* shown in FIG. 10A. Where applicable, this may be illustrated by the relative representations of links 1012*a/b*. Correspondingly shown in measurement profile 1010*b* is measurement value 1014*b* for measurement 1002*b* (e.g., which may be used to generate or obtain a derivative of a signal received via link 1012*b*) corresponding to link 1012*b* between display device 310 and analyte sensor system 308. Further shown in measurement profile 1010*b* is measurement value 1014*a* and measurement delta 1016*a* that, in this example, represents a difference between measurement values 1014*b* and 1014*a*. With respect to the measurement values described herein, in some cases, the user may be prompted to maintain a particular arrangement for a duration of time such that more accurate measurement values can be obtained. Once the duration of time has elapsed and/or an accurate measurement has been obtained, for example, the user may be notified by display device 310 and/or analyte sensor system 308 via audible, visual, and/or haptic feedback.

With respect to transitioning from arrangement 1000*a* to arrangement 1000*b*, several techniques may be employed in order to confirm/validate an initial selection/identification of display device 310 and analyte sensor system 308. In embodiments, measurement value 1014*b* may be monitored/determined/obtained and compared to threshold 1004. As such, it may be determined that while for arrangement 1000*a* measurement value 1014*a* fell below upper threshold 1004, in/after transitioning to arrangement 1000*b*, measurement value 1014*b* meets or is above upper threshold 1004. Measurement value 1014*b* having crossed upper threshold 1004 (in a positive or negative direction) may be used to indicate that the initial identification for selection and/or selection for connection was suitable/appropriate. As alluded to, in embodiments, the change between measurement values 1014*b/a* may be negative rather than positive. For example, measurement value 1014*b* may be measured initially, where upper threshold 1004 is met or exceeded. Then the user may be prompted to move display device 310 farther from analyte sensor system 308, thus transitioning to an arrangement like arrangement 1000*a* where measurement value 1014*a* is below upper threshold 1004.

Another technique that may be employed in example implementations involves comparing measurement delta 1016*a* or the like to a threshold value. By way of illustration, a threshold value for a measurement delta may be predetermined such that an initial identification for selection or selection for connection is confirmed if measurement delta 1016*a* exceeds the threshold value. In some cases, an absolute value of the measurement delta can be used for comparison purposes, such that movement either closer to or farther away from analyte sensor system 308 can be used to indicate that the initial identification/selection was suitable/appropriate. In this manner, for example, a user moving display device 310 a certain distance closer to or farther from analyte sensor system 308, where the distance moved is related in some way to the resulting change in measurement value (or a derivative of a signal received via the corresponding link), can confirm/validate that the identification/selection is appropriate. In some cases, use of measurement delta 1016*a* may be more robust than relying on the crossing threshold 1004 for selection validation. In some cases, measurement delta 1016*a* may be set so as to avoid false positive validation based on relatively minor fluctuations in measurement value 1014*a/b* (e.g., due to noise, reflections, and/or inadvertent movements). In some cases multiple measurement deltas may be employed in order to confirm pairing. For example, in addition to using a first measurement delta 1016*a* in connection with a first and second arrangement, a second measurement delta can be determined in connection with second and third arrangements. The first and second measurement deltas can then be compared, and if at least within a predetermined range of one another, pairing can be confirmed. The multiple measurement deltas can be used in connection with moving a display device 310 closer to analyte sensor system 308 and then farther away therefrom, or vice versa.

FIG. 10C illustrates arrangement 1000 of analyte sensor system 308 and display device 310. As shown, analyte sensor system 308 is connectable to display device 310 via communication medium 305 and is connectable to display device 310 by link 1012*c*. FIG. 10C will be referenced in connection with various embodiments of the present disclosure involving confirming/validating an initial selection or identification of display device 310 and analyte sensor system 308, in particular where a moderate amount of user interaction is considered suitable.

In example implementations, arrangement 1000*c* can result from the user being prompted to move display device 310 farther from analyte sensor 308 relative to arrangement 1000*a* shown in FIG. 10A. This is illustrated by the relative representations of links 1012*a/c*. Correspondingly shown in measurement profile 1010*c* is measurement value 1014*c* for measurement 1002*c* corresponding to link 1012*c* (e.g., measurement value 1002 may correspond to a distance between display device 310 and analyte sensor system 308 and/or radio conditions such as a path between display device 310 and analyte sensor system 308). In some cases first and second links may physically be the same in terms of distance, transmission, radio conditions generally, etc., but may be represented or referred to at different instances in time and thus referred to as being different links. For example a signal may be sent across a first link at a first time, and the signal being sent at a second time across the same physical link (e.g., in terms of distance etc.) may be referred to as being sent via a second link due to the different in time. Further shown in measurement profile 1010c is measurement value 1014a and measurement delta 1016b that, in this example, represents a difference between measurement values 1014a and 1014c.

With respect to transitioning from arrangement 1000a to arrangement 1000c, several techniques may be employed in order to confirm/validate an initial selection/identification of display device 310 and analyte sensor system 308. In embodiments, measurement value 1014c may be monitored/determined and compared to lower threshold 1006. As such, it may be determined that while for arrangement 1000a measurement value 1014a met or been above lower threshold 1006, in/after transitioning to arrangement 1000c measurement value 1014c falls below lower threshold value 1006. Measurement value 1014c having crossed lower threshold 1006 (in a positive or negative direction) may be used to indicate that the initial identification/selection was suitable/appropriate. As alluded to, in embodiments, the change between measurement values 1014c/a may be positive rather than negative. For example, measurement value 1014c may be measured initially, where lower threshold 1006 is not exceeded. Then the user may be prompted to move display device 310 closer to analyte sensor system 308, thus transitioning to an arrangement like arrangement 1000a where measurement value 1014a exceeds lower threshold 1006. As described in connection with FIGS. 10A and 10B, a measurement delta can also be employed here.

With further reference to FIGS. 10A-10C, additional features of the present disclosure relating to confirming/validating an initial selection/identification of display device 310 and analyte sensor system 308 will now be described. In particular, a multi-step process may be used for confirmation/validation. For example, it may first be determined that measurement value 1014a meets or is above lower threshold 1006 but not upper threshold 1004. The user may then be prompted to move display device 310 relatively close to analyte sensor system 308. In some cases, the prompt may be to move display device 310 very close, or to a defined position relative to the user's body and/or analyte sensor system 308, for example to the user's hip or abdomen, etc., or for example within six inches or the like of analyte sensor system 308. This may result in measurement value 1014b, which meets or is above upper threshold 1004, and may also result in measurement delta 1016a.

Next, in response to upper threshold 1004 being met or exceeded, the user may be prompted to move display device 310 farther away from analyte sensor system 308. In embodiments, the prompt may be to move display device 310 roughly an arm's length away or the like, or a defined position relative to the user's body or a certain distance away from the initial position (e.g., 24 inches). This may result in measurement value 1014c, which is below lower threshold 1006, and may result in measurement delta 1016c. The sequence of first crossing upper threshold 1004 (e.g., in a positive direction) and then crossing lower threshold 1006 (e.g., in a negative direction) with respect to measurement values, can thus be used to confirm/validate an initial selection/identification of display device 310 and analyte sensor system 308. Conversely, a sequence involving first crossing lower threshold 1006 (e.g., in a negative direction) and then crossing upper threshold 1004 (e.g., in a positive direction), can likewise be employed.

Many variations to the above are contemplated in connection with the present disclosure. For example, in some cases, in an initial arrangement (e.g., arrangement 1000b), display device 310 may be positioned relatively close to analyte sensor system 308 such that measurement value 1014b or the like may exceed upper threshold 1004. For example, the user may be holding display device 310 very close to analyte sensor system 308. This may occur, for example, if analyte sensor system 308 is placed on the user's abdomen and the user removes display device 310 from the user's front pocket near the user's abdomen. Here, one single measurement or derivative (e.g., RSSI measurement based on close proximity of display device 310 and analyte sensor system 308 may not be sufficient to perform accurate identification/selection). In this case, it may not be feasible for the user to move display device 310 closer to analyte sensor system 308. Thus, the user may first be prompted to move display device 310 away from analyte sensor system 308, for example far enough away that a threshold such as lower threshold 1006 is crossed and measurement value 1014c or the like is obtained. Then, the user may be prompted to move display device 310 closer to analyte display device 310, essentially restoring arrangement 1000b such that upper threshold 1004 is crossed and measurement value 1014b or the like is obtained.

Accordingly, and as described above, example solutions involve employing multiple thresholds. For example, if the detected RSSI meets or is above upper threshold value 1004 (e.g., when display device 310 and analyte sensor system 308 are relatively close), display device 310 may be configured to prompt the user to move display device 310 farther away from analyte sensor system 308. In some cases, the user is prompted to move display device 310 farther away until the RSSI is below lower threshold 1006. Or vice versa. In some cases, a measurement value being below lower threshold 1006 may be referred to as the measurement value meeting lower threshold 1006. Based on the two measurements, further operations can be implemented to confirm RSSI pairing. For example, upper and lower thresholds 1004 and 1006 can be compared to one another. Alternatively, threshold delta 1008 (which, e.g., may be an effective difference between the thresholds) between upper and lower thresholds 1004 and 1006 can be calculated. Or, both of these operations can be combined. If the measurements or calculations derived therefrom meet certain requirements, RSSI pairing can be confirmed.

With respect to example implementations employing threshold and/or measurement deltas for purposes of validation/confirmation, various configurations are contemplated in connection with the present disclosure. In embodiments, as mentioned above, a threshold delta can be used for validation confirmation. For example, with reference to FIGS. 10A and 10B, measurement value 1014a may be obtained in connection with arrangement 1000a. Then, display device 310 may be arranged into arrangement 1000b and measurement value 1014b can be obtained. Measurement delta 1016a may then be compared to a threshold delta, and if the threshold delta is exceeded, pairing can be confirmed.

In embodiments, the threshold delta may be set in conjunction with the manufacturing and/or setup process of analyte sensor system 310. For example, the threshold delta may initially be set based on an expected or average delta in a measurement value. With respect to RSSI-based pairing techniques, the threshold delta may be set based on expected use cases for pairing of display device 310 and analyte sensor system 308. One example expected use case is the user removing display device 310 from the user's pocket or other typical location and holding display device 310 out for viewing or the like. A typical user taking such action may result in a position change of display device 310 or approximately 16 inches, by way of example. Accordingly, an initial value for the threshold delta may be set to the expected change in RSSI corresponding to a position change of a value around 16 inches. In some specific examples by way of illustration, the change in RSSI may be approximately 20 dBm (e.g., +20 dBm if the devices are moved closer to one another or −20 dBm if the devices are moved farther away from one another). In embodiments, the initial value for the threshold delta may be determined based on the nature of aspects of analyte sensor system 308. For example, if aspects of analyte sensor system 308 such as sensor 10 are made variable (e.g., in terms of size) based on characteristics of an expected user, the value initially established for the threshold delta may likewise be varied (e.g., to accommodate an expected position change based on a difference in user size). In some cases, the threshold delta may be based on device type of display device 310.

It will be appreciated, however, that other display devices 310 may be in range of analyte sensor system 308 and may be changing positions relative to the same, thus potentially generating changes in RSSI that could satisfy the established threshold delta. To focus on display device 310 appropriate/suitable for pairing, additional features may be used in conjunction with the threshold delta. For example, upper threshold 1004 may be employed to determine whether at closer position, the measurement value (e.g., measurement value 1014*b*) exceeds upper threshold 1004. In another example, a determination may be made as to whether upper threshold 1004 and/or lower threshold 1006 is crossed as a result of rearranging display device 310. Alternatively or in addition, various measurement values can be compared to one another and the largest value can be chosen (e.g., in conjunction with a threshold delta determination or otherwise). The applied features or set of criteria may be adapted based on environmental conditions, such as the number of display devices 310 in range of analyte sensor system and/or the measurement values detected for one or more display devices 310.

In example implementations, the initially established threshold delta may be adapted and/or reprogrammed/recalibrated after deployment of analyte sensor system 308. By way of illustration, during setup of analyte sensor system 308, user information/characteristics may be determined (e.g., based on input received by analyte sensor system 308), including with respect to the user's size, for example. This information may be used to tailor the initial threshold delta for the user, e.g., based on the user's size or expected device usage. In embodiments, a profile may be established based on analyzing instances of validation/confirmation over time, and the profile may then be used to adjust the initially established threshold delta. For example, where the initially established threshold delta may have been set to 16 inches, the user may most frequently keep display device 310 on the user's office desk further away. After storing/analyzing information regarding instances of validation/confirmation over time, the threshold delta may be modified based on the user's actual behavior and/or confirmation of devices, such that the, for example, the threshold delta can be increased to 20 inches.

The following is a specific example of operations that may be used for confirming/validation an initial identification/selection using measurement such as RSSI. First, the user may connect analyte sensor 10 to sensor electronics module 12 of analyte sensor system 308 (with reference to, e.g., FIGS. 2A, 2B). Analyte sensor system 308 can then begin sending advertisement messages (with reference to, e.g., FIG. 7A and/or FIG. 7J). Next, display device 310 receives an advertisement message from analyte sensor system 308. This could occur, for example, in connection with arrangement 1000*a* (with reference to FIG. 10A). By way of illustration, measurement value 1014*a*, corresponding in this case to RSSI, may be approximately −20 dBm. For example, measurement value 1014*a* may be a derivative of a signal received via link 1012*a*.

Display device 310 may then, based on measurement value 1014*a* exceeding lower threshold 1006, notify the user that there is a discoverable analyte sensor system 308 available for connection. A user notification from display device 310 can include, for example, one or more of a visual indicator such as a light or screen/display effect, banner, or popup; an auditory indicator such as a beep or other sound; and/or haptic feedback. The notification can originate from analyte sensor system 308, display device 310, or both. Display device 310 may then prompt the user to, for example, move display device 310 closer to analyte sensor system 308.

The user may then move display device 310 closer to analyte sensor system 308. In embodiments, this may entail changing the position of display device 310 or analyte sensor system 308 or both. This may result, for example, in arrangement 1000*b* (with reference to FIG. 10B). By way of illustration, measurement value 1014*b*, corresponding in this case to a derivative based of a signal based on RSSI, may be approximately 0 dBm. Based on measurement value 1014*b* exceeding upper threshold 1004 (or, for example, measurement delta 1016*a* exceeding a threshold delta), display device 310 may validate/confirm the identification/selection and notify the user of the same.

In embodiments, identification/selection can be confirmed/validated with a moderate amount of user interaction and based on various factors in addition or alternatively to the RSSI measurement values. For example, it may be determined that display device 310 has identified and/or connected to analyte sensor system 308 previously (e.g., by way of the above steps for RSSI pairing or through other operations described herein with respect to identification/selection), and validation/confirmation can be based on this determination. It will also be appreciated that the above example operations can be used to connect display device 310 with a desired analyte sensor system 308, even in the event that there are multiple analyte sensor systems 308 within range of display device 310 and/or event in the event that there are multiple display devices 310 within range of analyte sensor system 308.

Referring again to FIG. 10D, arrangement 1020*a* and measurement profile 1030*a* are illustrated. In some cases, multiple analyte sensor systems 308*a*, 308*b* may attempt to connect to a single display device (e.g., display device 310*a*). For example, in a doctor's office, two patients may be using respective analyte sensor systems 308*a* and 308*b* and be relatively close in proximity to one another, and both patients may have respective display devices 310*a* and 310*b*. Because of the proximity of analyte sensor systems 308*a*, 308*b* to display devices 310*a*, 310*b*, both analyte sensor systems 308*a*, 308*b* may attempt to connect to one of the display devices 310*a* and 310*b*. In particular, with reference to arrangement 1020*a* and measurement profile 1030*a*, measurement values 1034*a*, 1034*c*, and 1034*d* may all be identified initially as indicating connections that may be established, for example, due to the proximity of display device 310a to analyte sensor system 308a (e.g., corresponding to measurement value 1034a) and analyte sensor system 308b (e.g., corresponding to measurement value 1034d), and display device 310b to analyte sensor system 308b (e.g., corresponding to measurement value 1034d). Whereas each of these measurement values exceeds threshold 1006, measurement value 1034b falls below threshold 1006, and thus analyte sensor system 308a may not be identified as being available for connection to display device 310b. In such circumstances, it may be more difficult for one of the display devices 310a, 310b to determine which analyte sensor system 308a, 308b is appropriate for connection, and due to the proximity of multiple devices, a single RSSI measurement may be insufficiently for pairing.

Accordingly, in embodiments of the present disclosure, for example, display device 310a can determine measurement values 1034a and 1034d (e.g., based on RSSI) for signals received from each of analyte sensor systems 308a and 308b and differentiate between the two analyte sensor systems 308a and 308b based on one of the measurement values exceeding a predetermined, adjustable, programmable, or adaptable threshold, such as upper threshold 1024 and/or lower threshold 1026. Alternatively, for example, display device 310a can compare the two measurement values (e.g., RSSI or a derivatives signal received via links) to one another and select analyte sensor system 308a associated with the larger of the two values (here measurement value 1034a, which may be an RSSI value).

In some cases, for example, both measurement values 1034a and 1034d (e.g., which may be RSSI values) exceed lower threshold 1026 and/or may be relatively close in magnitude, and thus display device 310a may not be able to easily differentiate between analyte sensor systems 308a and 308b based on measurements from one arrangement alone. Likewise, in some cases, analyte sensor system 308a may not be able to distinguish between display devices 310a, 310b using measurements for a single device arrangement.

Figure 10E:
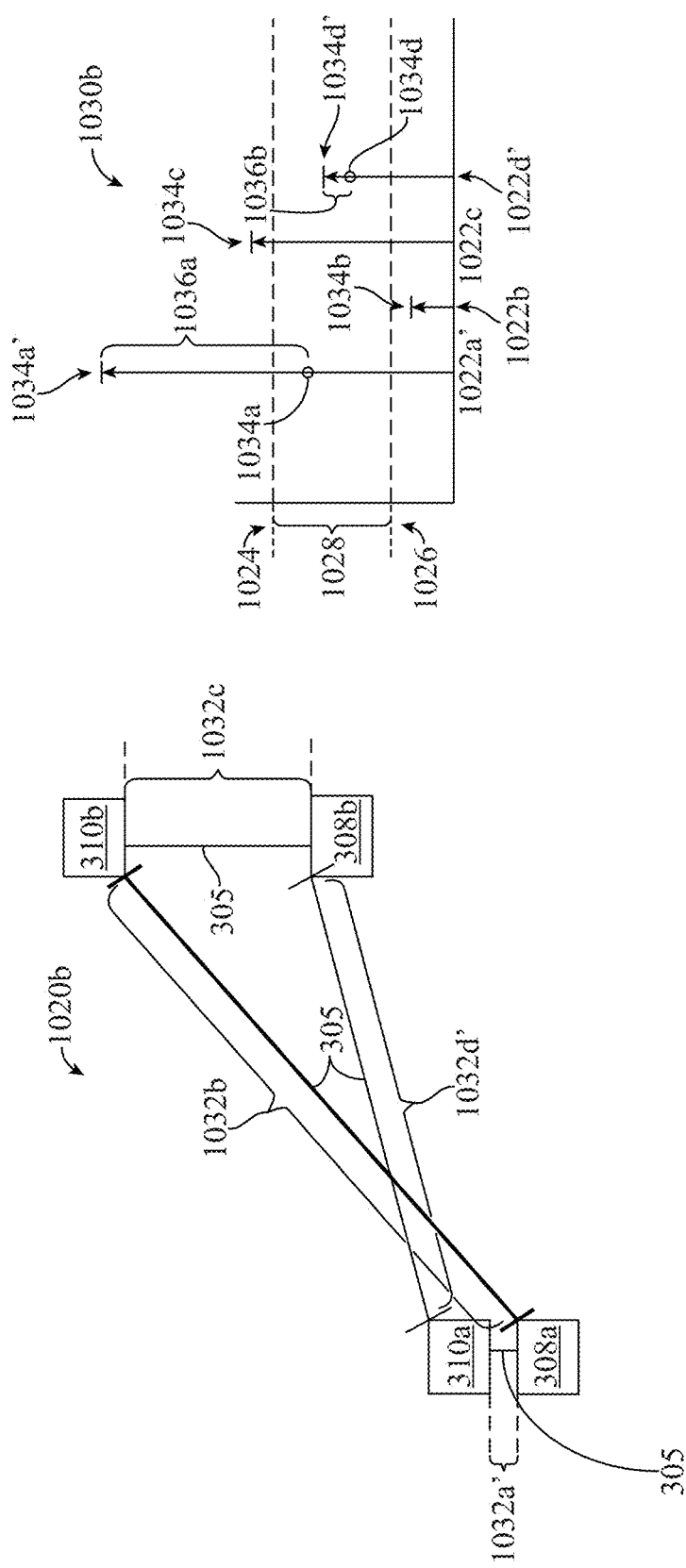
FIG. 10E illustrates aspects of an example system that may be used in connection with implementing embodiments of the disclosure.

One way of differentiating between devices involves moving one or more devices, as alluded to above in connection with FIGS. 10A-10C. With reference to FIGS. 10D and 10E, for example, in arrangement 1020b, display device 310a has been moved relatively close to analyte sensor system 308a in comparison to arrangement 1020a. As a result, measurement value 1034a' has increased according to measurement delta 1036a related to the distance change between links 1032a' and 1032a. Measurement delta 1036a may be compared to a threshold delta and based on the comparison it may be determined that display device 310a is validated/confirmed for pairing. Further, although measurement value 1034d' has also increased relative to measurement value 1034d, this increase is relatively small, and could be distinguished by comparison to a threshold delta. In embodiments, additional comparisons to additional thresholds described herein may be employed. In embodiments, if no conditions are satisfied that may confirm/validate a selection/identification, one or more of the thresholds (including threshold deltas) can be adjusted and measurements can be retaken.

In embodiments, as alluded to above, a threshold delta may be employed such that pairing is confirmed when display device 310 and analyte sensor system are brought closer together such that the threshold delta is met or exceeded by the change in the measurement values, and then display device 310 and analyte sensor system moved farther apart such that the threshold delta is again met or exceeded by the change in the measurement values. Here, an absolute value of the threshold delta may be employed. In some cases, rather than being based on the threshold delta being exceeded in both directions, pairing may be based on the threshold delta being met within a range or margin of error. For example, this may represent the distance moved in a first direction (e.g., closer) being close to or the same as a distance moved in the negative direction (e.g., farther away). Moving closer and then farther away or vice versa may be detected by obtaining derivatives of signals received at the links corresponding to the closer arrangement and the father away arrangement, and determining, for example, that an upper threshold was first crossed (in a positive direction) and then a lower threshold was crossed (in a negative direction). The converse could also be employed. Alternatively or in addition, moving closer and then farther away or vice versa may be detected by obtaining derivatives of signals received at the links corresponding to the closer arrangement and the father away arrangement, and determining, for example, that a first difference between the derivatives (resulting from moving closer) at least meets a positive threshold delta and then a second difference in the derivatives (resulting from moving farther away) at least meets a negative threshold delta. The converse could also be employed. In some cases, where a threshold is being used to determine whether a derivative of a signal has or derivatives of signals have crossed the threshold in a negative direction, a derivative falling below the threshold may be considered meeting or exceeding the threshold (e.g., in the negative direction).

Another way of differentiating between analyte sensor systems 308a, 308b is as follows. In embodiments, display device 310a can scan and detect identification information (e.g., identification numbers or the like) for each of analyte sensor systems 308a, 308b and provide the available analyte sensor systems 308a, 308b, etc. and their respective identification information to the user. The user can then use the display device GUI 340 to select the analyte sensor system 308a, 308b with the desired identification information.

Another potential issue involved in the selection/identification of analyte sensor systems such as analyte sensor system 308 arises from the possibility that in some cases not all analyte sensor systems 308a, 308b, etc. wake up or become active a uniform amount of time after analyte sensor 10 is coupled to the sensor electronics module 12 of analyte sensor system 308. That is, there may be a non-uniform time delay between the physical/electrical connection of sensor electronics module 10 to analyte sensor 12, and the powering up of sensor electronics module 12 and transmission of advertisement messages. As alluded to, this time delay can vary between analyte sensor systems 308a, 308b, etc.

This variance may result in, for example, display device 310 seeking to connect to first analyte sensor system 308a that has become active or woken up, even though the appropriate analyte sensor system 308b for connection is second analyte sensor system 308b that has not yet become active or woken up. As such, display device 310 may connect to a less-than-preferred analyte sensor system 308a instead of the preferred analyte sensor system 308b.

Figure 7B:
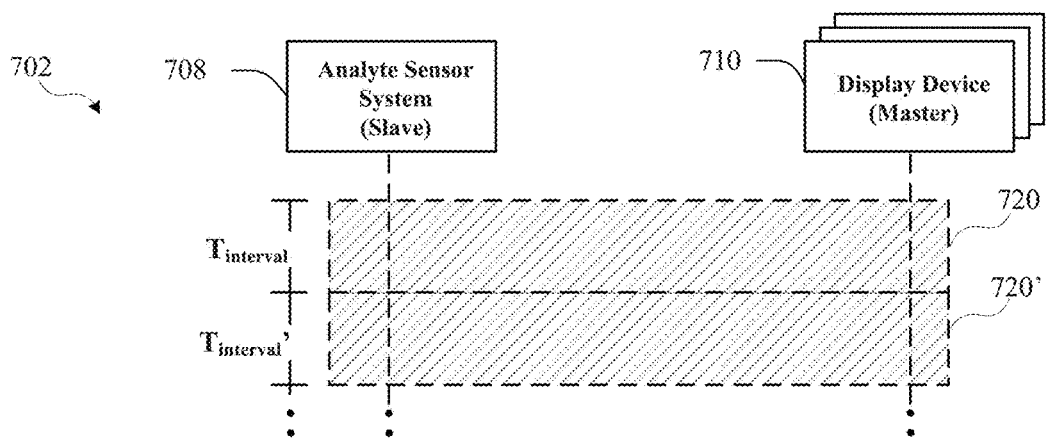
FIG. 7B is an operational flow diagram illustrating various operations that may be performed in accordance with embodiments of the disclosure.
Figure 7C:
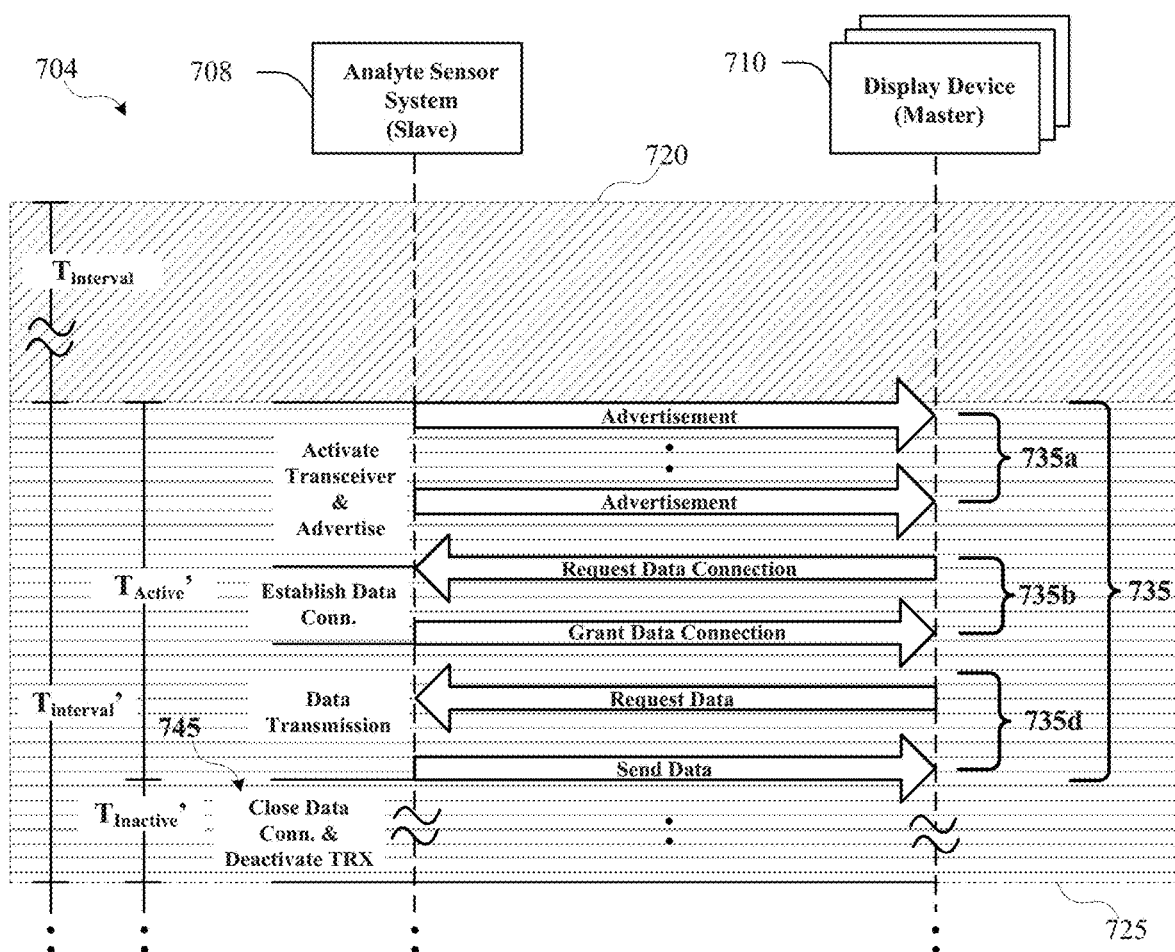
FIG. 7C is an operational flow diagram illustrating various operations that may be performed in accordance with embodiments of the disclosure.
Figure 7D:
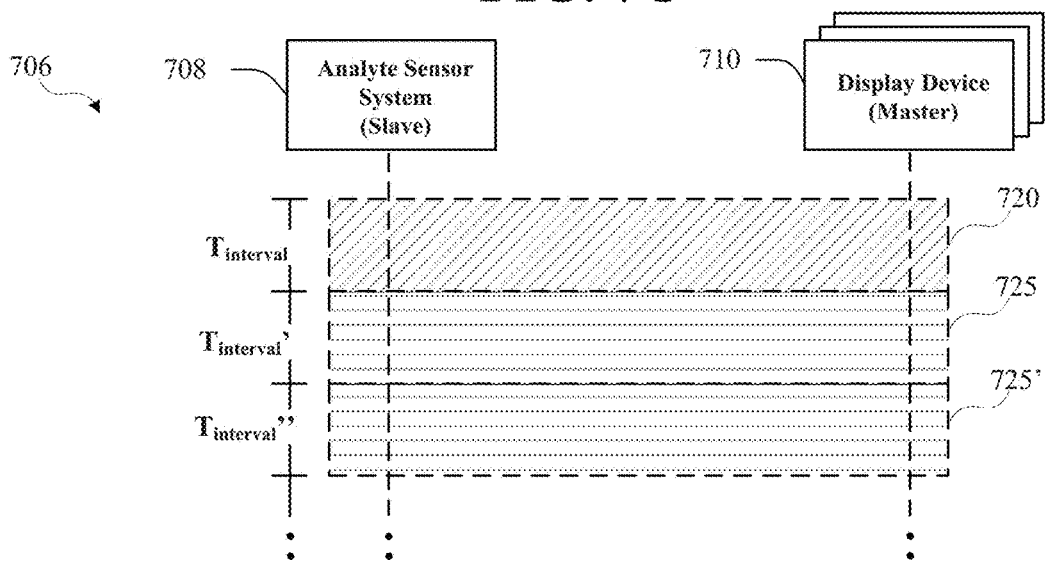
FIG. 7D is an operational flow diagram illustrating various operations that may be performed in accordance with embodiments of the disclosure.
Figure 7E:
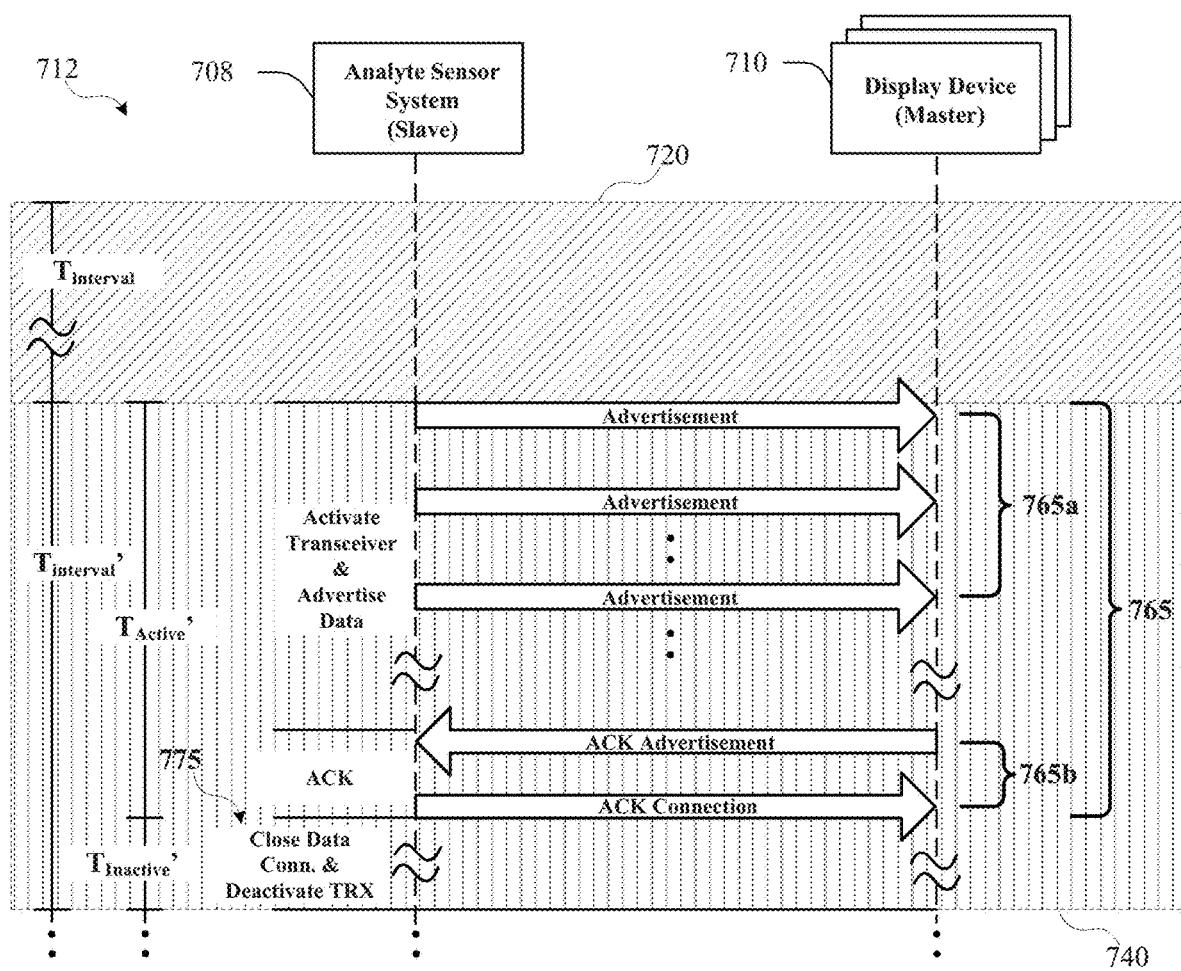
FIG. 7E is an operational flow diagram illustrating various operations that may be performed in accordance with embodiments of the disclosure.
Figure 7F:
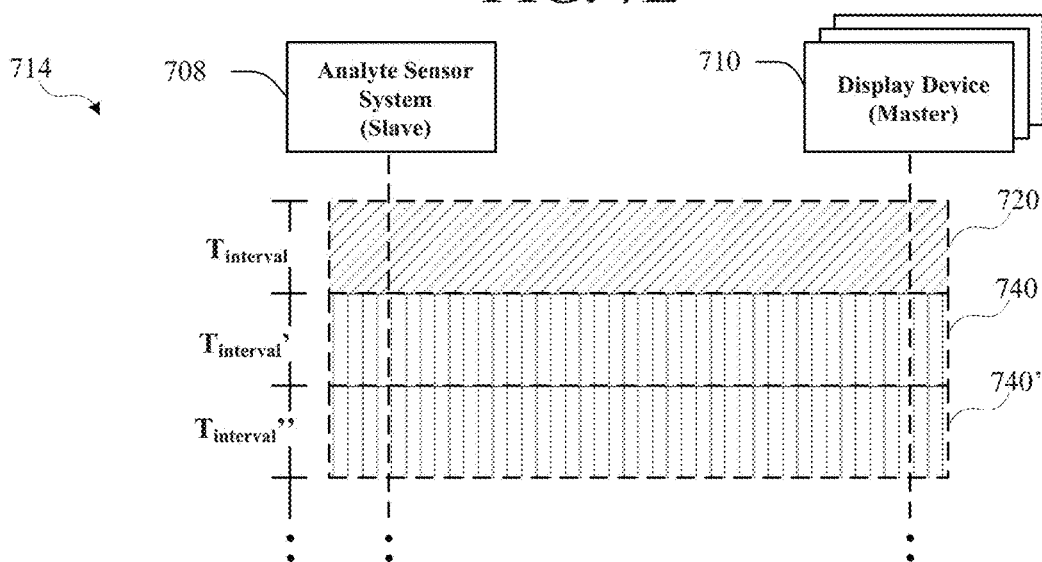
FIG. 7F is an operational flow diagram illustrating various operations that may be performed in accordance with embodiments of the disclosure.
Figure 7G:
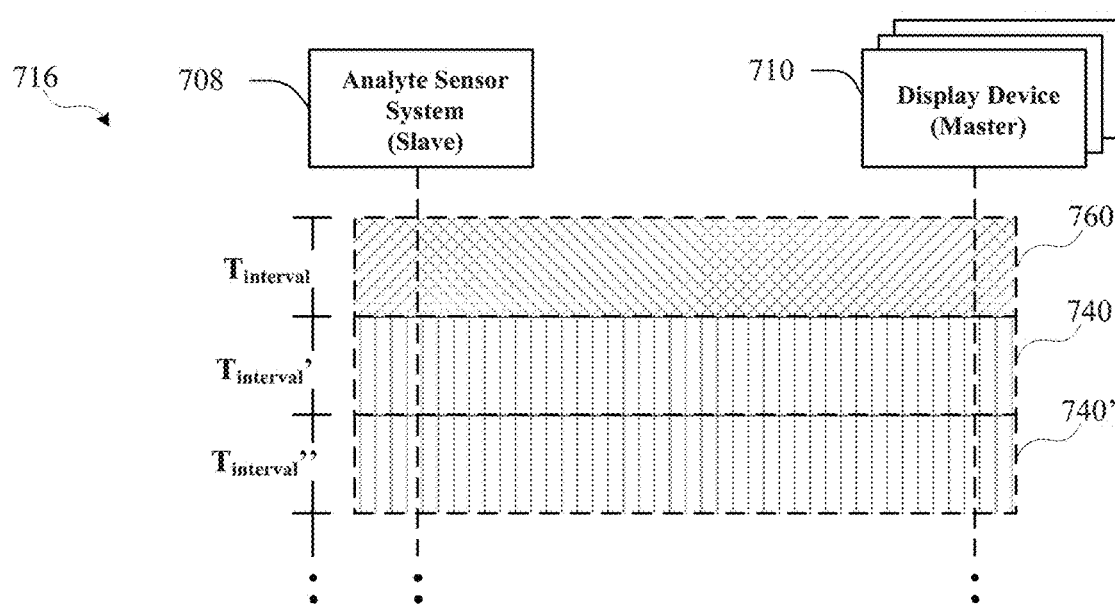
FIG. 7G is an operational flow diagram illustrating various operations that may be performed in accordance with embodiments of the disclosure.
Figure 7H:
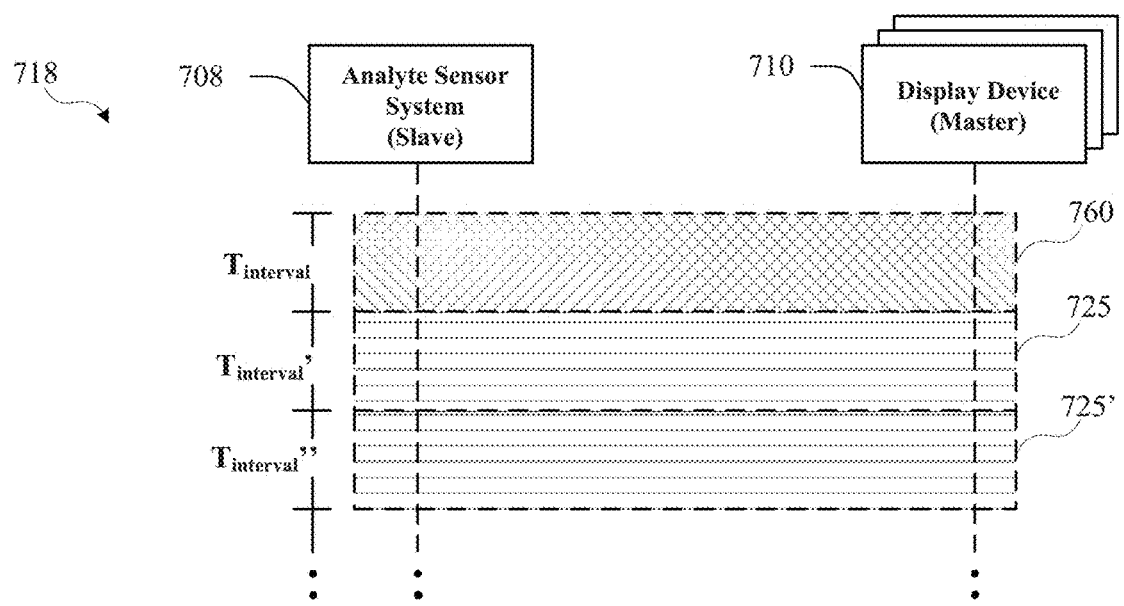
FIG. 7H is an operational flow diagram illustrating various operations that may be performed in accordance with embodiments of the disclosure.
Figure 7J:
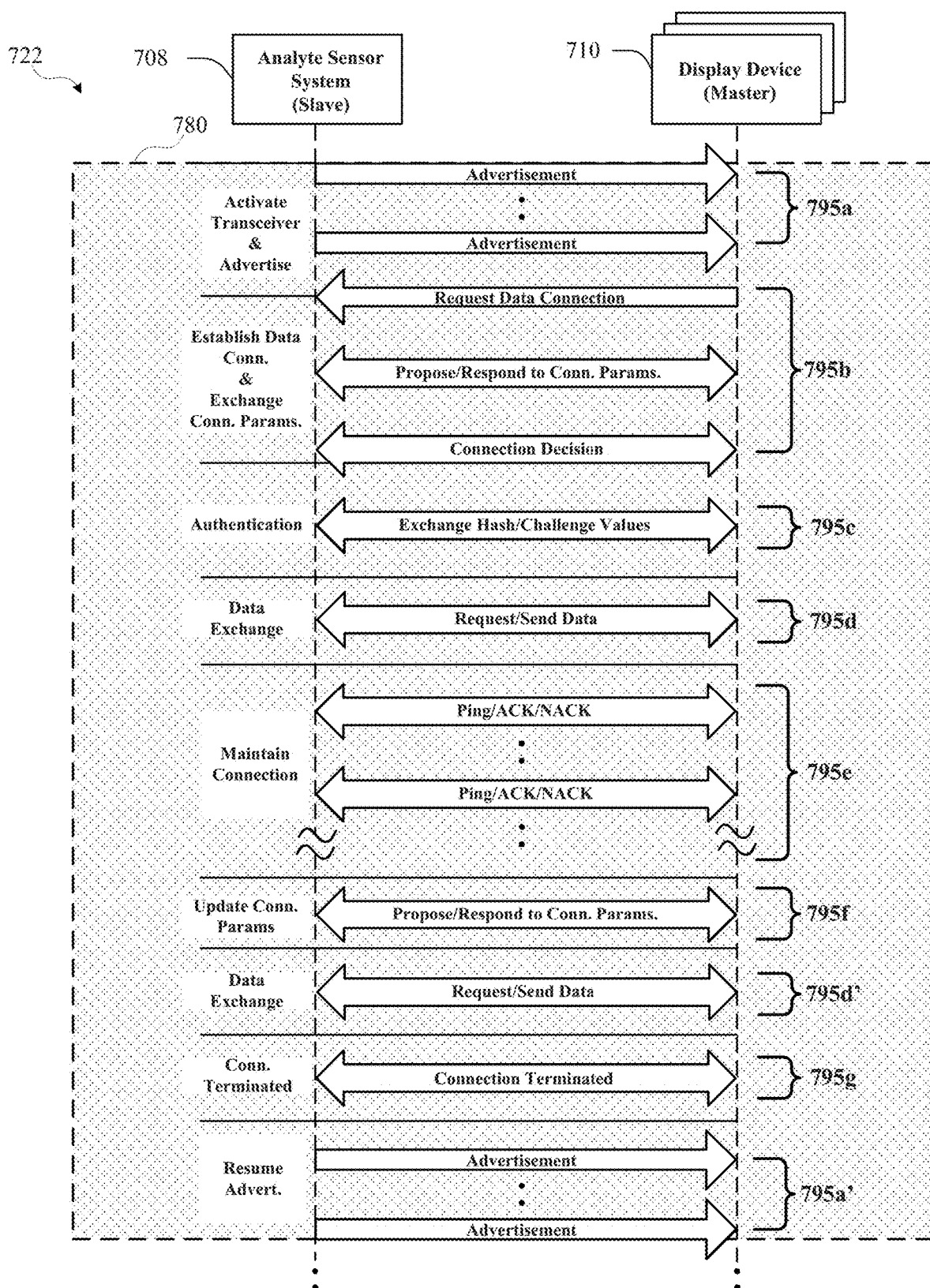
FIG. 7J is an operational flow diagram illustrating various operations that may be performed in accordance with embodiments of the disclosure.

Accordingly, embodiments of the present disclosure involve a wake up circuit that may be employed in analyte sensor systems 308 to implement a uniform wakeup time, or uniform time delay that occurs between the physical/electrical connection of sensor electronics module 12 to analyte sensor 10, and the powering up of sensor electronics module 12 and transmission of advertisement messages (e.g., at operation 795a with reference by way of example to FIG. 7J). The time delay may be variable or programmable and may be set to a very small or zero value, such that wakeup occurs nearly immediately upon connecting analyte sensor 10 to sensor electronics module 12. Or the time delay may be relatively larger. Regardless of the actual value of the time delay, the wakeup circuit may be employed to apply a uniform value across analyte sensor systems 308a, 308b, etc. In this manner, for example, first and second analyte sensor systems 308a, 308b wake up or become active at roughly the same time, and display device 310 can select and connect to the appropriate analyte sensor system 308b, for example as described above in connection with various pairing techniques involving various amounts of user interaction.

Yet another potential issue involved in the selection/identification of analyte sensor system 308 arises from side lobes that may be present on antennas of analyte sensor systems 308. These side lobes may create interference between signals and affect the calculation of RSSI and other measurements, thus potentially hampering the above-described semi-automated measurement-based pairing techniques (e.g., including techniques involving RSSI).

In embodiments of the present disclosure, and in some cases particularly when a plurality of analyte sensor systems 308 are in geographic proximity to one another, out-of-band pairing may be used by display device 310 for selection/identification of analyte sensor system 308a from among the plurality of analyte sensor systems 308a, 308b, etc. For example, near-field communications (NFC) may be used to select/connect analyte sensor system 308a and initiate pairing/connection therewith by display device 310a.

In embodiments, other techniques may be employed for selection/identification of analyte sensor system 308a from among the plurality of analyte sensor systems 308a, 308b, etc. Such techniques may include one or more of display device 310a taking a photograph of information borne on analyte sensor system 308a that is desired to be selected/identified, scanning a bar or QR code from analyte sensor system 308a or related packaging, using invisible ink on analyte sensor system 308a and/or product packaging thereof, and using thermal ink on analyte sensor system 308a and/or packaging.

In embodiments, analyte sensor system 308 and/or display device 310 may include an accelerometer, optical or infrared detector, microphone, or other sensor that can be used to aid in selecting/identifying analyte sensor system 308 and/or display device 310. For example, display device 310 can prompt the user to tap analyte sensor system 308 one or more times. This may cause analyte sensor system to begin sending advertisement messages. Subsequently, the user can initiate selection/identification of analyte sensor system 308 using RSSI or another of the above-describe techniques. Alternatively or in addition, the input to the accelerometer, optical or infrared detector, microphone, or other sensor that can be used to confirm/validate that the selected/identified analyte sensor system (e.g., by RSSI pairing) is the preferred device. In some embodiments, display device 310 may pair by selecting/identifying analyte sensor system 308a from among the plurality of analyte sensor systems 308a, 308b, etc., co-authenticating the analyte sensor system 308a and mobile application, and further exchange keys for data encryption, secured connection or links, and device privacy. In such embodiments, the display device 310 may initially generate and exchange short-term keys using modulated signals (e.g., modulated infrared signals), and the analyte sensor system 308a may employ a photo detector, a light pipe or an IR emitter to receive and decode or demodulate such signals. Following this, final keys exchange may be performed between the display device and the analyte sensor system over a BLE link that is encrypted using the short-term key.

In embodiments, gestures can be performed by the user holding display device 310 in order to confirm/validate a selected/identified display device and/or analyte sensor system. For example, by moving a device in a figure eight or the like, the user may confirm/validate a selection/identification. In embodiments, auditory input (e.g., voice recognition) may be used for confirmation/validation of a device. In embodiments, the user may also be instructed to tap or shake analyte sensor 308 and/or display device 310 in order to trigger validation/confirmation. Such gestures/accelerometer-based events may trigger advertisements that may be limited in time so as to be detectable and to potentially limit collisions caused by advertisement messages.

With respect to the above-described features related to a moderate amount of user interaction, it should be appreciated that in some cases, the described techniques may be employed for the purposes of identifying/selecting devices in the first instance, and not merely for confirming/validating an initial identification/selection.

Figure 13C:
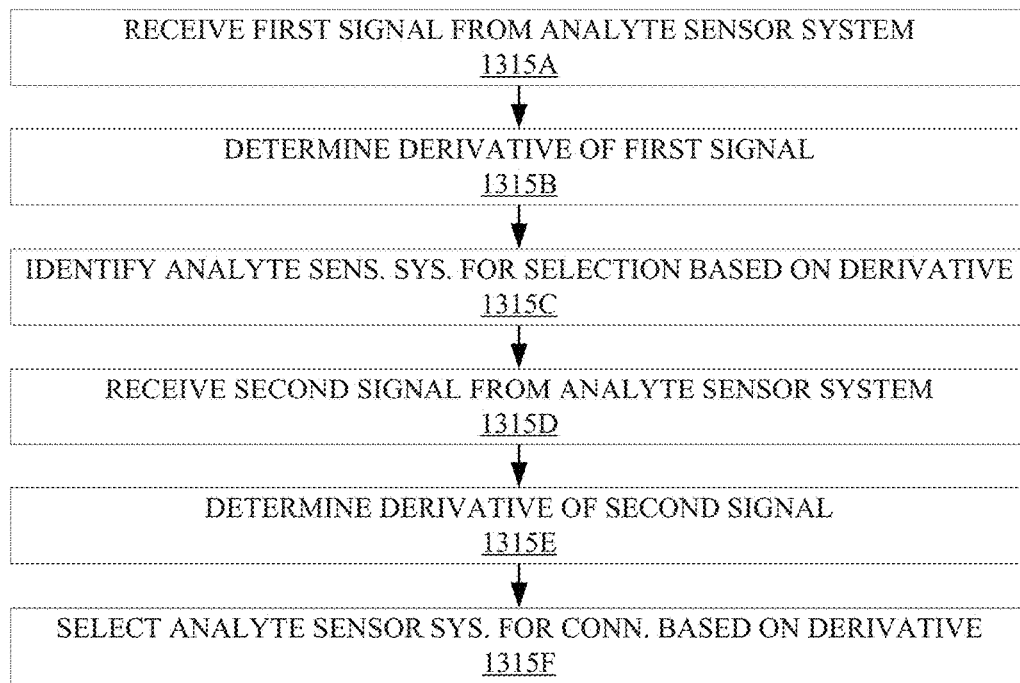
FIG. 13C is an operational flow diagram illustrating various operations that may be performed in accordance with embodiments of the disclosure.
Figure 13D:
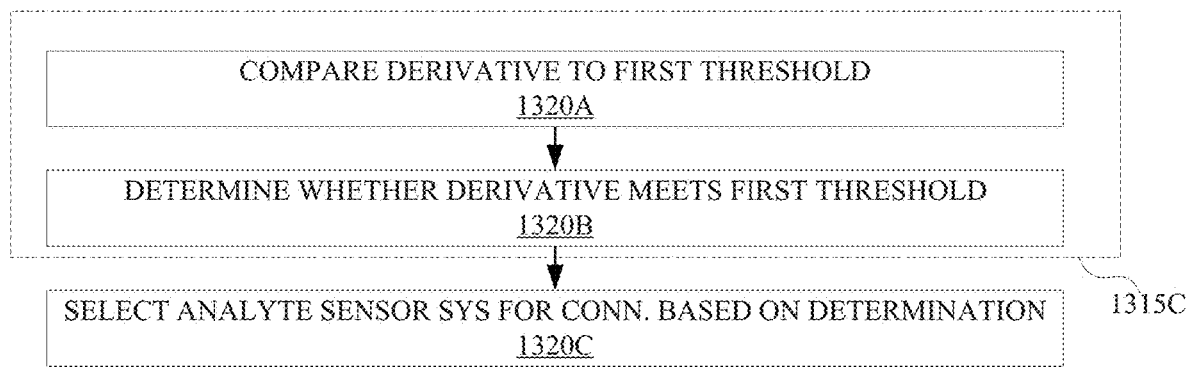
FIG. 13D is an operational flow diagram illustrating various operations that may be performed in accordance with embodiments of the disclosure.
Figure 13E:
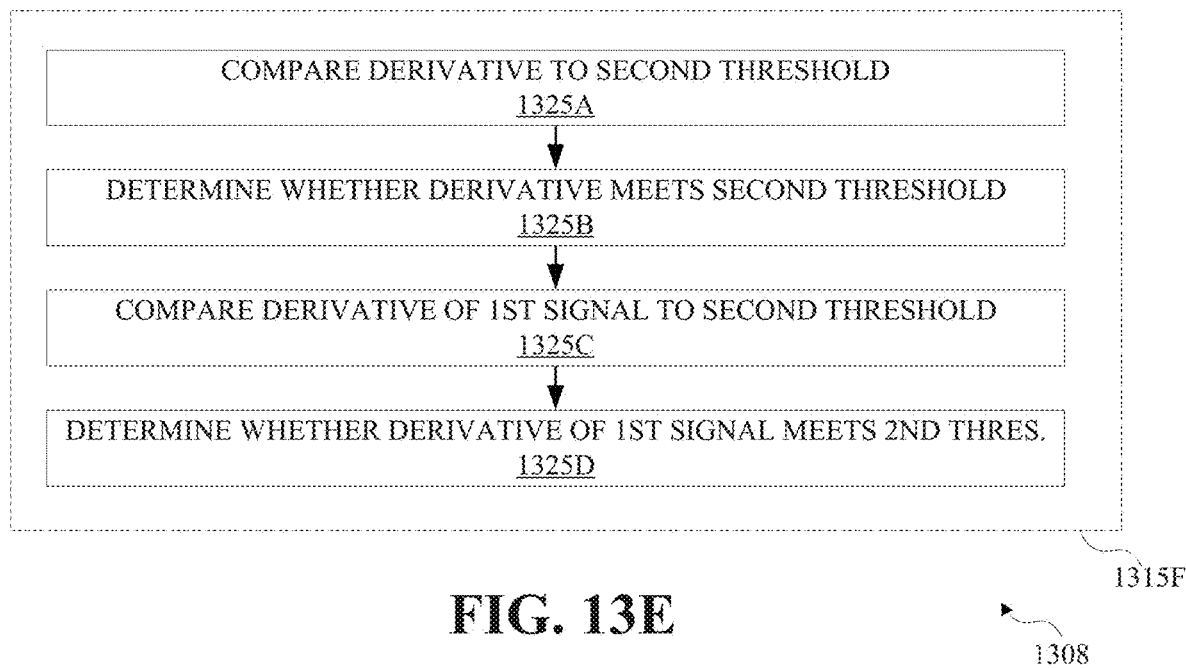
FIG. 13E is an operational flow diagram illustrating various operations that may be performed in accordance with embodiments of the disclosure.
Figure 13F:
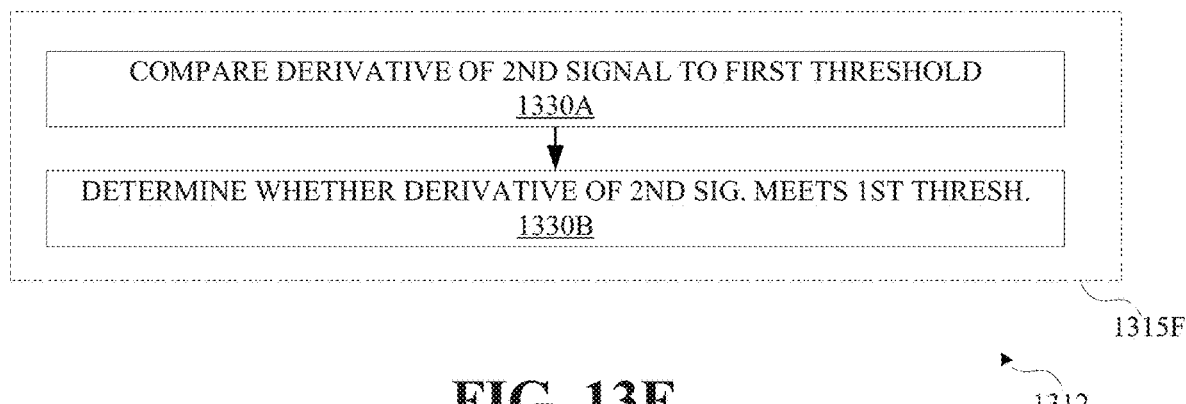
FIG. 13F is an operational flow diagram illustrating various operations that may be performed in accordance with embodiments of the disclosure.
Figure 13G:
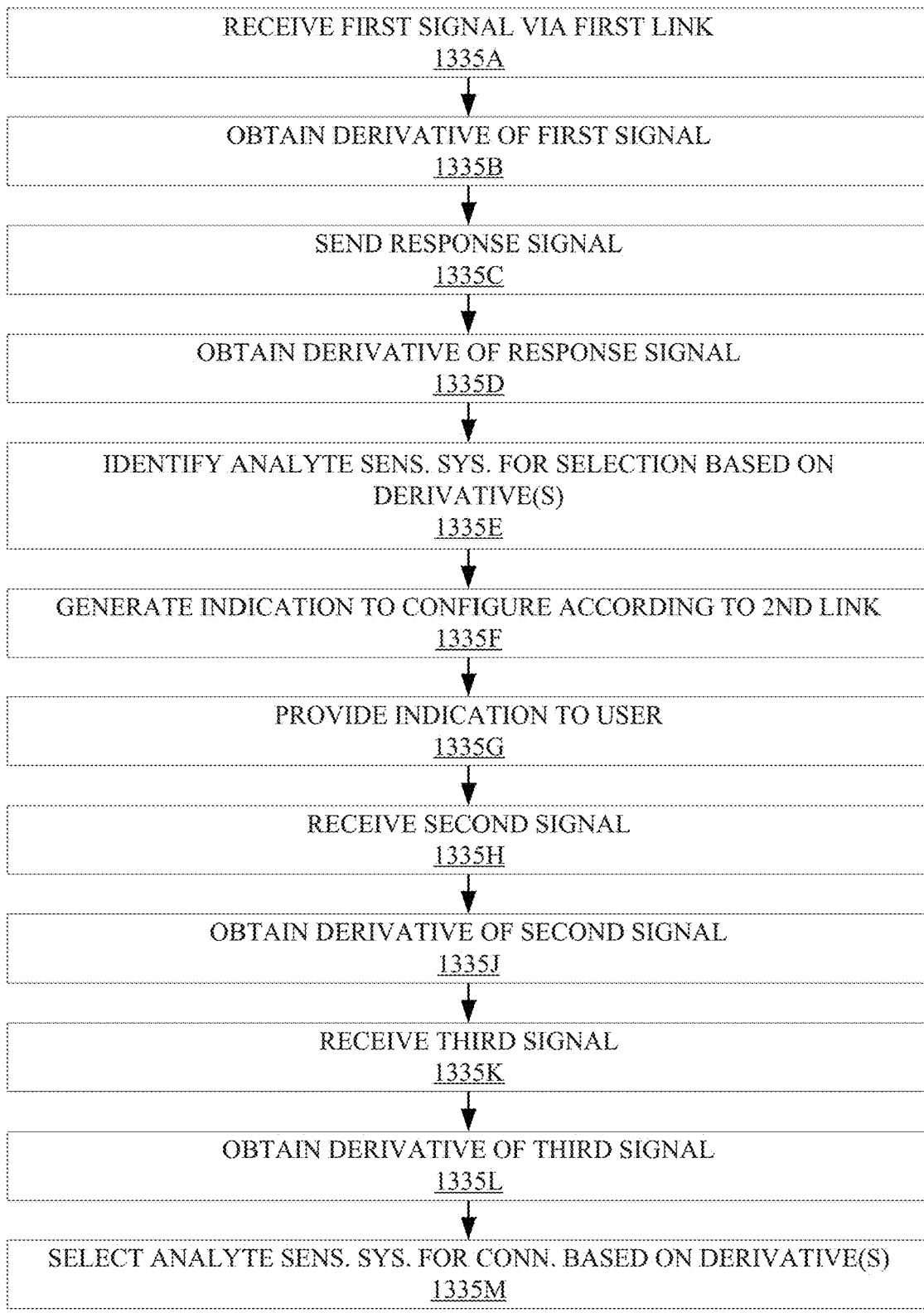
FIG. 13G is an operational flow diagram illustrating various operations that may be performed in accordance with embodiments of the disclosure.
Figure 13H:
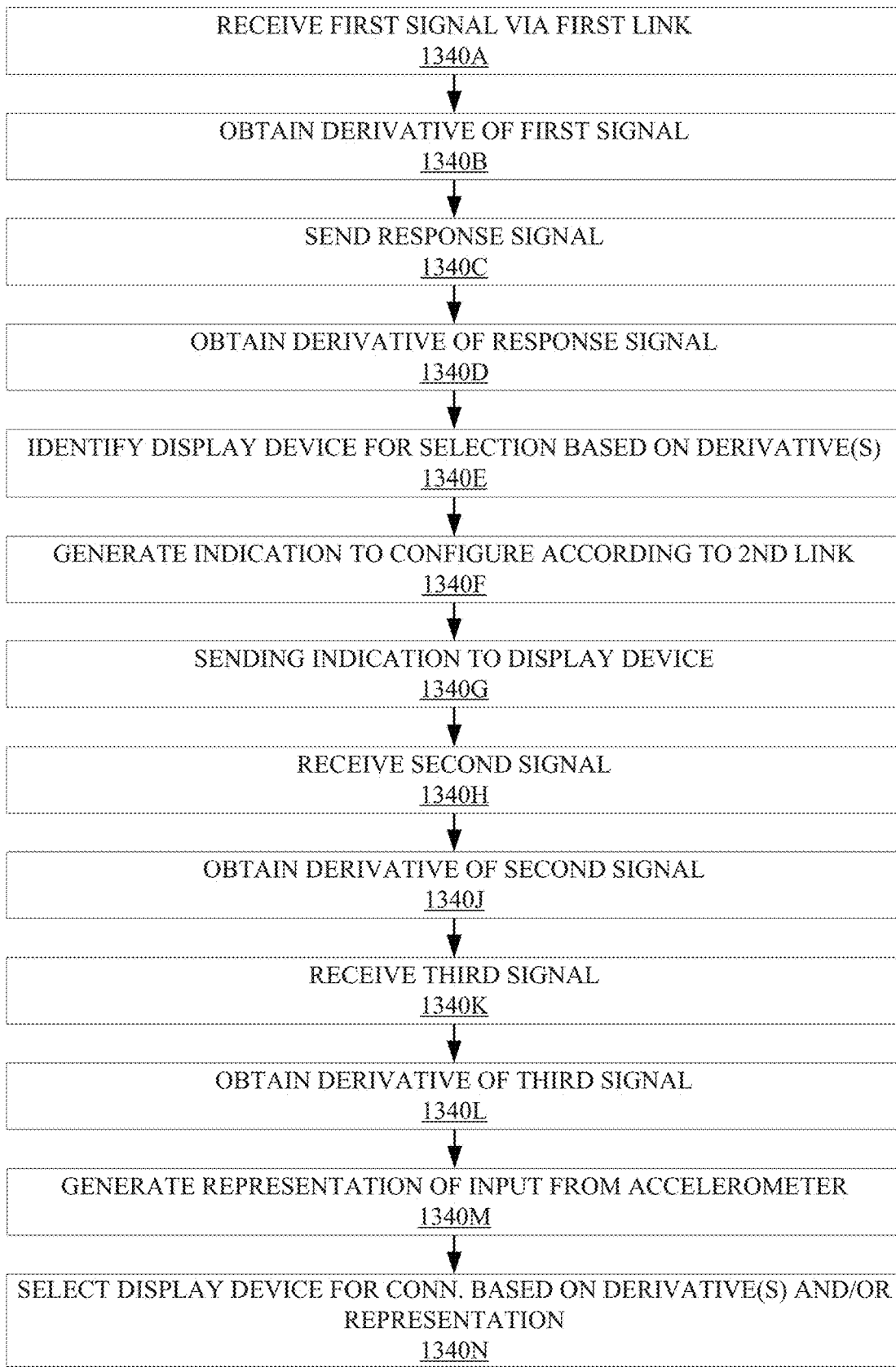
FIG. 13H is an operational flow diagram illustrating various operations that may be performed in accordance with embodiments of the disclosure.
Figure 13J:
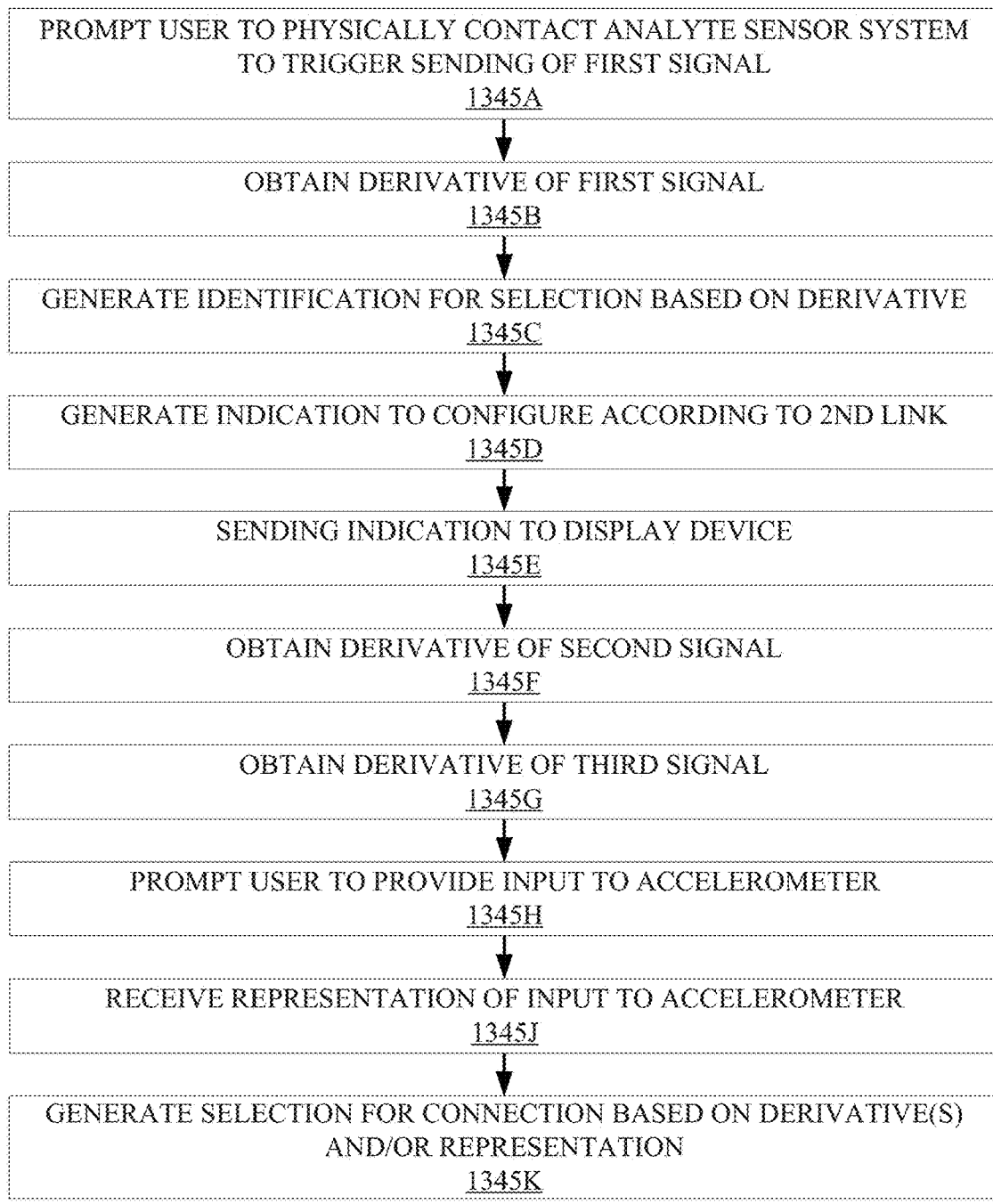
FIG. 13J is an operational flow diagram illustrating various operations that may be performed in accordance with embodiments of the disclosure.
Figure 13K:
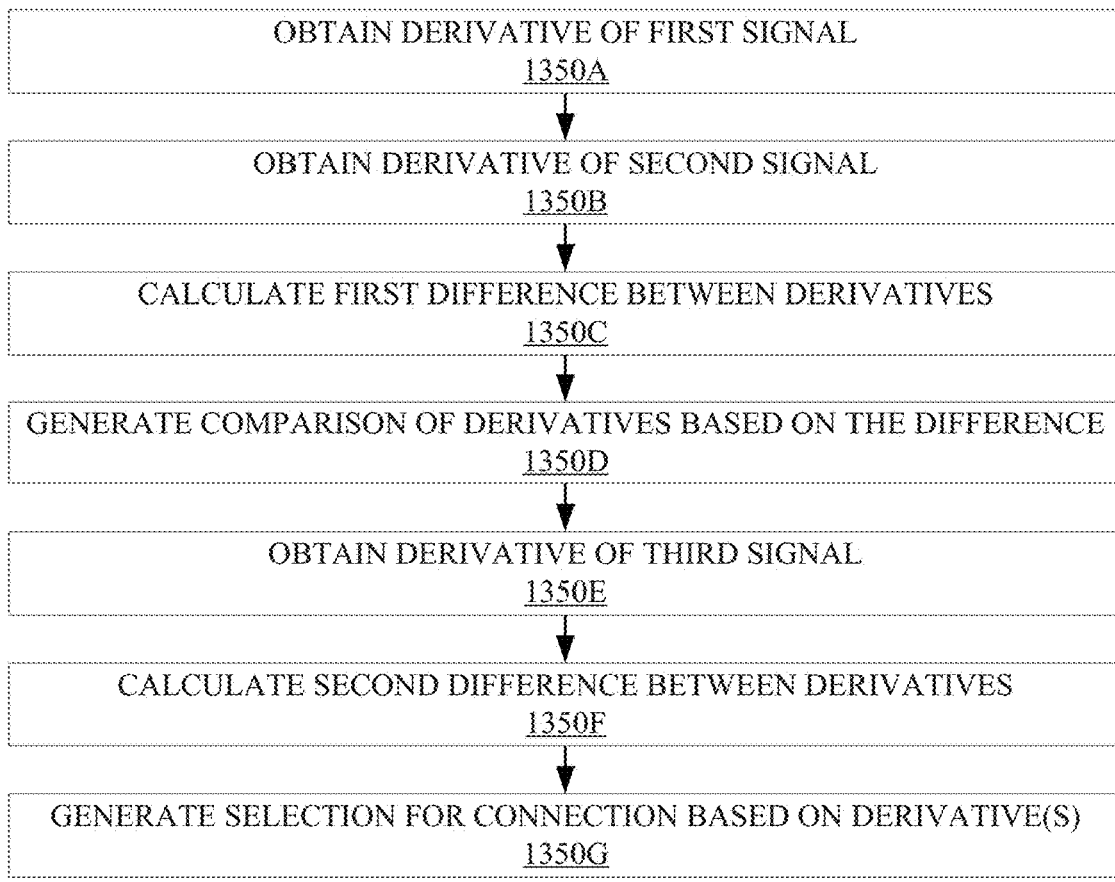
FIG. 13K is an operational flow diagram illustrating various operations that may be performed in accordance with embodiments of the disclosure.
Figure 13L:
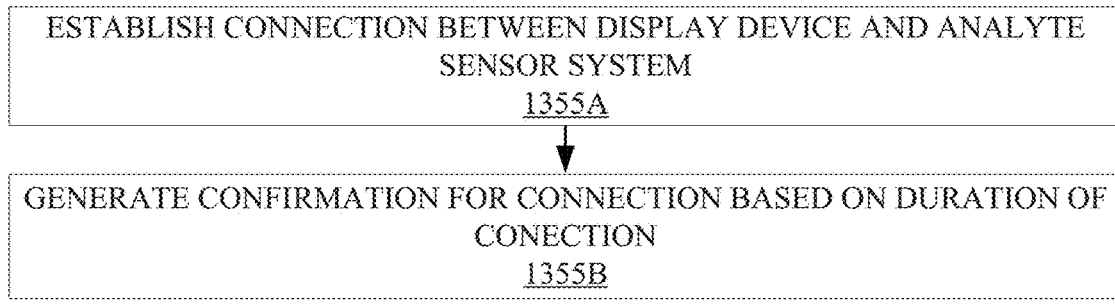
FIG. 13L is an operational flow diagram illustrating various operations that may be performed in accordance with embodiments of the disclosure.
Figure 13M:
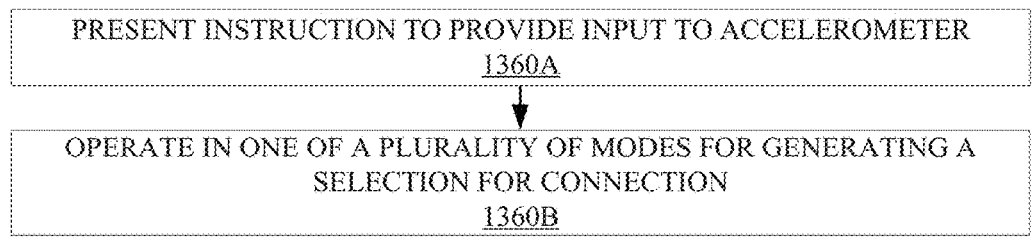
FIG. 13M is an operational flow diagram illustrating various operations that may be performed in accordance with embodiments of the disclosure.
Figure 13N:
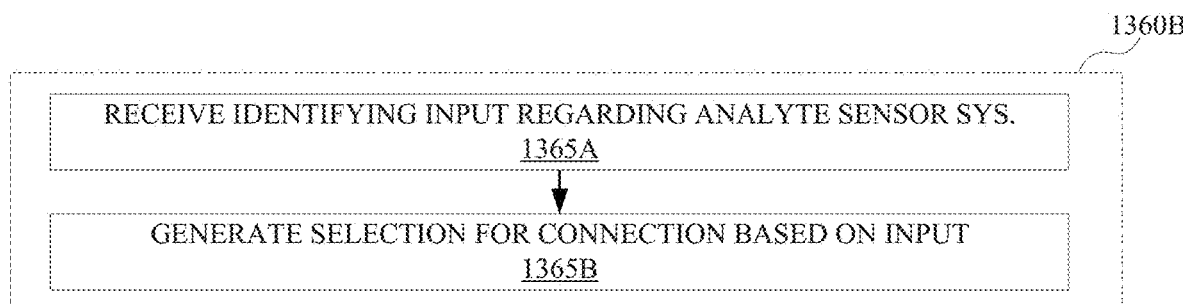
FIG. 13N is an operational flow diagram illustrating various operations that may be performed in accordance with embodiments of the disclosure.
Figure 13P:
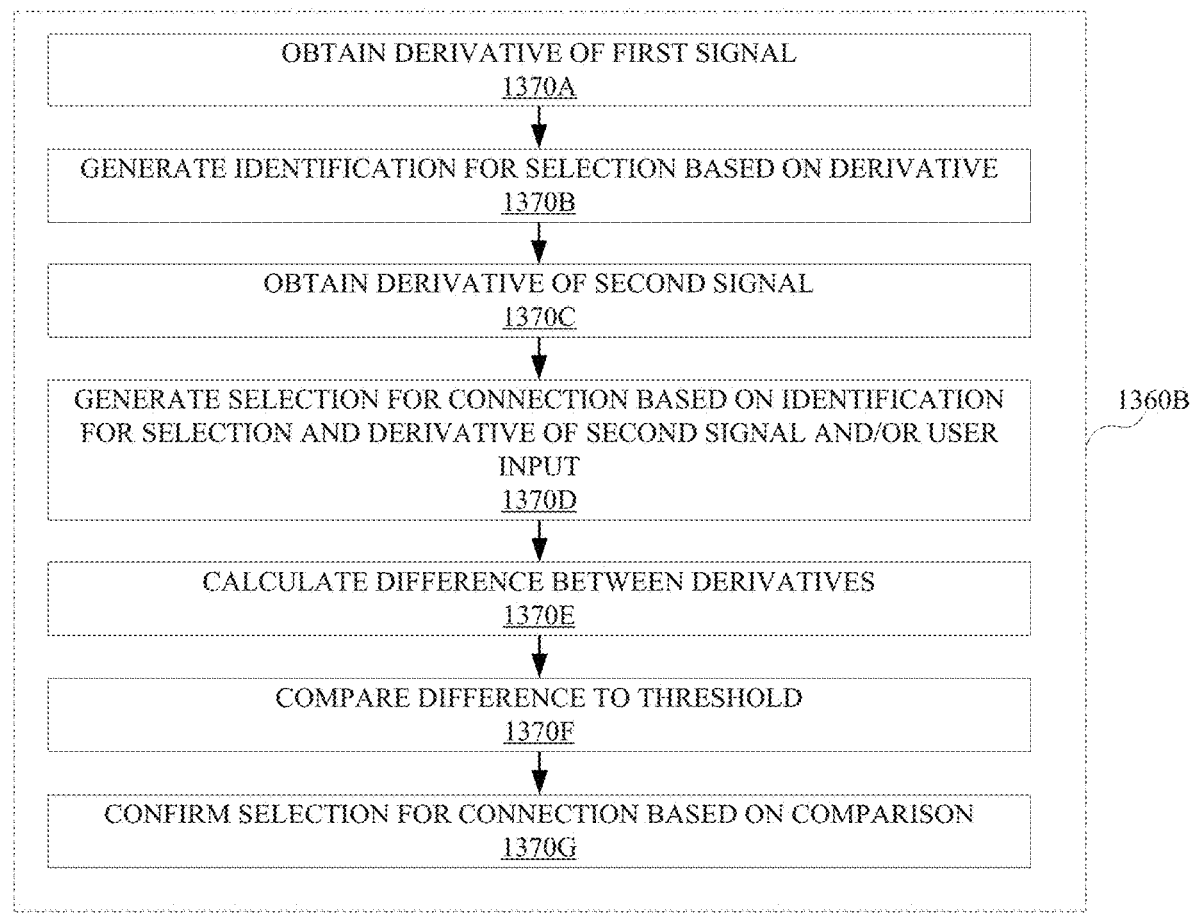
FIG. 13P is an operational flow diagram illustrating various operations that may be performed in accordance with embodiments of the disclosure.

FIGS. 13C to 13P provide operational flow diagrams illustrating various operations that may be performed in accordance with embodiments of the present disclosure, for example in connection with the second tier or level of user interaction described above. For illustration purposes, reference is made here to FIGS. 10A through 10E and numerals of components shown therein. Nevertheless, one of ordinary skill in the art will appreciate upon studying the present disclosure that like components from other FIGS. of the present disclosure may be included in the scope of the present description of FIGS. 13C to 13P.

Embodiments shown in FIG. 13C involve aspects of method 1304 for identifying a device for connection. At operation 1315A, method 1304 involves display device 310a receiving a first signal from analyte sensor system 310a among a set of analyte sensory systems 310a, 310b, etc. The first signal is received via a first link (e.g., link 1032a). Operation 1315B involves the display device determining a derivative of the first signal (e.g., resulting in measurement value 1034a). Operation 1315C involves display device 310a identifying analyte sensor system 308a for selection, based on the derivative of the first signal.

Turning now to FIG. 13D, embodiments involving aspects of method 1306, which includes further details regarding operation 1315C, mentioned above with reference to FIG. 13C, are shown. As shown in FIG. 13D, operation 1315C may include at operation 1320A, comparing the derivative of the first signal to a first threshold. Further, operation 1315C may include at operation 1320B determining whether the derivative of the first signal at least meets the first threshold. At operation 1320C, method 1306 may involve selecting analyte sensor system 308a for connection, based on determining that the derivative of the first signal at least meets the first threshold.

Referring again to FIG. 13C, at operation 1315D, method 1304 may include display device 310a receiving a second signal from analyte sensor system 308a (e.g., via first link 1032a or second link 1032a'). Operation 1315E involves display device 310a determining a derivative of the second signal. At operation 1315F, method 1304 may include selecting analyte sensor system 310a for connection, based on the derivative of the second signal.

FIG. 13E illustrates embodiments involving aspects of method 1308, which includes further details regarding operation 1315F, mentioned above with reference to FIG. 13C. As shown in FIG. 13E, operation 1315F may include at operation 1325A, comparing the derivative of the second signal to a second threshold. Further, operation 1315F may include at operation 1325B determining whether the derivative of the second signal at least meets the second threshold. At operation 1325C, operation 1315F optionally includes comparing the derivative to the first signal to the second threshold. At operation 1325D, operation 1315F may include determining whether the derivative of the second signal does or does not at least meet the second threshold.

FIG. 13F illustrates embodiments involving aspects of method 1312, which includes further details regarding operation 1315F, mentioned above with reference to FIG. 13C. As shown in FIG. 13F, operation 1315F may include at operation 1330A, comparing the derivative of the second signal to the first threshold. Further, operation 1315F may include at operation 1330B determining whether the derivative of the second signal at least meets or does not at least meet the first threshold.

Embodiments shown in FIG. 13G involve aspects of method 1314 for identifying a device for connection. At operation 1335A, method 1314 involves display device 310a receiving a first signal from analyte sensor system 308a among a set of analyte sensor systems 308a, 308b, etc. The first signal is received via a first link (e.g., link 1032a). Operation 1335B involves the display device obtaining a derivative of the first signal (e.g., measurement value 1034a). Method 1314 optionally includes at operation 1335C display device 310a sending a first response signal to analyte sensor system 308a via the first link. At operation 1335D, method 1314 may include display device 310a obtaining (e.g., from analyte sensor system 308a) a derivative of the first response signal. The derivative of the first response signal may be generated by and received from analyte sensor system 308a. At operation 1335E, method 1314 includes identifying analyte sensor system 310a for connection based the derivative of the first signal meeting or being above a lower threshold (e.g., lower threshold 1026). The identifying at operation 1335E may also be based on a comparison of the derivative of the first signal to the derivative of the first response signal. At operation 1335F, method 1314 optionally includes generating an indication to configure display device 310a according to a second link (e.g., link 1032a' in arrangement 1020b). Operation 1315C involves display device 310a identifying analyte sensor system 308a for selection, based on the derivative of the first signal. Operation 1335G involves display device 310a and/or analyte sensor system 308a providing the indication to the user of display device 310a.

At operation 1335H, method 1314 may include display device 310a receiving a second signal from analyte sensor system 308a (e.g., via a second link such as link 1032a'). Operation 1335J involves display device 310a obtaining a derivative of the second signal (e.g., display device 310a may generate the derivative itself of may receive the derivative from analyte sensor system 308a or another remote source). At operation 1335K, method 1314 may include display device 310a receiving a third signal from analyte sensor system 308a (e.g., via a third link). In some cases, the third link may be the same as, similar to, or within a predetermined window of values relative to the first link. Operation 1335L involves display device 310a obtaining a derivative of the third signal. At operation 1335M, method 1314 may include display device 310a selecting analyte sensor system 308 for connection, based on one or more of the derivatives of the first, second, and third signals. For example, display device 310a may select analyte sensor system 308 for connection based on one or more of: the derivative of the first signal meeting or being above an upper threshold (e.g., upper threshold 1024); the derivative of the first signal not meeting or being above the upper threshold; the derivative of the second signal meeting or being above the upper threshold; the derivative of the third signal being below the lower threshold (e.g., threshold 1026); a comparison of the derivative of second signal to the derivative of the first signal or vice versa; the derivative of the first signal meeting or exceeding the upper threshold and the derivative of the second signal being less than the derivative of the first signal; the derivative of the second signal meeting or exceeding the upper threshold and the derivative of the first signal being less than the derivative of the second signal; a comparison of the derivative of the third signal and the derivative of the second signal; etc.

Embodiments shown in FIG. 13H involve aspects of method 1316 for identifying a device for connection. At operation 1340A, method 1314 involves analyte sensor system 308a receiving a first signal from display device 310a among a set of display devices 310a, 310b, etc. The first signal is received via a first link (e.g., link 1032a). At operation 1340B, method 1316 optionally includes analyte sensor system 308a obtaining a derivative of the first signal (e.g., measurement value 1034a). At operation 1340C, method 1316 may include analyte sensor system 308a sending a response signal. At operation 1340D, method 1316 may include analyte sensor system 308a obtaining a derivative of the response signal (e.g., from display device 310a). The derivative of the response signal may be used in a similar fashion as described in connection with FIG. 13G. At operation 1340E, method 1316 includes analyte sensor system 308a selecting display device 310a for selection, based on the derivative of the first signal meeting or being above a lower threshold (e.g., lower threshold 1026). This selecting may additionally be based on the derivative of the response signal, similar to the manner described above with regard to FIG. 13G.

At operation 1340F, method 1316 may include generating an indication to configure display device 310a according to a second link (e.g., link 1032a'). The indication may be generated based on the derivative of the first signal being below an upper threshold (e.g., threshold 1024). This indication may in some cases be based on the derivative of the first signal meeting or being above an upper threshold (e.g., threshold 1024). Method 1316 may include at operation 1340G sending the indication to display device 310a for the indication to be provided to a user of display device 310a. In embodiments, analyte sensor system 308a may provide the indication directly to the user (e.g., visually, audibly, and/or haptically, etc.).

At operation 1340H, method 1316 optionally includes analyte sensor system 308a receiving a second signal from display device 310a (e.g., via the first or second link). Operation 1340J involves analyte sensor system 308a obtaining a derivative of the second signal. At operation 1340K, method 1316 may include analyte sensor system 308a receiving a third signal from display device 310a (see, e.g., the description of the third link set forth above in connection with FIG. 13G). Operation 1340L involves analyte sensor system 308a obtaining a derivative of the third signal. Embodiments or method 1316 include at operation 1340M generating a representation of user input from an accelerometer.

At operation 1340N, method 1316 optionally includes selecting display device 310a for connection. This selecting may be based on one or more of: the derivative of the first signal meeting or being above the upper threshold; the derivative of the second signal being below the lower threshold; the derivative of the second signal meeting or being above the upper threshold; the derivative of the first signal not meeting or being above the upper threshold; the derivative of the third signal being below the lower threshold; a comparison of the derivative of the second signal to the derivative of the first signal; the derivative of the first signal meeting or exceeding the upper threshold and the derivative of the second signal being less than the derivative of the third signal or vice versa; a comparison of the derivative of the third signal and the derivative of the second signal; the representation of the user input from the accelerometer; etc.

Embodiments shown in FIG. 13J involve aspects of method 1318 for identifying a device for connection. At operation 1345A, method 1318 optionally includes display device 310a prompting a user to physically contact analyte sensor system 308a in order to trigger analyte sensor system 308a to send a first signal to display device 310a. At operation 1345B, method 1318 includes display device 310a obtaining a derivative of a first signal received via a first link (e.g., first link 1032a). Operation 1345C involves display device 310a generating an identification for selection. This generating may be based on the derivative of the first signal meeting or being above a lower threshold (e.g., lower threshold 1026).

Method 1318 optionally includes at operation 1345D generating an indication to configure display device 310a according to a second link (e.g., link 1032a' in arrangement 1020b). This generating may be based on the derivative of the first signal being below an upper threshold (e.g., upper threshold 1024). Alternatives, this generating may be based on the derivative of the first signal meeting or being above the upper threshold. The indication may include, for example, an instruction for the user to move display device 310a closer to analyte sensor system 308a. At operation 1345E, method 1318 may include sending the indication to display device 310a for the indication to be provided to a user of display device 310a (e.g., via GUI 340).

At operation 1345F, embodiments of method 1318 include display device 310a obtaining a derivative of a second signal (e.g. received via the second link or the first link). At operation 1345G, method 1318 may include display device 310a obtaining a derivative of a third signal. The third signal may be received via a third link, which may be substantially similar in nature to the third link described above.

At operation 1345H, method 1318 may include presenting a prompt for the user to provide user input to an accelerometer (e.g., by tapping the accelerometer of a device housing the accelerometer, such as analyte sensor system 308a and/or display device 310a). At operation 1345J, method 1318 may include receiving a representation of user input into the accelerometer.

Method 1318 may include at operation 1345K display device 310a generating a selection for connection. This generating may be based on one or more of: the derivative of the first signal meeting or being above the upper threshold; the derivative of the second signal being below the lower threshold; the derivative of the second signal meeting or being above the upper threshold; the derivative of the first signal not meeting or being above the upper threshold; the derivative of the third signal meeting or being above the upper threshold; a comparison of the derivative of the second signal and the derivative of the first signal; the derivative of the first signal meeting or exceeding the upper threshold and the derivative of the second signal being less than the derivative of the first signal or vice versa; a comparison of the derivative of the third signal and the derivative of the second signal; the derivative of the second signal meeting or exceeding the upper threshold and the derivative of the third signal being greater than the derivative of the second signal or vice versa; etc.

Embodiments shown in FIG. 13K involve aspects of method 1322 for identifying a device for connection. At operation 1350A, method 1322 includes display device 310a obtaining a derivative of a first signal received via a first link (e.g., first link 1032a). Operation 1350B involves display device 310a obtaining a derivative of a second signal received via a second link (e.g., link 1032a'). At operation 1350C, method 1322 optionally includes calculating a difference between the derivative of the first signal and the derivative of the second signal. Operation 1350C involves generating a comparison of the derivative of the first signal and the derivative of the second signal, for example by comparing the difference or an absolute value of the difference to a predetermined value (e.g., a threshold delta). At operation 1350E, method 1322 optionally includes display device 310a obtaining a derivative of a third signal received via a third link. At operation 1350F, method 1322 may include calculating a difference between the derivative of the third signal and the derivative of the second signal. In such cases a comparison between the difference between the derivative third signal and the derivative of the second signal (e.g., a second difference), and the difference between the derivative first signal and the derivative of the second signal (e.g., a second difference), may be generated.

Operation 1350G involves display device 310a generating a selection for connection. This generating may be based on one or more of: the comparison of the derivative of the first signal and the derivative of the second signal; the comparison of the derivative of the second signal and the derivative of the third signal; the comparison of the first and second differences; etc.

In sum, with respect to the second tier of user interaction, may combinations of the above-described features may be employed depending upon the applicable use case.

A third tier or level of user interaction involved in the selection/identification of analyte sensor system 308 and/or display device 310 may be associated with a minimal amount of user interaction. In one example, an application (e.g., analyte sensor application 330) may be downloaded to or resident on display device 310 and/or in some cases analyte sensor system 308. Application 330 can monitor the duration of a connection established between display device 310 and analyte sensor system 308 and determine that analyte sensor system 308 is preferred based on the duration of the connection. For example, if display device 310 and analyte sensor system 308 remain connected for longer than a predetermined, adjustable, adaptable, or programmable amount of time (e.g., 1 hour), then application 330 may determine that display device 310 has selected/identified the appropriate analyte sensor system 380 for connection.

FIG. 13L provides an operational flow diagram illustrating various operations that may be performed in accordance with embodiments of the present disclosure, for example in connection with the third tier or level of user interaction described above. For illustration purposes, reference is made here to FIGS. 10A through 10E and numerals of components shown therein. Nevertheless, one of ordinary skill in the art will appreciate upon studying the present disclosure that like components from other FIGS. of the present disclosure may be included in the scope of the present description of FIG. 13L.

Embodiments shown in FIG. 13L involve aspects of method 1324 for identifying a device for connection. At operation 1355A, method 1334 includes display device 310a of a set of display devices 310a, 310b, etc. establishing a connection with analyte sensor system 308a of a set of analyte sensor systems 308a, 308b, etc. At operation 1355B, method 1334 includes display device 310a generating a confirmation for connection to analyte sensor system 308a based on a duration of the connection exceeding a predetermined, programmable, adaptable, and/or variable amount of time.

A fourth tier or level of user interaction involved in the selection/identification process may be associated with an adjustable, variable, and/or hybrid amount of user interaction. In one example, application 330 may be downloaded to or resident on display device 310. Operation according to the fourth tier of user interaction may involve employing combinations of the various techniques described above with respect to tiers one through three. In one specific example, the search and select method of tier one may be used and combined with the RSSI pairing described in tier two and/or other of the techniques described in connection with tiers two and three. Furthermore, the applicable amount of user interaction may be adjusted on the fly if, for example, no discoverable devices are successfully paired, if connections are interrupted unexpectedly or more often than expected, based on use input, based on performance characteristics gleaned over periods of time and from multiple systems, etc.

Some embodiments related to the tiers or levels of user interaction involved in the selection/identification process will now be described. In this respect, embodiments include display device 310 scanning for analyte sensor systems 308a, 308b, etc. in the vicinity of or discoverable to display device 310 and monitoring analyte sensor systems 308a, 308b, etc. to ascertain whether and how to establish connection with the same.

By way of example, display device 310 may receive advertisement messages from analyte sensor 308a, where one or more analyte sensor systems 308a, 308b, etc. may be in the vicinity of or discoverable to display device 310. Advertisement messages may also be received from analyte sensor systems 308b, etc. in certain situations. Display device 310 may then obtain a derivative (e.g., RSSI) of a first signal received from any of analyte sensor systems 308a, 308b, etc., and use the derivative and a condition (e.g., a threshold for the derivative) to identify and generate a selection for connection. In embodiments, the received signal may be the advertisement messages sent by sensor systems 308a, 308b, etc. Based on certain conditions, display device 310 may identify and then establish a first connection with analyte sensor system 308a using the selection for connection. For example, the first connection may be established if, during an amount of time (which, e.g., may be predetermined, adjustable, adaptable, programmable, variable, etc.), display device 310 does not receive an advertisement message from analyte sensor systems 308b, etc. other than analyte sensor system 308a or display device 310 has not obtained a derivative of a second signal that satisfies the condition, where the second signal is sent by analyte sensor systems 308b, etc. other than analyte sensor system 308a.

In other words, in this example, if, for an amount of time, only one analyte sensor system 308a is present, in the vicinity of display device 310, or otherwise discoverable or identifiable by display device 310, this may trigger connection establishment between analyte sensor system 308a and display device 310. Alternatively or additionally, where additional analyte sensor systems are present, in the vicinity of display device 310, or otherwise discoverable to display device 310, if, for an amount of time, only analyte sensor system 308a sends a signal for which the derivative satisfies a threshold, this may cause the display device to identify the analyte sensor system 308a as the preferred analyte sensor system to pair and then trigger connection establishment with analyte sensor system 308a. In specific cases, this may indicate that connection should be established between analyte sensor system 308a and display device 310 because no other sensor systems 308b, etc. have sent a strong enough signal (e.g., based on RSSI) during the amount of time to be suitable/correct for connection. It is contemplated that, pairing and subsequent data connections may be established based on various methods and processes described herein.

In some embodiments, display device 310 may continue monitoring various conditions (e.g., signal over a period of time) and obtaining a derivative of a signal from one of the other analyte sensor systems 308b, etc. while being connected to the analyte sensor system 308a and identifying and establishing a second connection between display device and the same using the derivative. For example, this may facilitate display device 310 identifying and then connecting to the most suitable or correct analyte sensor system 308b, 308c, etc., where the first connection established with analyte sensor system 308a as described above was or turned out to be perhaps not the most suitable or most correct.

In another example, it may be the case that a number of analyte sensor systems 308a, 308b, etc. present, in the vicinity of, or sending advertisement messages to display device 310 exceeds a predetermined number for display device 310. In such case, the derivative and amount of time alone may not be sufficient for identification and connection establishment purposes. As such, by way of example, display device 310 may provide a prompt to a user of display device 310, where the prompt relates to identification of the analyte sensor system and subsequent connection establishment. In one example, connection may be established between display device 310 and one of analyte sensor systems 308a, 308b, etc. based on input received at display device 310 in response to the prompt for identification. Such input may be of but is not limited to any of the various forms described above in connection with the first tier of user interaction.

Embodiments shown in FIG. 13M involve aspects of method 1326 for identifying a device for connection, including with respect to one or more of the first, second, third, and fourth tiers or levels of user interaction described above. At operation 1360A, method 1326 optionally includes presenting an instruction (e.g., via GUI 340 of display device 340 or via analyte sensor system 308a, including for example visually, audibly, and/or haptically) to a user to provide input to an accelerometer housed in analyte sensor system 308a and/or display device 310a, where the input initiates the transmission of signals (e.g., advertisement messages, pilot signals, etc.). At operation 1360B, method 1326 includes operating in one of a plurality of modes for generating a selection for connection between display device 310a and analyte sensor system 308a. The plurality of modes may correspond to the first, second, third, and so on, tiers of user interaction.

FIG. 13N illustrates embodiments involving aspects of method 1328, which includes further details regarding operation 1360B, mentioned above with reference to FIG. 13M. As shown in FIG. 13N, embodiments of operation 1360B involve operating in a first mode of the plurality of modes. The first mode may be associated with a first tier or level of user interaction. With respect to operating in the first mode, operation 1360B includes operation 1365A, which involves receiving input regarding analyte sensor system 308a that identifies analyte sensor system 308a from among a set of analyte sensor systems 308a, 308b, etc. At operation 1365B, operation 1360B may include generating the selection for connection with analyte sensor system 308a based on the received input. The input may be received at one or both of analyte sensor system 308a and display device 310a.

FIG. 13P illustrates embodiments involving aspects of method 1332, which includes further details regarding operation 1360B, mentioned above with reference to FIG. 13M. As shown in FIG. 13P, embodiments of operation 1360B involve operating in a second mode of the plurality of modes. Operating in the second mode may be associated with a second tier or level of user interaction. With respect to operating in the second mode, operation 1360B includes operation 1370A, which involves obtaining a derivative of a first signal received via a first link (e.g., link 1032a). This obtaining may be performed by either or both of analyte sensor system 308a and display device 310a. At operation 1370B, method 1332 includes generating an identification for selection based on the derivative of the first signal. At operation 1370C, method 1332 optionally includes obtaining a derivative of a second signal received over a second link (e.g., link 1032a'). Method 1332 further includes at operation 1370D generating a selection (e.g., of analyte sensor system 308a and/or display device 310a) for connection based on the identification for selection and one or more of the derivative of the second signal and user input.

In embodiments, operating in the second mode according to method 1332 further includes at operation 1370E calculating a difference between the derivative of the first signal and the derivative of the second signal. At operation 1370F, method 1332 may include comparing the difference to a threshold (e.g., predetermined, adaptable, variable, programmable, etc.). If the difference meets or exceeds the threshold, method 1332 may include confirming the selection for connection, at operation 1370G.

Figure 13Q:
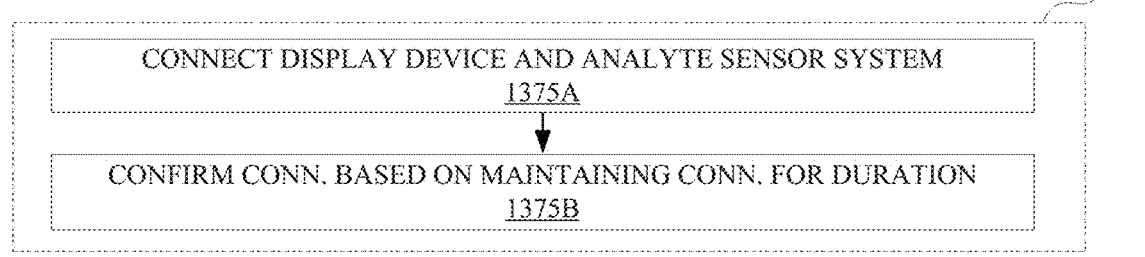
FIG. 13Q is an operational flow diagram illustrating various operations that may be performed in accordance with embodiments of the disclosure.

FIG. 13Q illustrates embodiments involving aspects of method 1334, which includes further details regarding operation 1360B, mentioned above with reference to FIG. 13M. As shown in FIG. 13Q, embodiments of operation 1360B involve operating in a third mode of the plurality of modes. The third mode of operation may be associated with a third tier or level of user interaction. With respect to operating in the third mode, operation 1360B includes operation 1375A, which involves forming a connection between display device 310a and analyte sensor system 308a. At operation 1375B, method 1334 includes generating a confirmation of the connection based on maintaining the connection for at least a predetermined, adaptable, variable, and/or programmable amount of time.

Accordingly, by flexibly employing the above-described tiers of user interaction, including in some cases combinations of the same, embodiments of the present disclosure can be optimally configured across various use cases, network and battery conditions and scenarios, user preferences and/or characteristics, and so on.

I. Authentication and Encryption

In scenarios involving the connection of two devices over a network (wireless or otherwise), authentication may be used in attempt to prevent unauthorized devices from making a connection. For example, where sensitive data is being exchanged, authentication can be used in attempt to prevent unauthorized devices or entities from gaining access to the data. In this regard, authentication protocols can be employed to establish or validate the identity of connecting devices. In some cases, authentication techniques may vary depending upon the connection model being employed. For example, if an intermittent connection model is being employed, a different authentication technique may be implemented than if a continuous connection model were being employed.

FIG. 7A is an operational flow diagram illustrating various operations that may be performed in connection with embodiments of method 700 for wireless communication of analyte data between analyte sensor system 708 and display device 710, as well as in connection with embodiments of related systems, apparatuses, and devices. In some instances, method 700 may be used in connection with authenticating display device 710 and/or analyte sensor system 708 (e.g., in a two-way authentication), such that analyte data may be exchanged under authorized conditions.

The various tasks performed in connection with the procedure illustrated in FIG. 7A may be performed, for example, by a processor executing instructions embodied in non-transitory computer-readable medium. The tasks or operations performed in connection with the procedure may be performed by hardware, software, firmware, or any combination thereof incorporated into one or more of computing devices, such as one or more of analyte sensor system 708 and display devices 710. It will be appreciated upon studying the present disclosure that the procedure may include any number of additional or alternative tasks or operations. The operations shown by way of example in FIG. 7A need not be performed in the illustrated order, and the procedure may be incorporated into a more comprehensive procedure or process having additional functionality not described in detail herein with specific reference to FIG. 7A.

In some examples described below, the analyte values are glucose values based on one or more measurements made by analyte sensor 10 (with reference to FIGS. 1A, 2A, and 2B) and/or sensor 405 (with reference to FIG. 4) for illustration purposes. Nevertheless, it should be understood upon studying the present disclosure that the analyte values can be any other analyte value described herein. The wireless data communication between analyte sensor system 708 and one or more of display devices 710 may happen periodically, at times separated by an update interval denoted "$T_{interval}$" that may correspond to a time duration between two consecutive wireless communication sessions between the transceiver 360 of analyte sensor system 708 and transceiver 320 of display device 710 (with reference to FIG. 3B). Alternatively or additionally, the update interval may be thought of as a period of obtaining and sending a recently measured glucose value. Transmitting advertisement signals or messages, establishing a data connection (e.g., a communication channel) and requesting and sending data may occur during wireless communication sessions each lasting an active time or period denoted "$T_{Active}$" within an update interval $T_{interval}$. One caveat here is that $T_{interval}$ and/or $T_{Active}$ can vary as between sessions. In between two consecutive wireless communication sessions, components of analyte sensor system 708 (e.g., transceiver 360) may enter LPM or a like mode, such as an inactive or sleep mode for an inactive period denoted as "$T_{inactive}$". This may enable the conservation of battery life and/or reduce peak voltage requirements, for example.

Accordingly, in some authentication and connection schemes used for the communication of analyte data, analyte sensor system 708 may periodically connect to display device 710. For example, communication session 720 may implement one such authentication and connection scheme. More specifically, as shown in FIG. 7A, communication session 720 may be implemented during a time interval $T_{interval}$. As alluded to above, $T_{interval}$ may include an active portion corresponding to $T_{Active}$ and an inactive portion corresponding to $T_{Inactive}$. Generally speaking, during $T_{Active}$, analyte sensor system 708 and display device 710 are connected and actively exchanging messaging (e.g., pursuant to operation 705 and/or sub-operations thereof), though there may be periods during $T_{Active}$ during which analyte sensor system 708 enters LPM or the like, as described above.

In terms of connecting, in example implementations, the analyte sensor system may transmit one or more advertisement messages at operation 705 during communication session 720. An advertisement message may be considered as an invitation for display device 710 to establish a data connection with analyte sensor system 708 (e.g., via transceiver 360). FIG. 8 illustrates an example structure for advertisement message 800 that in some cases may be transmitted for purposes of establishing a connection between two devices, according to various aspects of the present disclosure (e.g., with reference to FIG. 7A, at operation 705, and the like). The transmitted advertisement messages may then be received at display devices 710 (e.g., via transceiver 320). For purposes of authentication, the analyte sensor system may share an identification number with the display device, where the identification number is associated with the analyte sensor system.

In some embodiments illustrated by way of example in FIG. 7A, it is assumed that analyte sensor system 708 should engage in an initial system setup because, for example, analyte sensor system 8 has been recently turned on for the first time and/or is currently not paired with any display devices 710. By way of illustration, a user of display device 710 can identify a new or never-been used analyte sensor system 708 to be paired with display device 710 by entering identification information (e.g., a serial number) associated with analyte sensor system 708 via a custom application (e.g., application 330) running on display device 710 using a GUI 340 that may be presented on display 345 (e.g., a touchscreen display).

As alluded to above, during communication session 720, an authentication procedure may need to be performed in connection with a data connection process corresponding to operation 705b and/or a data transmission process corresponding to operation 705d. To establish a data connection with analyte sensor system 708, display device 710 may listen or scan continuously until an advertisement message transmitted by analyte sensor system 708 is received. Once analyte sensor system begins transmitting advertisement messages at operation 705a, it may take one, two, or more advertisement messages for display device 710 to receive an advertisement message and responds thereto. In some embodiments, analyte sensor system 708 stops sending additional advertisement messages once one of display devices 710 receives an advertisement message and responds thereto, for example, via an acknowledgement and/or by sending a connection request (e.g., as part of operation 705b). In other embodiments, analyte sensor system may continue to send additional advertisement messages even after receiving a response from one display devices 710, so that another of display devices 710 may receive and respond to one of the additional advertisement messages.

Accordingly, operation 705b may involve analyte sensor system receiving a connection request from display device 710 and responding thereto by granting or denying the request. If analyte sensor system 708 grant the connection request, an acknowledgement or other message may be transmitted to display device 710 as part of operation 705b. Then, a data connection between analyte sensor system 708 and display device 710 may be established. Nevertheless, according to operation 705c, an authentication procedure may be employed before data is actually exchanged at operation 705d. Authentication may involve the exchange of various messages, including challenge and hash values and signaling related thereto, between the analyte sensor system and the display device, in accordance with a one-way or two-way handshake process.

For example, as part of operation 705c, display device 710 may request a challenge value from analyte sensor system 708. In response to the request, analyte sensor system 708 sends a challenge value to display device 710. The display device may then generate a hash value based on both the challenge value received from analyte sensor system 708 and identification information associated with analyte sensor system 708. As yet another part of operation 705c, display device may then transmit the hash value to analyte sensor system 708. Display device 710 may transmit additional information as well (e.g., information related to the type of display device 710, whether display device is medical device or a personal electronic device, for example).

Analyte sensor system 708 (e.g., via transceiver 360) receives the hash value from display device 710, decodes the identification information from the hash value, and verifies that the received identification information matches identification information associated with the analyte sensor system 708, which may have been previously stored in storage 365 of analyte sensor system 708, such as during manufacturing/setup of analyte sensor system 708. Analyte sensor system 708 may also validate the hash value received from display device 710 by comparing the received hash value to a mirror hash value analyte system sensor 708 generated (e.g., based on the challenge value send previously). Upon verification, analyte sensor system 708 may send a signal confirming a successful authentication to display device 710. Once authenticated, the analyte sensor system 8 and display device 110, 120, 130, 140 may exchange information to determine how data will be exchanged (e.g., a specific frequency, time slot assignment, encryption, etc.). FIG. 12C also illustrates aspects of the above-described handshake process.

The above-described process may be thought of as a one-way authentication procedure. During a two-way authentication procedure (not shown specifically in FIG. 7A, but see, e.g., FIG. 12B), additional operations may take place as part of operation 705c. For example, in addition to the hash value transmitted from display device 710 to analyte sensor system 708, display device 710 can also send a new challenge value to analyte sensor system 708. Then, analyte sensor system 708 may generate an additional hash value using the new challenge value received from display device 710, and transmit the additional hash value back to display device 710. Upon receiving the additional hash value, display device 710 can validate the additional hash value. In example implementations, the validation of the additional hash value received from analyte sensor system 708 may be performed by display device 710 by comparing the received additional hash value to a mirror hash value that display device 710 generated (e.g., based on the new challenge value sent previously). In this manner, two-way authentication can be performed between analyte sensor system 708 and display device 710. Following authentication, data can be exchanged with the understanding that the data is being received by and from a valid (or approved) device. It will be appreciated that many various of operation 705*c* and sub-operations thereof are contemplated in the present disclosure. For example, analyte sensor system 708 and display device 710 may reverse roles with respect to operation 705*c*. That is, operation 705*c* may be initiated by analyte sensor system 708 requesting a challenge value from display device 710, thus triggering the above-described operations but in the reverse direction as between analyte sensor system 708 and display device 710.

Further, communication session 720 may also include exchanging an application key between analyte sensor system 708 and display device 710. For example, in the above-mentioned authentication process, the identification information associated with the analyte sensor system 708 may be used as an application key in order to encrypt data and other signaling transmitted between analyte sensor system 708 and display device 710. By the exchange of challenge and hash values described in connection with operation 705*c*, such an application key may effectively be shared between analyte sensor system 708 and display device 710. Thus, in embodiments, of the present disclosure, the application key may be used for both authentication and encryption purposes. The application key may be a random number in some cases. In some instances, the application key may literally be exchanged (whether encrypted or unencrypted) between analyte sensor system 708 and display device 710 (e.g., as a challenge value etc.). In other cases, the actual application key is not exchanged, but by exchanging the challenge and hash values, the application key can be derived respectively by the analyte sensor system 708 and display device 710. A such, the application key may be used for example by analyte sensor system 708 to encrypt analyte data for transmission to display device 710, and display device 710 may use the application key to decrypt the received analyte data. Of course, other exchanged information may likewise be encrypted.

In example deployments, the application key may be generated at a software/application level of analyte sensor system 708 and/or display device 710. In some such deployments, only the application key may be exchanged (i.e., no exchange of the hash and challenges) and then used for authentication and encryption. The application key may be, for example, a randomly generated number. Alternatively, the software-generated application key may be exchanged in addition to the hash/challenge values, for authentication and encryption purposes. Encryption, for example as described above, may be performed concurrently during authentication, or after authentication, or both, in various embodiments.

The application key, in example embodiments, may be obtained from server system 334. In some such embodiments, storage 334*b* may include identification information associated with analyte sensor system 708 (e.g., an identification number) and the application key. The identification information may simply be mapped to the application key, and/or the identification information may be hashed or otherwise combined with the application key in some cases. Display device 710 may request such information by sending a message to server system 334, where the message includes at least some of the identification information. By way of example, display device 710 may send an advertisement message to server system 334 that includes an identification number for a specific analyte sensor system 708 (this identification number may have been received through at least a partial pairing with analyte sensor system 708). In response, server system 334 may provide display device 710 with the application key for the relevant analyte sensor system 708. After receiving the application key, display device 710 may use the key to authenticate/communicate with analyte sensor system 708 and decrypt encrypted information received therefrom (and also encrypt information being sent thereto).

In some cases, analyte sensor system 708 may contain a mapping (e.g., in storage 365) that associates particular application keys with particular display devices 710 based on the identification information of analyte sensor system 708. As such, authentication can be performed based on the application key received by display device 710 from server system 334, and the application key can be used for encryption/decryption of analyte data sent by analyte sensor system 708. In this way, authorization regarding communications (including sharing of encrypted data) between analyte sensor 708 and a given display device 710 can be managed/established. In other cases, for example where the application key is associated with an identification number of analyte sensor system 708, the analyte sensor system 708 may derive an expected application key based on the identification number, and compare the expected application key to information regarding the application key as received from display device 710, in order to determine that data exchange with display device 710 is authorized.

Alternatively or in addition, exchanging the application key may be done directly between analyte sensor system 708 and display device 710 using WiFi or NFC. Exchanging the application key may involve sharing the application key between analyte sensor system 708 and display device 710 in a secluded and/or safe area (such as in a user's home) so as to avoid interception by a foreign or unknown device. Additionally, the application key may in turn be encrypted with an additional key for added security. Characteristics of the key may be based on one or more of the type of data to be encrypted with; the network environment; and user settings. By way of example, the encryption method applied using the application key may be based on the Advanced Encryption Standard (AES) 128. Alternatively or in addition, a proprietary encryption method may be used. Such an encryption method may be run on display device 710, including in some cases on an application (e.g., application 330) running on display device 710.

The complexity of the encryption scheme employed may be based on the level of desired security. For example, different levels of complexity may be employed for different types of data. A more complex encryption scheme may be employed for the exchange of analyte data (e.g., estimated glucose values) as compared to, for example, calibration data or time synchronization data. Characteristics of the application key may also be varied in different scenarios. By way of example, the length of the application key may be chosen based on the amount of security desired and/or on the encryption scheme or protocol being employed. The encryption scheme in some cases may employ salts that may be used in connection with the exchange of hash values, and the salts may be encrypted and exchanged between analyte sensor system 708 and display device 710.

The application key may also be modified from time to time, e.g., on an event-triggered, random, and/or periodic basis. This may be done responsive to, for example, the passage of a predetermined amount of time; analyte sensor system 708 of a subsystem thereof or display device 710 being restarted; a trigger related to another device (e.g., a rouge device) attempting to connect to analyte sensor system 708; and/or user input. For example, the application key may be configured to expire after the passage of a predetermined amount of time and may be refreshed or renewed thereafter. Alternatively or in addition, if analyte sensor system 708 and/or display device 710 restarts or experiences an interruption, a new application/encryption key may be generated and shared between analyte sensor system 708 and display device 710. In some cases, the application key may be modified according to a key rotation scheme. Moreover, the frequency with which the application key may be modified may be varied according to the level of desired security (e.g., with more frequent modification corresponding to increased level of security).

With further reference to FIG. 7A, after completion of the authentication process according to operation 705c, analyte sensor system 708 and connected display device 710 engage in data communication at operation 705d, during which connected display device 710 may request and receive desired information (e.g., analyte data, control information, identification information, and/or instruction) from analyte sensor system 708. When data communication at operation 705d is completed, the data connection may be terminated at operation 715 (e.g., by closing the established communication channel). At this point, transceiver 360 and/or processor 380 of analyte sensor system 708 (or with reference to FIG. 4, radio 425 and processor 420) can be deactivated. This may be done, for example, by causing transceiver 360 and/or processor 380 (etc.) to enter a LPM mode or the like, e.g., a sleep or inactive mode. In some embodiments, transceiver 360 (or radio 425) is completely powered down during a sleep mode. In other embodiments, transceiver 360 is in a low power mode using only a small fraction (e.g., 1-10%) of the normal current/power. In FIG. 7A, this period generally corresponding to operation 715 is denoted as $T_{Inactive}$.

FIG. 7B provides, by way of illustration, an example of typical intermittent communications schemes between analyte sensor system 708 and display devices 710, according to method 702 for wireless communication of analyte data between analyte sensor system 708 and display device 710. As shown in FIG. 7B, method 702 involves multiple occurrences of communication session 720. Communication session 720 occurs, having a length in time of $T_{interval}$. Subsequently, communication session 720' occurs, having a length in time of $T_{interval}'$, which may be the same as or different from $T_{interval}$, in various embodiments described herein.

It will thus be appreciated that in typical intermittent communications schemes between analyte sensor system 708 and display devices 710, the above-mentioned connection and authentication process may be repeated periodically (e.g., according to a time denoted by $T_{interval}$) for each subsequent data communication. For example, the process may involve the exchange of up to 20 or more messages before any data (e.g., analyte values) are communicated. Furthermore, the process may restart if exchanged messages fail or packets are dropped. This may result in drain of the battery of analyte sensor system 708.

Accordingly, aspects of the present disclosure include an improved authentication scheme. The improved authentication scheme of the present disclosure reduces the amount of messaging exchanged between analyte sensor system 708 and display device 710 connecting thereto, while maintaining a sufficient level of security for analyte and other data communicated between analyte sensor system 708 and display device 710. In this manner, the complexity and network load involved with communications between analyte sensor system 708 and display device 710 may be reduced, thus increasing the overall reliability of and power consumption involved with such communications. Generally, the improved authentication scheme involves stepping through the above-mentioned authentication process of communication session 720 (e.g., at operation 705c) that uses at least an application key for an authentication and connection between analyte sensor system 708 and display device 710, as well as for data encryption in embodiments, and then bypassing the authentication process in subsequent connections and/or communication sessions.

It will thus be appreciated that in some intermittent communications schemes employing the intermittent connection model between analyte sensor system 708 and display devices 710, the above-mentioned connection and authentication process may be repeated periodically (e.g., according to a time denoted by $T_{interval}$) for each subsequent data communication. For example, the process may involve the exchange of up to 20 or more messages before any data (e.g., analyte values) are communicated. Furthermore, the process may restart if exchanged messages fail or packets are dropped. This may result in drain of the battery of analyte sensor system 708.

Likewise, it will be appreciated that in some continuously connected communication schemes employing the continuous connection model between analyte sensor system 708 and display device 710, the connection and authentication process may be repeated, for example if connection is lost and subsequently reacquired, if the connection parameters are updated, if the connection model is switched from the intermittent connection model to the continuous connection model, etc. With brief reference to FIG. 7J for purposes of illustration, method 722 for communication of analyte data according to a continuous connection model includes various messages that may be communicated before any data is exchanged. For example, advertisements messages may be sent at operation 795a, data connection and connection parameter messaging may then be exchanged at operation 795b, and then authentication/encryption related messages may then be exchanged at operation 795c.

Thus, for various connection models, there exists a need to streamline the authentication process in order to reduce or in some cases eliminate repeating the authentication process at regular intervals or when otherwise avoidable, while still maintaining adequate levels of security and data protection.

Accordingly, aspects of the present disclosure include improved authentication schemes for both the intermittent connection model and the continuous connection model. The improved authentication schemes of the present disclosure reduce the amount of messaging exchanged between analyte sensor system 708 and display device 710 connecting thereto, while maintaining a sufficient level of security for analyte and other data communicated between analyte sensor system 708 and display device 710. In this manner, the complexity and network load involved with communications between analyte sensor system 708 and display device 710 may be reduced, thus increasing the overall reliability of and power consumption involved with such communications.

Generally, the improved authentication scheme involves stepping through the above-mentioned authentication process of communication session 720 (e.g., at operation 705c) or communication session 780 (e.g., at operation 795c) that uses at least an application key for an authentication and connection between analyte sensor system 708 and display device 710, as well as for data encryption in embodiments, and then bypassing the authentication process in subsequent connections, communication sessions, and/or exchanges of data. For example, and as will be described herein, for the intermittent connection model and/or the continuous connection model, the authentication process may be bypassed in subsequent connections and/or communication sessions. And in some cases, for example, for the continuous connection model, repeating the authentication process can be avoided by maintaining an authenticated connection following initiation authentication. With respect to both the intermittent and continuous connection models, an application key used for authentication purposes can also be used for encryption/encoding of data subsequently exchanged.

Referring now to FIG. 7C, method 704 for wireless communication of analyte data between analyte sensor system 708 and display device 710 is illustrated in connection with implementations of the improved authentication scheme alluded to above. Method 704 includes establishing a first connection between analyte sensor system 708 and display device 710. This may occur in connection with communication session 720. As such, establishing the first connection can include performing a two-way authentication between analyte sensor system 708 and display device 710 (e.g., based on the exchange of information related to the application key, at operation 705c for example).

Method 704 also includes establishing a second connection between analyte sensor system and display device 710. As shown in FIG. 7C, in embodiments, this may occur in connection with communication session 725. More specifically, as shown in FIG. 7C, communication session 725 may be implemented during a time interval $T_{interval}'$, which may be the same as or different from $T_{interval}$. $T_{interval}'$ may include an active portion corresponding to $T_{Active}'$ and an inactive portion corresponding to $T_{Inactive}'$. During $T_{Active}'$, communication session 725 may involve operation 735 and sub-operations thereof.

Here it should be noted that in communication session 725, establishing the second connection need not include the authentication process that may be included in communication session 720 (e.g., at operation 705c). Rather, at operations 735a and 735b, advertisement and connection may occur, and upon establishing the second connection in this manner, method 704 includes data transmission at operation 735d. More specifically, at operation 735d, analyte sensor system 708 may transmit, for example, encrypted analyte values and other data to display device 710, in response to a request for data sent by display device 710. The encrypted analyte value may have been encrypted using the application key used for authentication in the authentication process in communication session 720, and/or may involve the use of encryption key. Encrypting the transmissions using an application key can maintain privacy/security even in the absence of authentication procedures being performed during communication session 725. In other words, in communication session 725, the above-described authentication process, including the two-way authentication, can be bypassed. In this manner, the number of messages exchanged in establishing the second connection (and hence the power consumption) may be reduced. Moreover, the application key may also be used to decrypt encrypted data exchanged between analyte sensor 708 and display device 710. For example, during operation 735d, display device 710 may decrypt encrypted data (e.g., encrypted analyte data, which may include encrypted glucose data) received from analyte sensor 708, and vice versa.

When data communication at operation 735d is completed, the data connection may be terminated at operation 745. At this point, transceiver 360 and/or processor 380 of analyte sensor system 708 (or with reference to FIG. 4, radio 425 and processor 420) can be deactivated. In FIG. 7C, this period generally corresponding to operation 745 is denoted as $T_{Inactive}'$.

At this juncture, it should be noted that regardless of the connection model employed or which of the above-described communication sessions is used, the application key may be updated and/or shared between devices at predetermined, configurable, variable, programmable, and/or adaptable intervals. In some cases, during connection establishment or subsequent thereto, display device 710 and analyte sensor system 708 may negotiate an interval at which the application key is to be shared and/or updated.

FIG. 7D illustrates an example implementation of method 706 for wireless communication of analyte data between analyte sensor system 708 and display device 710 in connection with implementations of the improved authentication scheme discussed to above. As shown in FIG. 7D, method 706 involves communication session 720. Communication session 720 occurs, having a length in time of $T_{interval}$. Subsequently, an instance of communication session 725 occurs, having a length in time of $T_{interval}'$, which may be the same as or different from $T_{interval}$, in various embodiments described herein. Then, an instance of communication session 725' occurs, having a length in time of $T_{interval}''$, which may be the same as or different from $T_{interval}'$, in various embodiments described herein. Communication session 725' may be substantially similar to communication 725, aside from potentially having a different interval length.

By following communication session 720 with one or more instances of communications 725, 725', etc., the overall number of messages exchanged during communication of analyte data (and hence the power consumption) may be reduced. It will be noted here, however, that in some cases, method 706 may involve reverting back to communication session 720 after implementing communication session 725, 725', etc. for one or more connections. This may be done adaptively or based on user inputs, and may be done for security purposes based on network conditions or triggered events (e.g., a rogue device attempting to connect). In other words, reverting back to communication session 720 from time to time, for example to exchange information regarding a new/modified application key, as discussed above, may enable increased security.

Referring now to FIG. 7E, method 712 for wireless communication of analyte data between analyte sensor system 708 and display device 710 is illustrated in connection with implementations of the improved authentication scheme alluded to above. Method 712 includes establishing a first connection between analyte sensor system 708 and display device 710. This may occur in connection with communication session 720 corresponding to $T_{interval}$. As such, establishing the first connection can include performing a two-way authentication between analyte sensor system 708 and display device 710.

Method 712 also includes establishing communication session 740 that may be implemented during a time interval $T_{interval}'$ which may be the same as or different from $T_{interval}$. $T_{interval}'$ may include an active portion corresponding to $T_{Active}'$ and an inactive portion corresponding to $T_{Inactive}'$. During $T_{Active}'$, communication session 740 may involve operation 765 and sub-operations thereof.

Here it should be noted that communication session 740 may not include establishment of a second connection between analyte sensor system 708 and display device 710. For example, communication session 740 as illustrated does not include the data connection aspects of operation 735b shown in FIG. 7C in connection with communication session 725. Nor does communication session 740 as illustrated include the authentication process that may be included in communication session 720 (e.g., at operation 705c). Rather, at operation 765a, method 712 involves sending one or more advertisement messages to display device 710.

As such, as part of communication session 740, analyte sensor system 708 may transmit a first advertisement message (e.g., during operation 765a). The first advertisement message may include at least a first portion of the analyte value. The analyte value may but need not have been encrypted (e.g., using an application key) prior to transmission. In other words, with regard to communication session 740, analyte sensor system 708 may use one or more advertisement messages to transmit encrypted or non-encrypted analyte values or analyte data and/or other signaling (such as, e.g., timing and control information) in addition to other information that may be included in advertisement messages.

In some cases, as will be described in further detail with reference to FIG. 8 for example, an advertisement message may take the form of a packet. By way of example, the analyte value (whether encrypted or not) may be included in a reserved field in the advertisement message packet. Specifically, in some cases, a manufacturing data or other slot in the packet may include a reserved field of 1 byte or more. This reserved field is one example of how an analyte data or other form of payload may be included in the advertisement message. As alluded to above, in addition or instead of the analyte value, the advertisement message may also include a time stamp associated with the analyte value.

In some example implementations, however, there may be insufficient space in the advertisement message/packet for both the analyte value and the associated time stamp. In some such cases, method 712 may involve breaking the payload, which may include the (encrypted) analyte value and associated data, into multiple parts. The first advertisement message may then indicate that a second advertisement message includes a second portion of the analyte value and/or associated data. The first advertisement may so indicate by tagging the first portion of the payload, where the tag represents to display device 710 receiving the advertisement message that a subsequent advertisement message may include a second portion of the payload.

The above-mentioned tagging of the first portion of the payload may take various forms. For example, a relatively simple tag may indicate only that a subsequent advertisement message includes a second portion of the payload. A relatively more complex tag may additionally indicate the type of content that will be included in the second portion of the payload, or how the payload has been split or distributed amongst advertisement messages. The first portion may, for example, include an encrypted analyte value, and the tag applied may indicate that the subsequent advertisement message will include the associated time stamp.

In other words, according to communication session 740, advertisement messages may be transmitted during operation 765a for the purposes of communicating analyte data to display devices 710. With the payload encrypted using an application key, privacy/security can be maintained even in the absence of authentication procedures being performed during communication session 740. In other words, in communication session 740, the above-described authentication process, including the two-way authentication, can be bypassed. Likewise, because the payload is included in the advertisement messages, the data connection request and data transmission processes (e.g., operations 735b and 735d, respectively) can also be bypassed or avoided. In this manner, the number of messages exchanged in pursuant to communication session 740 (and hence the power consumption) may be reduced relatively to other communication sessions.

Returning to FIG. 7E, communication session 740 may also include, at operation 765b, display device 710 acknowledging receipt of the advertisement message(s) sent during operation 765a, by sending an acknowledgement (ACK) message. In some cases this acknowledgement may trigger a data connection process between analyte sensor system 708 and the acknowledging display device 710. For example, analyte sensor system 708 may in turn send an ACK to display device 710 and thus form a connection. The data connection process established in connection with operation 765b, in example deployments, may be used for renewing the application and/or encryption key(s) and/or for exchanging other data, such as, for example, calibration data, timing information, and the like. When communications at operation 765 are completed, data transmission may be terminated at operation 775. At this point, transceiver 360 and/or processor 380 of analyte sensor system 708 (or with reference to FIG. 4, radio 425 and processor 420) can be deactivated. In FIG. 7E, this period generally corresponding to operation 775 is denoted as $T_{Inactive}'$.

FIG. 7F illustrates an example implementation of method 714 for wireless communication of analyte data between analyte sensor system 708 and display device 710 in connection with implementations of the improved authentication scheme discussed above. As shown in FIG. 7F, method 714 involves communication session 720. Communication session 720 occurs, having a length in time of $T_{interval}$. Subsequently, an instance of communication session 740 occurs, having a length in time of $T_{interval}'$, which may be the same as or different from $T_{interval}$, in various embodiments described herein. Then, an instance of communication session 740' occurs, having a length in time of $T_{interval}''$, which may be the same as or different from $T_{interval}'$, in various embodiments described herein. Communication session 725' may be substantially similar to communication 725, aside from potentially having a different interval length.

By following communication session 720 with one or more instances of communication sessions 740, 740', etc., the overall number of messages exchanged during communication of analyte data (and hence the power consumption) may be reduced. It will be noted here, however, that in some cases, method 714 may involve reverting back to communication session 720 after implementing communication session 740, 740', etc. for one or more connections. This may be done adaptively or based on user inputs, and may be done for security purposes based on network conditions or triggered events (e.g., a rogue device attempting to connect). In other words, reverting back to communication session 720 from time to time may enable increased security.

FIG. 7G illustrates an example implementation of method 716 for wireless communication of analyte data between analyte sensor system 708 and display device 710 in connection with implementations of the improved authentication scheme discussed above. As shown in FIG. 7G, method 716 involves communication session 760. In example deployments of method 716, communication session 760 involve the exchange of information related to pairing, application keys, and timing parameters related to potential communications between analyte sensor system 708 and display device 710 using a first wireless protocol. But such an exchange may be streamlined by using certain types of wireless protocols. By way of example, the first wireless protocol may be WiFi or Near Field Communication (NFC). In other examples, the first wireless protocol may utilize RFID, another proximity based wireless connection, or the like.

In this manner, authentication, such as may occur using BLE (e.g., according to operation 705c with reference to FIG. 7A) may be circumvented, along with the typically associated exchange of numerous messages. By way of illustration, NFC may be used between analyte sensor system 708 and display device 710 in order to exchange information such as pairing, encryption information (e.g., application key information and/or scheme), advertising parameters (including, e.g., frequency/period, duration, timing, and/or nature of advertisements), connection interval information, and information related to display device 710 (e.g., type of display device, preferences, etc.). The exchanged information may then be used by display device 710 to receive and decrypt (where applicable) analyte values transmitted by analyte sensor system 708. Using NFC to exchange authentication related information in this fashion may extend the battery life of analyte sensor system 708 and increase the reliability of communications between analyte sensor system 708 and display device 710.

As shown in FIG. 7G, after communication session 760 is used to exchange information, communication session 740 occurs, having a length in time of $T_{interval}$. In some deployments, communication session 740, including, for example, establishing connection and transmitting the analyte values, may be carried out using a second wireless protocol different than the first wireless protocol used in connection with communication session 760. The second wireless protocol may be Bluetooth Low Energy (BLE), for example. Communication session 740 occurs, having a length in time of $T_{interval}'$, which may be the same as or different from $T_{interval}$, in various embodiments described herein. Then, an instance of communication session 740' may occur, having a length in time of $T_{interval}''$, which may be the same as or different from $T_{interval}'$, in various embodiments described herein.

With further reference to FIG. 7G, by following using communication session 760 before one or more instances of communication sessions 740, 740', etc., the overall number of messages exchanged for communication of analyte data (and hence the power consumption) may be reduced, particularly with regard to the above-described authentication process and exchange of pairing information and the like. It will be noted here, however, that in some cases, method 716 may involve reverting back to communication session 760 after implementing communication session 740, 740', etc. for one or more connections. This may be done adaptively or based on user inputs, and may be done for security purposes based on network conditions or triggered events (e.g., a rogue device attempting to connect). In other words, reverting back to communication session 760 from time to time may enable increased security.

FIG. 7H illustrates an example implementation of method 718 for wireless communication of analyte data between analyte sensor system 708 and display device 710 in connection with implementations of the improved authentication scheme discussed above. In some respects, method 718 is substantially similar method 716. One difference is that after implementing communication session 760, method 718 involves implementing communication session 725 rather than communication session 740. Subsequently, an instance of communication session 725' may occur, having a length in time of $T_{interval}''$, which may be the same as or different from $T_{interval}'$, in various embodiments described herein. It will be appreciated, however, that various of the above-described communications sessions (e.g., 720, 725, 740, 760) may be mixed and matched in accordance with the above-described methods.

Figure 14:
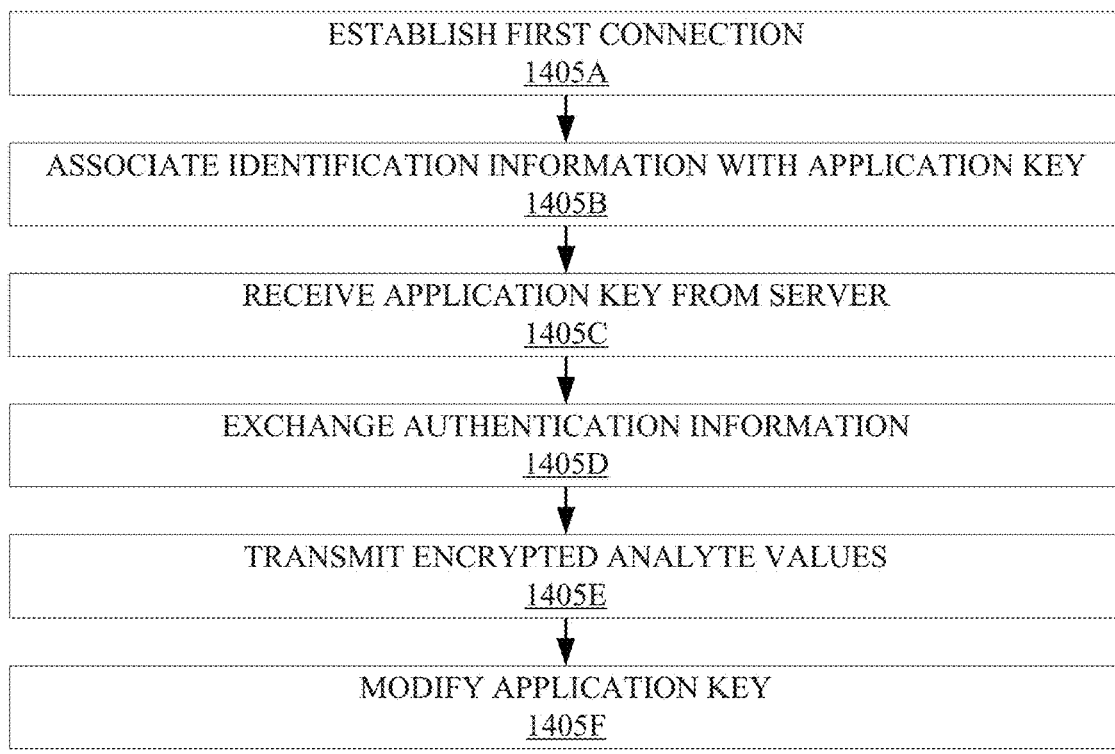
FIG. 14 is an operational flow diagram illustrating various operations that may be performed in accordance with embodiments of the disclosure.

Improved authentication schemes may also be facilitated by the user of a remote service or cloud server, including, for example, aspects of server system 334 with reference to FIG. 3A. In this regard, FIG. 14 is an operational flow diagram illustrating various operations that may be performed in accordance with embodiments of the present disclosure, for example in connection with methods for wireless communication of analyte data. For illustration purposes, reference is made here to FIGS. 3A and 7A through 7K, FIG. 10D, as well as numerals of components shown therein. Nevertheless, one of ordinary skill in the art will appreciate upon studying the present disclosure that like components from other FIGS. of the present disclosure may be included in the scope of the present description of FIG. 14.

Embodiments shown in FIG. 14 involve aspects of method 1400 for wireless communication of analyte data. Method 1300 includes at operation 1405A establishing a first connection between analyte sensor system 308 and display device 310, where analyte sensor system 308 is one of a set of analyte sensor systems 308a, 308b, etc. (see, e.g., FIG. 10D). At operation 1405B, method 1400 optionally includes server system 334 associating, for each analyte sensor system (e.g., 308) of the set of analyte sensor systems (e.g., 308a, 308b, etc., with reference to FIG. 10D), an application key with identification information for the analyte sensor system 308. At operation 1405C, method 1400 optionally includes display device 308 receiving the application key from server system 334 associated with the identification information for the analyte sensor system 308. For example, the application key may be received by display device 310 from server system 334 responsive to display device 310 providing server system 334 with the identification information for analyte sensor system 308.

At operation 1405D, method 1400 includes, during the first connection, exchanging information related to authentication between analyte sensor system 308 and display device 310. The information related to authentication includes the application key. At operation 1405E, method 1400 includes analyte sensor system 308 transmitting an encrypted analyte value to display device 310, where the encrypted analyte value has been generated based on the application key. At operation 1405F, method 1400 may include modifying the application key responsive to one or more of: the passage of a predetermined, adaptable, variable, and/or programmable amount of time; analyte sensor system 308 and/or display device 310 being restarted or cycling through sleep or power/shut down modes; a trigger related to another device (e.g., a rouge device) attempting to connect to analyte sensor system 308; and user input.

J. Intermittent Connection Model

As alluded to above, aspects of the present disclosure also include various connected models for communications between analyte sensor system 708 and display devices 710. One connection model for communications may be referred to as a connect/disconnect or intermittent/periodic connection model. In accordance with an intermittent or connect/disconnect scheme, communications between analyte sensor system 708 and display device 710 may be periodic or intermittent in nature, following a defined or event-based/asynchronous schedule. For example, display device 710 may establish connection with analyte sensor system 708 periodically (e.g., once every five minutes) in order to receive analyte and other data from analyte sensor system 708 and/or in order to transmit data thereto.

It may be the case, however, that even if display device 710 successfully connects to analyte sensor system 708 (which is not guaranteed, per se), analyte sensor system 708 may not have data ready to be transferred. In such a case, the length of time between successive receipts of data by display device 710 may be increased. This may in some instances result in in stale measurements data, such as analyte data or values, being received by and presented at display device 710. Nevertheless, in some use cases, the intermittent connection model may result in power savings relative to other connection models. Accordingly, if battery power is a primary concern relative to packet loss and/or latency, then continuous connection model may be preferable to the intermittent connection model. Additionally, it will be appreciated that according to the intermittent connection model, two display devices 710 in example implementations are not connected to analyte sensor system 708 at the same time. Rather, different display devices 710 in some cases connect for different, limited amounts of time. Which display devices 710 can connect and when such devices can connect to analyte sensor system 708 may be controlled, for example, using a list such as a whitelist.

K. Continuous Connection Model

In some situations, the intermittent model may be suitable and/or preferable. One such situation may be if a user prefers to monitor an analyte value using multiple display devices. For example, if the user has Type 1 diabetes, monitoring of analyte (e.g., glucose) data may be relatively more critical, and hence, multiple display devices may be employed for greater coverage/redundancy. In other circumstances, however, A continuous connection model may be suitable and/or preferable. For example, a user may prefer to or may be limited to using a single display device (e.g., for convenience purposes, or if the user is traveling, or if other display devices become unavailable, e.g., if the devices break, run out of battery, are lost, are unable to connect/function, or are being used primarily for other purposes). Other circumstances may also include, for example, that the user has Type 2 diabetes and thus monitoring of glucose data may be relatively less critical, such that multiple display devices need not be employed for redundancy/coverage purposes.

In yet additional circumstances, an analyte sensor system such as analyte sensor system 708 may be used for a relatively short amount of time (e.g., two weeks). In such a case, analyte sensor system 708 may be less sensitive to battery/power consumption constraints and instead a higher priority may be placed on reliability and/or latency. The continuous connection model, as described in further detail herein, may be preferable overall in such instances. Additionally, attempting to connect and/or disconnect to a display device such as display device 710 after a relatively long amount of time may in some ways be burdensome to analyte sensor system 708 (e.g., in terms of power consumption or computing/processing/radio resources). The continuous connection model may be provided as a way of diminishing and/or removing the burdens that may be associated with such connection/disconnection.

Accordingly, the present disclosure includes employing a continuous connection model. Such a connection model may in some cases reduce latency between the collection of analyte data at analyte sensor system 708 and the transmission of such data to display devices 710 connecting thereto, while maintaining a sufficiently low power consumption for analyte sensor system 708. Furthermore, the continuous connection model may increase reliability and predictability of the connection between analyte sensor system 708 and display device 710. At a high level, the continuous connection model can involve an initial pairing between analyte sensor system 708 and display device 710, after which analyte sensor system 708 and display device 710 remain connected, essentially not closing the connection or disconnecting. That is, connection and the exchange of data is not done periodically or intermittently as with the intermittent connection model (e.g., as discussed with reference to FIGS. 7A-7D etc.), but instead, the connected devices periodically exchange messaging to maintain the connection. Once data is available at analyte sensor system 708 (e.g., gathered by sensor 405 and/or processed by processor 420, with the note that FIG. 4 as shown pertains primarily to the intermittent connection model but may be modified as described hereinabove to pertain to the continuous connection model as well), the data can be transmitted to display device 710 in near in at least near real time. In this manner, the overall accuracy and responsiveness of communications related to analyte data may be increased. An additional advantage associated with the continuous connection model is that analyte sensor system 708 may be enabled to better mitigate against interferences caused by undesired devices (e.g., in some cases, undesired display devices 710) seeking to connect with analyte sensor system 708. Hence, reliability of data exchange may be increased.

In this connection, FIG. 7J illustrates example implementations of method 722 for wireless communication of analyte data between analyte sensor system 708 and display device 710 according to example implementations of the continuous connection model alluded to above.

Communication session 780 can be initiated in connection with method 722. More specifically, as shown in FIG. 7J, communication session 780 may involve operations 795a through 795g and 795a', though in embodiments, not all of these operations are performed. With respect to the continuous connection model, analyte data may be dropped or lost if the connection between the display device and the analyte sensor system is not maintained. This may in turn lead to improper or inaccurate representation of analyte information, such as estimated glucose values. Thus, embodiments herein related to the continuous connection model involve sustaining and/or maintaining a connection established between analyte sensor system 708 and display device 710. Further, with respect to maintaining the connection, it may at times be useful to monitor the connection status to derive and/or provide an indication regarding the same. One way this may be done is using connection parameters, as will be described further herein with reference to FIG. 7J.

At operation 795a, method 722 may involve activating a transmitter of analyte sensor system 708 and/or transmitting advertisement messages. This transmission of advertisement messages may be substantially similar to operation 705a described above. The advertisement messages transmitted at operation 795a may be received by one or more display devices 710.

At operation 795b a connection may be established between analyte sensor system and a responding display device 710. As shown in FIG. 7J, typically in response to receiving one or more advertisement messages, display device 710 can request a connection with analyte sensor system 708 as part of operation 795*b*. Also as part of operation 795*b*, connection parameters can be exchanged between analyte sensory system 708 and display device 710 in response to the connection request being sent. In this regard, analyte sensor system 708 and/or display device 710 may propose and set up a set of connection parameters upon which aspects of a connection between analyte sensor system 708 and display device 710 may be based.

Examples of connection parameters include a connection interval (in some cases referred to herein as a pinging interval), slave latency, and supervision timeout. Analyte sensor system 708 and/or display device 710 can use one or more of such connection parameters to maintain a connection lasting as long as is desired for continuously monitoring analyte levels, as well as to modify characteristics of the connection depending on various criteria, such as, for example criteria related to analyte sensor system 708, display device 710, the connection between the two devices (e.g., link quality), and/or user preferences or feedback. As shown in FIG. 7J, connection parameters can be exchanged and determined, by way of example, in conjunction with connection establishment (e.g., in relation to operation 795*b*) vis-à-vis analyte sensor system 708 and display device 710. In connection with operation 795*b*, analyte sensor system 708 and display device 710 in example implementations negotiate and ultimately agree (or disagree) on aspects of the set of connection parameters.

For example, with reference to operation 795*b*, if display device 710 requests a data connection with analyte sensor system 708, connection parameters may be sent from analyte sensor system 708 and proposed to display device 710, or vice versa. In other examples, connection parameters may be sent/proposed irrespective of whether or not a data connection request has been received. Display device 710 (or analyte sensor system 708) can then, for example, either accept or deny the proposed connection parameters. If display device 710 (or analyte sensor system 708) accepts or approves the proposed connection parameters, the proposed conditions related to the connection parameters can then be applied to the connection ultimately established between analyte sensor system 708 and display device 710. Such connection parameters may include, by way of example, a connection (or pinging) interval, a slave latency connection parameter, and a supervision timeout parameter. The conditions specified for each of these connection parameters may involve values, ranges of values for the connection parameters, and/or a set of rules or guidelines for one or more of the connection parameters.

Aspects of the connection interval parameter will now be described. In embodiments employing the continuous connection model, connection between, for example, analyte sensor system 708 and display device 710, can be maintained by the periodic exchange of messaging (e.g., ping messages). This is illustrated in FIG. J by operation 795*e*, for example. At operation 795*e*, messing is periodically exchanged between analyte sensor system 708 and display device 710 in order to maintain a connection. For example, such messages may be transmitted to/from analyte sensor system 708 simply to indicate that the transmitting device is still connected to the receiving device (e.g., a "ping"). This may be done periodically according to a predetermined connection interval (e.g., once every 2 seconds or any amount of time) as defined by the connection parameters. The established period may in some case be selected/varied according to criteria such as network parameters or conditions, the type or other characteristic of display device 710 connected to analyte sensor system 708, the frequency with which data is being transmitted or generated/gathered by analyte sensor system 708, and so on.

Through the periodic exchange of messaging, connection between analyte sensor system 708 and display device 710 may be maintained, thus allowing for gathered analyte data to be exchanged in at least near real time. The connection can be maintained for as long as is needed, including in some instances through the lifetime of analyte sensor system 708. While the connection is maintained, analyte sensor system 708 in some examples does not send advertisement messages. Rather, the connection may continue unless it becomes necessary to issue a disconnect command or until certain criteria are not met, as will be described herein.

In other words, analyte sensor system 708 (and/or display device 710) can send a ping message to display device 710 (and/or analyte sensor system 708) according to a time interval (e.g., periodically). In response, the receiving device, for example display device 710 (and/or analyte sensor system 708) may then respond by sending an acknowledgment message (ACK) acknowledging reception of the ping message. Alternatively, the receiving device, for example display device 710 (and/or analyte sensor system 708) may send a negative acknowledgement (NACK) indicating no ping message was received. A NACK may be sent, for example, if no ping message was received when expected according to the established connection interval (e.g., within a predetermined amount of time). In this manner, the exchanged messaging can indicate to analyte sensory system 708 and/or display device 710 that the connection is maintained and ongoing (e.g., if an ACK is sent at operation 795*e*), or is not being maintained as expected (e.g., if a NACK or no response is sent at operation 795*e*). As will be described in further detail herein, if no response to a sent ping message is provided, and/or if a NACK message is sent, this may indicate that an established connection should be terminated and/or that other action(s) should be taken.

With respect to the connection interval, as mentioned previously, a value or range of values can be established in conjunction with connection establishment vis-à-vis analyte sensor system 708 and display device 710. For example, in some embodiments, every connection interval, analyte sensor system 708 may send and/or receive a ping message and then receive and/or send a response thereto in order to maintain the connection according to operation 795*e*, as mentioned above. A smaller connection interval with more frequent ping messages exchanged may reduce packet loss between analyte sensor system 708 and display device 710, whereas a larger connection interval may allow for more packet loss. Each ping message can in some cases be configured to indicate when the next ping message will be sent (e.g., the scheduled amount of time between the sequential exchange of ping messages).

The device proposing this connection parameter in conjunction with operation 795*b* (which may be analyte sensor system 708 or display device 710), may propose a value and/or range of values for the connection interval that may be based on a number of factors. For example, the value or range for the connection interval may be based on the expected lifespan of analyte sensor system 708. The expected lifespan may be a suggested length of use, for example, as determined by the manufacturer of analyte sensor system 708, and/or this value may be programmed into analyte sensory system 708 as part of the manufacturing process. In another example, the user may determine and/or set this value during product setup or at another time. Additionally, display device 710 may also be subject to power, computational, memory, and/or data constraints or other factors that make suitable a particular value and/or range of values for the connection interval. Accordingly, in example implementations, the connection interval can be based on factors drawn from one or both of analyte sensor system 708 and display device 710.

As mentioned, in example embodiments, the expected lifespan of analyte sensor system 708 and/or the expected battery life of analyte sensor system 708 may play a part in the determination of the value and/or range of values for the connection interval. In embodiments, for example, the connection interval may be proportional to the expected lifespan of analyte sensor system 708. That is, a higher value for the connection interval (e.g., ping messages sent less often) may use less battery life and thus may be more likely to sustain a longer expected lifespan. Likewise, a lower value for the connection interval (e.g., ping messages sent more often) may use more battery life and thus may be more likely to sustain a longer expected lifespan. If, for example, the expected lifespan for analyte sensor system 708 were 14 days, analyte sensor system 708 may be willing to set the connection interval to between 2 and 10 seconds. It will be appreciated that these numbers are provide by way of illustration only.

In some cases, the value and/or range of connection intervals to be employed can be negotiated as between analyte sensor system 708 and display device 710. It should be noted, however, that in some cases analyte sensor system 708 may dominate the negotiation. For example, if analyte sensory system 708 proposes a value and/or range for the connection interval, display device 710 can accept the proposed value, can choose a value for the connection interval according to the range provided by analyte sensor system 708, or can simply reject the range. Alternatively or in addition, display device 710 can respond in other ways besides an acceptance or denial of the provided range. For example, display device 710 may indicate that its battery will soon run out and thus it will not accept the range of connection intervals nor will it accept connection to analyte sensor system 708. In this regard, display device 710 and/or analyte sensor system 708 may include power management circuitry for monitoring local battery conditions. The power management circuitry may provide input that may be used for setting, proposing, and/or updating values for connection parameters. For example, a processor (e.g., processor 335 or 380, with reference to FIG. 3B) may use input from power management circuitry as a trigger point for setting, modifying, or updating connection parameters. In example embodiments, display device 710 may provide a counter response including a different range of connection intervals based on various conditions, as will be described below. Here, it will be appreciated that the proposal of the connection interval or other connection parameters could likewise be provided by display device 710 to analyte sensory 708, and that the response to the proposal could be provided from analyte sensor system 708 to display device 710.

Moreover, the proposed and/or counter-proposed connection interval may be based on various factors, including for example the current analyte value and/or a trend in the analyte value. For example, analyte sensor system 708 and/or display device 710 may monitor the analyte value and/or a trend thereof (derivative, second derivative, etc.) and request a shorter connection interval when the value falls outside a given threshold window. This may provide for a more responsive connection during critical times (e.g., as defined by the analyte value). In example embodiments, the value/range for the connection interval may be based on information derived about the user, whether based on user input or gathered based on monitoring the user over time. For example, the value/range may be based on the user's physical characteristics, health conditions, and/or medical history (including, for example, historically measured analyte values).

With respect to the slave latency connection parameter, this connection parameter may relate to the number of dropped packets or ping messages (e.g., to be sent at operation 795*e* according to the connection interval describe above) that is allowable before the connection may be terminated or considered terminated, or before a condition related to the termination of the connection is triggered. In embodiments, slave latency can be employed such that, for example, even if a certain number of packets or ping messages are missed/dropped, the connection can still be considered active. This connection parameter may be exchanged during connection establishment in conjunction with operation 795*b* and/or may be modified subsequently (e.g., in conjunction with operation 795*f*). Slave latency can be based on or modified depending upon various factors, such a quality of service (QoS), time of day, location of analyte sensor system 708, location and/or type of display device 710, battery power of analyte sensor system 708 and/or display device 710, expected lifespan of analyte sensor system 708, current and/or historical analyte values or trends therein, user characteristics, etc.). The slave latency may be proposed/counter-proposed in conjunction with connection establishment as a value and/or range of values, and may in some cases be defined according to a set of rules. One or both of analyte sensory system 708 and display device 710 can define and/or update the slave latency.

In some cases, if the slave latency is triggered (e.g., a sufficient number of packets or ping messages are missed), the response can be to modify one or more connection parameters so as to attempt to avoid slave latency being triggered going forward. For example, the system can adapt the connection parameters on the fly in order to maintain the connection between analyte sensor system 708 and display device 710. Such a response may be based on a predetermined set of conditions (e.g., QoS, time of day, location of analyte sensor system 708, location and/or type of display device 710, battery power of analyte sensor system 708 and/or display device 710, expected lifespan of analyte sensor system 708, current and/or historical analyte values or trends therein, user characteristics, etc.), in example embodiments.

With respect to the supervision timeout parameter, this parameter may be used to determine how strictly to enforce slave latency. For example, a larger supervision timeout will allow a more friendly null packet exchange for maintaining the connection. For example, supervision timeout may monitor slave latency and can allow for violations of slave latency to be ignored in some cases, based on various factors, for example power considerations and/or radio conditions, etc. In other words, in some cases, even if enough ping messages are missed such that slave latency is triggered, supervision timeout may be used to effectively override the consequences (e.g., disconnection of analyte sensor system 708 and display device 710, etc.). As with other connection parameters, the supervision timeout parameter may be proposed/counter-proposed in conjunction with connection establishment at operation 795*b* as a value and/or range of values, and may in some cases be defined according to a set of rules. One or both of analyte sensor system 708 and display device 710 can define and/or update (e.g., at operation 7950 the supervision timeout parameter. As with other connection parameters, supervision timeout may in some cases be managed by the system without user intervention, including without user visibility into the same, or in other examples may be managed by or at least visible to the user.

In some cases, supervision timeout can be modified (e.g., in conjunction with operation 7950 so as to attempt to avoid slave latency being triggered going forward. For example, the system can adapt the supervision timeout connection parameter on the fly in order to manage the connection between analyte sensor system 708 and display device 710. Such a response may be based on a predetermined set of conditions (e.g., QoS, time of day, location of analyte sensor system 708, location and/or type of display device 710, battery power of analyte sensor system 708 and/or display device 710, expected lifespan of analyte sensor system 708, current and/or historical analyte values or trends therein, user characteristics, etc.), in example embodiments.

Referring further to FIG. 7J, a connection decision can be made as an additional aspect of operation 795*b*, either by analyte sensor system 708 or display device 710 or both, and connection can thus be established. In other cases, as alluded to above, if in conjunction with connection establishment, analyte sensor system 708 and display device 710 do not agree on a set of connection parameters, it may be the case that no connection is established. That is, the connection decision may be not to establish a connection between analyte sensor system 708 and display device. In other cases, the connection decision may be for analyte sensor system 708 and display device 710 to connect using a connection model other than the continuous connection model (e.g., to connect using the intermittent connection model). In such a case, communication session 780 may terminate and another communication session (e.g., communication session 720 or 725) may be initiated.

Following a connection decision that results in establishing a connection of analyte sensor system 708 and display device 710, at operation 795*c*, method 722 may involve authentication. For example, authentication may include the exchange of hash and/or challenge values, and may be a one-way or two-way authentication, similar to operation 705*c* described with regard to FIG. 7A. Additionally, it should be noted here that authentication may be bypassed or otherwise not performed in some cases. Display device 710, for example, may already have been authenticated for exchanging data with analyte sensory system 708. As such, in some cases, data can be exchanged between analyte sensor system 708 and display device 710 under trusted conditions, and/or with encryption applied (e.g., using an application key known to analyte sensor system 708 and display device 710), at operation 795*d* without authentication being performed within communication session 780.

At operation 795*d*, embodiments of method 722 include exchanging data between analyte sensor system 708 and display device 710. For example, display device 710 can request data from analyte sensor system 708 and, in response, analyte sensor system 708 can send data. The requested/sent data may be analyte data (e.g., glucose values) and/or control signaling. Exchanged data may be encrypted in some cases, for example using an application key. The application key may have been shared between analyte sensor system 708 and display device 710 in conjunction with operation 795*c* and/or may have been received using other means (e.g., from a cloud server).

With respect to the continuous connection model, operation 795*d* may be repeated periodically, as data becomes available for transmission (e.g., in some cases aperiodically), and/or whenever data is requested to be exchanged (e.g., on-demand). The exchange of data according to operation 795*d* may be interspersed with the exchange of other messaging, such as, for example, ping messaging, exchanged between analyte sensor system 708 and display device 710. In FIG. 7J, this is represented by way of example using the operations intervening operation 795*d* and 795*d'*.

In embodiments, connection parameters agreed upon in conjunction with connection establishment (e.g., as part of operation 795*b*) can be updated/modified subsequently, for example, after a connection decision is made. Accordingly, at operation 795*f*, method 722 may involve updating one or more of the connection parameters. Updating the connection parameters may involve analyte sensory system 708 and/or display device 710 proposing or requesting a modification to an existing connection parameter. In another example, a value for a connection parameter that has not been previously established can be proposed/requested in conjunction with operation 795*f*. The proposal/request can result in several outcomes, including, for example, denial, acceptance, or counterproposal.

Furthermore, operation 795*f* may involve a negotiation between analyte sensor system 708 and display device 710 regarding the update to the connection parameters. As is described in relation to exchanging connection parameters in conjunction with operation 795*b*, connection parameters can be proposed/requested etc. in the form of ranges and/or values. It will also be appreciated that various aspects of operation 795*b* can be applied with respect to operation 795*f*. Various scenarios are possible in this regard. For example, one or both of analyte sensor system 708 and display device 710 may propose and/or request a modification to/of one or more of the connection parameters. A counterproposal for a connection parameter value (or range) may be provided in response to the proposal/request. In some cases, if the proposal/request or counterproposal is denied, connection according to the connection parameters previously established may be maintained/continued. Acceptances and denials can be conveyed in the form of ACK/NACK messages, as shown at operation 795*f*, where, for example, an ACK represents an acceptable of the proposal/request and a NACK represents a denial and/or counterproposal. In this regard, the NACK may contain or be accompanied by additional information such as the counterproposal. In some cases, the counterproposal may include a range of acceptable values for the connection parameter. Once analyte sensor system 708 and display device 710 agree upon a set of modified or unmodified connection parameters, connection can resume, including operations 795*d*, 795*e*, and 795*d'*.

If, however, analyte sensor system 708 and display device 710 are not able to agree upon modified values or ranges for the connection parameters and/or do not agree to maintain a connection based on the previously established connection parameters, analyte sensor system 708 and display device 710 may terminate the connection or may switch from the continuous connection model to another connection model, such as, e.g., the intermittent connection model. For example, display device 710 may receive a notification indicating that analyte sensor system 708 is available for a new or modified connection according to certain connection parameter values to be used with the continuous connection model, but these values may result in a shorter lifetime (e.g., 6 days instead of 14 days). Thus, analyte sensor system 708 may suggest that the intermittent connection model can be employed to extend the lifetime. In some but not all cases with respect to the intermittent connection model, the values for connection parameters are not updated or modified over the lifespan of analyte sensor system 708. In other cases, however, the connection parameters may be updated/modified, for example, in a fashion substantially similar to that described in connection with operation 795*f*. Moreover, once connection is established according to the new or modified connection parameters, the connection parameters can be subsequently maintained/modified (e.g., according to operation 795*f*, as described above).

With respect to updating the connection parameters according to operation 795*f*, in some cases, an application running on display device 710 (e.g., application 330) may not have access to the connection parameters in order to make modifications thereto. For example, access to these connection parameters may lie with the operating system of display device 710 rather than the application. In such cases, however, the application can cause display device 710 to request analyte sensor system 708 to request the connection parameters pertaining to display device 710 to be updated. In embodiments, this request can be made by display device 710 sending a value for a connection parameter (e.g., in a message or packet) to analyte sensor system 708. Analyte sensor system 708 can then send a message to display device 710 to update and/or apply the value for the connection parameter(s), and the connection parameter(s) can be updated accordingly (e.g., via the operating system of display device 710). In this manner, the application can be used to configure the connection parameters. In implementations, analyte sensor system 708 makes a determination regarding whether the proposed value for the connection parameter is acceptable, and sends the update message to display device 710 responsive to determining that the proposed value is acceptable. Here, reference is made to FIG. 15B described in detail elsewhere herein. Alternatively or additionally, analyte sensor system 708 may reject the proposed value and so indicate, or may provide a counterproposal for the value. The display device 710 may accept the counter-proposed value as a matter of course, or may make a further determination as to whether the counter-proposed value is acceptable (e.g., based on various criteria as discussed herein). In example embodiments, GUI control can be provided to a user through GUI 340 display device 710, thus allowing the user to attempt manual setup and/or update of connection parameters. As shown in FIG. 3G, for example, access to connection parameters may be provided through option 314*c*.

As shown at operation 795*g*, in some cases, the connection between analyte sensor system 708 and display device 710 may be terminated or lost. There may be various causes for this. For example, and as alluded to above, it may be that analyte sensor system 708 and display device 710 are unable to agree on a proposed or modified set of connection parameters (e.g., in conjunction with operations 795*b* and/or 795*o*, or that ping messages are not responded to such that, e.g., slave latency is violated. For example, if display device 710 goes out of range from analyte sensor system 708, ACK messages may not be received in response to ping messages. In another example, display device 710, may be turned off, or the link to display device 710 may be degraded temporarily or permanently, such that the exchange of messaging according to operation 795*e* is unfeasible.

In response to connection being lost at operation 795*g*, analyte sensor system 708 may send advertisement messages according to operation 795*a*'. In accordance with example embodiments of the continuous connection model, upon analyte sensor system 708 and display device 710 becoming disconnected, analyte sensor system 708 may resume sending advertisement messages in some cases at least almost immediately. A faster advertising pattern may be employed, for example, during a limited window in order to reacquire connection with display device 710. By way of illustration, with reference to FIG. 9, advertisement message interval 915 may be reduced such that advertisement messages 920 are sent more frequently during advertisement duration 910.

Furthermore, the user may not be aware that there has been a disconnection according to operation 795*g*. This may in some cases lead to packet drop or data loss. Thus, in some cases, analyte sensor system 708 may resume advertisement automatically without user intervention. Alternatively or in addition, advertisement can be resumed based on a trigger provided via NFC by the user. For example, the user may receive a notification via GUI 340 that connection has been lost. The notification may prompt the user to bring display device 710 into relatively close proximity with analyte sensor system 708, such that NFC signaling can be exchanged. Other techniques can be employed to manually trigger resumed advertisement. For example, the user may be prompted to tap analyte sensor system 708. In other example, alternatively or in addition to NFC- and accelerometer-based triggers, the user may be prompted to bring display device 710 into relatively close proximity with analyte sensor system such that RSSI-based triggers can resume advertisement messaging. Once resumed, advertisement can be made to occur for an indefinite amount of time and for relatively long duration windows.

In some cases, when advertising is resumed, a very short advertisement period (or advertisement message interval 915, with reference to FIG. 9) can be employed for a first advertisement duration 910 and then a longer period (or advertisement message interval) can be employed for a second advertisement duration (e.g., in connection with advertisement duration structure 935', with reference to FIG. 9). If there is still no connection established with display device 710, analyte sensor system 708 can, for example, then opt to switch to the intermittent connection model, as will be described in further detail below. Alternatively, analyte sensor system 708 can terminate advertising and remain disconnected. In such a case, analyte sensor system 708 may send a message to display device 710 that causes the user to be prompted to provide a trigger for analyte sensor system 708 to resume advertisement (e.g., at operation 795*a*'). As mentioned, such a trigger may be provided in the form of NFC, for example. Upon receiving the trigger, analyte sensor system 708 can resume advertising with a short advertisement message period to increase the chances of connecting to display device 710. Such an advertisement scheme may likewise be employed when analyte sensor system 708 is first activated, in order to connect to display device 710. Alternatively or in addition, analyte sensor system 708 may advertise for connection to other known display devices 710 with the hopes that they will form a more reliable connection.

According to embodiments of the continuous connection model, when display device 710 is not connected to analyte sensor system 708 (e.g., where the connection has been terminated or otherwise), display device 710 continuously scans for analyte sensor system 708 (e.g., by looking for advertisement messages sent by analyte sensor system 708). In such cases, analyte sensor system 708 may advertise as much as is permitted under the circumstances. For example, analyte sensor system 708 may employ a smaller advertisement messaging period, according to which advertisement messages are sent more frequently. In this manner, analyte sensor system 708 can attempt to quickly acquire or reacquire connection with display device 710 previously connected to analyte sensor system 708, or another display device 710. The extent or intensity of advertising may in some instances be limited, however, based on battery constraints of analyte sensor system 708. Thus, analyte sensor system 708 may send advertisement messages according to periodic advertisement windows (e.g., as may be employed in connection with the intermittent connection model), such as described herein with reference to FIG. 9.

In some cases, the continuous connection model may be considered to be state based. That is, for example, if display device 710 attempts to read an analyte value from analyte sensor system 708, display device 710 would only receive the analyte data when there is a new or updated value available. Some examples of the continuous connection model, however, may be only partially state based. That is, in some cases, a two-way communication may take place. For example, display device 710 may request analyte data or other information, such as sensor information, or may send data to analyte sensor system 708. Based on the request/sent data, analyte sensor system 708 may provide new analyte data along with updated calibration data and updated sensor data, etc. In other examples, as alluded to above, analyte sensor system 708 may send data when new data is available (e.g., if battery power is low). That is, analyte sensor system 708 may operate in more of a state based manner.

Figure 18:
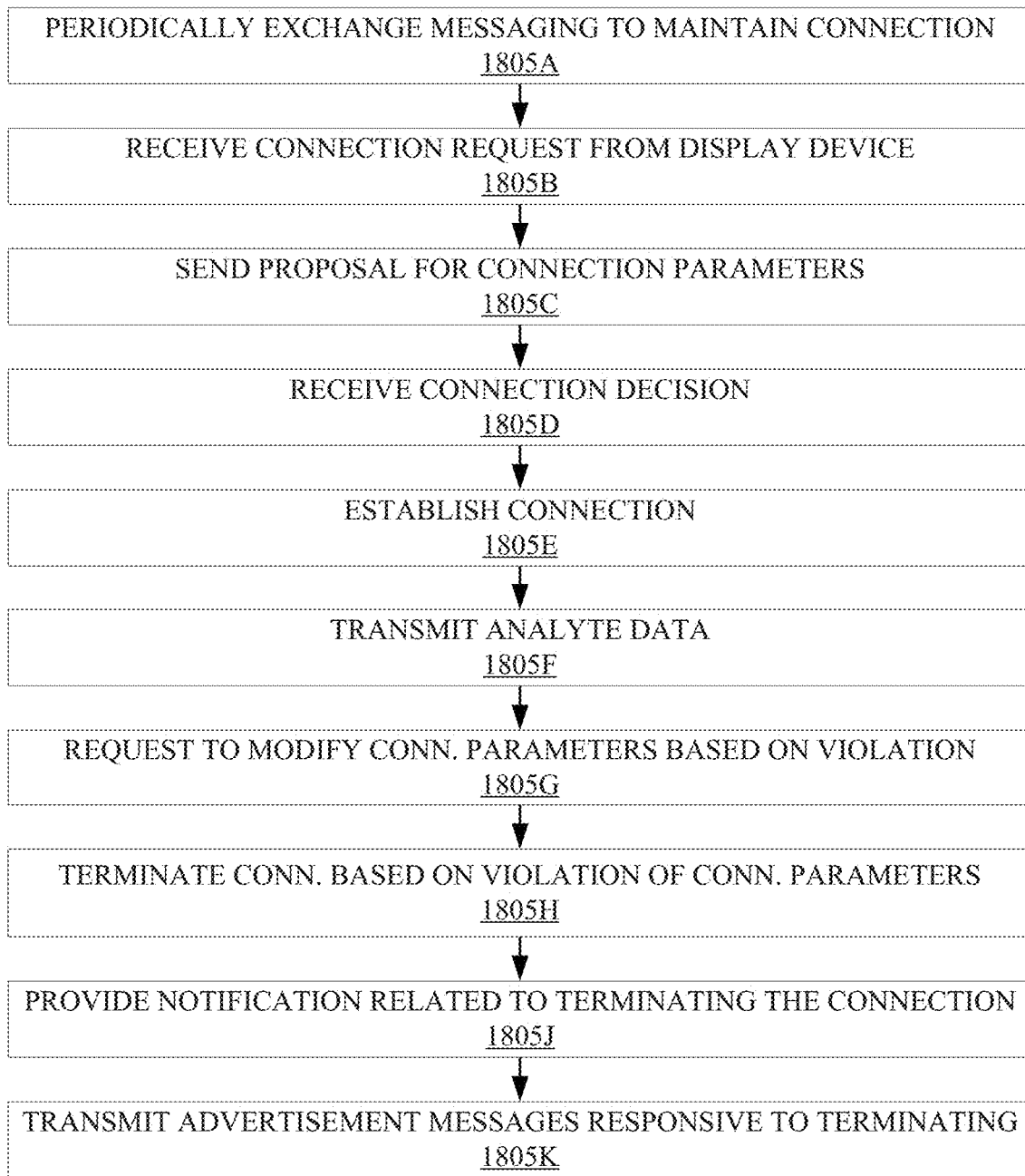
FIG. 18 is an operational flow diagram illustrating various operations that may be performed in accordance with embodiments of the disclosure.

With further regard to the continuous connection model, FIG. 18 provides an operational flow diagram illustrating various operations that may be performed in accordance with embodiments of the present disclosure. For illustration purposes, reference is made here to FIG. 7J, as well as numerals of components shown therein. Nevertheless, one of ordinary skill in the art will appreciate upon studying the present disclosure that like components from other FIGS. of the present disclosure may be included in the scope of the present description of FIG. 18.

Embodiments shown in FIG. 18 involve aspects of method 1800 for wireless communication of analyte data, including, for operating according to a continuous connection model as described in instances herein. In this regard, method 1800 includes at operation 1805A analyte sensor system 708 periodically exchanging messaging with display device 710 such that analyte sensor system 708 and display device 710 maintain a connection. Here, reference is made by way of example to operation 795e shown in FIG. 7J.

At operation 1805B, method 1800 may involve receiving a connection request from display device 710. Here reference is made by way of example to operation 795b shown in FIG. 7J. Method 1800 optionally includes at operation 1805C analyte sensor system 708 sending a proposal for a set of connection parameters to display device 710, responsive to receiving the connection request. Here again reference is made by way of example to operation 795b, and also to operation 795f. At operation 1805D, method 1800 may include receiving a connection decision from display device 710, based on the proposal. Here again reference is made by way of example to operation 795b, and also to operation 795f.

It should be understood that operations 1805B through 1805D can be performed before, after, and/or during the periodic exchange of messaging of operation 1805A. For example, operations 1805B through 1805D may be executed in connection with establishing a connection that is maintained according to operation 1805A. Alternatively or additionally, operations 1805B through 1805D may be executed in connection with modifying a connection maintained according to operation 1805A. In this regard, periodically exchanging messaging at operation 1805A may be done based on the set of connection parameters proposed at operation 1805C, responsive to the connection decision received at operation 1805D including an acceptance of the proposal and/or a connection being established. Operation 1805E involves establishing a connection between analyte sensor system 708 and display device 710 based on the connection decision received at operation 1805D. Accordingly, operation 1805E may precede operation 1805A in some cases. For example, with reference to FIG. 7J, see operations 795b and 795e. At operation 1805F, method 1800 includes analyte sensor system 708 transmitting analyte data to display device while analyte sensor system 708 and display device 710 maintain the connection. Reference is made here by way of example to operation 795d in FIG. 7J.

At operation 1805G, method 1800 may include requesting to modify one or more of the connection parameters, responsive to a violation of one or more of the connection parameters (e.g., connection interval, slave latency, and supervision timeout). Here, reference is made by way of example to operation 795f. At operation 1805H method 1800 may include terminating the connection, based on a violation of one or more of the connection parameters. At operation 1805J, method 1800 optionally includes providing a notification related to terminating the connection (e.g., visual, audible, and/or haptic). At operation 1805K, method 1800 may include analyte sensor system 708 transmitting advertisement messages, responsive to terminating the connection at operation 1805H. Here, reference is made to operation 795a' in FIG. 7J.

Figure 19:
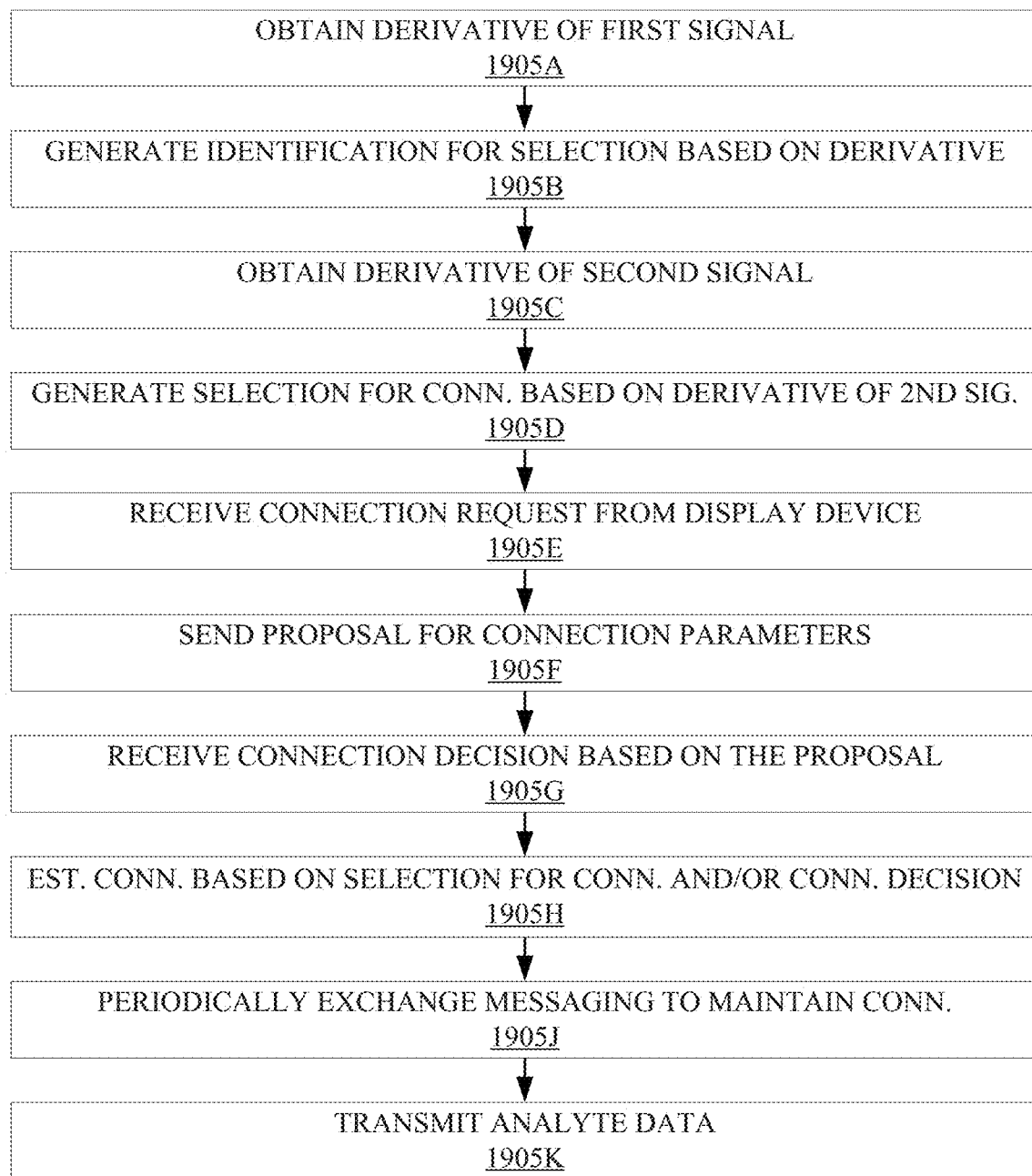
FIG. 19 is an operational flow diagram illustrating various operations that may be performed in accordance with embodiments of the disclosure.

With further regard to the continuous connection model, FIG. 19 provides an operational flow diagram illustrating various operations that may be performed in accordance with embodiments of the present disclosure. For illustration purposes, reference is made here to FIG. 7J and FIGS. 10A through 10E, as well as numerals of components shown therein. Nevertheless, one of ordinary skill in the art will appreciate upon studying the present disclosure that like components from other FIGS. of the present disclosure may be included in the scope of the present description of FIG. 19.

Embodiments shown in FIG. 19 involve aspects of method 1900 for wireless communication of analyte data, including, for operating according to a identifying and/or selecting a device for connection according to the continuous connection model as described in instances herein. In this regard, method 1900 includes at operation 1905A obtaining a derivative of a first signal received via a first link (e.g., link 1032a). At operation 1905B, method 1900 includes generating an identification for selection, based on the derivative of the first signal. Operation 1905C involves obtaining a derivative of a second signal received via a second link (e.g., 1032a'). Operation 1905D involves generating a selection for connection, based on the derivative of the second signal.

At operation 1905E, method 1900 optionally includes receiving a connection request from display device 710. Here, reference is made by way of example to operation 795b in FIG. 7J. Method 1900 may include at operation 1905F analyte sensor system 710 sending a proposal for a set of connection parameters to display device 710, responsive to receiving the connection request. Here, reference is made by way of example to operations 795b and 795f in FIG. 7J. At operation 1905G, method 1900 may include receiving a connection decision from display device 710, based on the proposal. Reference is made here by way of example to operations 795*b* and 795*f*/795*g* in FIG. 7J.

At operation 1905H, method 1900 includes establishing a connection between display device 710 and analyte sensor system 708, based on the selection for connection and/or the connection decision. For example, the connection may be established responsive to the connection decision including an acceptance of the proposal for the set of connection parameters send at operation 1905F. Reference is made here by way of example to operations 795*b* and 795*f* in FIG. 7J. Operation 1905J involves periodically exchanging messaging to maintain the connection, for example based on the set of connection parameters. Reference is made here by way of example to operation 795*e* in FIG. 7J. At operation 1905K, method 1900 includes analyte sensor system 710 transmitting analyte data to display device 710 while analyte sensor system 708 and display device 710 maintain the connection.

Figure 20:
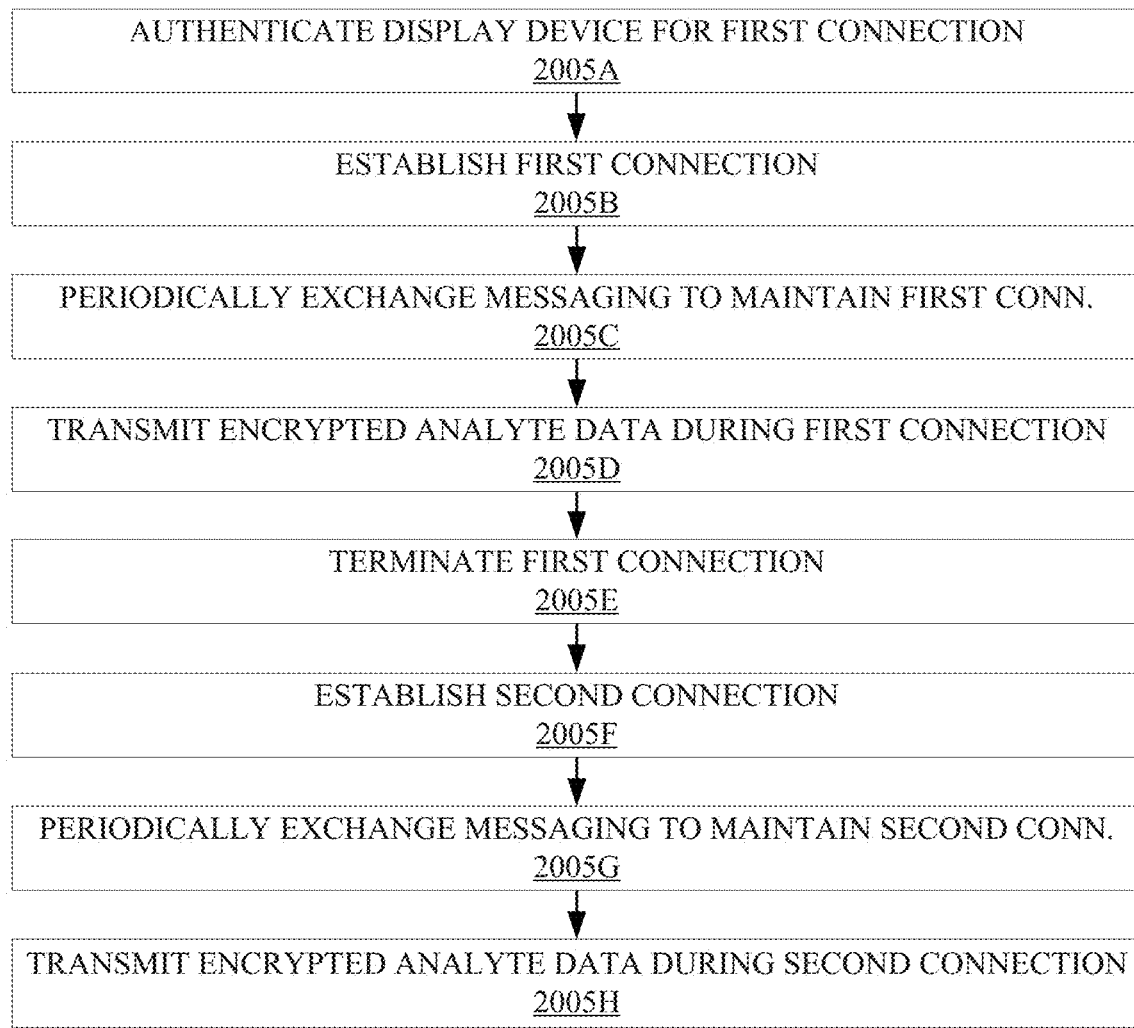
FIG. 20 is an operational flow diagram illustrating various operations that may be performed in accordance with embodiments of the disclosure.

With further regard to the continuous connection model, FIG. 20 provides an operational flow diagram illustrating various operations that may be performed in accordance with embodiments of the present disclosure. For illustration purposes, reference is made here to FIGS. 7C and 7J, as well as numerals of components shown therein. Nevertheless, one of ordinary skill in the art will appreciate upon studying the present disclosure that like components from other FIGS. of the present disclosure may be included in the scope of the present description of FIG. 20.

Embodiments shown in FIG. 20 involve aspects of method 2000 for wireless communication of analyte data, including, for implementing an improved authentication scheme in conjunction with operation according to a continuous connection model as described in instances herein, in order to for example, reduce the number of messages exchanged before analyte data can be securely transmitted (e.g., in an encrypted fashion between authenticated devices).

In this regard, at operation 2005A, method 2000 includes authenticating display device 710 for a first connection (e.g., with analyte sensor system 708) by exchanging information related to authentication between analyte sensor system 710 and display device 708. Here, reference is made by way of example to operation 795*c* in FIG. 7J. At operation 2005B, method 2000 optionally includes establishing the first connection between display device 710 and analyte sensor system 708. Here, reference is made by way of example to operation 795*b* in FIG. 7J. At operation 2005C, method 2000 includes, analyte sensor system 708 periodically exchanging messaging with display device 710 to maintain the first connection. Periodically exchanging the messaging at operation 2005C is in this case based on authenticating at operation 2005A. Here, reference is made by way of example to operation 795*e* in FIG. 7J. At operation 2005D, method 2000 includes analyte sensor system 708 transmitting encrypted analyte data to display device 710 during the time the first connection is maintained. Reference is made here for example to operations 795*d* and 795*d'* in FIG. 7J.

Embodiments of method 2000 includes at operation 2005E terminating the first connection. For illustration purposes, reference is made to operation 795*g* in FIG. 7J. At operation 2005F, method 2000 optionally includes establishing a second connection between analyte sensor system 708 and display device 710. Operation 2005G involves analyte sensor system 708 periodically exchanging messaging with display device 710 to maintain the second connection. At operation 2005H, method 2000 may include analyte sensor system 708 transmitting encrypted analyte data to display device 710 during the time the second connection is maintained. For the second connection, the periodically exchanging the messaging at operation 2005G and the transmitting encrypted analyte data at operation 2005H are based on authenticating display device 710 for the first connection at operation 2005A. Thus, in connection with these aspects of method 2000, authentication may not be repeated where a prior authentication can be sued to reduce the amount of messaging exchanged before the transmission of analyte data.

L. Switching Between Connection Models

As mentioned above, there are various embodiments where the intermittent connection model and/or the continuous connection model may be implemented. Moreover, in some embodiments, various parameters such as battery power of the analyte sensor system and/or the display device, reliability, and availability of the wireless connections, etc. may be taken into consideration during the implementation of one or more of the connection models.

Accordingly, embodiments of the present disclosure involve switching between these connection models in order to provide a flexible and adaptable system that may be optimized for a variety of use cases, operating conditions, and user/system preferences. Switching adaptively (whether in an automated fashion or based on user input, both of which are contemplated herein) may allow for optimization of battery power usage as well as transmission efficiency and data accuracy. In addition, device performance and behavior can, in accordance with example embodiments, be tracked over time and be used to develop an optimization profile with respect to circumstances in which various connection models may be preferable.

As alluded to above, in some cases, the connection model may be switched on an automated basis depending on various criteria. For example, the connection model may be set depending upon the type of display device being connected to the analyte sensor system (e.g., smartphone vs. medical device). In another example, the connection model may be set based on the number of display devices being used—e.g., if a single, dedicated device is being used (e.g., for a predetermined amount of time), then the system may switch to the continuous connection model. In another example, the connection model may be switched based upon current or projected battery life. The quality of exchanged signals may also be used to determine whether a switch between connection models is appropriate. Further, a switch in connection models may be based on the time of day and/or the location of analyte sensor system 708 and/or display device 710. The switch could be initiated by display device 710 and/or analyte sensor system 708.

In embodiments, the switch may be based on user input or may be semi-automatic. For example, a user may navigate a GUI such as GUI 340 to implement the switch. In particular, with reference to FIG. 3G, the user may select the connection status ("Conn. Status) option 314*f* to vary the connection model employed. In some cases, different buttons 316*f* may be presented via GUI 340, where each button (or soft key) corresponds to a different connection model. In other cases, such as is shown in FIG. 3G, a single button may be used to select between connection models. In some such cases, a drop-down menu may be provided so that the user can select between different connection models. In other cases, a number or letter or other character can be used to indicate the desired connection model. In another example, the switch may be triggered automatically in turn triggering a prompt being presented to the user on display device 710 via GUI 340. The user may then approve or deny the switch (thus, the switch can be made semi-automatic). The prompt may provide the user with information regarding the connection model currently employed, the reason for the proposed switch, and in some cases the consequences of rejecting and/or accepting the proposed switch, including tradeoffs related to the same.

Figure 7K:
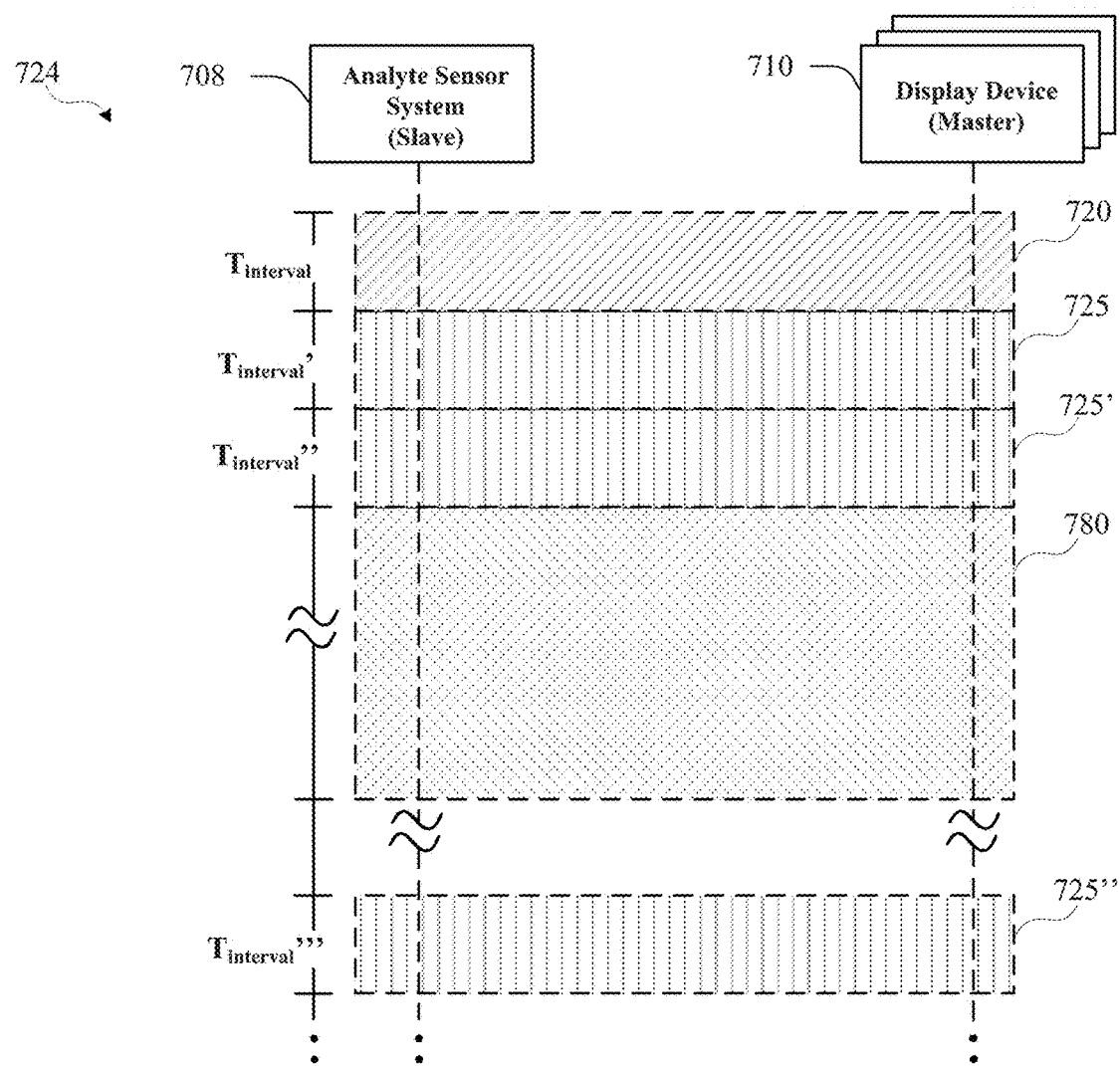
FIG. 7K is an operational flow diagram illustrating various operations that may be performed in accordance with embodiments of the disclosure.

FIG. 7K illustrates by way of example, embodiments involving the employment of various connection models, as well as features related to the same. Namely, method 724 includes the use of several connection models being employed in an example sequence. A shown, at $T_{interval}$, communication session 720 may occur. Communication session 720 involves employing the intermittent connection model, and with reference to FIG. 7A, may involve such features as advertising at operation 705a, authentication at operation 705c, and data transmission at operation 705d. FIG. 7K also illustrates, at operation $T_{interval}'$, the occurrence of communication session 725, which involves the intermittent connection model. With reference to FIG. 7C, communication session 725 may involve such features as advertising at operation 735a, and data transmission at operation 735d. Notably, embodiments of communication 725 may not include authentication, for example where authentication was performed previously in conjunction with communication 720, or in other situations where authentication can be skipped or bypassed, as described herein. Referring again to FIG. 7K, communication 725' is shown occurring at $T_{interval}''$, where the intermittent connection model may again be employed. $T_{interval}'$ may be the same as or different from $T_{interval}$, in various embodiments described herein. Likewise, $T_{interval}''$ may be the same as or different from $T_{interval}$ and $T_{interval}'$ in various embodiments described herein.

Following communication 725' in FIG. 7K, communication 780 is shown to occur. With reference to FIG. 7J, communication 780 involves employing the continuous connection model. It should be noted here that less than all operations or aspects of communication session 780 as shown in FIG. 7J may occur in connection with certain instances of communication session 780. For example, with reference to FIG. 7K, authentication may already have been performed previously in conjunction with communication session 720. As a result, authentication at operation 795c of communication 780 may not occur. Also, in some cases, connection parameters may have been established previously in conjunction with one or more of communication sessions 720, 725, 725', etc. Or for example, connection parameters may have been established in conjunction with a previous instance of communication session 780 or other communication session employing the continuous connection model or otherwise involving connection parameters. In such cases, the established connection parameters can be used in making a connection decision at operation 795b, such that the exchange of connection parameters described with respect to operation 795b need not occur. This can allow for quicker connection establishment with reduced signaling.

With further reference to FIG. 7K, after communication session 780 has been active for an indefinite amount of time, disconnection may occur, a new communication session may be initiated, and/or the employed connection model may be changed. For example, as shown at operation 795g (referencing FIG. 7J), connection may be lost for various reasons, such as user preference/input, network or power conditions, and so on. In the illustrated example of FIG. 7K, analyte sensor system 708 and display device 710 are disconnected for some time, after which communication session 725'' is initiated during $T_{interval}'''$ and the intermittent connection model is employed. It will be appreciated, however, that no disconnection need occur in order to switch connection models. Rather, in embodiments, communication session 780 involves the exchange of messaging while in a connected state, where the messaging signals that a transition from the continuous connection model to, for example, the intermittent connection model, should occur. Such signaling can occur at almost any point during communication session 780, one example being in conjunction with operation 795f. Likewise, similar signaling can be exchanged in conjunction with a communication session involving the intermittent connection model in order to initiate a transition to the continuous connection model.

In embodiments, one of the continuous connection model, in which analyte data can be exchanged upon or shortly after the data becoming available for transmission, or the intermittent connection model, is employed responsive to an indication, such as, for example, an indication of a use preference related to display device 710. The indication may be communicated to/from analyte sensor system 708 at various points. In example cases, the indication can be communicated before connection is established. For example, advertisement messages transmitted from analyte sensor system 708 (e.g., at operations 705a, 735a, and/or 795a) may contain the indication signaling that the continuous connection model is preferable, should be employed, or is required, or that there is not preference for a particular connection model. By way of illustration, this may be done using a flag in an advertisement packet (e.g., packet 800 with reference to FIG. 8) or by otherwise modifying the information carried in the advertisement packets. In response, the request for data connection (e.g., at operation 705b, 735b, and/or 795b) can then indicate whether the indication regarding the connection model is agreeable.

Alternatively or in addition, the indication may be exchanged in response to advertisement messages being received at display device 710, for example, in conjunction with a connection request/grant (e.g., at operations 705b, 735b, and/or 795b) or other message related to connection establishment. In such examples, subsequent messaging such as the grant of a data connection e.g., at operation 705c, 735c, and/or 795c), authentication messaging (the request for data connection (e.g., at operation 705b and/or 795b), etc. can then indicate whether the indication regarding the connection model is agreeable.

As another example, the indication may be exchanged in conjunction with a request or transmission of data (e.g., at operations 705d, 735d, and/or 795d). With respect to communication session 780, the indication may be exchanged in conjunction with messaging used to maintain the connection (e.g., at operation 795e) and/or in conjunction with messaging used to update connection parameters (e.g., at operation 795f). In some embodiments, the indication can be exchanged at other points during or outside of a connection between analyte sensor system 708 and display device 710. For example, the indication may be sent in real time or at least near real time, or at other predetermined times not mentioned heretofore.

With respect to generating the indication, in one example situation, the user of display device 710 may indicate that the continuous connection model is preferred relative to the connect/disconnect model, or vice versa. For example, if the user prefers a first display device 710 (e.g., a smartphone), such that, e.g., it is the only display device 710 the user will be using to capture analyte data, then analyte sensor system 708 may operate in the continuous connection mode according to communication session 780 after connecting to the preferred display device 710. The user's preference may be indicated manually by the user (e.g., via GUI 340 and the "Dedicated", "Priority", or Preferences options), or may be derived from data relating to usage of first display device 710 as well as other display devices, for example, as is described in detail herein. Deriving the user's preference may be done based on data relating to the user's analyte data values/trends, the time of day, location, radio link conditions (including, e.g., RSSI), packet loss rates, and network parameters, for example.

In some embodiments, a prioritization scheme may be configured with respect to multiple display devices 710. In order to implement the priority scheme for a particular display device 710, communication session 780 may be used for that particular display device 710. In some cases, for example, if packet loss increases above a threshold, the continuous connection model may be employed in order to decrease packet loss. In some cases, the continuous connection model or the intermittent connection model may serve as a default connection model, and the corresponding communication session (e.g., 720, 725, 740, 780) can be employed by default. The default model may be selectable, e.g., according to user input or adaptively based on various of the parameters/criteria described above.

To illustrate, analyte sensor system 708 and a first display device 710 may be communicating analyte data using the intermittent connection model as described above (e.g., with respect to FIGS. 7A, 7B, and 7E). In this scenario, the first display device 710 may, for example, be a user's smartphone. Analyte sensor system 708 may also, according to the connect/disconnect model, be communicating analyte data with a second display device 710, which may, for example, be a medical device (e.g., an insulin pump, medical device 136, or the like) or a proprietary display device (e.g., a device designed specifically for the communication of analyte data, such as display device 110, with reference to FIG. 1A; examples of such are also referred to herein at times as an analyte display device). The user may then provide, for example via GUI 340, an indication that the user will only be using the smartphone and not the medical device. As mentioned, this may be done via GUI 340 provided on the smartphone in connection with an application, such as application 330, that may be related to the communication of analyte data. For example, with reference to FIG. 3G, the user may select one of options 316e to indicate that a display device 710 should be dedicated or not dedicated, or another option (not specifically shown/enumerated) that the devices is preferred or not preferred (e.g., "Priority" and/or "Preferences").

The smartphone (or other type of display device 710) in this example may then transmit the user's indication to analyte sensor system 708, which upon receiving the indication may initiate operation under the continuous connection model according to communication session 780, since the user selected the device to be dedicated. With reference to FIG. 7J, the user's indication may be transmitted from display device 710 to analyte sensor system 708 at operation 795b, in the form of a request message. Although other display devices 710 (including, e.g., a medical device such as medical device 136) can listen to the analyte sensor system 708 (that is, receive messages therefrom) in this scenario, only the preferred display device 710—in this example, the smartphone—is operating under the connected model, and hence potentially exchanging analyte data relatively more frequently.

In embodiments, the continuous connection model, e.g., according to communication session 780, is employed adaptively. For example, depending on the time of day, there may be an advantage to operating under the continuous connection model according to communication session 780 (as opposed to, for example, employing the intermittent connection model or using another form of communication session described herein) for some users and/or display devices 710. Particular users may experience more severe glucose level variations during certain times of day. Such variations, for example, may be more rapid and/or large in magnitude at certain times. In some instances, such variations may not be ideally addressed by analyte sensor system 708 operating under the intermittent connection model according to communication sessions 720, 725, and/or 740, for example, since analyte values may in some cases be exchanged relatively less frequently. Thus, during times when glucose level variations are typically severe, analyte sensor system 708 and/or display device 710 may initiate operation under the connected model pursuant to communication session 780. Accordingly, the connection model used can be changed/toggled/switched adaptively.

In another example, network parameters, network conditions, the quality of the radio link (e.g., RSSI etc.), the number of display devices 710 seeking connection to or in communication with analyte sensor system 708, and/or a prioritization scheme (e.g., as determined by a user or otherwise), may serve as the basis for operating under the continuous connection model (e.g., per communication session 780) or the intermittent connection model on an adaptive basis. With respect to network parameters or conditions, and/or with respect to radio link quality, a degradation may result in packet loss. Such packet loss, as alluded to above, may be more critical to the exchange of analyte data under the intermittent connection model, since data is in some cases not exchanged as frequently relative to the continuous connection model. Accordingly, in order to mitigate degradation of network parameters or conditions, and/or radio link quality, when such degradation is detected, analyte sensor system 708 and display device 710 may initiate operation under the continuous connection model pursuant to communication session 780. As mentioned above, analyte sensor system 708 and/or display device 710 may monitor network parameters, network conditions, and/or radio link quality. These measurements may then be compared to thresholds such that switching the employed connection model (e.g., between various communication sessions) may be done adaptively responsive to the threshold being crossed.

With respect to the number of devices seeking a connection to analyte sensor system 708, and/or being in communication therewith, adaptation of the operating mode/connection model can be described as follows. A large number of display devices 710 may be in range from analyte sensor system 708, and attempting to connect thereto may result in interference, and hence packet loss and/or increased power consumption. To avoid such packet loss and increased power consumption, even in the face of numerous display devices 710 seeking a connection, analyte sensor system 708 may initiate operation under the continuous connection model with a preferred display device 710.

This may be done by analyte sensor system 708 maintaining a count of the number of display device 710 devices seeking a connection thereto, and signaling a preferred display device 710 to enter operation under the continuous connection model if the count surpasses a threshold. Such signaling may be implemented in conjunction with various operations of communication sessions described herein, for example. Alternatively or additionally, packet loss may be monitored (e.g., at display device 710 and/or analyte sensor system 708). Further, the source of such packet loss may be determined, or estimated/approximated, e.g., at display device 710 and/or analyte sensor system 708. If the source of the packet loss is determined to be interference (due, for example, to numerous display devices 710 attempting to connect to analyte sensor system 708), operation under the continuous connection model may be initiated.

Here, the preferred display device 710 may also be determined instantaneously or nearly so, may be determined on the fly, and may be determined without user intervention. For example, the preferred display device 710 may be determined based on frequency of use, a previously determined prioritization scheme, the quality of connection or radio link (e.g., based on signal power, channel loss, bit error rate, RTT, RSSI, etc.), available battery life and/or processing power, the time of day, etc. Alternatively or in addition, the user may be queried via GUI 740, e.g., as part of application 330 running on display device 710, as to the preferred display device 710.

With respect to terminating the connection established and maintained pursuant to communication session 780, several techniques may be employed. As mentioned above, operation 795e may involve the exchange of messaging according to a connection interval. Such messages may be thought of as "ping" messages.

The sequential exchange of such messaging may involve a first message and a second message that is successively transmitted with respect to the first message, and so on with respect to third, fourth, and fifth messages, etc. The first such message may be configured to include a connection interval that indicates when the next message in the sequence will be exchanged between analyte sensor system 708 and display device 710, or in other words may include a scheduled amount of time between the sequential exchange of the first and second ping messages.

This connection interval may be varied between the messages exchanged at operation 795e. If display device 710 does not receive the second message within the expected connection interval, the connection between display device 710 and analyte sensor system 708 may be terminated at operation 795g. In another instance, the connection may be terminated if a proposed connection interval is NACKed or otherwise rejected, e.g., at operation 795b or operation 795f. That is, if analyte sensor system 708 and display device 710 do not agree upon a connection interval, the connection may be closed/terminated. An ACK/NACK may also be sent following each ping message (e.g., multiplexed ACK/NACK) or following a predetermined or adaptively varied number of such messages (e.g., bundled ACK/NACK), e.g., at operation 795e.

In embodiments, one or more messages exchanged at operation 795e may include a timeout value. As mentioned above, supervision timeout and related techniques may also be employed with respect to the continuous connection model. For example, upon expiry of the timeout value, if a second ping message has not been received, method 722 may involve terminating the connection at operation 795g. When the connection is terminated, communication session 780 may end. At this point, transceiver 360 and/or processor 380 of analyte sensor system 708 can be deactivated in some cases. Alternatively, as mentioned above, analyte sensory system 708 can initiate advertisement at operation 795a'. In some cases, the decision to deactivate or advertise can be based on an apparent reason the connection was terminated. For example, if the connection was terminated concurrently with interference events, degraded radio conditions, or loss of battery power, analyte sensor system 708 may initiate advertisement per operation 795a' in order to reacquire the display device 710 previously connected or another display device 710.

Generally, an instance of communication session 780, in which analyte sensor system 708 and display device 710 are continuously connected, may remain last until the connection is closed or terminated or lost for various of the potential reasons described above. A request to modify the connection model (e.g., send according to operation 795f) may result in the terminating the connection established as part of communication session 780, and the triggering of a different connection model, for example by initiating communication session 725". In some cases, the employed connection model may be controlled manually via GUI 340. With reference to FIG. 3G, a user may be presented with sub-menu 314f which allows selection of a connection model using options 316f, thus initiating a switch in the employed connection model. Method 722 thus provides a highly flexible and adaptable technique for the communication of analyte data.

With regard to connection models described herein, in embodiments of the present disclosure, different connection models can be used for different connected devices (e.g., display devices 710). With reference to FIG. 3C, for example, communication session 780 can be employed as between display devices 310a and 310b, while at the same time a different communication session (e.g., 720, 725, 740, etc.) can be employed as between display devices 310a and/or 310b, on the one hand, and analyte sensor system 708 on the other hand. In embodiments, one of display devices 310a and 310b may not be connected to analyte sensor system 708 but may nevertheless receive analyte data therefrom via another display device 310b or 310a that is connected to analyte sensor system 708. In some cases, this may be referred to as tethering. Such configurations can be implemented, for example, using sub-menu 314a presented by GUI 340, with reference to FIGS. 3F and 3G.

Turning now to FIGS. 3C-3E, embodiments of the present disclosure involve configuring and/or setting up a kind of mesh network using various of the connection models described herein. For example, two or more display devices 310a and 310b can be connected to analyte sensor system 308 using different connection models. With reference to FIG. 3C and the illustrated system 304, analyte sensor system 308 may be connectable to display devices 310a and 310b via communication medium 305a. Further, display devices 310a and 310b may be connectable to one another via communication medium 305b. It will be appreciated that although two display devices 310a and 310b are shown in FIGS. 3C-3E, more than two display devices may be included in the mesh-like networks described herein and/or using various connection models.

FIG. 3D shows that in connection with system 306a, analyte sensor system 308 may be connectable to display devices 310a and 310b, respectively, using various communication media (e.g., communication medium 305) and/or connection models (e.g., intermittent connection model, continuous connection model, etc.), represented by way of illustration as Connections A and B. Additionally, display devices 310a and 310b may be connectable to one another using various communication media and/or connection models, represented by way of illustration here as Connection C. For example, when two display devices 310a and 310b are in range of analyte sensor system 308, analyte sensor system 308 and display device 310a may connect using the continuous connection model. Display device 310b may then connect to analyte sensor system 308 using the intermittent connection model. In this manner, with display device 310b connected to display device 310a, display device 310a can essentially act as a gateway device for display device 310b. In some other embodiments, analyte sensor system 308 may simultaneously connect with both display device 310a and display device 310b via the continuous connection model. (e.g., both Connection A and Connection B may use continuous connection model). It is contemplated that multiple display devices may simultaneously connect with the analyte sensor system using the continuous connection model.

It will be appreciated here that the respective connection models used display devices 510a and 510b may switch. It will also be appreciated that both display devices 310a and 310b can connect to analyte sensor system using the intermittent connection model. Regardless of the connection models employed between analyte sensor system 306a, on the one hand, and display devices 310a, 310b on the other hand, display devices 310a, 310b may connect to one another using either intermittent connection model or the continuous connection model. Furthermore, any of the communication media and/or connection models employed (e.g., in Connections A, B, and C) can switch to a different connection model subsequent to connection establishment.

Turning now to FIG. 3E, another example of configuring and/or setting up a mesh network using various of the connection models described herein is illustrated. As shown in connection with system 306b, analyte sensor system 308 may be connectable to a series of display devices 310a, 310b, 310c, with various connection models and/or communication media 305 being employed for each of the respective connections. It will be appreciated that any of the connection models described herein may be used for Connections D, E, and/or F, etc. Furthermore, any of the connection models employed (e.g., Connections D, E, and F) can switch to a different connection model subsequent to connection establishment. It will also be appreciated that in example implementations of system 306b, one or more display devices can be connected to analyte sensor system 308 in parallel with display devices 310a, 310b, and 310c. Each display devices may also have connected thereto a chain of display devices, as is shown with respect to display devices 310a, 310b, and 310c.

In embodiments relating to the configurations shown in FIGS. 3C to 3E, a user interface such as GUI 340, with reference to FIGS. 3F and 3G, can present to the user information regarding the mesh network, such that the user may maintain some level of control and/or input into the configuration thereof. For example, the topography of the mesh network might be provided, and the user may be enabled to access connection links to alter the connection model employed or the connection parameters used, advertisement characteristics, etc. associated with the various connections. Moreover, the user may be able to switch among display devices 310a, 310b, etc. in terms of which device can act as a gateway to other devices.

Figure 15A:
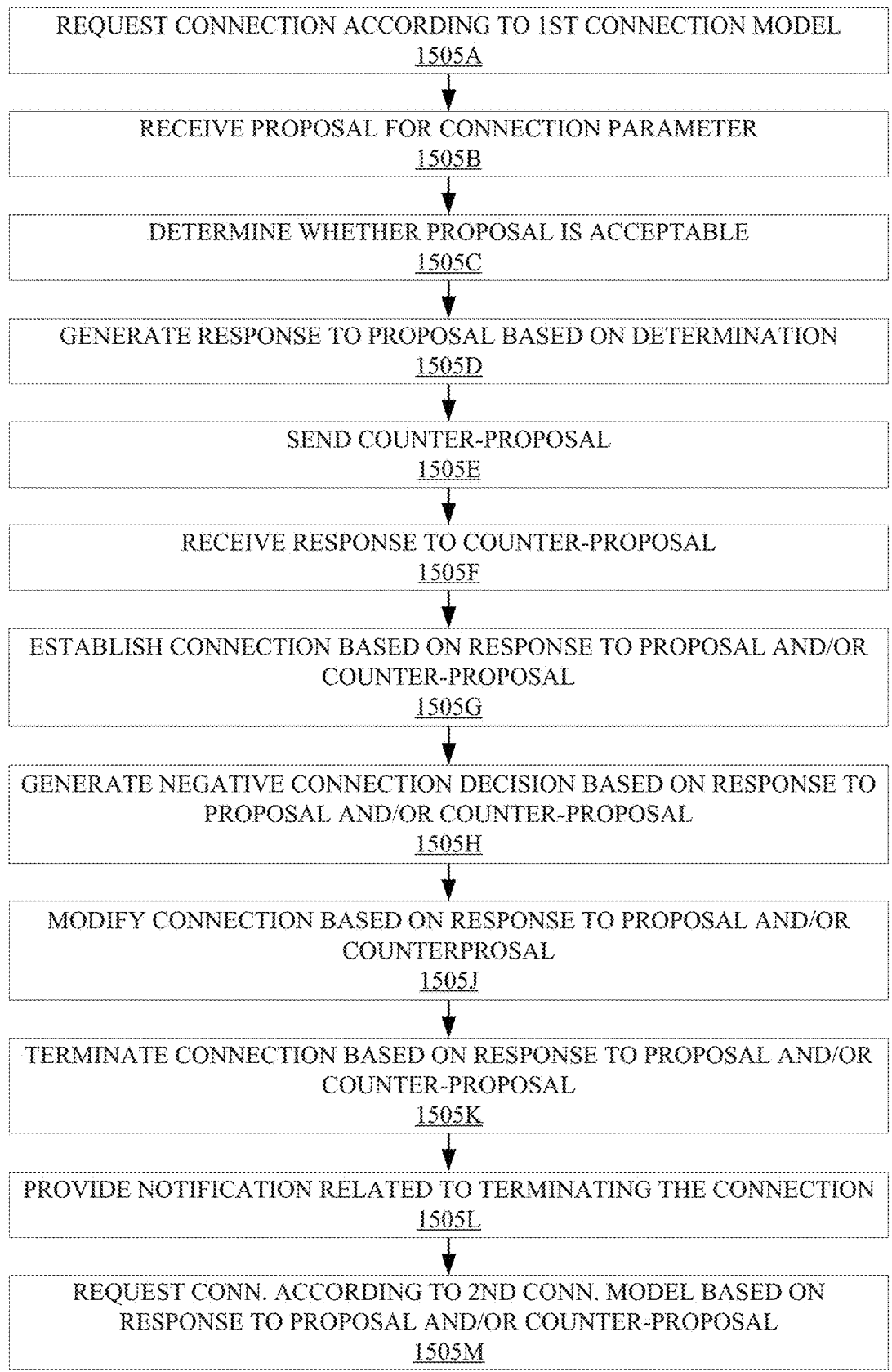
FIG. 15A is an operational flow diagram illustrating various operations that may be performed in accordance with embodiments of the disclosure.
Figure 15B:
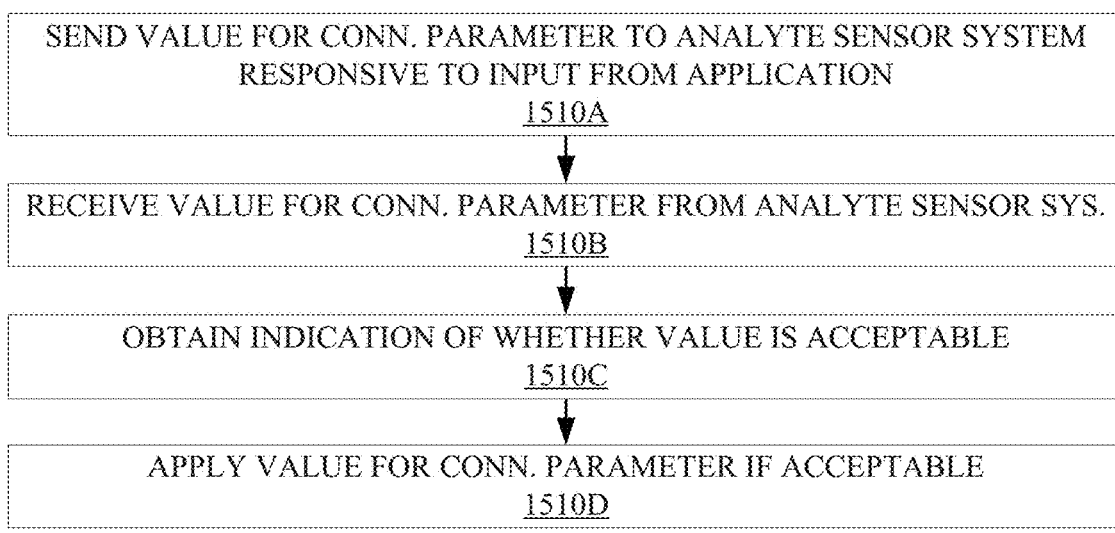
FIG. 15B is an operational flow diagram illustrating various operations that may be performed in accordance with embodiments of the disclosure.

Referring now to FIGS. 15A and 15B, some embodiments of the present disclosure related to the above-described connection parameters will now be described. In this regard, FIGS. 15A and 15B provide operational flow diagrams illustrating various operations that may be performed in accordance with embodiments of the present disclosure, for example in connection with setting and/or modifying connection parameters in accordance with various connection models described herein. For illustration purposes, reference is made here to FIG. 7J, as well as numerals of components shown therein. Nevertheless, one of ordinary skill in the art will appreciate upon studying the present disclosure that like components from other FIGS. of the present disclosure may be included in the scope of the present description of FIGS. 15A and 15B. It will also be noted at this juncture that while the setting, negotiation, and/or modification of connection parameters may be related in some cases to switching between connection models, in other cases, the setting, negotiation, and/or modification of connection parameters may be related to operating according to a single connection model for a given amount of time. Nevertheless, discussion of these features is included in this portion of the disclosure for the reader's convenience.

Embodiments shown in FIG. 15A involve aspects of method 1500 for wireless communication of analyte data, including, for example the exchange, negotiation, and setting of connection parameters and related features. In this regard, method 1500 may include at operation 1505A requesting a connection according to a first connection model. For example, display device 710 may request a connection to analyte sensor system 708 in conjunction with operation 795b shown in FIG. 7J. The first connection model could be an intermittent connection model or a continuous connection model. At operation 1505B, method 1500 includes receiving a proposal for a connection parameter. The proposal includes one or more proposed values for the connection parameter. Proposals for multiple connection parameters can be sent simultaneously or nearly so in some cases. The proposal may be received at analyte sensor system 708 and/or display device 710. At operation 1505C, method 1500 includes determining whether the proposal is acceptable. Operation 1505D involves generating a response to the proposal, based on determining whether the proposal is acceptable.

At operation 1505E, method 1500 optionally includes sending a counter-proposal, if the response generated at operation 1505E indicates a preference of a value for the connection parameter other than the proposed values for the connection parameter. The counter-proposal may include one or more counter-proposal values for the connection parameter. Embodiments of method 1500 also include at operation 1505F receiving a response to the counter-proposal. Based on the response received to the proposal of values and/or the counter-proposal of values, various actions may be taken.

At operation 1505G, method 1500 may include establishing a connection between display device 710 and analyte sensory system 708 based on one or more of: an acceptable proposal value of the one or more proposed values, if the response indicates an acceptance of the acceptable proposed value; at least one of the counter-proposal values, if the response to the counter-proposal indicates an acceptable of one or more of the counter-proposal values. At operation 1505H, method 1500 may include generating a negative connection decision, if the response to the counter-proposal indicates a denial of the counter-proposal values. In some cases, a negative connection decision may also be generated at operation 1505H based on a denial of at least one of the propose values. At operation 1505J, method 1500 optionally includes modifying a connection between display device 710 and analyte sensor system 708 based on one or more of: an acceptable proposed value of the one or more proposed values, if the response indicates an acceptance of the acceptable proposed values; and at least one of the counterproposal values, if the response to the counter-proposal indicates an acceptance of one or more of the counter-proposed values.

At operation 1505K, method 1500 may include terminating a connection between display device 710 and analyte sensor system 708, for example: if the response to the counter-proposal indicates a denial of the counter-proposal values; if the response to the proposal indicates a denial of at least one of the propose values; and responsive to determining that the proposal is not acceptable. At operation 1505L, embodiments of method 1500 includes providing a notification related to terminating the connection (e.g., at operation 1505K). In embodiments, method 1500 includes requesting a connection according to a second connection model (e.g., that is different from the first connection model), responsive to determining that the proposal and/or counter-proposal is not acceptable.

FIG. 15B illustrates embodiments of the present disclosure related to aspects of method 1502 for wireless communication of analyte data, including, for example the exchange, negotiation, and setting of connection parameters and related features. In this regard, method 1502 may include at operation 1510A, responsive to input from an application running on display device 710 (e.g., application 330 with reference by way of example to FIG. 3B), display device 710 sending to analyte sensor system 708 a messing that includes a value for a connection parameter. At operation 1510B, method 1502 includes display device 710 receiving from analyte sensor system 708 the value for the connection parameter.

At operation 1510C, method 1502 may include obtaining an indication of whether the value is acceptable. This obtaining may be accomplished, for example, by display device 710 receiving from analyte sensor system 708 a determination of whether the value is acceptable. At operation 1510D, method 1502 includes an operating system of display device 710 (e.g., as may be stored in storage 325 and executed/controlled at least partially by processor 335, with reference by way of example to FIG. 3B) applying the value for the connection parameter, based on a determination that the value is acceptable. For example, the value may be applied to a connection established or to be established between analyte sensor system 708 and display device 710.

Figure 16A:
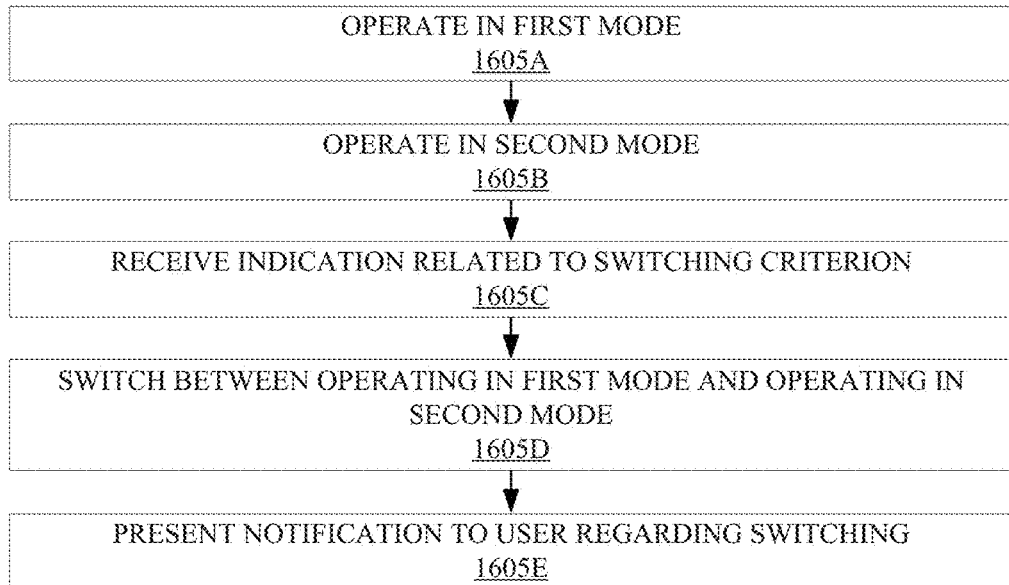
FIG. 16A is an operational flow diagram illustrating various operations that may be performed in accordance with embodiments of the disclosure.
Figure 16B:
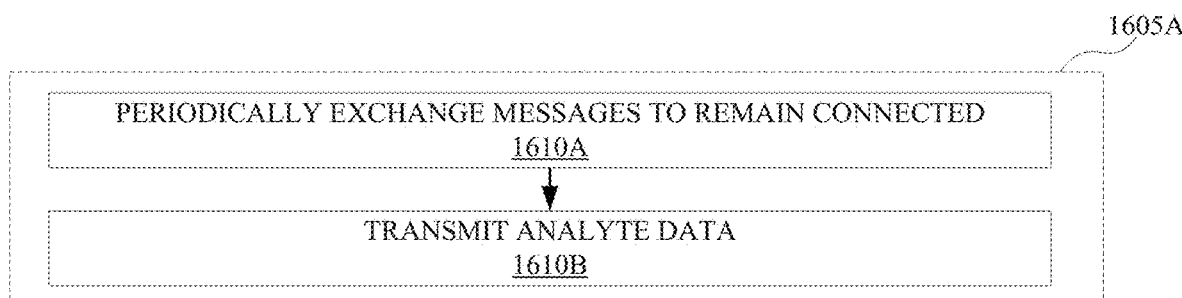
FIG. 16B is an operational flow diagram illustrating various operations that may be performed in accordance with embodiments of the disclosure.
Figure 16C:
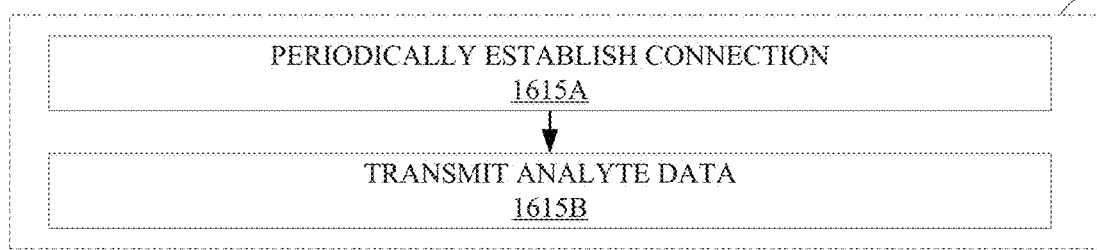
FIG. 16C is an operational flow diagram illustrating various operations that may be performed in accordance with embodiments of the disclosure.

With further regard to switching between connection models, FIGS. 16A through 16C provide operational flow diagrams illustrating various operations that may be performed in accordance with embodiments of the present disclosure. For illustration purposes, reference is made here to FIG. 7A through FIG. 7K, as well as numerals of components shown therein. Nevertheless, one of ordinary skill in the art will appreciate upon studying the present disclosure that like components from other FIGS. of the present disclosure may be included in the scope of the present description of FIG. 16A through 16C.

Embodiments shown in FIG. 16A involve aspects of method 1600 for wireless communication of analyte data, including, for example switching between operating according to different connection models described herein. In this regard, method 1600 includes at operation 1605A operating in a first mode. Additionally, at operation 1605B, method 1600 includes operating in a second mode. FIGS. 16B and 16C illustrate further detail with respect to operations 1605A and 1605B. FIG. 16B illustrates embodiments involving aspects of method 1602, which includes further details regarding operation 1605A, mentioned above with reference to FIG. 16A. As shown, operation 1605A includes at operation 1610A analyte sensor system 708 periodically exchanging messaging with display device 710 such that analyte sensor system 708 and display device 710 remain connected. Here, reference is made by way of example to operation 795e shown in FIG. 7J. Operation 1610B involves, while analyte sensor system 708 and display device 710 remain connected, analyte sensor system 708 transmitting analyte data to display device 710.

FIG. 16C illustrates embodiments involving aspects of method 1604, which includes further details regarding operation 1605B, mentioned above with reference to FIG. 16A. As shown, operation 1605B includes at operation 1615A periodically establishing a connection between analyte sensor system 708 and display device 710. Here, reference is made by way of example to FIGS. 7A and 7B (e.g., communication sessions 720 and 720' and operation 705b). Operation 1615B involves, while the connection is established, transmitting analyte data to display device 710.

Referring back to FIG. 16A, at operation 1605C, method 1600 may include receiving an indication related to one or more switching criteria (e.g., such criteria may related to batter conditions and/or management as described herein). At operation 1605D, method 1600 optionally includes switching from operating in the first mode to operating in the second mode or switching from operating in the second mode to operating in the first mode. The switching at operation 1605C may be based on user input and/or one or more switching criteria. At operation 1605E, method 1600 may include presenting a notification to the user related to the switching.

M. Reading Data Using a Characteristic-Based Profile

By way of background, some profiles described herein may be control based, linear, and employ a number of characteristics that may be configured in a sequence. In some cases, after going through a number of characteristics in the sequence (e.g., reading sync time, authentication, etc.) display device 710 can request EGV values from analyte sensor system 708. That is, some example profiles request and/or require a particular sequence of commands and operations to be followed and executed before EGV is exchanged.

In accordance with embodiments of the present disclosure, profiles are provided based on characteristics. That is, for reading or receiving EGV data by display device 710 while operating according to the continuous connection model or the intermittent connection model (e.g., as described above), a characteristics based profile may be implemented. This may allow display device 710 to read CGM data directly, as opposed to first executing a number of communications-related operations or characteristics before reading the CGM data. Direct reading of CGM data may be at least partially facilitated by the above-described authentication scheme because no additional authentication needs to be performed following initial authentication. Thus, in some cases, the disclosed profiles may include an increased number of characteristics without needing to exchange an increased number of messages prior to the exchange of data. One such characteristic may be used for or in some cases dedicated to encrypted EGV. As such, display device 710 may skip directly to the EGV characteristic and read encrypted EGV, rather than first passing through all the other characteristics (as may be required according to existing control based profiles). This may result in power savings as well as responsiveness and reliability increases.

A typical sequence of reading EGV data according to embodiments of the presently disclosed characteristic based profiles may be as follows. Where different steps may be taken depending on the connection model employed (e.g., the continuous connection model or the intermittent connection model), the same is noted in the following description. First, analyte sensor system 708 and display device 710 may establish connection. Analyte sensor system 708 may then indicate to display device 708 what and how many characteristics are included in the applicable profile (e.g., analyte sensor system 708 may indicate that it has three or four characteristics). For the intermittent connection model, analyte sensor system 708 may then disconnect and/or go to sleep for a time before waking back up. Alternatively or additionally, for the continuous connection model, the connection is maintained after analyte sensor system 708 indicates the number of characteristics to display device 710. Display device 710 may then at any time during the connection for example request to read a specific characteristic from analyte sensor system 708 regardless of the characteristics may be arranged in a sequence. For example, the request may be made according to characteristic numbers. Thus, for example, display device 710 may request to read characteristic numbers one and three, which may be time sync and encrypted EGV, for example.

That is, in the above-described profile implementation, (encrypted) EGV can be read directly without stepping through other characteristics (e.g., characteristic number two in this example) that may be unnecessary (at least at the time). Accordingly, the number of messages/communications exchanged between analyte sensor system 710 and display device 708 before the reading of (encrypted) EGV can be reduced.

Figure 12B:
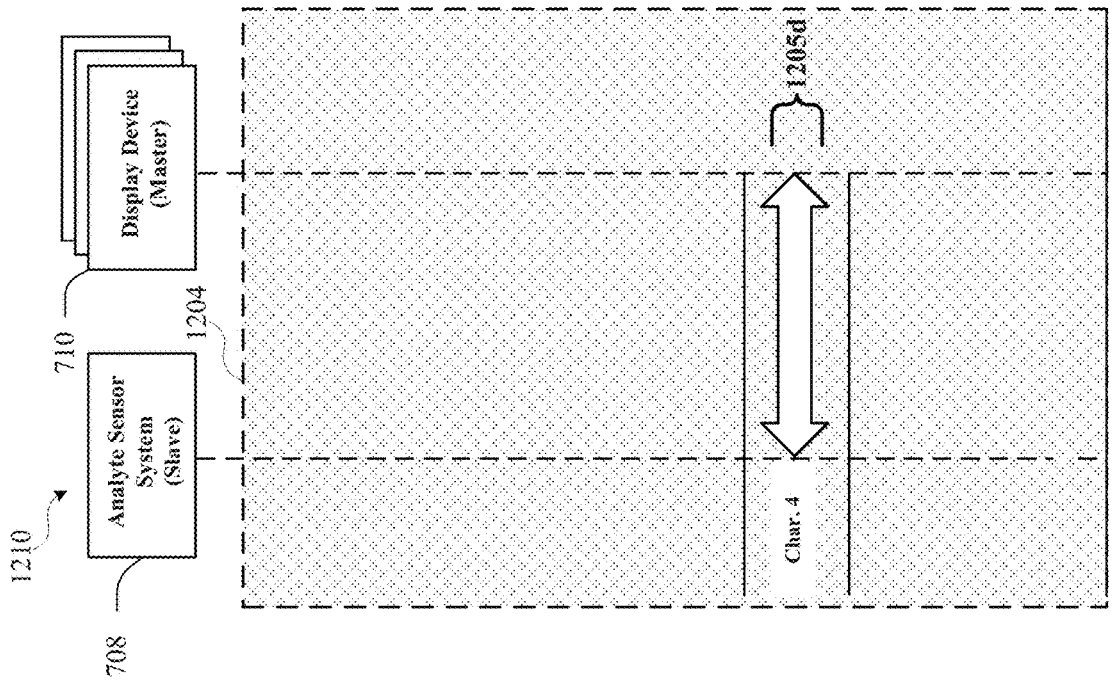
FIG. 12B is an operational flow diagram illustrating various operations that may be performed in accordance with embodiments of the disclosure.
Figure 12A:
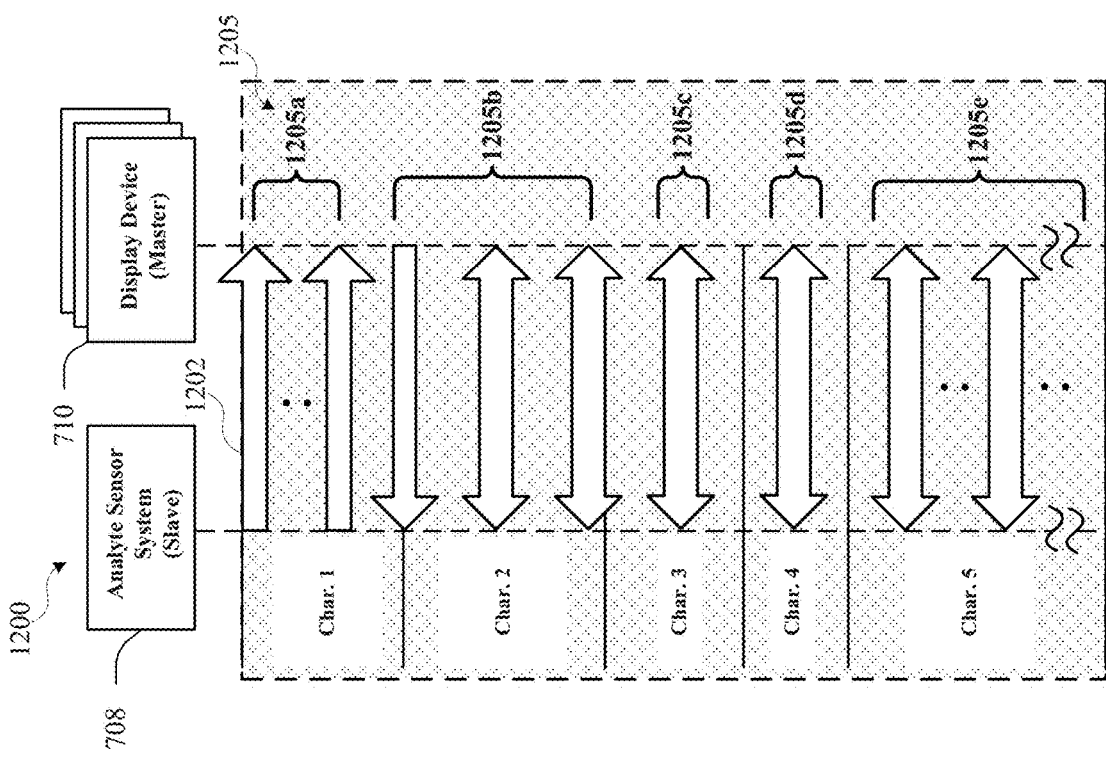
FIG. 12A is an operational flow diagram illustrating various operations that may be performed in accordance with embodiments of the disclosure.

FIGS. 12A and 12B show by way of example, embodiments involving the employment of characteristic profiles, as well as features related to the same. Namely, method 1200 includes communication session 1202 and the use of characteristic profile 1205 being employed in an example sequence, namely, characteristics 1205*a*, 1205*b*, 1205*c*, and so on. Characteristic profile 1205 may include characteristics 1205*a*, 1205*b*, etc., which may involve, for example, advertising in conjunction with characteristics 1205*a* and/or 1205*e*, establishing a connection in conjunction with characteristic 1205*b*, authentication in conjunction with characteristic 705*c*, and data transmission in conjunction with characteristic 1205*d*. It will be appreciated these characteristics are provided by way of illustration only, and that additional or fewer characteristics may be included in characteristics profile 1205.

As mentioned above, analyte sensor system 708 and display device 710 may establish connection. Analyte sensor system 708 may then indicate to display device 708 what and how many characteristics are included in characteristic profile 1205. As represented in FIG. 12B, display device 710 may request to read a characteristic 1205*d* (e.g., read an encrypted estimated glucose value) from analyte sensor system 708 without performing each of the characteristics in the sequence shown in FIG. 12A, e.g., according to characteristic profile 1205. It will be appreciated at this juncture that communication sessions 1202 and/or 1204 may employ an intermittent connection model, a continuous connection model, or both.

Figure 17:
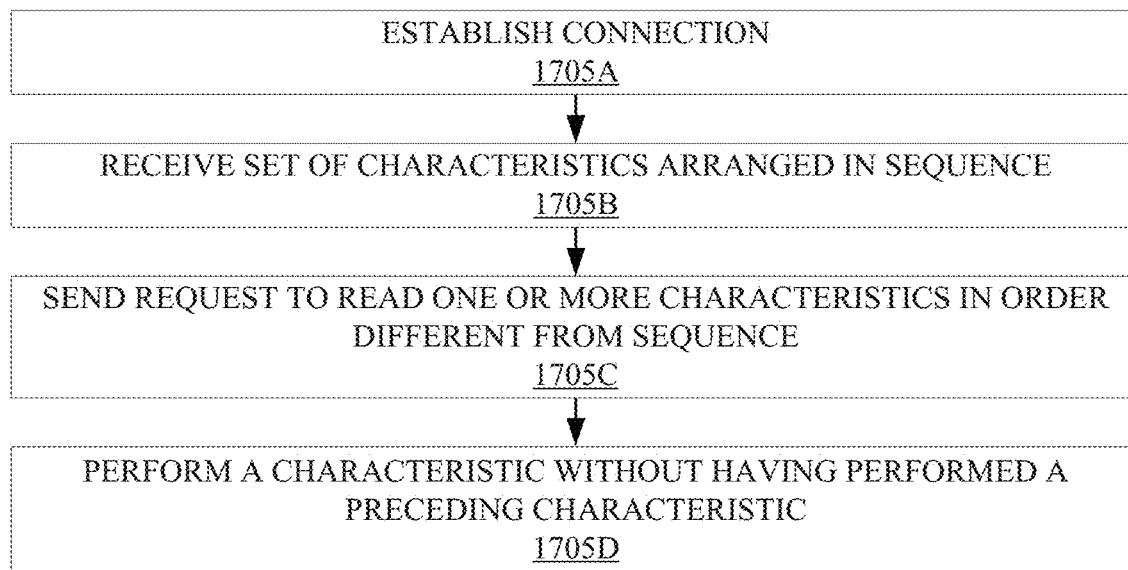
FIG. 17 is an operational flow diagram illustrating various operations that may be performed in accordance with embodiments of the disclosure.

With further regard to the characteristic-based profiles, FIG. 17 provides an operational flow diagram illustrating various operations that may be performed in accordance with embodiments of the present disclosure. For illustration purposes, reference is made here to FIGS. 12A and 12B, as well as numerals of components shown therein. Nevertheless, one of ordinary skill in the art will appreciate upon studying the present disclosure that like components from other FIGS. of the present disclosure may be included in the scope of the present description of FIG. 17.

Embodiments shown in FIG. 17 involve aspects of method 1700 for wireless communication of analyte data, including, for employing aspects of characteristic profiles. In this regard, method 1700 includes at operation 1705A establishing a connection between analyte sensor system 708 and display device 710. At operation 1705B, method 1700 includes receiving a set of characteristics associated with analyte sensor system 708. The characteristics may be arranged in a sequence. In embodiments, method 1700 includes operation 1705C, which involves sending to analyte sensor system 708 a request to read one or more of the characteristics in an order different from the sequence. At operation 1705D, method 1700 optionally includes performing a characteristic of the set of characteristics without having performed one or more other characteristics preceding the performed characteristic in the sequence.

N. Additional Embodiments

One of skill in the art will appreciate upon studying the present disclosure that various additional embodiments not described explicitly herein are within the spirit and scope of the present disclosure.

Figure 11:
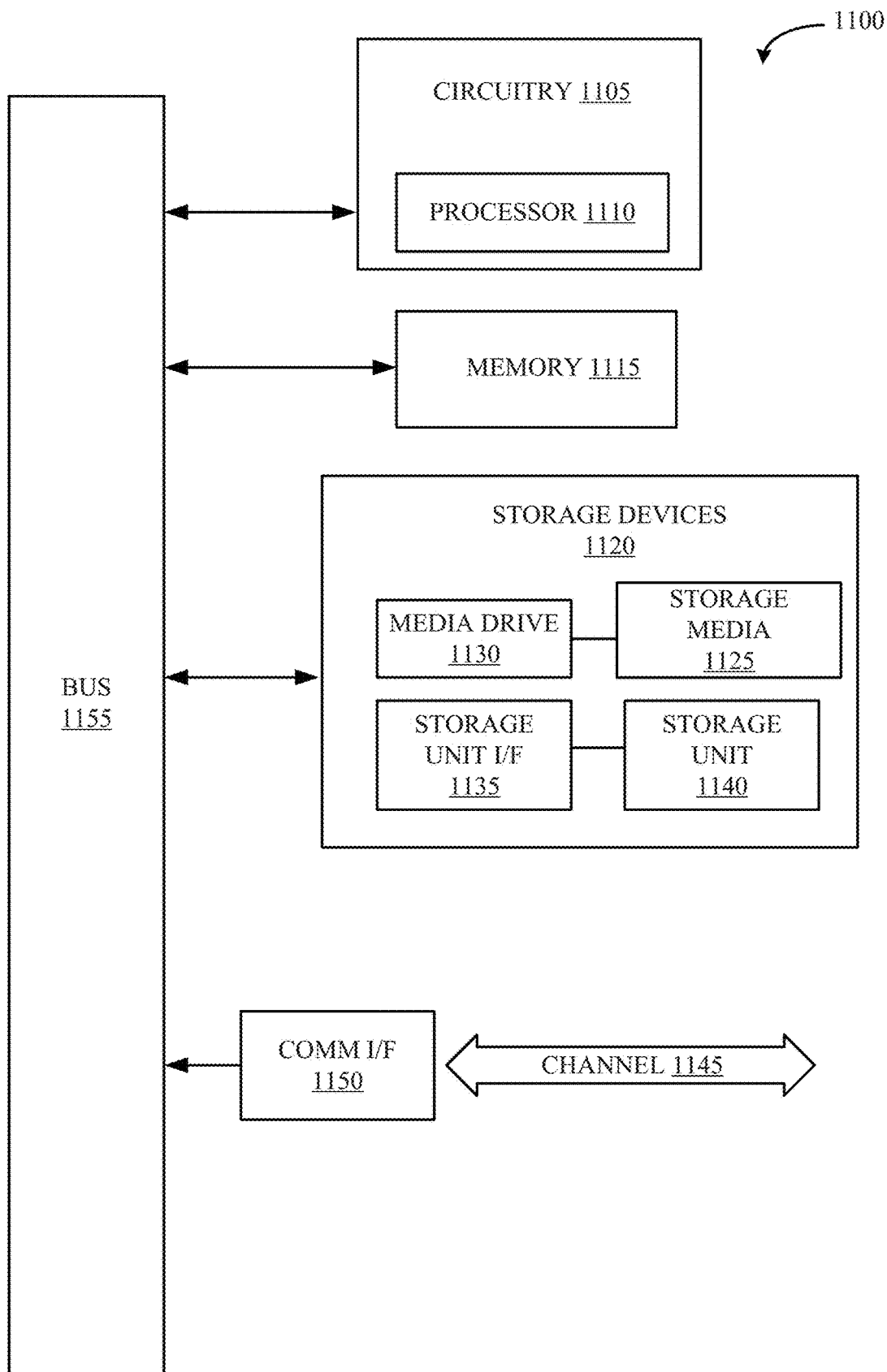
FIG. 11 illustrates an example computing module in accordance with embodiments of the present disclosure.

FIG. 11 illustrates example computing module 1100, which may in some instances include a processor/microprocessor/controller resident on a computer system (e.g., in connection with server system 334, any of the display devices described herein (e.g., display devices 120, 130, 140, 310(*a*, *b*), 710 (*a*, *b*), as well as analyte display device 110 and medical device 136), and/or analyte sensor system 8, 308, 708, etc. Computing module 1100 may be used to implement various features and/or functionality of embodiments of the systems, devices, apparatuses, and methods disclosed herein. With regard to the above-described embodiments set forth herein in the context of systems, devices, apparatuses, and methods described with reference to the various FIGS. of the present disclosure, including embodiments analyte sensor system 708, analyte display device 110, display devices 710*a*, 710*b*, etc., server system 334 and components thereof, etc., one of skill in the art will appreciate additional variations and details regarding the functionality of these embodiments that may be carried out by computing module 1100. In this connection, it will also be appreciated by one of skill in the art that features and aspects of the various embodiments (e.g., systems, devices, and/or apparatuses, and the like) described herein may be implemented with respected to other embodiments (e.g., methods, processes, and/or operations, and the like) described herein without departing from the spirit of the disclosure.

As used herein, the term module may describe a given unit of functionality that may be performed in accordance with one or more embodiments of the present application. As used herein, a module may be implemented utilizing any form of hardware, software, or a combination thereof. For example, one or more processors, controllers, ASICs, PLAs, PALs, CPLDs, FPGAs, logical components, software routines or other mechanisms may be implemented to make up a module. In implementation, the various modules described herein may be implemented as discrete modules or the functions and features described may be shared in part or in total among one or more modules. In other words, as would be apparent to one of ordinary skill in the art after reading this description, the various features and functionality described herein may be implemented in any given application and may be implemented in one or more separate or shared modules in various combinations and permutations. Even though various features or elements of functionality may be individually described or claimed as separate modules, one of ordinary skill in the art will understand that these features and functionality may be shared among one or more common software and hardware elements, and such description shall not require or imply that separate hardware or software components are used to implement such features or functionality.

Where components or modules of the application are implemented in whole or in part using software, in one embodiment, these software elements may be implemented to operate with a computing or processing module capable of carrying out the functionality described with respect thereto. One such example computing module is shown in FIG. 11. Various embodiments are described in terms of example computing module 1100. After reading this description, it will become apparent to a person skilled in the relevant art how to implement the application using other computing modules or architectures.

Referring now to FIG. 11, computing module 1100 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); other display devices, application-specific devices, or other electronic devices, and the like, depending on the application and/or environment for which computing module 1100 is specifically purposed.

Computing module 1100 may include, for example, one or more processors, microprocessors, controllers, control modules, or other processing devices, such as a processor 1110, and such as may be included in circuitry 1105. Processor 1110 may be implemented using a special-purpose processing engine such as, for example, a microprocessor, controller, or other control logic. In the illustrated example, processor 1110 is connected to bus 1155 by way of circuitry 1105, although any communication medium may be used to facilitate interaction with other components of computing module 1100 or to communicate externally.

Computing module 1100 may also include one or more memory modules, simply referred to herein as main memory 1115. For example, random access memory (RAM) or other dynamic memory may be used for storing information and instructions to be executed by processor 1110 or circuitry 1105. Main memory 1115 may also be used for storing temporary variables or other intermediate information during execution of instructions to be executed by processor 1110 or circuitry 1105. Computing module 1100 may likewise include a read only memory (ROM) or other static storage device coupled to bus 1155 for storing static information and instructions for processor 1110 or circuitry 1105.

Computing module 1100 may also include one or more various forms of information storage devices 1120, which may include, for example, media drive 1130 and storage unit interface 1135. Media drive 1130 may include a drive or other mechanism to support fixed or removable storage media 1125. For example, a hard disk drive, a floppy disk drive, a magnetic tape drive, an optical disk drive, a CD or DVD drive (R or RW), or other removable or fixed media drive may be provided. Accordingly, removable storage media 1125 may include, for example, a hard disk, a floppy disk, magnetic tape, cartridge, optical disk, a CD or DVD, or other fixed or removable medium that is read by, written to or accessed by media drive 1130. As these examples illustrate, removable storage media 1125 may include a computer usable storage medium having stored therein computer software or data.

In alternative embodiments, information storage devices 1120 may include other similar instrumentalities for allowing computer programs or other instructions or data to be loaded into computing module 1100. Such instrumentalities may include, for example, fixed or removable storage unit 1140 and storage unit interface 1135. Examples of such removable storage units 1140 and storage unit interfaces 1135 may include a program cartridge and cartridge interface, a removable memory (for example, a flash memory or other removable memory module) and memory slot, a PCMCIA slot and card, and other fixed or removable storage units 1140 and storage unit interfaces 1135 that allow software and data to be transferred from removable storage unit 1140 to computing module 1100.

Computing module 1100 may also include a communications interface 1150. Communications interface 1150 may be used to allow software and data to be transferred between computing module 1100 and external devices. Examples of communications interface 1150 include a modem or soft-modem, a network interface (such as an Ethernet, network interface card, WiMedia, IEEE 802.XX or other interface), a communications port (such as for example, a USB port, IR port, RS232 port Bluetooth® interface, or other port), or other communications interface configured to operation with the communication media described herein. Software and data transferred via communications interface 1150 may in examples be carried on signals, which may be electronic, electromagnetic (which includes optical) or other signals capable of being exchanged by a given communications interface 1150. These signals may be provided to/from communications interface 1150 via channel 1145. Channel 1145 may carry signals and may be implemented using a wired or wireless communication medium. Some non-limiting examples of channel 1145 include a phone line, a cellular or other radio link, an RF link, an optical link, a network interface, a local or wide area network, and other wired or wireless communications channels.

In this document, the terms "computer program medium" and "computer usable medium" and "computer readable medium", as well as variations thereof, are used to generally refer to transitory or non-transitory media such as, for example, main memory 1115, storage unit interface 1135, removable storage media 1125, and/or channel 1145. These and other various forms of computer program media or computer usable/readable media may be involved in carrying one or more sequences of one or more instructions to a processing device for execution. Such instructions embodied on the medium, may generally be referred to as "computer program code" or a "computer program product" or "instructions" (which may be grouped in the form of computer programs or other groupings). When executed, such instructions may enable the computing module 1100, circuitry related thereto, and/or a processor thereof or connected thereto to perform features or functions of the present disclosure as discussed herein (for example, in connection with methods described above and/or in the claims), including for example when the same is/are incorporated into a system, apparatus, device and/or the like.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense. It will be appreciated that, for clarity purposes, the above description has described embodiments with reference to different functional units. However, it will be apparent that any suitable distribution of functionality between different functional units may be used without detracting from the invention. For example, functionality illustrated to be performed by separate computing devices may be performed by the same computing device. Likewise, functionality illustrated to be performed by a single computing device may be distributed amongst several computing devices. Hence, references to specific functional units are only to be seen as references to suitable means for providing the described functionality, rather than indicative of a strict logical or physical structure or organization.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; the term "set" should be read to include one or more objects of the type included in the set; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Similarly, the plural may in some cases be recognized as applicable to the singular and vice versa. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic, circuitry, or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration. Moreover, the operations and sub-operations of various methods described herein are not necessarily limited to the order described or shown in the figures, and one of skill in the art will appreciate, upon studying the present disclosure, variations of the order of the operations described herein that are within the spirit and scope of the disclosure. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

It should be appreciated that all methods and processes disclosed herein may be used in any glucose or other analyte monitoring system, continuous or intermittent. It should further be appreciated that the implementation and/or execution of all methods and processes may be performed by any suitable devices or systems, whether local or remote. Further, any combination of devices or systems may be used to implement the present methods and processes.

In addition, the operations and sub-operations of methods described herein may be carried out or implemented, in some cases, by one or more of the components, elements, devices, modules, circuitry, processors, etc. of systems, apparatuses, devices, environments, and/or computing modules described herein and referenced in various of FIGS. of the present disclosure, as well as one or more sub-components, elements, devices, modules, processors, circuitry, and the like depicted therein and/or described with respect thereto. In such instances, the description of the methods or aspects thereof may refer to a corresponding component, element, etc., but regardless of whether an explicit reference is made, one of skill in the art will recognize upon studying the present disclosure when the corresponding component, element, etc. may be used. Further, it will be appreciated that such references do not necessarily limit the described methods to the particular component, element, etc. referred to. Thus, it will be appreciated by one of skill in the art that aspects and features described above in connection with (sub-) components, elements, devices, modules, and circuitry, etc., including variations thereof, may be applied to the various operations described in connection with methods described herein, and vice versa, without departing from the scope of the present disclosure.

What is claimed is:

1. A glucose monitoring system configured for monitoring glucose data, the glucose monitoring system comprising:
   a transcutaneous glucose sensor configured to generate glucose sensor data associated with a glucose concentration in a host;
   a display device configured to display information related to the glucose sensor data;
   a sensor electronics unit coupled to the transcutaneous glucose sensor and configured to:
      process the generated glucose sensor data;
      wirelessly transmit a first data packet containing information associated with the processed glucose sensor data to the display device over a communication channel at a first time;
      wirelessly transmit a second data packet containing information associated with the processed glucose sensor data to the display device over the communication channel at a second time;
      maintain a connected state of the communication channel in an interval between wirelessly transmitting the first data packet and the second data packet by transmitting messages between the sensor electronics and the display device, wherein the messages comprise:
         a proposal for a connection parameter for the communication channel between the sensor electronics unit and the display device, wherein the proposal comprises one or more proposed values for the connection parameter;
         a response to the proposal for a connection parameter, based on a determination that the proposal is acceptable; and
      modify a connection between the display and the sensor electronics unit based on another acceptable proposed value of the one or more proposed values.

2. The glucose monitoring system of claim 1, wherein the messages further comprise a counter-proposal, if the response indicates a preference of a value for the connection parameter other than the proposed values for the connection parameter; wherein the counter-proposal comprises one or more counter-proposal values for the connection parameter.

3. The glucose monitoring system of claim 2, wherein the messages further comprise a response to the counter-proposal.

4. The glucose monitoring system of claim 3, wherein the sensor electronics unit is further configured to modify a connection between the display device and the analyte sensor system based on at least one of the counter-proposal values, if the response to the counter-proposal indicates an acceptance of one or more of the counter-proposed values.

5. The glucose monitoring system of claim 3, wherein the sensor electronics unit is further configured to terminate a connection between the display device and the glucose monitoring system, if the response to the counter-proposal indicates a denial of the counter-proposed values.

6. The glucose monitoring system of claim 3, wherein the sensor electronics unit is further configured to establish a connection with the display device based on at least one of the counter-proposal values, if the response to the counter-proposal indicates an acceptance of one or more of the counter-proposed values.

7. The glucose monitoring system of claim 1, wherein the messages further comprise ACK/NACK messages.

* * * * *

UNITED STATES PATENT AND TRADEMARK OFFICE
CERTIFICATE OF CORRECTION

PATENT NO. : 11,019,411 B2
APPLICATION NO. : 15/782782
DATED : May 25, 2021
INVENTOR(S) : Mandapaka et al.

It is certified that error appears in the above-identified patent and that said Letters Patent is hereby corrected as shown below:

On the Title Page

On page 2, in Column 1, item (57), Abstract, Line 1, delete "and. Yet" and insert -- and yet --.

On page 3, in Column 2, item (56), U.S. Patent Documents, Line 21, delete "Varsaysky" and insert -- Varsavsky --.

In the Drawings

In sheet 35 of 41, FIG. 15A, reference numeral 1505J, Line 2, delete "COUNTERPROSAL" and insert -- COUNTERPROPOSAL --.

In the Specification

In Column 3, Line 16, delete "signal" and insert -- signal. --.

In Column 27, Line 23, delete "andrenostenedione;" and insert -- androstenedione; --.

In Column 27, Line 39, delete "diptheria" and insert -- diphtheria --.

In Column 27, Line 46, delete "perioxidase;" and insert -- peroxidase; --.

In Column 27, Line 55, delete "sissomicin;" and insert -- sisomicin; --.

In Column 27, Line 59, delete "duodenalisa," and insert -- duodenalis, --.

In Column 27, Line 67, delete "Trepenoma pallidium," and insert -- Treponema pallidum, --.

In Column 28, Line 1, delete "stomatis" and insert -- stomatitis --.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*

In Column 28, Line 37, delete "(FHIAA)." and insert -- (5-HIAA). --.

In Column 31, Line 9, delete "911);" and insert -- 911; --.

In Column 36, Line 17, delete "132,/or" and insert -- 132, or --.

In Column 45, Line 30, delete "(e.g.," and insert -- e.g., --.

In Column 47, Line 32, delete "and or" and insert -- and/or --.

In Column 57, Line 15, delete "a an" and insert -- an --.

In Column 69, Line 30, delete "1034d)" and insert -- 1034d --.

In Column 80, Line 62, delete ""$T_{inactive}$"." and insert -- "$T_{Inactive}$". --.

In Column 88, Line 58, delete "$T_{interval}$'" and insert -- $T_{interval}$', --.

In Column 93, Lines 38-48, delete "A....purposes." and insert the same in Column 93, Line 37 as the continuation of same paragraph.

In Column 95, Line 54, delete "FIG. J" and insert -- FIG. 7J --.

In Column 98, Line 27, delete "etc.)." and insert -- etc. --.

In Column 99, Line 1, delete "7950" and insert -- 795f) --.

In Column 99, Line 8, delete "7950" and insert -- 795f) --.

In Column 101, Line 55, delete "7950," and insert -- 795f), --.

In Column 106, Line 56, delete "795c)," and insert -- 795c, --.

In Column 108, Line 43, delete "("Conn. Status)" and insert -- ("Conn. Status") --.

In Column 108, Line 43, delete "(the" and insert -- the --.

In Column 113, Line 10, delete "model." and insert -- model, --.

In Column 115, Line 54, delete "16C" and insert -- FIG. 16C --.

In Column 118, Line 31, delete "(e.g.," and insert -- e.g., --.